United States Patent [19]

Vandenbark

[11] Patent Number: 5,614,192
[45] Date of Patent: Mar. 25, 1997

[54] T CELL RECEPTOR PEPTIDES AS THERAPEUTICS FOR IMMUNE-RELATED DISEASE

[75] Inventor: Arthur A. Vandenbark, Portland, Oreg.

[73] Assignee: Connective Therapeutics, Inc., Palo Alto, Calif.

[21] Appl. No.: 59,020

[22] Filed: Mar. 16, 1993

Related U.S. Application Data

[63] Continuation of Ser. No. 735,612, Jul. 16, 1991, abandoned, which is a continuation-in-part of Ser. No. 708,022, May 31, 1991, abandoned, which is a continuation-in-part of Ser. No. 554,529, Jul. 19, 1990, abandoned, which is a continuation-in-part of Ser. No. 467,577, Jan. 19, 1990, abandoned, which is a continuation-in-part of Ser. No. 382,804, Jul. 19, 1989, abandoned.

[51] Int. Cl.$^6$ .................... A61K 38/00; C07K 14/725
[52] U.S. Cl. .................... 424/185.1; 424/184.1; 424/193.1; 514/2; 514/12; 514/16; 530/300; 530/324; 530/328; 530/868
[58] Field of Search .................... 424/88, 184.1, 424/185.1, 193.1; 514/2, 8, 12–16; 530/300, 350, 868, 324–8; 435/69.3

[56] References Cited

U.S. PATENT DOCUMENTS

| | | | |
|---|---|---|---|
| 4,634,590 | 1/1987 | Cohen et al. | 424/88 |
| 4,716,038 | 12/1987 | Stanford et al. | 424/92 |
| 4,845,026 | 7/1989 | Kung et al. | 435/5 |
| 4,873,190 | 10/1989 | Saito et al. | 435/172.3 |
| 4,874,845 | 10/1989 | Saito et al. | 530/395 |
| 4,886,743 | 12/1989 | Hood et al. | 435/5 |
| 5,114,721 | 5/1992 | Cohen et al. | 424/534 |
| 5,316,925 | 5/1994 | Davis et al. | 435/91.2 |
| 5,340,921 | 8/1994 | Brenner et al. | 530/350 |
| 5,436,319 | 7/1995 | Kung et al. | 530/350 |

FOREIGN PATENT DOCUMENTS

| | | | |
|---|---|---|---|
| 1197480 | 12/1985 | Canada | 195/1.11 |
| 0291046 | 11/1988 | European Pat. Off. | G01N 33/80 |
| 296786 | 12/1988 | European Pat. Off. | |
| 0304279 | 2/1989 | European Pat. Off. | C07K 7/04 |
| 340109 | 11/1989 | European Pat. Off. | |
| 0403156 | 12/1990 | European Pat. Off. | C07K 15/06 |
| WO8606413 | 11/1986 | WIPO | C12Q 1/68 |
| WO8703600 | 6/1987 | WIPO | C07K 3/00 |
| 9117268 | 11/1991 | WIPO | |
| 9508572 | 3/1995 | WIPO | |

OTHER PUBLICATIONS

Desquenne–Clark, L. et al., P.N.A.S. (USA) 88:7219–7223 (Aug. 1991), "T–Cell Receptor Peptide Immunization Leads to Enhanced and Chronic Experimental Allergic Encephalomyeitis".

Esch, T. et al., Critical Reviews in Immunology 11(5): 249–264 (1992), "Observations Legends Conjectures Concerning Restricted T–cell Receptor Usage and Autoimmune Disease".

Howell, M.D. et al., Science 246:688–670 (1989).

Janeway, C.A., Nature 341:482–483 (1989).

Happ, M.P. et al., J. Neuroimmunol. 19:191–204 (1988).

Hashim, G., et al., "Suppression . . . peptide," FASEB Journal, vol. 4, No. 7, 26 Apr. 1990, p. A2023.

Paul, W. F. (ed), Fundamental Immunology, 3rd edition (1993), pp. 679–685 (Immunological Tolerance), 903–915 (Immunosuppression), and 1033–1095 (Autoimmunity and Autoimmune Diseases).

Urban, J. L., et al., Cell 54:577–592 (Aug 12, 1988), "Restricted use of T cell receptor V genes in murine autoimmune encephalomyelitis raises possibilities for antibody therapy".

Vandenbark, A. A., et al., Nature 341:541–544 (12 Oct. 1989), "Immunization with a synthetic T–cell receptor V–region peptide protects against experimental autoimmune encephalomyelitis".

Wraith, D. C., et al. Cell 57:709–715 (Jun. 2, 1989), "T cell recognition as the target for immune intervention in autoimmune disease".

Acha–Orbea, et al., Cell 54:263–273 (Jul. 15, 1988), "Limited heterogeneity of T cell receptors from lymphocytes mediating autoimmune encephalomyelitis specific immune intervention".

Ben–Nun, A., et al., Nature 292:60–61 (1981), "Vaccination against autoimmune encephalomyelitis with T–lymphocyte line cells reactive against myelin basic protein".

Brostoff, S., Immunol. Ser. 59:203–218 (1993), "Vaccination with T–cell receptor peptides".

Holoshitz, J., et al., J. Immunol. 131(6):2810–2813 (1983), "Autoimmune encephalomyelitis (EAE) mediated or prevented by T lymphocyte lines directed against diverse antigenic determinants of myelin basic protein. Vaccination is determinant specific".

Howell, M. D., et al., Science 246:668–670 (1989), "Vaccination against experimental allergic encephalomyelitis with T cell receptor peptides".

Kappler, J. W., et al., Cell 49:263–271 (Apr. 24, 1987), "A T cell receptor Vβ segment that imparts reactivity to a class II major histocompatibility complex product".

Hafler, D. A.., Immunology Today 17(4): 152–159, "TCR usage in human and experimental demyelinating disease". Apr. 1996.

(List continued on next page.)

Primary Examiner—Thomas M. Cunningham
Attorney, Agent, or Firm—David A. Lowin; Richard J. Warburg; Lyon & Lyon

[57] ABSTRACT

Peptides and pharmaceutical compositions comprising immunogenic peptides of a marker T cell receptor (TCR) characteristic of an immune-related disease, capable of preventing, suppressing, or treating the disease, are disclosed. In a preferred embodiment, the amino acid sequence of the peptide corresponds to at least part of the second complementarity determining region (CDR2) of the TCR. Antibodies and/or T cells immunologically reactive to the TCR peptide capable of preventing, suppressing, or treating an immune-related disease by passive transfer are also disclosed.

56 Claims, 27 Drawing Sheets

OTHER PUBLICATIONS

Steinman, L., Annals N. Y. Acad. Sci. 636: 147–153, "Prospects for immunotherapy directed to the T cell receptor in human autoimmune disease". 1991.

Vandenbark, A. A. et al., J. Neurosci. Res. 43:391–402, "T cell receptor peptides in treatment of autoimmune disease: rationale and potential". 1996.

Brostoff, S., "The development and use of T cell receptor peptide vaccines" in Immunobiology of Proteins and Peptides VIII (M. Z. Atassi, ed.), Plenum Press, New York. 1995.

Brostoff, S. W. et al., Annals of the New York Academy of Sciences, vol. 636, pp. 71–78. Dec. 1991.

Brostoff, S. in Monoclonal Anitbodies and Peptide Therapy in Autoimmune Diseases, J. Bach, editor, Chapter 13, pp. 203–218, "Vaccination with T cell receptor peptides". 1993.

Davis, M. D. et al., Nature 334:395–403, "T–cell antigen receptor genes and T–cell recognition". Aug. 4, 1988.

Barth et al., "The Murine T–Cell Receptor Uses A Limited Repertoire of Expressed Vβ Gene Segments," Nature 316:517–523 (1985).

Ben–Nun et al., "The Rapid Isolation of Clonable Antigen–Specific T Lymphocyte Lines Capabhe of Mediating Autoimmune Encephalomyelitis," European Journal of Immunology 11:195–199 (1981).

Berzofsky, "T–Cell Activation by Antigen: Promising Clues to Reception Genes and Molecules," Immunology Today 4:299–301 (1983).

Clark et al., "Identification of a Diversity Segment of Human T–Cell Receptor β–Chain, and Comparison with the Analogous Murine Element," Nature 311:387–389 (1984).

Clevers et al,. "The T–Cell Receptor/CD3 Complex: A Dynamic Protein Ensemble," Annual Review of Immunology 6:629–662 (1988).

Cohen and Weiner, "T–Cell Vaccination," Immunology Today 9:332–335 (1988).

Offner et al., "T Cell Receptor Peptide Therapy Triggers Autoregulation of Experimental Encephalomyelitis," Science 251:430–432 (1991).

Terasaki et al., "Multiple Sclerosis and High Incidence4 of a B Lymphocyte Antigen," Science 193:1245–1247 (1976).

Vandenbark et al., "TCR Peptide Therapy Decreases the Frequency of Encephalitogenic T Cells in the Periphery and the Central Nervous System," J. Neuroimmunology 39:251–260 (1992).

Vandenbark et al., "Human T Lymphocyte Response to Myelin Basic Protein: Selection of T Lymphocyte Lines from MPB–Responsive Donor," J. of Neuroscience Research 23:21–30 (1989).

Gaur et al., "Requirement of CD8+ Cells in T Cell Receptor Peptide–Induced Clonal Unresponsiveness", Science 259:91–93 (1993).

Karpus et al., "CD4+ Suppressor Cells of Autoimmune Encephalomyelitis Respond to T Cell Receptor–Associated Determinants on Effector Cells by Interleukin–4 Secretion", Eur. J. Immunol. 22:1757–1763 (1992).

Kumar et al., "The Involvement of T Cell Receptor Peptide–Specific Regulatory CD4+ T Cells in Recovery From Antigen–Induced Autoimmune Disease", J. Exp. Med. 178:909–916 (1993).

Stevens et al., "Studies of Vβ8 T Cell Receptor Peptide Treatment in Experimental Autoimmune Encephalomyelitis" J. Neuroimmunol. 37:123–129 (1992).

Chou et al., "Immunity to TCR Peptides in Multiple Sclerosis", Amer. Assoc. of Immun., (1994) pp. 2520–2529.

Vainiene et al., "Common Sequence on Distinct Vbeta Genes Defines a Protective Idiotope in Experimental Encephalomyelitis", 31 Journal of Neuroscience Res. 413–420, 1992.

Cohen, "Regulation of Autoimmune Disease Physiological and Therapeutic", Immunological Reviews 1986, No. 94, pp. 5–21.

Katz et al., "The V–region disease hypothesis: evidence from autoimmune encephalomyelitis", Immunology Today, vol. 10(5): 164 (1989).

Bourdette et al., "Immunity to TCR Peptides in Multiple Sclerosis", Amer. Assoc. of Immun. (1994) pp. 2510–2519.

Kitzin et al., "Preferential T–cell receptor beta–chain variable gene use in myelin basic protein–reactive T–cell clones from patients with multiple sclerosis", 88 Proc. Nat'l Acad. Sci, USA 9161–9165, 1991.

Sakai, K. et al., Proc. Natl. Acad. Sci. USA 85: 8608–8612 (1988).

Wraith, D. C. et al., Cell 59:247–255 (1989).

Urban, J. L. et al., Cell 59: 257–271 (1989).

Kumar, V. et al., Ann. Rev. Immunol. 7:657–682 (1989).

Heber–Katz, E. et al., Immunol. Today 10:164–169 (1989).

Holoshitz, J. et al., J. Immunol. 131:2810–2813 (1983).

Cohen, I.R. Prog. Immunol. VI:491–499 (1986).

Lider, O. et al. Science 239:181–183 (1988).

Lider, O. et al., J. Autoimmun. 2:87–99 (1989).

Cohen, I. R. Hosp. Prac. pp. 57–64 (1989).

Sun, D. et al., Nature 332:843–845 (1988).

Sun, D. et al., Europ. J. Immunol. 18:1993–1999 (1988).

Chluba, J. et al., Europ. J. Immunol. 19:279–284 (1989).

Sun, D. et al., J. Immunol. 143:2867–2872 (1989).

Zamvil, S. et al., J. Exp. Med. 167:1586–1596 (1988).

Padula, S.J. et al., J. Clin. Invest. 81:1810–1818 (1988).

Beall, S.S. et al., J. Neuroimmunol. 21:59–66 (1989).

Brostoff, S.W. et al., J. Neuroimmunol. 13:233–240 (1986).

Oksenberg, J.R. et al., Human Immunol. 22:111–121 (1988).

Seboun, E. et al., Cell 87:1095–1100 (1989).

Acha–Orbea, H. et al., Ann. Rev. Immunol. 7:371–405 (1989).

Heber–Katz, E. et al., Ann. N.Y. Acad. Sci. 540:576–577 (1988).

Wraith, D.C. et al., Cell 57:709–715 (1989).

Owhashi, M. et al., J. Exp. Med. 168:2153–2164 (1988).

Urban, J. L. et al., Cell 54:577–592 (1988).

Kappler, J.W. et al., Nature 332:35–40 (1988).

Gascoigne, N.R.J. et al., Proc. Natl. Acad. Sci., USA 84:2936–2940 (1987).

Offner, H. et al., J. Neuroimmunol. 21:13–22 (1989).

Claverie, J.M. et al., Immunol. Today 10(1):10–14 (1989).

Oksenberg, J.R. et al., Proc. Natl. Acad. Sci. USA 86:988–992 (1989).

Burns, F.R. et al., J. Exp. Med. 169:27–39 (1989).

Zamvil, S. et al., Nature 324:258–260 (1986).

Zamvil, S. et al., Nature 317:355–358 (1985).

MacDonald, H.R. et al., Nature 332:40–45 (1988).

Lipoldova, M. et al., J. Autoimmun. 2:1–13 (1989).

Londei, M. et al., Science 228:85–89 (1985).

Stamenkovic, I. et al., Proc. Natl. Acad. Sci. USA 85:1179–1183 (1988).

Rothbard, J.B. et al., EMBO J. 7(1):93–100 (1988).

Margalit, H. et al., J. Immunol. 138(7): 2213–2229 (1987).

Ota, K. et al., Nature 346:183–187 (1990).

Allegretta et al., Science 247:718–721 (1990).

Link et al., *Neurology* 40(Suppl. 1) :283 (1990).
Offner et al., *J. Exper. Med.* 170:355–367 (1989).
Zamvil et al., *J. Immunol.* 139(4):1075–79 (1987).
Waksman et al., *Proc. Sco. Exp. Biol. Med.* 175:282–94 (1984).
Bourdette et al., *Cell. Immunology* 112:351–63 (1988).
Whitman et al., *Cell. Immunology* 126:290–303 (1990).
Hafler et al., *J. Immunology* 139(1):68–72 (1987).
Richert et al., *J. Neuroimmunol.* 23:55–66 (1989).
Oksenberg, J.R. et al., *Nature* 345:344–346 (1990).
Wucherpfennig, K.W., et al., *Science* 248:1016–1019 (1991).
Chou, C.-H. J. et al., *J. of Neurochem.* 28:115–119 (1977).
Eyler, E.H. et al., *J. of Biol. Chem.* 246(18):5770–5784 (1971).
Cohen, J.A. et al., *Cell. Imm.* 108:203–213 (1987).
Geha, R.S., *Clin. Immunol. and Immunopath.* 19:196–205 (1981).
Sohnle, P.G. et al., *J. Immunol.* 127(2):612–615 (1981).
Ford, D. et al., *Cell. Immunol.* 79:334–344 (1983).

Olsson, T. et al., *J. Clin. Invest.* 86:981–985 (1990).
Gammon, G. et al., *Immunol. Rev.* 98:53–73 (1987).
Offner, H. et al., *J. Immunol.* 141(11): 3828–3832 (1988).
Vandenbark, A.A. et al., *J. Immunol.* 135(1):229–233 (1985).
Vandenbark, A.A. et al., *Dynamic Interactions of Myelin Proteins* pp. 93–108 (1990).
Chou, Y.K. et al., *J. Neurosci Res.* 22:181–187 (1989).
Hashim, G.A. et al., *J. Immunol.* 144(12):4621–4627 (1990).
Alvord, Jr., E.C., *Exp. Allergic Encephalomyelitis* pp. 523–537 (1984), A.R. Liss. Pub., New York.
Higgins, P.J. et al., *J. Immunol.* 140(2):440–445 (1988).
Williams, W.V. et al., *Immunol. Res.* 7:339–350 (1988).
Chou, Y.K. et al., *J. Neurosci. Res.* 23:207–216 (1989).
Bourdette, D.N. et al., *J. Neuroimmunol.* 26:81–85 (1990).
Kappler, J. et al., *Science* 244:811–813 (1989).
Hashim, G.A. et al., *J. Neurosci. Res.* 24:222–230 (1989).
Tuohy, V.K. et al., *J. Immunol.* 140(6):1868–1873 (1988).

Vβ8-

Vβ8+

Vβ8-

Vβ8+

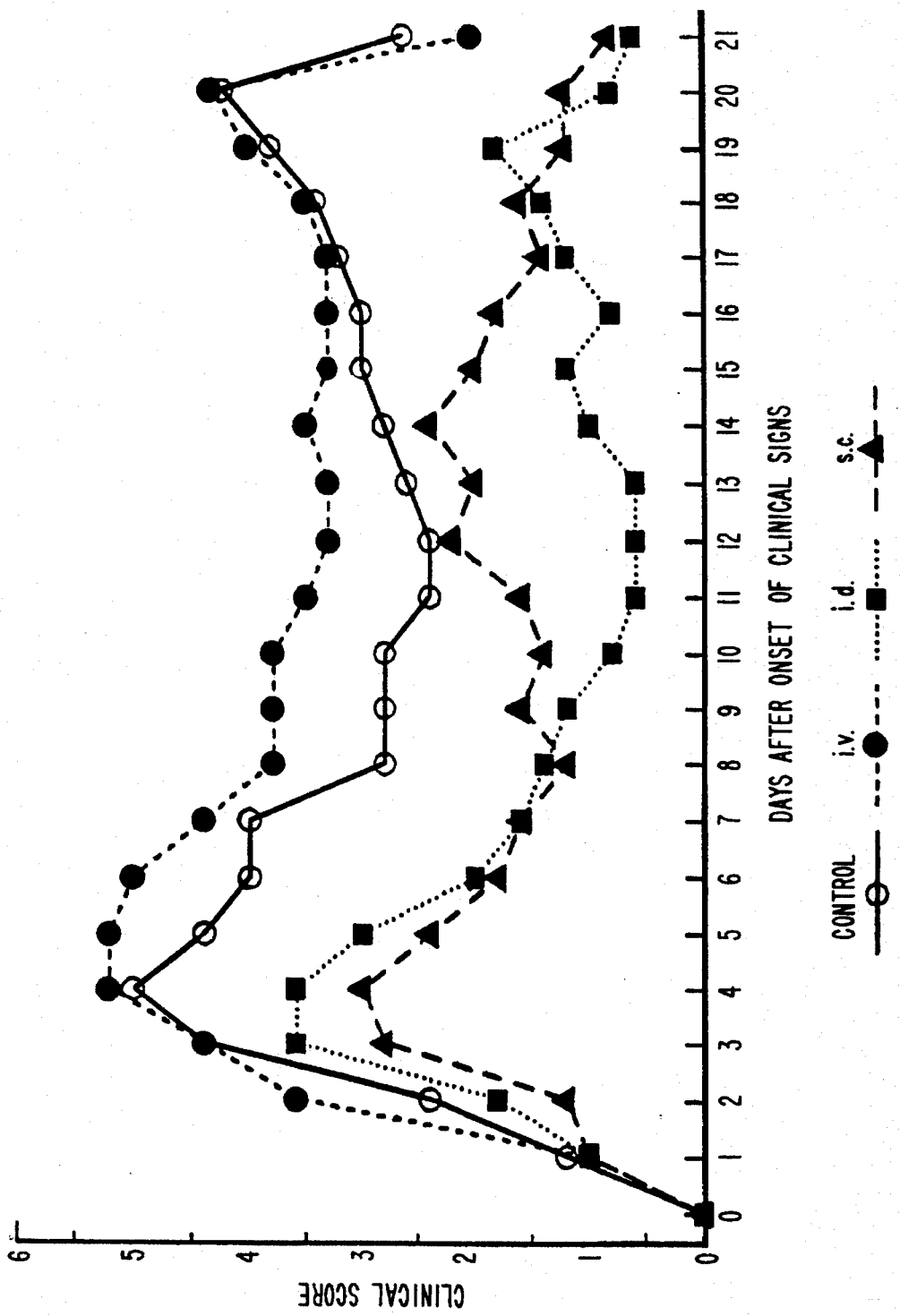
FIG. 9. TREATMENT OF SJL MICE WITH Vβ17 (1-17)

Vα GENE FAMILIES

FIG. 11A.

| PATIENTS | H CLONES | 1 | 2 | 3 | 4 | 5 | 6 | 7 | 8 | 9 | 10 | 11 | 12 | 13 | 14 | 15 | 16 | 17 | 18 | NT |
|---|---|---|---|---|---|---|---|---|---|---|---|---|---|---|---|---|---|---|---|---|
| NL | 14 | 4 |  |  |  |  |  |  |  |  |  |  |  |  |  |  |  |  |  | 10 |
| MR | 10 | 2 | 2 |  |  |  |  | 2 | 3 |  | 2 | 1 |  |  |  |  |  |  |  | 3 |
| WS | 6 | 2 |  |  |  |  |  | 1 | 1 |  | 1 |  |  |  |  |  |  |  |  |  |
| MD | 9 |  | 1 |  | 1 |  | 1 | 2 |  |  |  |  | 1 | 1 | 2 |  |  |  |  | 3 |
| JH | 7 |  | 1 |  |  |  |  | 1 |  |  |  | 2 | 1 | 1 |  | 1 |  | 1 |  |  |
| SO | 3 |  |  |  |  |  |  |  |  |  |  |  | 1 |  |  |  |  |  |  | 2 |
| RB | 1 |  |  |  |  |  |  |  |  |  |  |  |  |  |  |  |  |  |  | 1 |
| TOTAL | 50 | 4 | 4 | • | 1 | • | 5 | 5 | • | 4 | 3 | 3 | 2 | 2 | 1 | • | • | 1 | 20 |

Vα GENE FAMILIES

FIG. 11B.

| PATIENTS | H CLONES | 1 | 2 | 3 | 4 | 5 | 6 | 7 | 8 | 9 | 10 | 11 | 12 | 13 | 14 | 15 | 16 | 17 | 18 | NT |
|---|---|---|---|---|---|---|---|---|---|---|---|---|---|---|---|---|---|---|---|---|
| MA | 13 |  | 1 |  |  |  |  |  |  |  |  |  | 2 | 1 |  |  |  |  |  | 11 |
| JT | 10 |  | 4 |  |  |  |  |  |  |  |  |  |  |  | 3 |  |  |  |  | 4 |
| BP | 7 | 1 | 3 |  |  |  |  |  |  |  |  |  | 1 |  | 4 |  |  |  |  |  |
| LT | 6 |  | 4 |  |  |  |  | 1 |  |  |  | 1 |  |  | 1 |  |  |  |  |  |
| DB | 4 |  |  |  |  |  |  |  |  |  |  |  |  |  |  |  |  |  |  | 4 |
| HY | 1 |  |  |  |  |  |  |  |  |  |  |  |  |  |  |  |  |  |  | 1 |
| TOTAL | 41 | 1 | 12 | • | • | • | • | 1 | • | • | • | 1 | 3 | • | 8 | • | • | • | • | 20 |

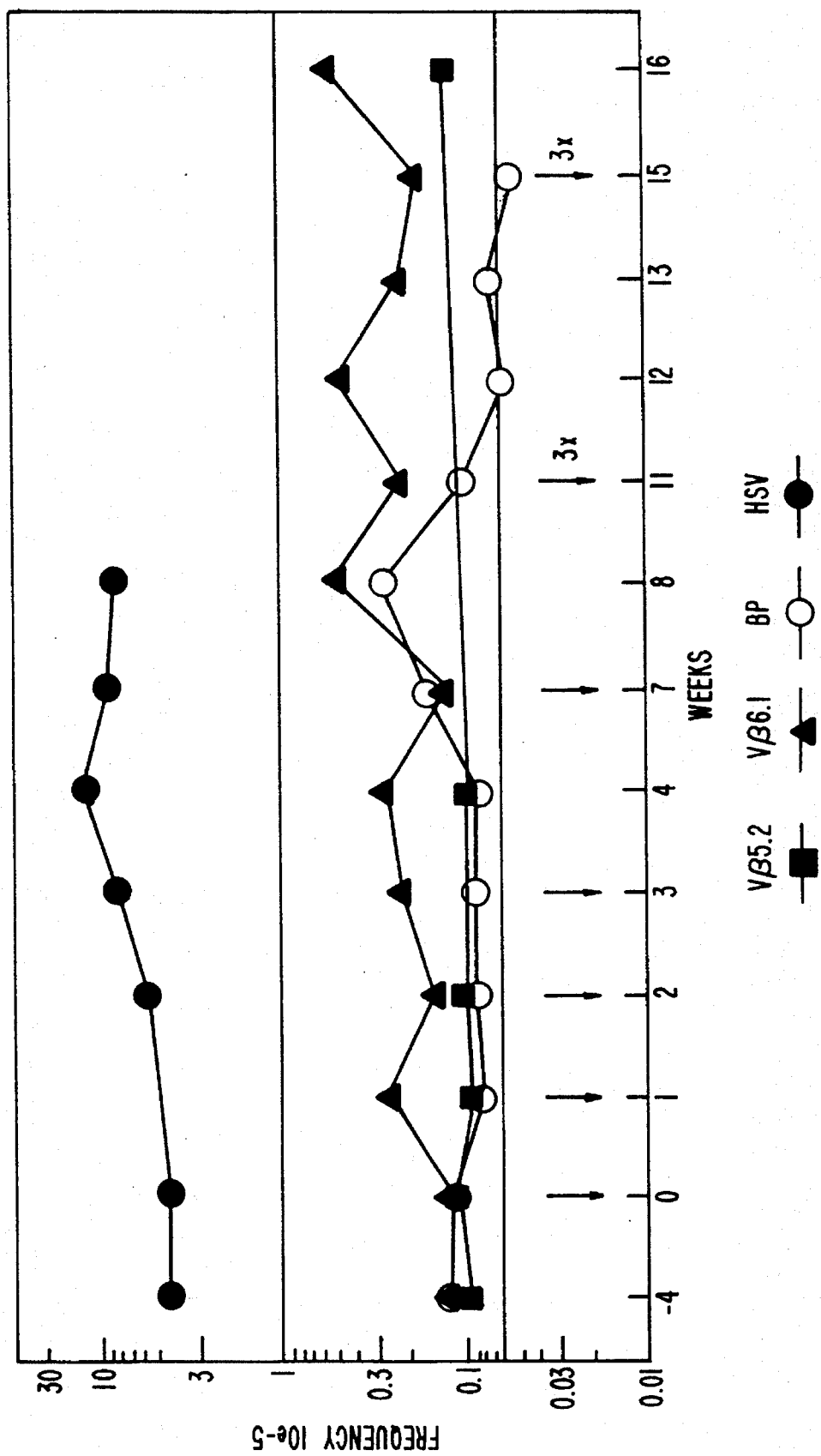

FIG. 18.

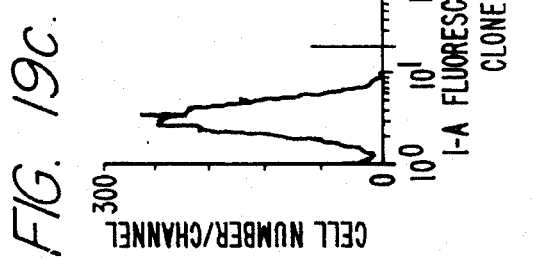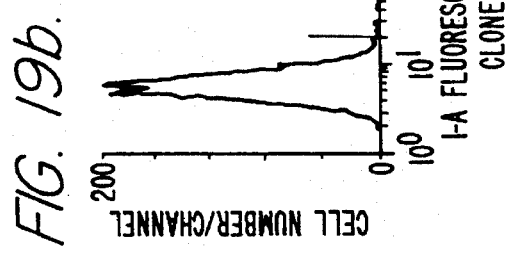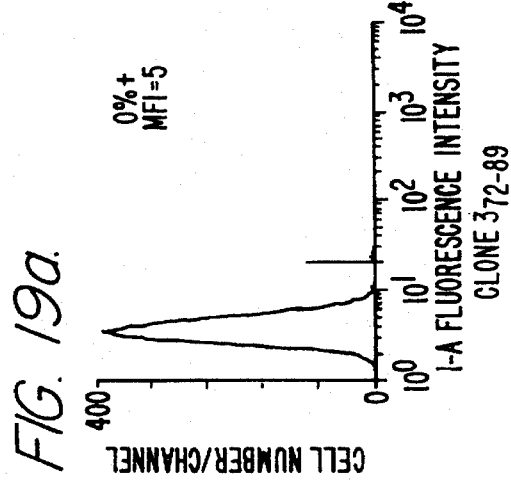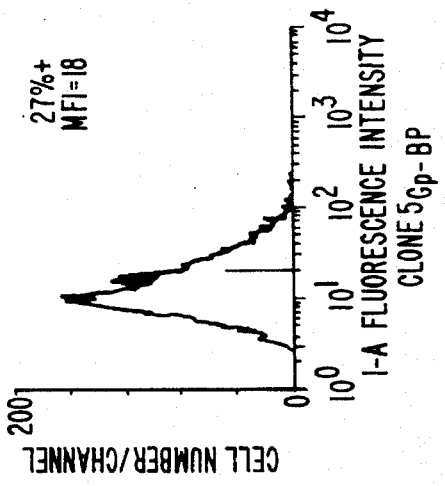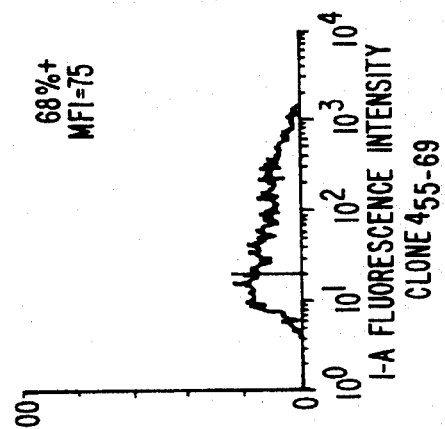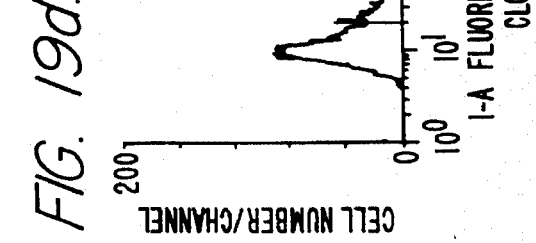

T CELL RECEPTOR PEPTIDES AS THERAPEUTICS FOR IMMUNE-RELATED DISEASE

CROSS-REFERENCE TO RELATED APPLICATIONS

This application is a continuation of application Ser. No. 07/735,612, filed 16 Jul. 1991, now abandoned; which is a continuation-in-part of U.S. patent application Ser. No. 07/708,022, filed 31 May 1991 (now abandoned) which is a continuation-in-part of U.S. patent application Ser. No. 07/554,529 (now abandoned) filed Jul. 19, 1990, which is a continuation-in-part of U.S. patent application Ser. No. 07/467,577, filed Jan. 19, 1990 (now abandoned), which is a continuation-in-part of U.S. patent application Ser. No. 07/382,804, filed Jul. 19, 1989 (now abandoned).

BACKGROUND OF THE INVENTION

1. Field of the Invention

The invention in the field of immunology and immunotherapy is directed to peptides and their pharmaceutical compositions which are capable of preventing, suppressing or treating immune-related diseases. Specifically, the invention provides a therapy that results in clinical improvement of MS patients.

2. Description of the Background Art

Autoimmune diseases are characterized by an unwanted and unwarranted attack by the immune system on the tissues of the host. While the mechanism for progress of these diseases is not well understood, at least some of the details with respect to antigen presentation in this (and other) contexts are being elucidated. It is now thought that antigens, including autoantigens, are processed by antigen-presenting cells (APC), and the resulting fragments are then associated with one of the cell surface proteins encoded by the major histocompatibility complex (MHC). As a result, recognition of a peptide antigen is said to be MHC "restricted." When the MHC/antigen fragment complex binds to a complementary T cell receptor (TCR) on the surface of a T lymphocyte, it leads to activation and proliferation of the clone or subpopulation of T cells that bear that particular TCR. Once activated, T cells have the capacity to regulate other cells of the immune system which display the processed antigen and to destroy cells or tissues which carry epitopes of the recognized antigen.

A review of the role of TCRs in autoimmune diseases by Acha-Orbea et al. (*Ann. Rev. Immunol.* 7:371–405 (1989)) discussed the tremendous variation in TCRs available in the immune system of an individual and the generation of this diversity by germ line gene organization and rearrangement of the DNA encoding TCR $\alpha$ and $\beta$ chains. The $\alpha$ chains are encoded by various combinations of variable (V), junction (J) and constant (C) region gene segments. TCR $\beta$ chains are additionally encoded by a diversity (D) region gene segment, and, thus comprise a rearranged VDJC sequence. Due to allelic exclusion, a clone of T cells expresses only one type of TCR $\alpha$-$\beta$ heterodimer.

A growing number of human diseases have been classified as autoimmune in nature (see, Theofilopoulos, A., In: D. P. Stites et al., eds., *Basic and Clinical Immunology*, Lange Medical Publications, Los Altos, Calif., 1988) of which several examples are rheumatoid arthritis (RA), myasthenia gravis (MG), multiple sclerosis (MS), systemic lupus erythematosus (SLE), autoimmune thyroiditis (Hashimoto's thyroiditis), Graves' disease, inflammatory bowel disease, autoimmune uveoretinitis, polymyositis and certain types of diabetes. Animal models have been developed for a number of these human autoimmune diseases. Among the best studied model is experimental allergic encephalomyelitis (EAE, also called experimental autoimmune encephalomyelitis), a model for MS.

Because it is now known that these and other autoimmune diseases involve the action of T helper cells stimulated by the binding of their TCR to an MHC/autoantigen (or nonautoantigen) complex, prevention and/or treatment strategies have been proposed which are based on the disruption of interactions between the MHC/antigen complex and the TCR. Wraith, D. C. et al., *Cell* 57:709–715 (1989)), proposed approaches based on this principle, including vaccination with whole T cells (as initially described by I. R. Cohen's laboratory, discussed below), passive blockade using antibodies which bind to the TCR, passive blockade using antibodies that bind to the MHC portion of the complex, administration of antibodies reactive with the T helper cell marker, CD4, and the use of peptides which mimic the antigen of interest and compete for binding to the MHC or the TCR molecule.

Myelin basic protein, MBP, is the major autoantigen involved in EAE and is the leading candidate as an encephalitogen involved in MS.

Heber-Katz's group (Heber-Katz, E. et al., *Ann. N.Y. Acad. Sci.* 540:576–577 (1988); Owhashi et al., *J. Exp. Med.* 168:2153–2164 (December 1988)) has analyzed the fine specificity of recognition of MBP epitopes by rat T cells. When T cells from rats immunized with MBP were hybridized to a mouse T lymphoma line and cloned, the pattern of fine specificity and Southern blot analysis of the TCR V$\beta$ gene rearrangement indicated a polyclonal response, even though 75% of the clones reacted to the 68–88 encephalitogenic determinant. A monoclonal antibody (mAb), designated 10.18, directed at one encephalitogenic T cell hybridoma proved to be an anti-idiotype or anti-clonotype which reacted only with T cell clones specific for the MBP 68–88 epitope. The mAb could block or reverse EAE when injected with, or 5 days after, the encephalitogenic MBP peptide. Soluble mAb 10.18 blocked the specific T cell clones, and immobilized mAb 10.18 stimulated their proliferation. Following induction of EAE with MBP, the proportion of mAb 10.18-binding cells increased from initially very low frequencies. The authors concluded that the 10.18[+] T cells probably represent the dominant pathogenic T cell repertoire of EAE in Lewis rats. However, it was not known whether mAb 10.18 recognized a V region or an idiotypic determinant.

T cells expressing the TCR $\alpha\beta$ heterodimer can induce idiotypic and V gene family-specific antibodies that can regulate T cell function (Owhashi et al., supra; Gascoigne et al., *Proc. Natl. Acad. Sci., USA* 84:2936 (1987); Kappler et al., *Nature* 332:35 (1988); Kappler et al., *Cell* 49:263 (1987); MacDonald et al., *Nature* 332:40 (1988)). For example, antibodies that recognize the TCR V$\beta$8 sequence have been effective in the prevention and treatment of autoimmunity in mice and rats (Owhashi et al., supra; Acha-Orbea et al., *Cell* 54:263–273 (1988); Urban et al., *Cell* 54:577–592 (1988)). Obtaining such antibodies selective for V region gene products has been dependent upon the availability of T cell clones that express TCR encoded by the relevant V gene family, and requires a laborious screening procedure using whole cells to establish specificity.

While antibody therapies in which antibodies are directed to MHC molecules and CD4 molecules have been generally successful in several animal models of autoimmunity, these approaches may be too nonspecific and potentially overly suppressive, since 70% of T cells bear the CD4 marker, and since all T cell-mediated responses and most antibody responses require MHC-associated antigen presentation.

Multiple sclerosis (MS) is an immune-mediated disease characterized by central nervous system mononuclear cell infiltration and demyelination. Although the pathogenesis of MS is unknown, both genetic and environmental factors have been implicated in the disease process. Major elements of the genetic predisposition include an association of disease with particular class II major histocompatibility complex (MHC) halotypes, in particular HLA-DR21 and -DQw1 (Terasaid et al., *Science* 1933:1245–1247 (976); Ho et al., *Immunogenetics* 15:509–517 (1982); Spielman et al., *Epidemiol. Rev.* 4:45–65 (1982); Francis et al., *Lancet* 1:211 (1986); Elian et al., *Disease Markers* 5:89–99 (1987)), as well as with certain polymorphisms within the T cell receptor (TCR) α-chain and β-chain gene complexes (Beall et al., *J. Cell. Biochem.* 11D:223 (1987); Hauser et al., *J. Neurol.* 89:275–277 (1989); Seboun et al., *Cell* 57:1095–1100 (1989)). These studies suggest that the disease involves $CD4^+$ T-cells bearing αβ TCR. In support of this idea, $CD4^+$ T cells represent a major component of mononuclear cells in the brains of active patients α-chain T cell receptors are present within central nervous system tissue of MS patients but not controls (Terasaid et al., *Science* 193:1245–1247 (976).

T lymphocytes that recognize myelin basic protein (BP) have been shown to have potent demyelinating and encephalitogenic activity in animals (Ben-Nun et al., *Eur. J. Immunol.* 11:195–199 (1981); McFarlin et al., *New Eng. J. Med.* 307:1183–1188 (1982); Mokhtarian et al., *Nature* 309:356–358 (1984); Vandenbark et al., *J. Immunol.* 135:223–228 (1985); Zamvil et al., *Nature* 317:355–358 (1985); Bourdette et al., *Cell. Immunol.* 112:351–363 (1988). Accumulating evidence also suggests that BP-specific T cells may contribute to the pathogenesis of MS. Thus, cells selected from MS patients on the basis of in vivo activation have specificity for BP. The frequencies of BP-reactive T cells are also increased in the blood and cerebrospinal fluid (CSF) of MS patients compared to normal individuals or patients with other neurological diseases. Furthermore, recent studies have demonstrated a marked selective enrichment of BP-reactive T cells in the CSF relative to the blood of individual MS patients. In animals, a limited set of TCR α-chain variable (Vα) and β-chain variable (Vβ) genes are utilized by T cells specific for BP (Acha-Orbea et al., *Cell* 54:263–273 (1988); Urban et al., *Cell* 54:577–592 (1988); Burns et al., *J. Exp. Med.* 169:27–39 (1989); Heber-Katz et al., *Immunol. Today* 10:164–169 (1989)). Monoclonal antibodies directed to these regions or synthetic peptides with sequences common to these TCR variable regions can both protect and treat animals with clinical signs of experimental autoimmune encephalomyelitis (EAE) (Acha-Orbea et al., *Cell* 54:263–273 (1988); Urban et al., *Cell* 54:577–592 (1988); Vandenbark et al., *Nature* 341:541–544 (1989); Howell et al., *Science* 246:668–670 (1989)). In order for a similar approach to be applied to MS patients, it is critical to know if potentially pathogenic T cells also preferentially utilize a limited set of V region genes.

I. R. Cohen's laboratory has developed an approach to the immunospecific treatment of autoimmunity which utilizes whole live or attenuated T lymphocytes as vaccines to treat or prevent EAE, experimental autoimmune thyroiditis (EAT), and experimental arthritis. This approach is reviewed in Cohen, I. R., *Immunol. Rev.* 94:5–21 (1986), which discusses several animal models of autoimmune disease wherein vaccination with disease-specific T lymphocytes has been used to generate prophylactic or therapeutic effects. The fine specificity of vaccination was dictated by the fine specificity of the T cell recognition, possibly implicating the TCR. For example, two different anti-MBP T cell lines, each reactive to a different epitope of MBP, were found to vaccinate against EAE specifically induced by the particular epitope, indicating some form of anti-idiotypic immunity. However, when attempts were made to isolate clones of MBP-specific or thyroglobulin-specific T cells (in a thyroiditis model) from the non-clonal cell lines, only clones producing disease, but not resistance, were obtained. This led to the finding that appropriate aggregation or rigidification of cell membranes, by either hydrostatic pressure or chemical cross-linking, yielded cells which could induce protection more consistently. Similarly, low doses (sub-encephalitogenic) of MBP-specific cells could also induce resistance to lethal EAE. The protective state was termed "counter-autoimmunity." This state involves T cell clones which can specifically proliferate in response to the vaccinating T cells, can suppress effector clones in vitro (non-specifically, presumably through release of a suppressive lymphokine), and can adoptively transfer counter-autoimmunity in vivo. Such counter-autoimmunity is accompanied by suppressed delayed hypersensitivity (DH) responses to the specific epitope and prevention or remission of clinical disease.

A major difficulty with the foregoing approaches is that they require the use of complex biological preparations which do not comprise well-defined therapeutic agents. Such preparations suffer from complex production and maintenance requirements (e.g., the need for sterility and large quantities of medium for producing large number of "vaccine" T cells), and lack reproducibility from batch to batch. The T cell "vaccine" preparations, to be useful in humans, must be both autologous and individually specific, that is, uniquely tailored for each patient. Furthermore, the presence of additional antigens on the surface of such T cells may result in a broader, possibly detrimental, immune response not limited to the desired T cell clones (Offner et al., *J. Neuroimmunol.* 21:13–22 (1989).

There is a great need, therefore, for agents and pharmaceutical compositions which have the properties of specificity for the targeted autoimmune response, predictability in their selection, convenience and reproducibility of preparation, and sufficient definition to permit precise control of dosage.

Currently, no effective treatment for MS is known. (*Harrison's Principles of Internal Medicine,* 12th ed. Wilson et al., McGraw Hill, Inc. 1991). Therapeutic efforts are directed toward amelioration of the acute episode, prevention of relapses or progression of the disease, and relief of symptoms. The clinical manifestations of MS depend upon which nerve group or region of the brainstem, cerebellar or spinal cord is involved. Spinal cord involvement is the predominating feature in most advanced cases of MS.

In acute episodes of disease, glucocorticoid treatment has been suggested as having the potential to lessen the severity of symptoms and speed recovery, however, even its proponents point out that ultimate recovery is not improved by this drug nor is the extent of permanent disability altered. ACTH is the preferred glucocorticoid of clinicians since the only controlled trials which demonstrated any efficacy of glucocorticoid therapy in episodes of MS and optic neuritis were performed with this drug. However, use of long term steroids is not advised.

Immunosuppressive agents such as azathioprine and cyclophosphamide have been claimed to reduce the number of relapses in several series, but there is no consensus about the efficacy of these drugs either.

The current recommendations for the treatment of MS revolve around attempting to avoid exacerbation of the symptoms. Patients are advised to avoid excess fatigue and extremes of temperature and eat a balanced diet. (The above discussion is primarily from Chapter 356 of *Harrison's Principles of Internal Medicine*, 12th ed 1991.)

SUMMARY OF THE INVENTION

This invention was made in response to a clear need for therapeutic agents and compositions capable of preventing, suppressing or treating immune-related diseases in a clone-specific manner, without causing generalized suppression of immunity, as is the case with most current immunotherapeutic and immunopharmacologic approaches. The invention was developed from the knowledge that lines or clones of T cells specific for autoantigens, which actually mediated autoimmune disease, could be converted into therapeutics by complex attenuation protocols, and injected directly into animals to prevent or treat the disease.

The inventor's attempts to achieve such cellular immunotherapy, based on the teachings of previous researchers, resulted in less than optimal results. When using attenuation methods disclosed in the prior art, the inventor achieved varying, unpredictable levels of protection, and the resultant immunity was not clonally limited, presumably because whole cell "vaccines" introduce a variety of antigens.

In an attempt to simplify and standardize this general approach and achieve highly specific immunity wherein only those clones of T cells that recognized the disease-associated antigen were affected, the inventor conceived of the present invention. It was recognized for the first time by the present inventor that an immunogenic peptide can be synthesized which mimics a portion of a disease-associated immunological "marker," such as the TCR of T cells involved in the disease process. Unexpectedly, immunization of a subject with the peptide directs the host immune response against the "marker" and thereby prevents or suppresses the development of the disease or treats the ongoing disease.

One hallmark of the invention is a method for selecting which peptide to use for preventing, suppressing or treating an immune-related disease, based on identifying the amino acid sequence of a marker TCR associated with the disease, predicting which segment of the TCR sequence is immunogenic based on several known algorithms, and determining which site or sites in the TCR structure is an appropriate target for an immune response which will result in protection from the disease.

One embodiment of the invention is a peptide having about 15–30 amino acids comprising an amino acid sequence of a TCR which is a marker TCR associated with an immune-related disease. The peptide, or its functional derivative is capable of inducing protection from the disease.

A related embodiment is a method of treating MS patients comprising administering an effective amount of one or a combination (cocktail) of the following peptides:

Vβ5.2(26–43), Vβ5.2(39–59), Vβ5.2(59–78), Vβ6.1(1–22), Vβ6.1(39–59), Vβ6.1(70–88), Vβ8.2(39–59), Vβ8(44–54), Vβ8.6(39–59) and Vα2.

Other embodiments of the invention are directed to the above peptide, the sequence of which is encoded by a TCR V gene or specific portions of the V gene, such as the VDJ region, at least a part of a complementarity determining region (CDR) of the TCR such as CDR2, or at least part of a hypervariable region. The invention also encompasses the peptide conjugated to a carrier, such as an additional heterologous amino acid sequence, in order to enhance the peptide's immunogenicity.

The invention is also directed to a pharmaceutical composition comprising the peptide or its functional derivative, in admixture with a pharmaceutically acceptable excipient.

Thus, the invention provides chemically defined peptides and therapeutics which can be specifically applied to designated immune-related diseases to disrupt the specific immunological responses responsible for induction or promotion of the disease process.

The diseases for which the invention is particularly useful include autoimmune diseases, such as rheumatoid arthritis, adjuvant arthritis, myasthenia gravis, encephalomyelitis, multiple sclerosis, thyroiditis, diabetes, inflammatory bowel disease and systemic lupus erythematosus. The invention is also directed to malignant disease, such as T cell leukemias and lymphomas wherein the TCR serves as a tumor marker.

The invention provides methods for preventing, suppressing, or treating an immune-related disease comprising administering one of the above TCR peptides, their functional derivatives, or a pharmaceutical composition comprising the peptide.

One embodiment of the invention is a method for selecting a peptide having an amino acid sequence of a T cell receptor which is a immune-related disease marker, comprising:

(a) removing T cells from a subject susceptible to the disease;

(b) expanding the T cells in culture in the presence of an an autoantigen preparation; (c) identifying the TCR V genes expressed by the expanded T cells; and (d) selecting the peptide from the amino acid sequence of the TCR.

The TCR V genes are identified through the use of TCR-specific antibodies or by determining the TCR amino acid sequence.

The invention further provides a method for preparing a peptide having an amino acid sequence of a TCR associated with an immune-related disease, comprising;

(a) selecting a peptide, as described above; and (b) synthesizing the peptide by chemical or recombinant means.

Other embodiments of the invention are directed to polyclonal, monoclonal, or chimeric antibodies specific for the TCR peptide which are capable of protecting a subject from an immune-related disease, and to methods for preparing such antibodies. Also encompassed by this invention are the antibodies conjugated to cytotoxic agents, including ribosomal inhibiting proteins such as the ricin A chain.

The invention also includes methods for preventing, suppressing or treating autoimmune disease by passive immunization with one of the above antibody preparations.

An additional embodiment provides protective T cells capable of preventing, suppressing, or treating autoimmune disease, and methods for preparing such T cells which comprise:

(a) removing T cells from a subject susceptible to the disease;

(b) expanding the T cells of step (a) in culture in the presence of TCR-bearing material such as a TCR peptide; and (c) preparing protective T cell from the expanded cultured T cells.

BRIEF DESCRIPTION OF THE DRAWINGS

FIG. 9. Treatment of relapsing EAE with TCR Vβ17 peptide.

Vβ5.2 is the only positive Vβ band in this autoradiogram. The primer used for amplification of Vβ5.2 cDNA is specific for a sequence common to Vβ5.2 and 5.3 (Choi et al., *Proc. Natl. Acad. Sci. USA* 86:8941–8945 (1989)). Control PCR reactions without added cDNA template but with oligomers specific for Vβ5.2/5.3 showed no Vβ bands.

Figure 10A:
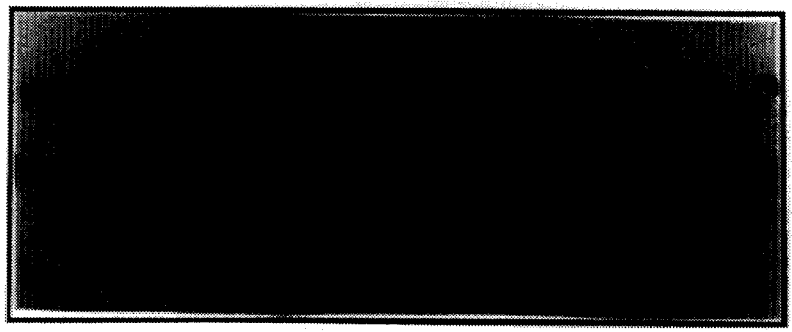
FIG. 10A. Analysis of TCR Vβ expression in clone #41 from patient MR. Autoradiogram shows TCR products amplified by PCR. Total RNA was prepared from the cloned T cells and used for the synthesis of first strand cDNA as described (Choi et al., *Proc. Natl. Acad. Sci. USA* 86:8941–8945 (1989)). Each PCR reaction contained specific oligonucleotide primers to expand the particular Vβ gene segment indicated (170–220 bp) as well as a Cα gene segment (~600 bp). The sequences of the specific primers used and details of the PCR have been described (Choi et al., *Proc. Natl. Acad. Sci. USA* 86:8941–8945 (1989)). Amplified products were separated on 2% agarose gels, dried, and exposed to x-ray film. Incorporation of $^{32}$P end-labeled 3' primers was used to identify amplified products.
Figure 10B:
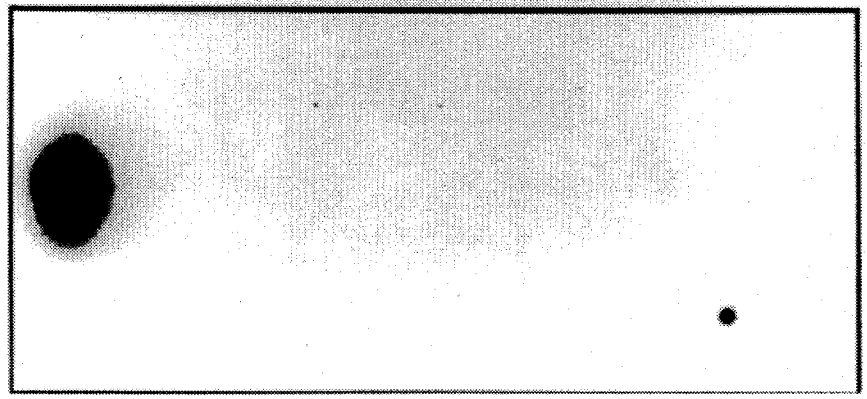

FIG. 10B. Analysis of TCR Vα expression of clone #41 from patient MR. Autoradiogram shows detection of PCR-amplified Vα products. Methods are similar to those described for FIG. 10A except that Vα cDNA was amplified using Vα-specific primers as described (Oksenberg et al., *Nature* 345:344–346 (1990)). In addition, after gel separation and transfer to nylon membranes, Southern Blots were hybridized by the use of a $^{32}$P-kinase probe (5'-AATATC-CAGAACCCTGACCCT-3') corresponding to an internal Cα region (Oksenberg et al., *Nature* 345:344–346 (1990)) and autoradiographed. The size of amplified Vα products ranged from about 320–420 base pairs (Oksenberg et al., *Nature* 345:344–346 (1990)). Vα1 is the only positive band in this Southern blot. For some experiments, slot blots rather than Southern blots were hybridized with the labeled Cα probe. Both detection techniques gave identical results.

FIGS. 11A and B. Summary of usage of Vα genes in BP-reactive T cell clones from MS patients (FIG. 11A) and normal individuals (FIG. 11B). Only the predominant Vα band for each clone is included in this summary analysis. Since some clones had two bands of nearly equal intensity, the total a number of Vαs may be greater than the number of clones analyzed. NT indicates the number of clones that were not tested for Vα expression.

FIG. 12. Frequencies of antigen reactive T cells in MS patient J. M.

Figure 13:
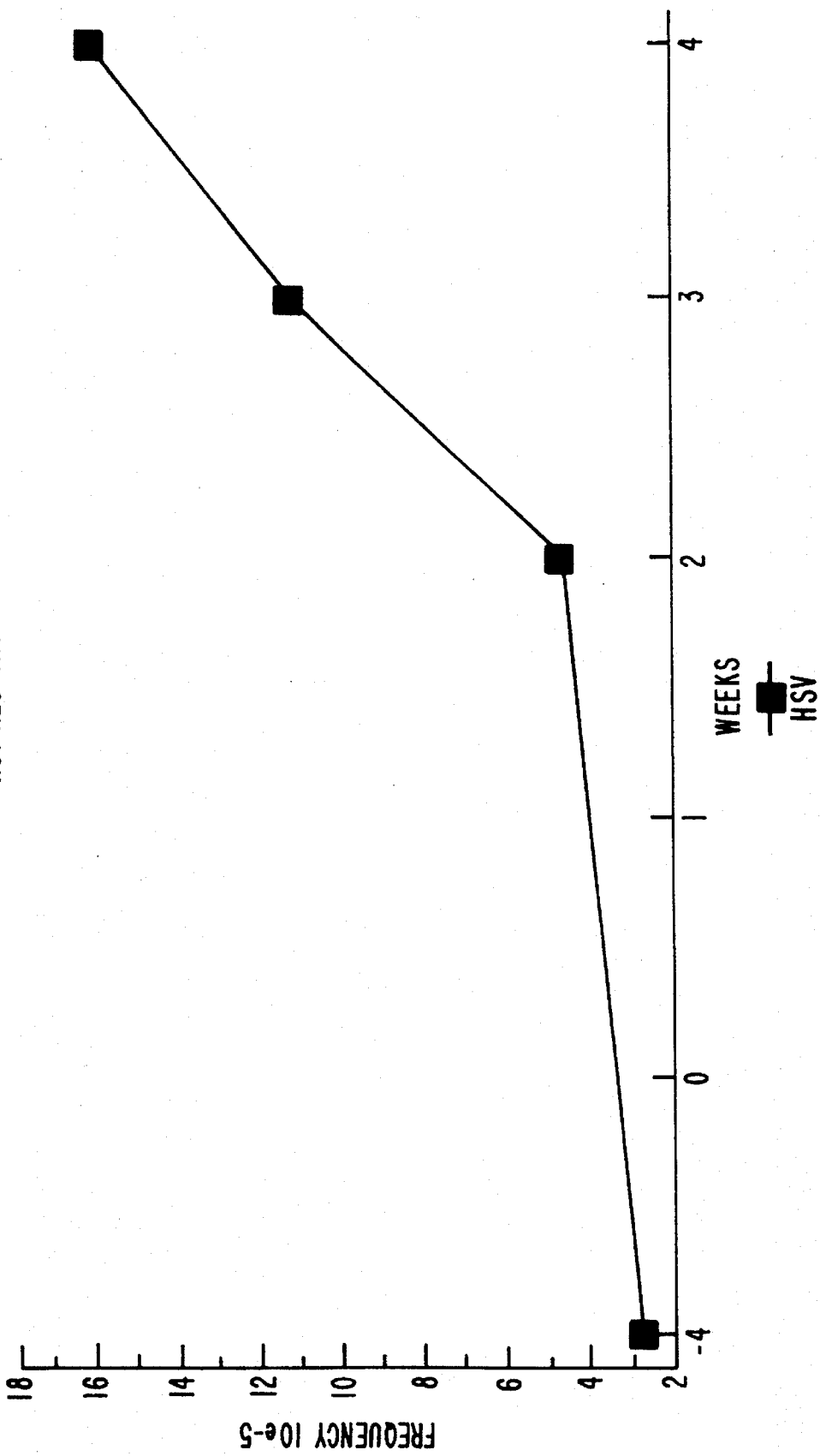

FIG. 13. HSV response in J. M.

Figure 14:
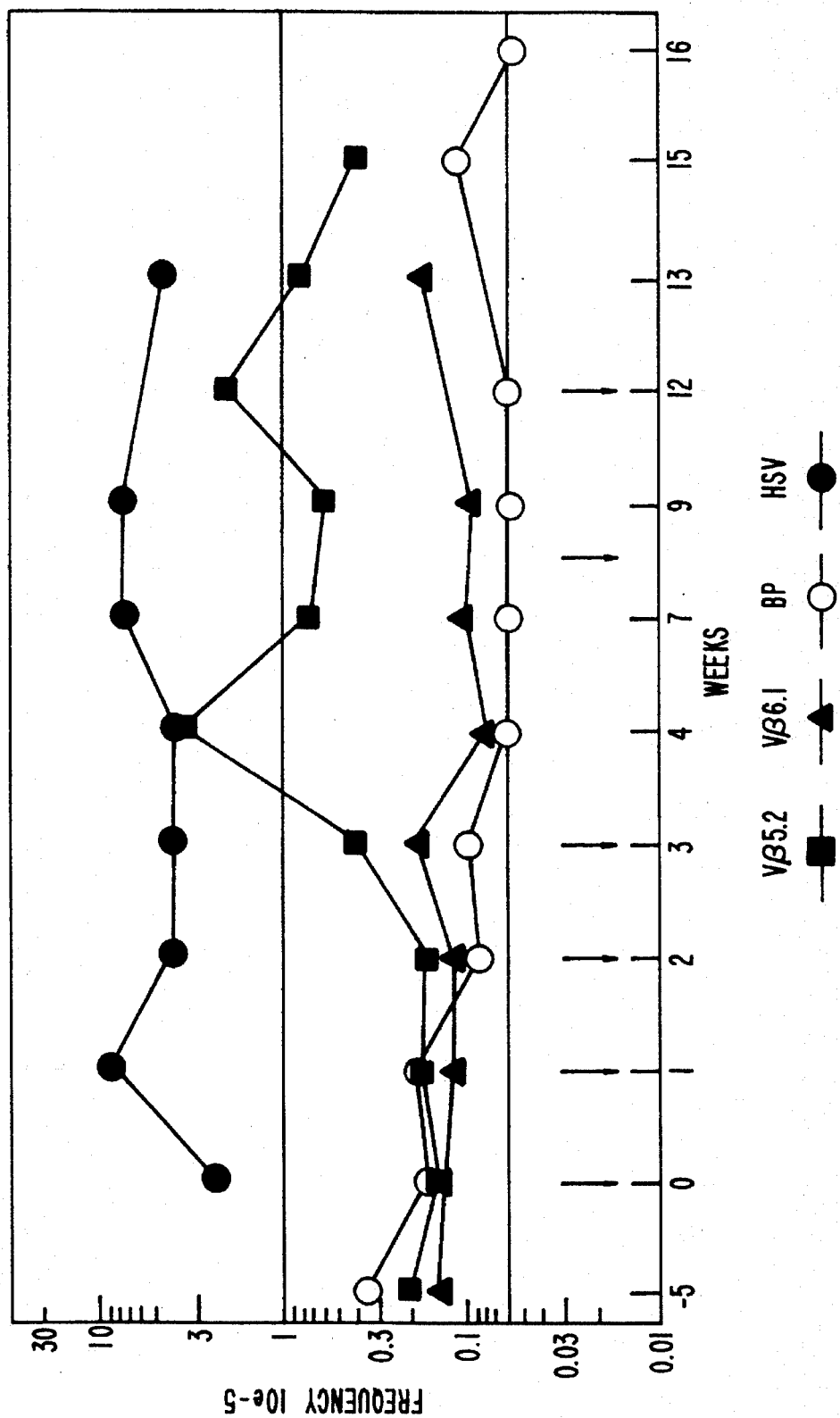

FIG. 14. Frequencies of antigen reactive T cells in MS patient M. R.

Figure 15:
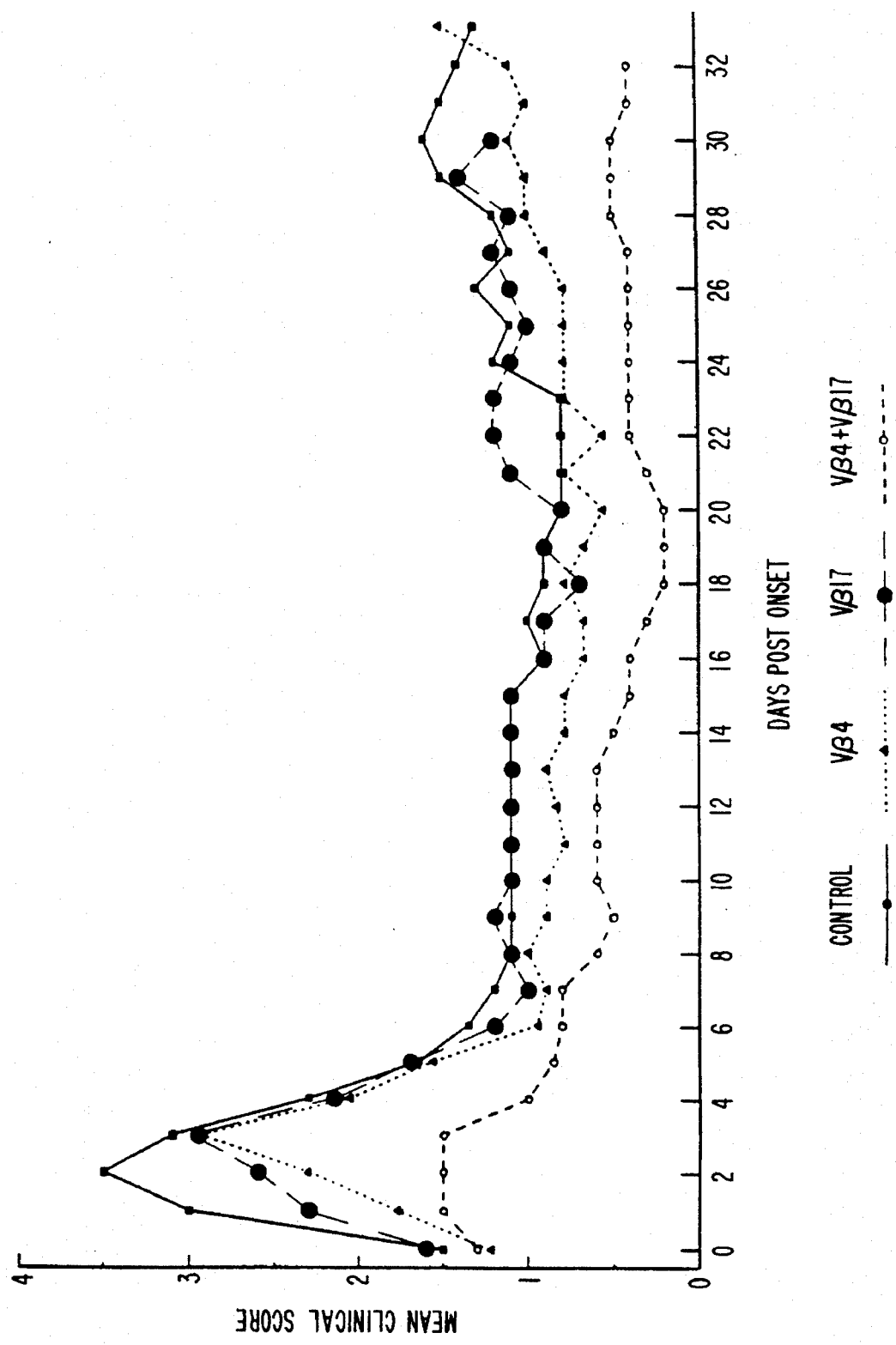

FIG. 15. TCR treatment in SJL mouse. PLP (proteolipoprotein) was used as the antigen to induce EAE.

Figure 16:
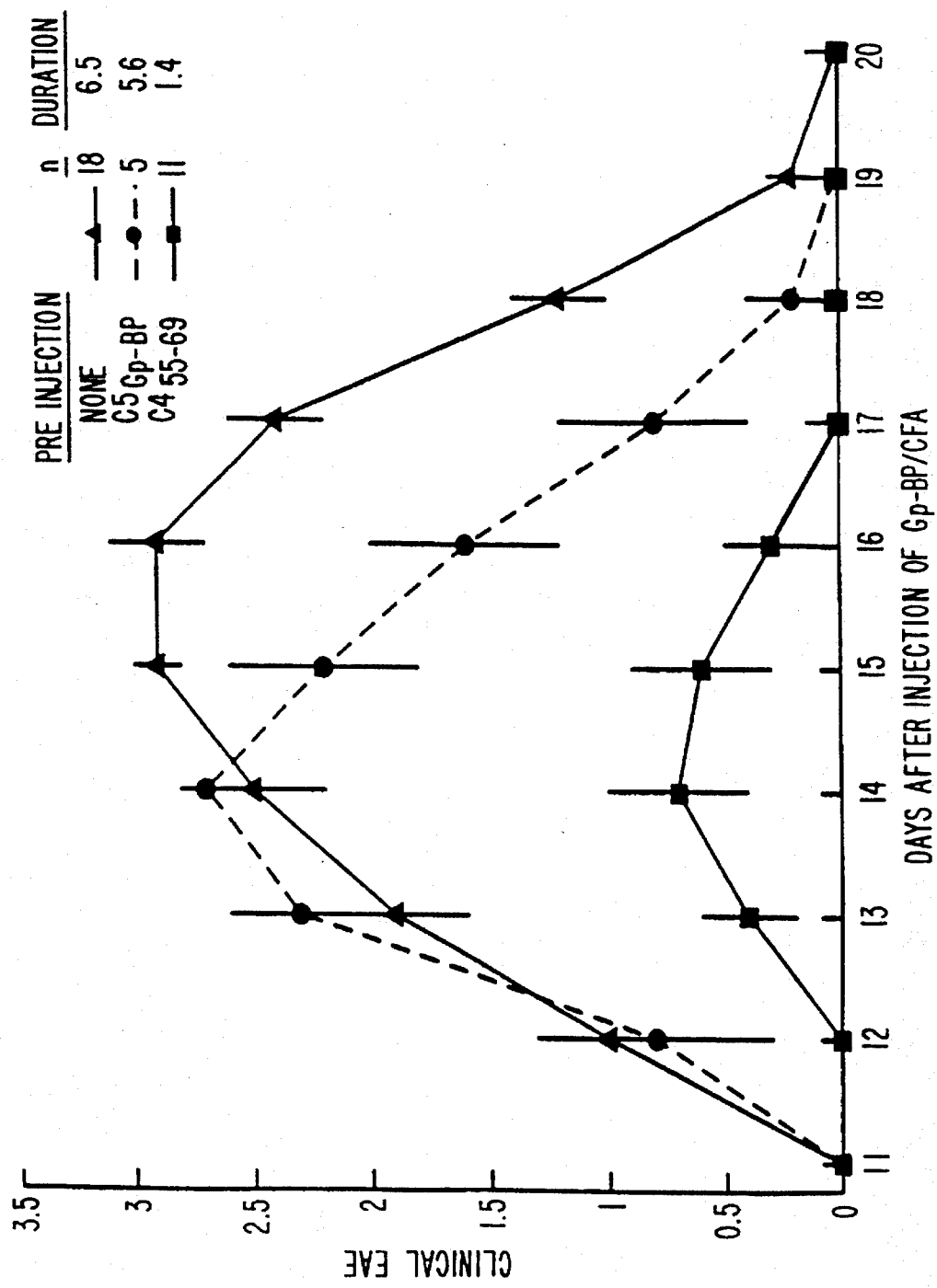

FIG. 16. Pre-immunization with Gp-BP-55-69 inhibits the induction of EAE. Rats were injected with either 100 μg Gp-BP-55-69/CFA or CFA alone for 4 weeks prior to challenge with 10 μg Gp-BP/CFA. Clinical EAE was assessed daily in both groups according to the scale described in Methods (Example XII).

Figure 17:
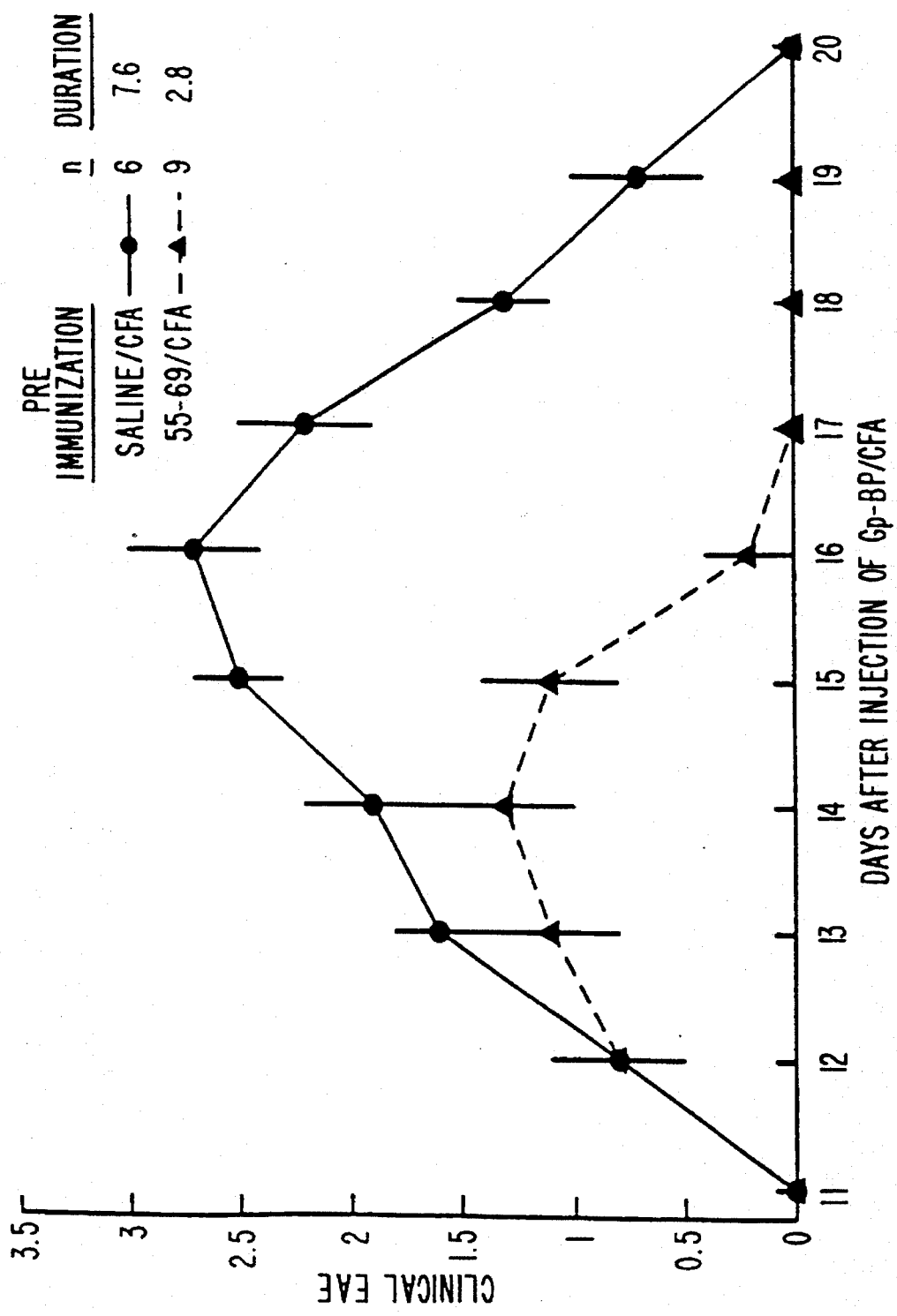

FIG. 17. Passive transfer of clone C4$_{55-69}$ inhibits the induction of EAE. Rats were injected with 10 million activated C4$_{55-69}$ or C5$_{Gp-BP}$ cloned T cells for 14 days prior to challenge with Gp-BP/CFA.

Figure 18:
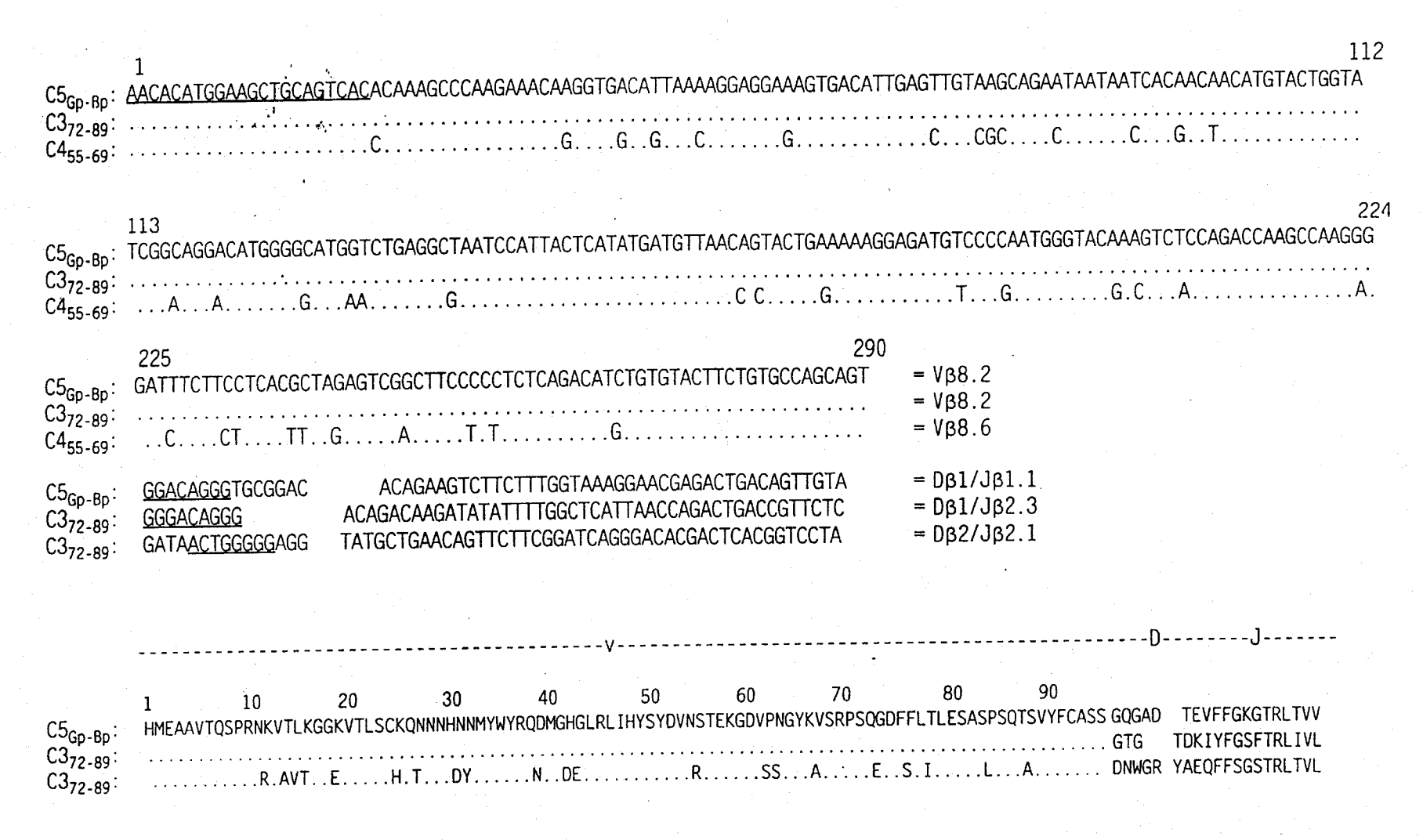

FIG. 18. Nucleotide (upper section) of TCR-Vβ chains utilized by anti-MBP clones. Bases 1–22, shown underlined, are derived from oligonucleotide used in PCR amplification (see Methods, Example XII). Underlined bases in the D region indicate germline sequences, and the remaining bases indicates N region additions. Lower section indicates predicted amino acid sequence of TCR-Vβ chains used by anti-MBP clones. Bases and amino acid residues that differ from the Vβ8.2 sequence are indicated below the sequence for clone C5$_{Gp-BP}$.

Figure 19I:
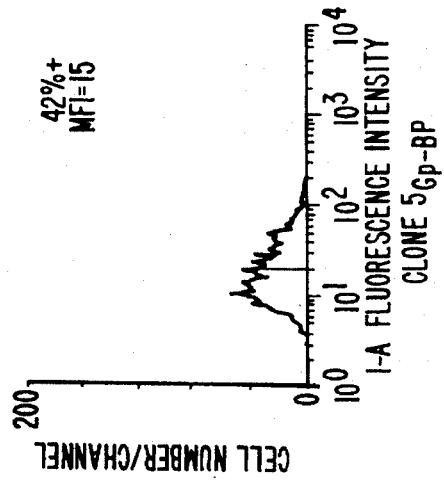
Figure 19H:
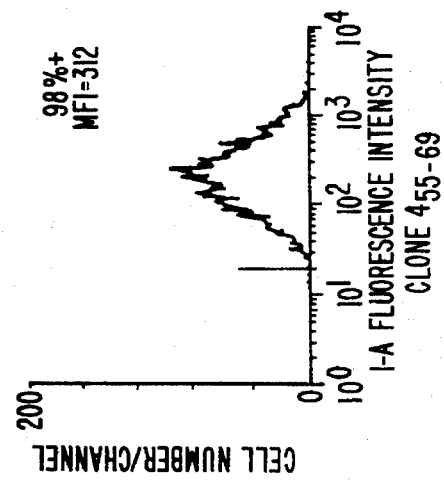
Figure 19G:
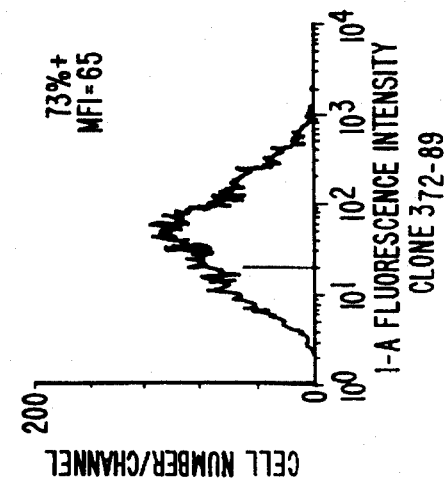

FIG. 19. Expression of I-A by activated and resting T cell clones from EAE-recovered rats. Cells were stained with OX-6 and counterstained with FITC-conjugated goat anti-rat IgG either 3 days after activation with Gp-BP (19g–i) or after an additional 7 days growth in IL-2 rich supernatant (19d–f). FIGS. 19a–c indicate the background level of staining with isotype control antibody.

Figure 20A:
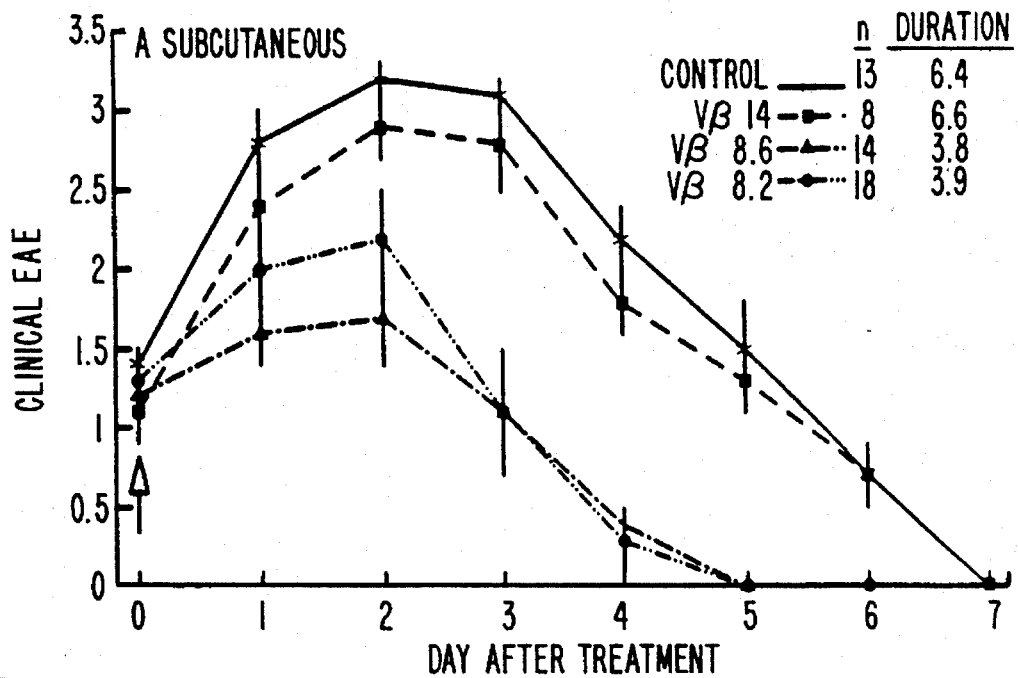
Figure 20B:
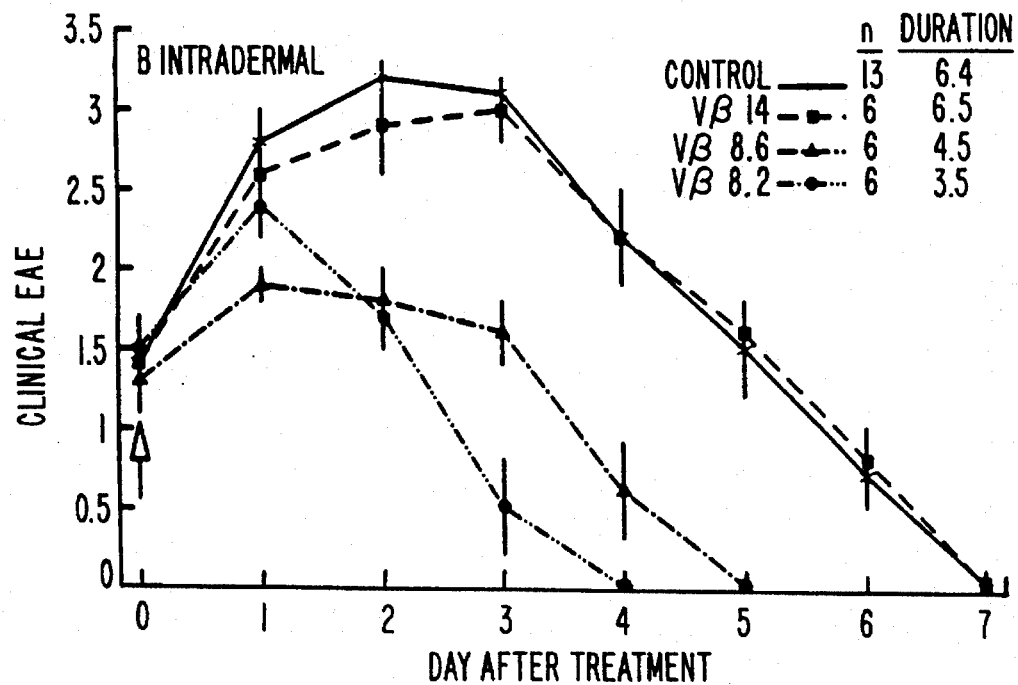

FIG. 20(A and B). Treatment of EAE with TCR Vβ8.6$_{39-59}$ and TCR Vβ8.2$_{39-50}$ peptides. Rats were injected with the indicated doses of TCR peptides either subcutaneously (20A) or intradermally (20B) on the first day of onset of clinical signs, usually day 12 after injection of Gp-BP/CFA. Control groups received TCR Vβ14$_{39-59}$ peptide or no peptide.

Figure 21A:
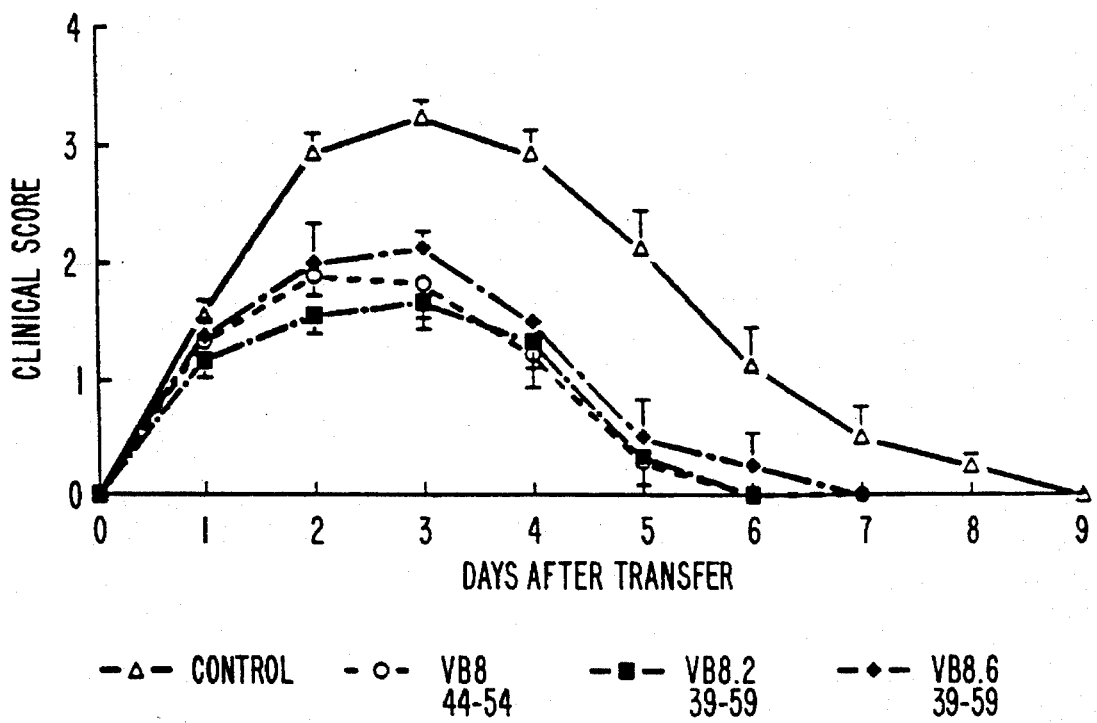
Figure 21B:
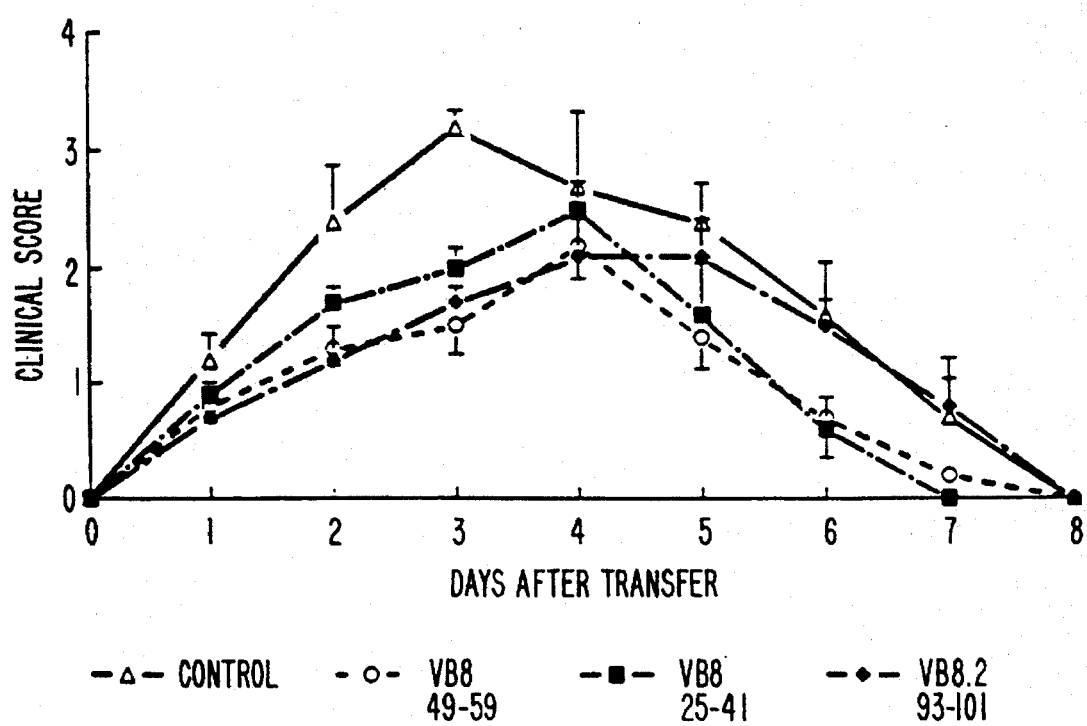

FIG. 21(A and B). Treatment of actively induced EAE with different sets of TCR Vβ8 peptides.

Figure 22:
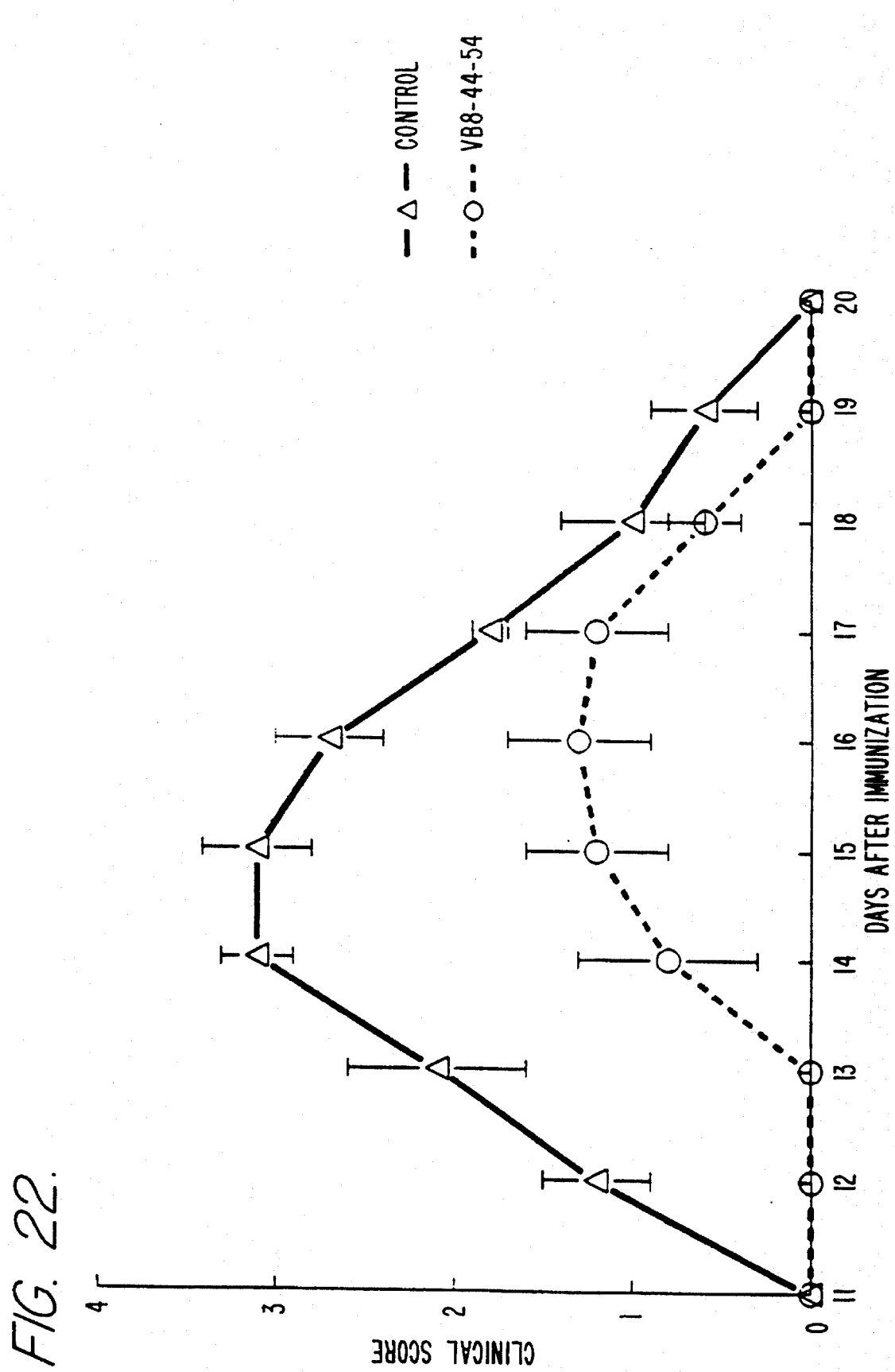

FIG. 22. Treatment of passively induced EAE with TCR Vβ8 peptides.

Figure 23A:
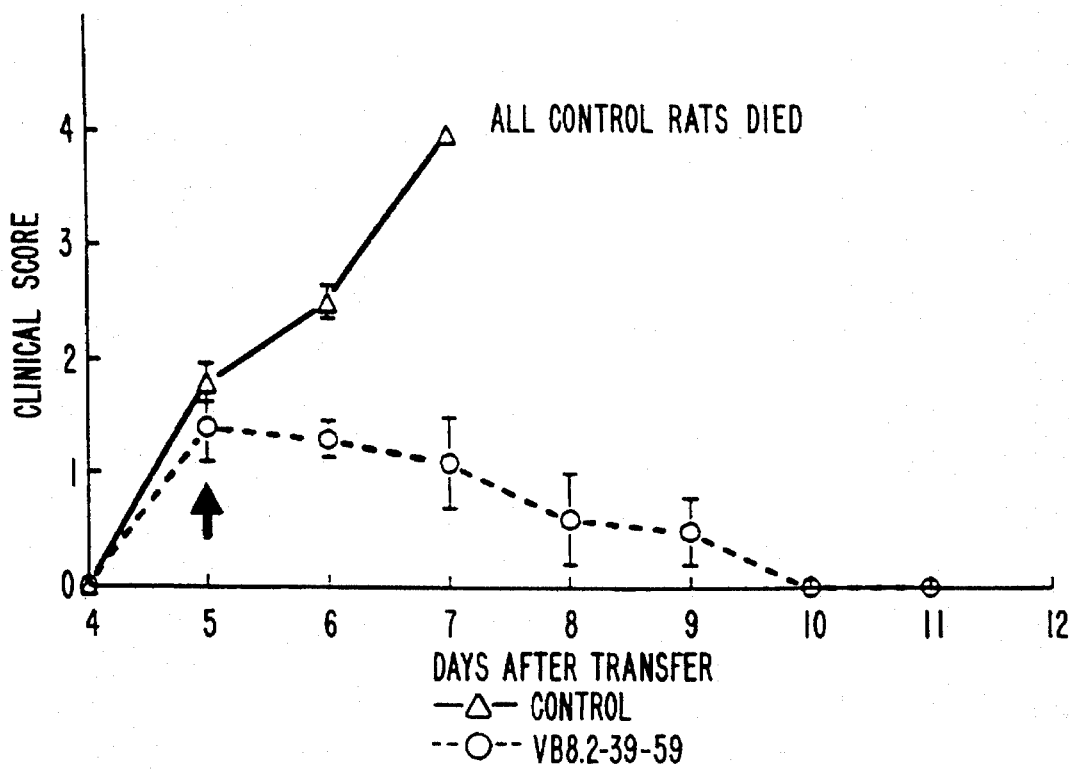
Figure 23B:
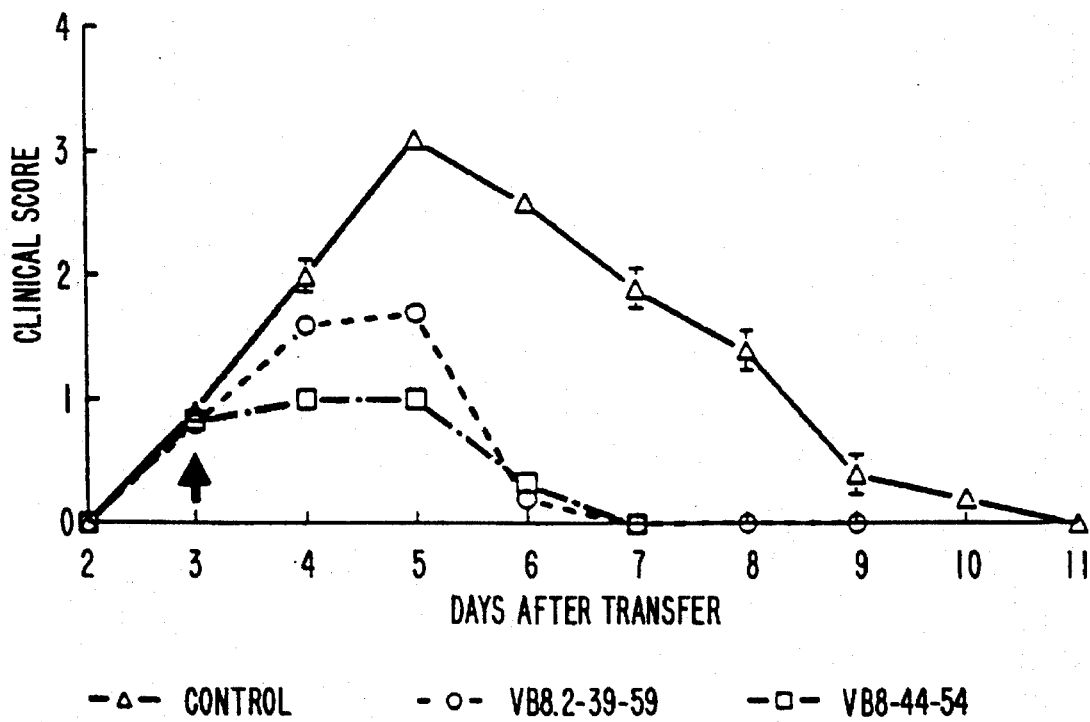

FIG. 23(A and B). FIGS. 23A and B show that T line cells specific for TCR Vβ8–44–54 or Vβ8–39–59 transfer protection against EAE.

Figure 24:
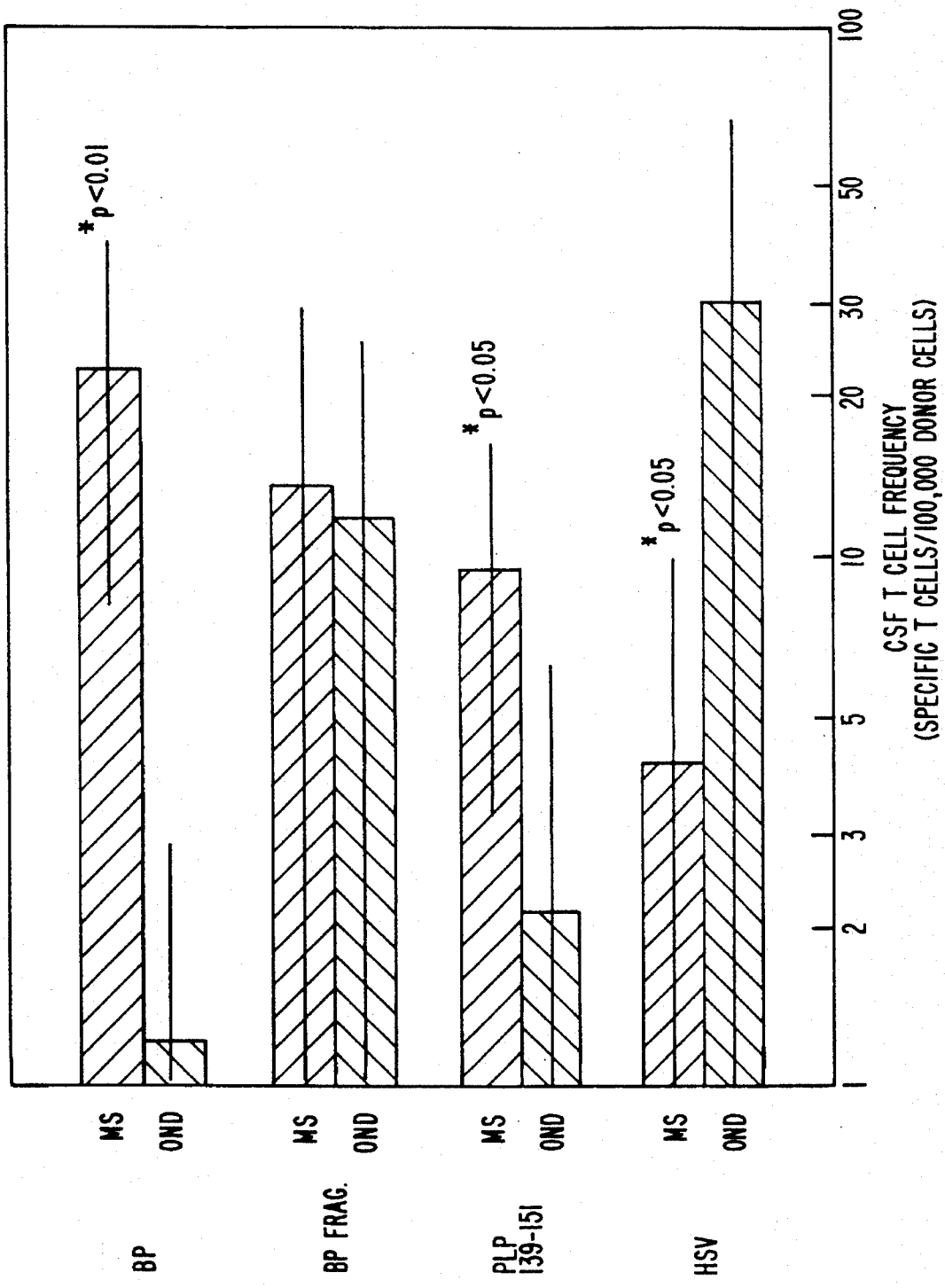

FIG. 24. Frequency of myelin antigen and HSV reactive T cells in the CSF of MS patients and controls. The frequency of antigen specific T cells from the CSF was calculated by dividing the number of antigen reactive clones recovered from each donor by the total number of CSF T cells analyzed. The values presented represent the mean ±S.D. for the 9 MS patients and 6 OND patients analyzed.

Figure 25:
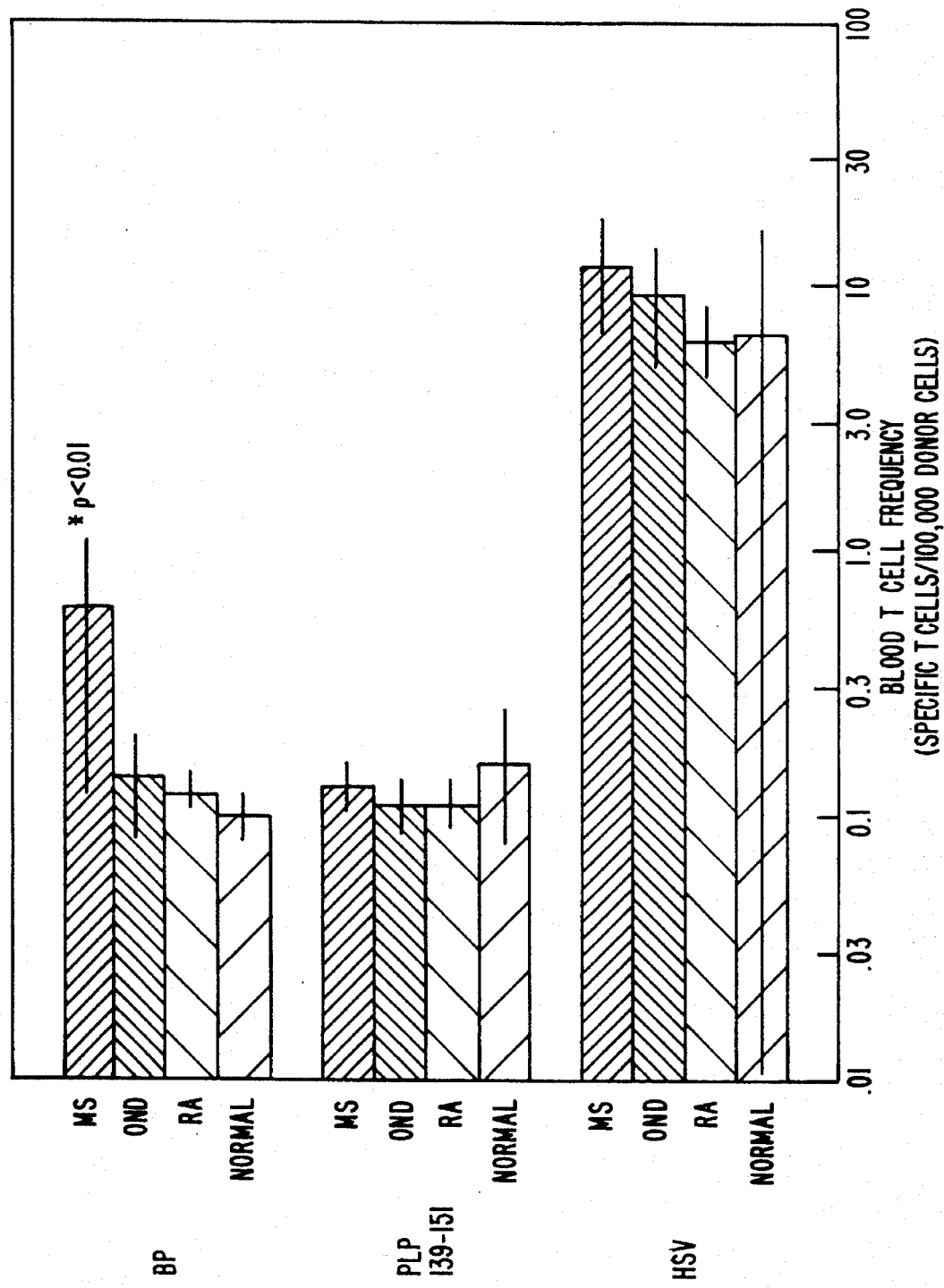

FIG. 25. Frequency of myelin antigen and HSV reactive T cells in the blood of MS patients and control. The blood MNC of each patient were separated by Ficoll density gradient centrifugation and subjected to a limiting dilution analysis (Lefkovits et al., *Immun. Today* 5:265–268, 295–298 (1984)), in which the range of cell dilutions tested were 0.31–5.0×10$^5$ cells per well for BP (50 μg/ml) and PLP$_{139-151}$ (50 μg/ml), and 0.01–0.16×10$^5$ cells per well for HSV antigen (½₀₀ of stock solution, Whittaker, Bethesda, Md.). Positive proliferation responses to antigens had either a stimulation index greater than 3.0 or a delta CPM of 1,000 over background. The mean percentage of non-responding microcultures of all donors was calculated at each cell dilution, and its negative logarithm was plotted on the y axis and the cell input per well on a linear scale on the x axis. At least two experimental points were used to fit a straight line passing through the origin (20%), representing two interactive cell types. The number of cells containing an average of one precursor cell was determined at the level of 37% non-responding cultures (Lefkovits et al., *Immun. Today* 5:265–268, 295–298 (1984)).

Figure 26:
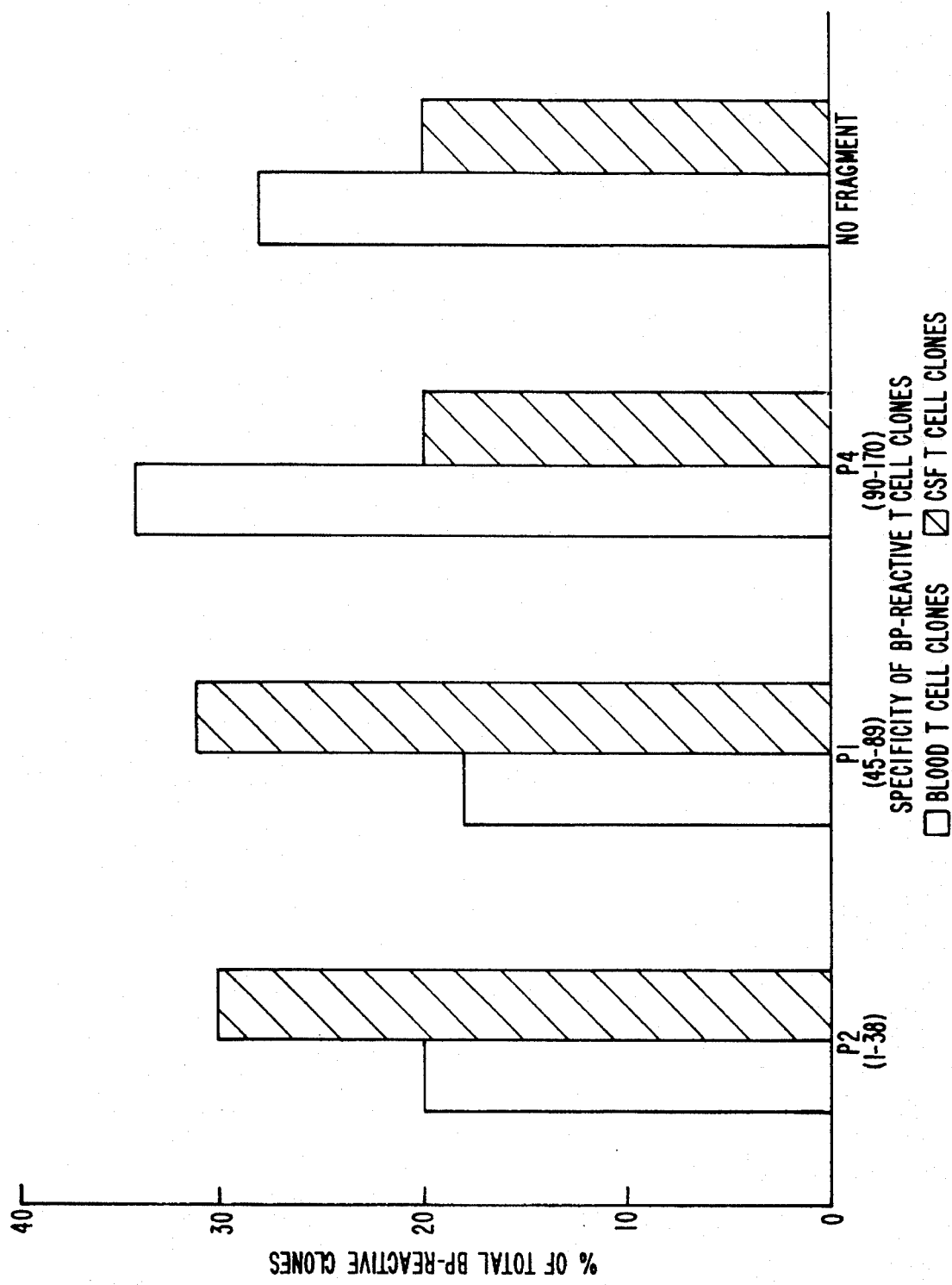

FIG. 26. Comparison of peptide specificities of Hu-BP reactive T cell clones in CSF and blood of MS patients. CSF T cells (1000/well) were expanded in IL-2 and IL-4-enriched medium with irradiated (4,500 rad) autologous MNC (1×10$^5$) without Hu-BP stimulation prior to the assay. Blood T cell clones were obtained by limiting dilution of Hu-BP specific T cell lines that had been restimulated twice with Hu-BP. The specificity of both CSF and blood T cells was evaluated by thymidine uptake 72 hr after incubating 2×10$^4$ T cells with 1×10$^5$ irradiated (4.500 rad) autologous MNC in 0.2 ml triplicate cultures in a round-bottomed 96-well microtiter plate in the absence of antigens and in the presence of 2 μg/ml Concanavalin A, 50 μg/ml Hu-BP, 50 μg/ml Hu-BP fragments: P1, P2, and P4. All clones responded with a stimulation index of >3.0 or >500 CPM over background. The data represent paired analysis of 71 CSF T cell clones and 50 blood T cell clones from 9 donors.

DESCRIPTION OF THE PREFERRED EMBODIMENTS

In the following description, reference will be made to various methodologies known to those of skill in the art of immunology, cell biology, and molecular biology. Publications and other materials setting forth such known methodologies to which reference is made are incorporated herein by reference in their entireties as though set forth in full.

The compositions, methods, and products of this invention are applicable to human and veterinary uses.

The peptides of the present invention comprise sequences of about 15–30 amino acids which are immunogenic, that is, capable of inducing an immune response when injected into a subject.

By "functional derivative" is meant a "fragment," "variant," "analog," or "chemical derivative" of the peptide, which terms are defined below.

It is understood that the amino acid sequence comprising the peptide of this invention can be used alone or bound to, or contained within the sequence of, a longer peptide. The longer peptide may carry additional sequence derived from TCR of interest or may include sequences of an unrelated peptide, such as a carrier protein used to enhance the immunogenicity of the TCR oligopeptide. Such carriers are well known in the art and include heterologous proteins such as, for example, keyhole limpet hemocyanin (KLH), bovine serum albumin, tetanus toxoid and the like. Also included within the scope of this invention is the peptide conjugated to an antibody, and the peptide conjugated to a toxin. The toxins of this invention include the ribosomal inhibitory protein, such as, for example, the ricin A chain or Pseudomonas toxin.

As used herein, "marker TCR" refers to a TCR which is characteristic of a specified immune-related disease, such as autoimmune disease or malignant disease (i.e. cancer).

The term "immune-related disease" as used herein refers to a disease in which the immune system is involved in the pathogenesis of the disease, or in which appropriate stimulation of the immune system can result in protection from the disease. A preferred example of an immune-related disease to which this invention is directed is an autoimmune disease. Non-limiting examples of the autoimmune diseases contemplated by this invention are rheumatoid arthritis (RA), myasthenia gravis (MG), multiple sclerosis (MS), systemic lupus erythematosus (SLE), autoimmune thyroiditis (Hashimoto's thyroiditis), Graves' disease, inflammatory bowel disease, autoimmune uveoretinitis, polymyositis and certain types of diabetes.

Thus, a marker TCR for MS is a TCR which is capable of binding the complex between serf MHC and the MBP fragment (or the MBP fragment alone), the MBP comprising the major autoantigen characteristic of this disease. In other autoimmune diseases, other TCRs serve as markers, as they are specific for the complex between MHC molecules and the autoantigens involved in these diseases. For example, in myasthenia gravis (MG), the autoantigen is thought to be the nicotinic acetylcholine receptor (AChR). Therefore, an identifiable TCR which binds AChR in the context of self MHC (or directly) and is expressed by AChR-reactive T cells which mediated the disease is a "marker TCR" for MG. Those of skill will recognize that determination of a marker TCR and of immunogenic peptides may be accomplished with the exercise of routine skill, using screening methods as are well-known in the art, when the teachings of the present invention are fully appreciated.

Also intended as immune-related diseases as used herein are malignancies wherein the tumor cell carries a tumor marker, such as a tumor antigen, capable of being recognized and responded to by the immune system. The TCR can serve as a tumor marker on T cell leukemia or T cell lymphoma cells.

In a subjected afflicted with, or susceptible to, an immune-related disease, introduction of the peptide carrying the amino acid seqeuence of a portion of the marker TCR results in generation of an immune response directed to the TCR and protection from the immune-related disease.

By the term "protection" from the disease as used herein is intended "prevention," "suppression" or "treatment" of the disease. "Prevention" involves administration of the protective composition prior to the induction of the disease. Thus, for example, in the animal model, EAE, successful administration of a protective composition prior to injection of the encephalitogen that induces the disease results in "prevention" of the disease.

"Suppression" involves administration of the composition after the inductive event but prior to the clinical appearance of the disease. Again, using the EAE example, successful administration of a protective composition after injection of the encephalitogen, but prior to the appearance of neurological symptoms comprises "suppression" of the disease.

"Treatment" involves administration of the protective composition after the appearance of the disease. In the EAE example, successful administration of a protective composition after injection of the encephalitogen and after clinical signs have developed comprises "treatment" of the disease.

It will be understood that in human medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

For the embodiment of the invention directed to autoimmune disease, the subject's immune response is directed to the particular TCRs which mark those T cells mediating the autoimmune process, thus inhibiting the function of the pernicious T cells.

In general, the peptide sequence represents a portion of the TCR itself and preferably corresponds to a portion of the TCR which is extracellular, exposed to antibody or other T cells, and is of biological importance in the activity of the T cell bearing the TCR. For the purposes of this invention, the peptide must be immunogenic, as defined below.

Peptides of the invention include those corresponding to a portion of the V region of the TCR. More preferably, the peptide corresponds to a segment of the VDJ region of the TCR β chain or the VJ region of the TCR α chain. In a preferred embodiment, the peptide corresponds to at least part of one of the three complementarity determining regions (CDRs) of the TCR heterodimer, such as second CDR (CDR2). Also intended within the scope of this invention are peptides corresponding to at least part of the TCR γ and TCR δ chains, their V regions, and CDR structures or their homologs in the γδ heterodimer (see Strominger, J. L., *Cell* 57:895–898 (1989); and Clevers et al., *Ann Rev. Immunol.* 6:629–662 (1988)).

The CDRs of the TCR are defined by analogy to the structure of the immunoglobulin molecule wherein the CDRs comprise the amino acid sequences of the heavy or light chain variable regions which contact antigen and constitute crucial portions of the antigen-binding site. All three TCR CDRs are believed to participate in binding to antigen and MHC (Davis, M. M. et al., *Nature* 334:395–402 (1988); Claverie et al., *Immnun. Today* 10:10–14 (1989)). By directing the immune response of the subject, the protective antibodies or the protective T cells of this invention against one of the CDRs of the "marker TCR," the likelihood of disrupting necessary binding or recognition events between the autoimmunity-associated T cell the autoantigen and/or MHC is increased.

A "fragment" of the peptide of the present invention, refers to any subset of the molecule, that is, a shorter peptide.

A "variant" of the peptide refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

Preparation of a peptide variant in accordance herewith is preferably achieved by site-specific mutagenesis of DNA that encodes an earlier prepared variant or a nonvariant version of the TCR protein or peptide. Site-specific mutagenesis allows the production of peptide variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. The technique of site-specific mutagenesis is well known in the art, as exemplified by Adelman et al., *DNA* 2:183 (1983). Typical vectors useful in site-directed mutagenesis include vectors such as the M13 phage, for example, as disclosed by Messing et al., *Third Cleveland Symposium on Macromolecules and Recombinant DNA*, Walton, A., ed., Elsevier, Amsterdam (1981). These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant peptide. An oligonucleotide primer bearing the desired mutated sequence is prepared, generally synthetically, for example, by the method of Crea et al.,

*Proc. Natl. Acad. Sci.* (USA) 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells and clones are selected that include recombinant vectors bearing the mutated sequence arrangement.

The mutated protein region may be removed and placed in an appropriate vector for protein production, generally an expression vector of the type that may be employed for transformation of an appropriate host.

An example of a terminal insertion includes a fusion of a signal sequence, whether heterologous or homologous to the host cell, to the N-terminus of the peptide molecule to facilitate the secretion of mature peptide molecule from recombinant hosts.

Another group of variants is those in which at least one amino acid residue in the peptide molecule, and preferably, only one, has been removed and a different residue inserted in its place. Such substitutions preferably are made in accordance with the following list when it is desired to modulate finely the characteristics of a peptide molecule.

| Original Residue | Exemplary Substitutions | Original Residue | Exemplary Substitutions |
|---|---|---|---|
| Ala | gly; ser | Leu | ile; val |
| Arg | lys | Lys | arg; gln; glu |
| Asn | gly; his | Met | leu; tyr; ile |
| Asp | glu | Phe | met; leu; tyr |
| Cys | ser | Ser | thr |
| Gln | asn | Thr | ser |
| Glu | asp | Trp | tyr |
| Gly | ala; pro | Tyr | trp; phe |
| His | asn; gln | Val | ile; leu |
| Ile | leu; val | | |

Substantial changes in functional or immunological properties are made by selecting substitutions that are less conservative than those in the above list, that is, by selecting residues that differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. The substitutions that in general are expected are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the peptide molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the peptide molecule-encoding nucleic acid, expression of the variant nucleic acid in recombinant cell culture, and, optionally, purification from the cell culture, for example, by immunoaffinity adsorption on an anti-peptide antibody column (to absorb the variant by binding it to at least one epitope).

The activity of the cell lysate or purified peptide variant is then screened in a suitable screening assay for the desired characteristic. For example, a change in the immunological character of the peptide molecule, such as binding to a given antibody, is measured by a competitive type immunoassay. Changes in T cell recognition of the variant peptide are measured by a DH assay in vivo or a T cell proliferation assay in vitro. Modifications of such peptide properties as redox or thermal stability, hydrophobicity, susceptibility to proteolytic degradation or the tendency to aggregate with carriers or into multimers are assayed by methods well known to the ordinarily skilled artisan.

An "analog" of a peptide refers to a non-natural molecule substantially similar to either the entire molecule or a fragment thereof.

A "chemical derivative" of a peptide of this invention contains additional chemical moieties not normally a part of the peptide. Covalent modifications of the peptides are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophanyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or theonyl residues, methylation of the α-amino groups of lysine, arginine, and histidine side chains (T. E. Creighton, Proteins: *Structure and Molecule Properties,* W. H. Freeman & Co., San Francisco, pp. 79–86 (1983)), acetylation of the N-terminal amine, and, in some instances, amidation of the C-terminal carboxyl groups.

Such derivatized moieties may improve the peptide's solubility, absorption, biological half life, and the like. The moieties may alternatively eliminate or attenuate any undesirable side effect of the peptide and the like. Moieties capable of mediating such effects are disclosed, for example, in *Remington's Pharmaceutical Sciences,* 16th ed., Mack Publishing Co., Easton, Pa. (1980).

Malignant Disease

Also susceptible to methods of the invention are lymphomas and leukemias. Lymphomas and many leukemias are tumors made up of lymphocytes that undergo uncontrolled proliferation (e.g., are malignant). Since several classes of leukemia and lymphoma are composed of T cells derived from a single malignant T cell precursor, all of the tumor cells bear the same TCR, which thus serves as a "tumor marker" which can be the target of protective compositions of this invention. Similarly, surface immunoglobulins can serve as tumor markers for B cell leukemias or lymphomas.

One embodiment of the invention is directed to the enhancement of an anti-tumor response by targeting the TCR of those T cells reacting against the "tumor marker" rather than the tumor marker itself. Thus, an immune response directed to the TCR on a tumor-specific T cell can be used to upregulate the antitumor response for the benefit of the host.

In fact, it will be appreciated that any disease involving a cell having a surface molecule that distinguishes that cell from other cells of the same histological type and from cells of a different histological type, contains a characteristic "marker," and will be susceptible to treatment by compositions which induce an immune response to the "marker," thereby altering activity of the cell bearing the "marker."

According to the present invention, the marker molecule itself may be relatively nonimmunogenic; it requires, at minimum, a characteristic antigenic epitope. This epitope itself may be inherently immunogenic, or it can be rendered immunogenic by treatments well known in the art, such as conjugation to an immunogenic carrier molecule. Thus, an epitope of a marker protein, either as a free peptide or in a form rendering it immunogenic, is capable of eliciting an antibody response, a cell-mediated immune response, or both, as conceived in the invention. Therefore, a composition which incorporates not the entire marker protein, but rather, a specific peptide region which is immunogenic or antigenic, will comprise a useful preparation for treating an immune-related disease characterized by this marker.

Identification of Marker TCR-Bearing T Cells

The present invention utilizes a synthetic peptide that represents a region of the TCR having biological importance in ligand/MHC binding, such as CDR2, and that is characteristic of a TCR V gene family. The invention therefore provides a much simpler approach for obtaining TCR V region-specific antibodies or T cells. Using other sequences from the same β chain to induce a spectrum of TCR V region-specific antibodies or T cells, those of skill will be able to map exposed epitopes of the TCR, and to establish the importance of these regions in ligand/MHC binding, with the exercise of routine skill.

Marker TCRs associated with a given disease are identified using known techniques. A genetic approach using patients known to have MG or MS was described by Oksenberg et al., *Proc. Natl. Acad. Sci.* USA 86:988–992 (1989). Sequences of the appropriate TCR β chain have been obtained by genomic analysis using restriction fragment length polymorphisms found in families having a prevalence of the particular autoimmune disease, as described by Seboun et al., *Cell* 87:1095–1100 (1989); Burns et al., *J. Exp. Med.* 169:27–39 (1989)).

It thus will be appreciated that, for the purposes of the present invention, determination of the marker TCR associated with an autoimmune disease and identification of peptides comprising an immunogenic sequence do not require that the autoantigen be characterized. It is sufficient that (a) the autoimmune disease involves a T cell-mediated immune response as a necessary part of the pathogenetic process, and (b) the disease has an organ-, tissue- or cell-specific target. In fact, as is known in the art (see, for example, Theofilopoulos, A., supra), the autoimmune disease may not involve an autoantigen at all at the inductive stage, but rather, may represent a response to an exogenous antigen, such as a bacterial or viral antigen, which is cross-reactive with serf antigens, or results in an immunopathologic response directed to the exogenous antigen present in the host.

T cells recognizing an autoantigen or autoimmune disease-associated antigen (such as certain vital or bacterial antigens) are cloned, and may be fused to an immortalizing cell, such as a long term T cell line, a T cell lymphoma line or a T cell hybridoma, and are grown in culture. The cultured cells serve as the source of cDNA encoding the appropriate TCR. Such cDNA is cloned and expressed by methods well known in the art. (See, for example, Maniatis et al., *Molecular Cloning: A Laboratory Manual* (1982)).

In addition to the foregoing approaches, it will be appreciated that advantage may be taken of animal models to identify the TCR variable region loci which are associated with the autoimmune disease. Animals which are susceptible to any of a number of autoimmune diseases, non-limiting examples of which include EAE, experimental MG, experimental autoimmune thyroiditis, adjuvant arthritis, collagen-induced arthritis, and the like, have a particular TCR variable locus associated with the disease which can be identified in vitro.

By the term "susceptible to a disease" is intended a state in which the animal possesses a gene or genes known to be associated with the disease, thereby increasing the risk that the individual with that gene or genes will develop that disease compared to the general population. Genes known to be associated with autoimmune diseases, for example, include MHC genes (especially class II), immunoglobulin V genes, TCR V genes, and the like. The term "susceptible" is also intended to encompass those individuals who actually have the disease. While a complete correlation between an autoimmune disease and the usage of a particular TCR is neither expected nor necessary to successfully practice the present invention, high correlations of about 60–70% have been found for presence or expression of a particular variable region gene and susceptibility to autoimmune disease in animals.

In an alternate embodiment of this invention, T cells isolated from humans who are susceptible to an autoimmune disease, and in particular susceptible individuals who have the autoimmune disease, are expanded in culture. Techniques for T cell expansion are described by Zamvil et al., *Nature* 319:355–358 (1985), and *Nature* 324:258–260 (1986).

In one embodiment employing this method, patient peripheral blood lymphocytes are removed and stimulated with the autoantigen or a specific peptide derived therefrom or related thereto, which is capable of stimulation comparable to that of the autoantigen. The autoantigen (or related peptide) is added to the lymphocyte cultures for several days. In one embodiment, cells are simulated with autoantigen for 5–6 days. In other embodiments, cells are stimulated for longer periods of time. The time required for stimulation is a function of the proportion of reactive cells in the blood sample, the activation state of these cells, and the potency of the stimulating preparation, and is readily determinable by one of skill in the art. After culture under such selective conditions, about $5 \times 10^5$ viable cells are isolated and restimulated with about $3 \times 10^7$ autologous antigen-presenting cells (irradiated to prevent their proliferation, such as with about 2500–4500 rad) and about 20 µg/ml of the autoantigen (or related peptide). About 7 days later, viable cells are collected and cloned by limiting dilution in the presence of about $10^3$–$10^6$ antigen presenting cells, for example about $5 \times 10^5$ antigen-presenting cells, and human IL-2 or crude or pure combinations of lymphocyte growth factors (such as, for example, IL-4). The cells of such a T cell line are expanded and grown in tissue culture flasks for about one to two weeks. Such lines can be multiply restimulated with antigen-presenting cells, autoantigen preparations, and IL-2. Restimulation can typically be carried out once a week. If desired, such T cells can be cloned by any of a number of methods known in the art, such as, for example, limiting dilution or by picking cells from colonies growing in soft agar, generally about 2 days after restimulation.

In another embodiment, lymphocytes from an organ or body fluid are first cultured in the presence of IL-2. Under these conditions, selection will occur for cells already activated and only such cells grow. Subsequently, such T cells are stimulated with antigen-presenting cells and an autoantigen preparation. Using this approach, MBP-specific T cells from the spinal cord of rats with EAE can be selectively expanded in vitro.

As used in the present invention, the term "autoantigen" is not intended to be limiting to a defined or known macromolecule. For example, in the case of type I diabetes, the particular antigen associated with pancreatic islet (or beta) cells that is the trigger or target antigen of the T cell-mediated autoimmune response is unknown. For the present invention, the autoantigen used to stimulate cells in vitro, as described above, can comprise whole pancreatic islet cells, crude membrane preparations derived from such cells, partially purified purified membrane components, or when identified, the diabetogenic autoantigen. The same is true for other autoimmune diseases for which a unique autoantigen has not yet been identified, including Hashimoto's thyroiditis, arthritis in which the autoantigen is not collagen, Sjogren's disease, polymyositis, arteriosclerosis, and the like. One of skill will appreciate that as long as the immunogenic moiety to which the T cells respond is present in the stimulatory preparation, the methods of the invention can be carried out as described.

The presence of autoantigen-specific reactive T cells in the cloned, expanded T cell population can be readily determined by testing the ability of the cells to be activated in the presence of the autoantigen. Many assays are available, and well known in the art, to measure early or late events in the T cell activation process. Example of such methods include, but are not limited to, T cell proliferation (which can be measured as the uptake of radiolabeled thymidine), the secretion of interleukin-2, intracellular calcium mobilization, translocation of particular membrane enzymes involved in inositol phosphate metabolism, and changes in expression of cell surface molecules (which can be determined by flow cytometry).

The TCR expressed by a T cell clone responding to a particular autoantigen can be identified using TCR-specific antibodies, either polyclonal, monoclonal or chimeric (see below) which are specific for a TCR variable segment to detect surface expression, employing techniques of fluorescence microscopy, flow cytometry, immunocytochemistry, or other techniques known in the art. Such antibodies have been described for a number of TCR αβ chain V regions (see, for example, Owhashi et al., supra; Gascoigne et al., supra; Kappler et al., 1987, 1988 (supra); and MacDonald, H. R., supra).

Alternatively, the DNA or mRNA of the T cell clone can be probed directly, or after amplification by the polymerase chain reaction (Synha et al., *Science* 239:1026 (1988); Saiki et al., *Nature* 324:163 (1986), by specific hybridization with nucleic acid probes for the various TCR gene families, using hybridization methods well known in the art. The TCR sequence, or a part thereof, can then be obtained directly from the amplified, rearranged DNA or mRNA.

Expression of a particular TCR can also be identified by determining the nucleic acid sequence encoding at least part of the TCR, for example, after cloning the TCR V gene, or by determining the amino acid sequence of at least part of a TCR protein. It will be apparent that any of the abovementioned approaches, or additional approaches known to one of skill in the art, will result in the identifying of the TCR expressed on a T cell or clone or line of T cells. This information is needed for the selection of an amino acid sequence which comprises the peptide or pharmaceutical preparations of this invention.

Where no specific autoantigen has been identified, the oligoclonality of T cells in the anatomic region associated with the disease can be used as a basis for enrichment of reactive T cells. For instance, cells uniquely associated with rheumatoid arthritis are found in the synovial fluid of the joint; cells uniquely associated with MS are found in the cerebrospinal fluid (CSF); and disease-associated T cells infiltrate the thyroid tissue in Hashimoto's thyroiditis and in Graves' disease. In these instances, T cells are isolated from the relevant anatomical location, and the cells expanded in culture as described above. (See also, Londei et al., *Science* 228:85-89 (1985); Londei et al. *Acta Endocrinol.* 115 (suppl. 281):86-89 (1987); Stamenkovic et al. *Proc. Natl. Acad. Sci.* USA 85:1179-1183 (1988); Lipoldova et al. *J. Autoimmun.* 2:1-13 (1989); Oksenberg et al., supra). The DNA or mRNA of such cells is isolated, cDNA prepared, and the differences in sequences of cDNA encoding the variable TCR loci are established by comparison of afflicted with unafflicted subjects. As an alternative to expanding the cells in culture, cellular DNA or, preferably, cDNA made from mRNA, can be obtained directly from T cells isolated from the subject, and the nucleic acid expanded by the PCR reaction, as above.

The antigens associated with a number of human and animal model autoimmune diseases are presently known. Type II collagen and *Mycobacterium tuberculosis* 65 kD heat shock protein are antigens associated with rheumatoid arthritis; AChR is associated with MG, and with experimental allergic myasthenia gravis (EAMG) which can be induced in mice. Thyroglobulin is known to be the antigen associated with experimental allergic thyroiditis (EAT) in mouse. A similar disease, Hashimoto's thyroiditis involves an immune response to an antigen on thyroid follicular cells. In Graves' disease, the immune response is directed to the thyrotropin receptor on thyroid cells. Myelin basic protein (MBP) and proteolipid protein (PLP) are known to be associated with experimental allergic encephalomyelitis (EAE) in mouse and rat. EAE is a recognized model for multiple sclerosis in humans.

Therefore, those of skill will appreciate that the present invention is directed in one aspect to identification of peptides useful for prevention or therapy of human and animal diseases, including but not limited to those mentioned above.

Selection of Antigenic Peptides

An important embodiment of this invention comprises the combined method of identifying a TCR associated with an autoimmune disease, determining which oligopeptide sequence of the TCR is both immunogenic and important for T cell action in the disease process, synthesizing that peptide, and using it as a therapeutic agent.

Regions of relevant TCR sequences are identified for synthesis on the basis of their predicted antigenic or immunogenic properties. By the term "immunogenic" is intended the capacity of a peptide to induce an immune response, either T cell-mediated, antibody, or both. By the term "antigenic" is intended the capability of a peptide to be recognized, in free form by antibodies and in the context of MHC molecules in the case of antigen-specific T cells. Regions of a protein or peptide that are likely to be immunogenic or antigenic for T cells are identified, for example, using the approaches and algorithms described by Margalt et al. (*J. Immunol.* 138:2213-2229 (1987) and Rothbard et al. *EMBO J.* 7:93-100 (1988)). The Margalt et al. approach is based on analysis of immunodominant helper T cell antigenic sites leading to development of an algorithm based on an amphipathic helix model, in which antigenic sites are postulated to be helices with one predominantly polar and one predominantly apolar face. The approach of Rothbard et al., recognizes motifs similar to epitopes recognized preferentially by T helper or T cytotoxic cell clones, which can predict accurately areas within protein sequences that are capable of being recognized by MHC class I and II molecules, such recognition being assumed as necessary for T cell immunogenicity and antigenicity.

In one approach for selecting TCR peptides, the regions of the TCR which are of immunoregulatory importance for the purposes of this invention (based on current models of the structure of the TCR and analogy to antibody structure) fall within CDR1, CDR2, or CDR3, or in TCR hypervariable regions not strictly part of a CDR, such as residues 39–49 of the Vβ segment (see Davis et al., *Nature* 334:395–402 (1988)).

The use of the above approach to select peptide sequences for use in treating MS in human patients and EAE in rats exemplifies the success of this approach. For example, a peptide comprising 16 amino acids corresponding to CDR1 of the marker TCR for EAE in Lewis rats, Vβ8 (25–41) was predicted by the above algorithms not to be immunogenic for T cells. In fact, this peptide does not induce T cell immunity and does not protect Lewis rats from EAE. A peptide corresponding to the CDR1 of a different TCR β chain which is not associated with EAE, Vβ14(25–41), was predicted to be immunogenic for T cells, and indeed was found to induce T cell immunity in Lewis rats, but, as expected, did not protect from EAE. Similarly the CDR2 peptide, Vβ14(39–59), corresponding to an TCR not associated with EAE, was predicted to be immunogenic, and did induce immunity, but, again, did not provide protection from EAE. According to the invention, the CDR2-related peptide of the relevant TCR, Vβ8(39–59), was predicted to be both immunogenic and protective in EAE, and indeed, was shown to be so (see Examples, below).

The size of the peptide selected for use in this invention is largely determined by the requirement for immunogenicity, while maintaining the minimal epitope structure such that a T cell or antibody specific for the peptide will recognize and react with the TCR on an intact T cell. For example, peptides of this invention, in order to be sufficiently immunogenic and to have a high probability of including the relevant epitope of the TCR which can lead to modulation of T cell activity, are of the range of about 15–30 amino acids, although peptides of differing length are also contemplated. The successful use of a 21 amino acid TCR peptide present on the TCR β chain associated with EAE in rats to treat EAE according to the methods of this invention is amply demonstrated in the Examples below.

Immunogenicity of peptides useful in the present invention can be screened by well-known methods, such as use of a DH response in an animal. In such a response, an animal is "sensitized" by injection of an appropriate dose of an antigen, typically subcutaneously (SC), frequently with an adjuvant, such as complete Freund's adjuvant (CFA). Generally about 5–15 days later, the response is "elicited" by challenging the animal, typically intradermally (ID), with an appropriate dose of the antigen, typically in saline or other buffer. The response is assessed 24–48 hours later. Non-limiting examples of assay methods which measure DH include size of erythema (redness) and induration (swelling) at the site of antigen injection, ear swelling, footpad swelling, tail swelling, accumulation of systemically injected $^{125}$I-labeled iododeoxyuridine in the challenge site, accumulation of intravenously (IV) injected radiolabeled serum protein, such as albumin, in the challenge site, and accumulation of IV-injected labeled inflammatory cells, such as lymphocytes or neutrophils, in the challenge, site. For example, an ear swelling response upon appropriate ID challenge in the ear pinna of about 0.15–0.25 mm, and preferably about 0.20 mm (in a Lewis rat) represents a positive DH response. One skilled in the art will understand that variations in peptide size, dose, route of sensitization or elicitation of DH, carriers used, adjuvants used, etc., will affect the timing and extent of the DH response.

For a peptide to be considered immunogenic, as intended here, a dose of about 10–200 µg per animal, and preferably about 25–100 µg of the peptide per animal, should be able to sensitize an animal for a DH response. Furthermore, in a sensitized animal, a dose of about 1–100 µg, and preferably about 5–50 µg, of the peptide is able to elicit a DH response upon ID challenge.

Synthesis of Peptides and Assay

The desired peptides, with sequences determined as described above, are prepared using standard synthesis techniques including solution and solid phase sequential amino acid conjugation and recombinant production in prokaryotic or eukaryotic hosts. Verification that the peptide prepared is immunogenic can easily be determined using a DH reaction in an animal (e.g., mouse or rat), as described above. The peptide is administered subcutaneously, and the animal is challenged about 9–14 days later ID in the ear pinna. The ear swelling response, measured 24 or 48 hours after challenge, serves as a simple and reliable measure of the presence of T cell-mediated immunity to the peptide.

Verification of the ability of the immunogenic peptide to actually modulate autoimmunity may be attained using an appropriate animal model, taking into account the species differences in the TCR-related peptides. For example, although it is preferred to use a sequence representing the CDR2 of a human marker TCR in treating humans, the corresponding region of the marker TCR for the animal disease model is used in the animal disease.

Animal model systems which can be used to screen the effectiveness of the peptides in protecting against or treating the disease are available, as discussed above. Of course, the identical peptides may not be effective in humans since they may not correspond to an appropriate site of the disease-associated human TCR, or may not be sufficiently immunogenic in humans. It is to be understood that modifications of the peptide sequence delineated in a particular animal model may be required in order to treat subjects belonging to other species, including humans. Thus, verification that, for example, a particular CDR2-associated peptide sequence is effective in protecting against a particular disease can be obtained in these models, leading to predictions that the corresponding human sequence would be a preferred candidate as an effective peptide therapeutic for humans. Determination of the corresponding TCR sequence in the human (or in different nonhuman animal species), using approaches described above, thus permits modification of the peptide for use in the human (or other species).

The following is a non-exclusive list of animal disease models of human autoimmune diseases with which a TCR peptide can be assessed for its ability to modify disease, and to induce antibodies and T cells which are capable, upon transfer, of modifying disease. Systemic lupus erythematosus (SLE) is tested in susceptible mice as disclosed by Knight et al., *J. Exp. Med.* 147:1653 (1978) and Reinertsen et al., *N. Eng. J. Med.* 299:515 (1978). MG is tested in SJL/J female mice by inducing the disease with soluble AChR protein from another species as described in Lindstrom et al., *Adv. Immunol.* 42:233–284 (1988). Arthritis is induced in a susceptible strain of mice by injection of Type II collagen as described by Stuart et al., *Ann. Rev. Immunol.* 2:199–218 (1984). Adjuvant arthritis is induced in susceptible rats by injection of Mycobacterial heat shock protein as described by Van Eden et al., *Nature* 331:171–173 (1988). Thyroiditis is induced in mice by administration of thyroglobulin as described by Maron et al., *J. Exp. Med.* 152:1115–1120 (1980). Insulin-dependent diabetes mellitus (IDDM) occurs naturally or can be induced in certain strains of mice such as those described by Kanasawa et al., *Diabetologia* 27:113 (1984). Other mouse strains can be caused to exhibit this disease by transferring lymphocytes from this strain.

EAE in mouse and rat serves as a model for MS in humans. In this model, the demyelinating disease is induced by administration of myelin basic protein (MBP) or proteolipid protein (PLP), or Theiler's virus, as described by Paterson, P. Y., *Textbook of Immunopathology* (Mischer et al., eds.), Grune and Stratton, New York, pp. 179–213 (1986); McFarlin, D. E., et al., *Science* 179:478–480 (1973); and Satoh, J., et al., *J. Immunol.* 138:179–184 (1987).

For measuring preventative, suppressive, or therapeutic benefit of the compositions of this invention in humans, certain clinical outcome measures are used. In MS, for example, quantitative parameters include: (a) clinical disability, (b) on-study exacerbation rate, and (c) magnetic resonance imaging (MRI) brain plaque load (which is an important recent parameter used to evaluate MS patients). These measures involve separate blinded examination or unblinded examination by a treating physician. Neuropsychological measures of cognitive impairment are used as an independent determinant of disability. Clinical disability is typically measured by the McAlpine Scale, the Kurtzke Score, a modification Kurtzke Score termed the Expanded Disability Status Score (EDSS). An improvement of ½ unit on the EDSS (Range of 1–9) is considered significant. One clinical measure, the patient's ability to walk, is rated by the Ambulation Index, wherein an improvement of 1 or more units is considered significant. These clinical measures are well known in the art and are described in detail in McAlpine et al., *Multiple Sclerosis*, Livingston Press, Edinburgh (1955); Binken, P. J. et al., *Handbook of Clinical Neurology*, Volume 9, Amsterdam-North Holland Publishers, Amsterdam (1970); and Field, E. J. et al., *Multiple Sclerosis: A Critical Review*, M.M.T.P Press, Ltd., Lancaster, England, (1977).

Measurement of improvement in RA, for example, is based on a number of primary clinical endpoints, including resolution or reduction of swelling, reduction in duration of morning stiffness, decreased erythrocyte sedimentation rate and/or C-reactive protein, resolution of rheumatoid-associated conditions as rheumatoid nodules, and reduction in lymphocyte counts. Secondary endpoints include reduction in fatigue and improvement in overall condition as assessed by the patient and the physician. Clinical outcomes are divided into the following: (a) Complete Response—greater than 90% decrease in joint swelling, tenderness, and morning stiffness; (b) Marked Response—50–90% decrease in joint swelling, tenderness, and morning stiffness; (c) Moderate Response—30–50% decrease in joint swelling, tenderness, and morning stiffness; and (d) No Response—≦30% decrease in joint swelling, tenderness, and morning stiffness.

Similar measurements which allow evaluation of the preventive, suppressive, or treatment effects of the peptides, antibodies, T cells and other compositions of the present invention in additional immune-related disease are known to those of skill in the art.

Passive Immunity

In addition to the use of a TCR peptide for active immunization, further embodiments of the present invention involve T cells which have been activated by the TCR peptide, and antibodies specific for the TCR peptide, for passive transfer of anti-TCR immunity. Passive antibody-mediated immunity may involve any of a number of effector mechanisms, such as, for example, antibody-dependent cellular cytotoxicity, or complement-dependent cytotoxicity. Alternatively, the antibody is used to deliver a toxic agent in a specific manner, such as ricin A chain, for example.

For passive vaccination, a subject animal is injected with the appropriate peptide, as described below, and the peripheral blood lymphocytes or lymphocytes from another organ, such as a draining lymph node, are harvested. The T cells may be used directly to transfer immunity. Alternatively, the T cells may be grown in culture in the presence of the TCR peptide as a selective stimulus, expanded with the aid of IL-2 or other T cell growth factors which are known in the art, maintained as a T cell line or clone, and then used to transfer immunity. B cells may be recovered from the initial cell population taken from the TCR peptide-immunized animal, and immortalized by fusion to cell line fusion partners using standard techniques to produce hybridomas for production of monoclonal antibodies specific for the TCR peptide. Hybridomas producing appropriate antibodies are screened by conventional immunoassays, such as direct ELISA assays, for reactivity with the TCR peptide antigen or with the relevant T cells.

Monoclonal antibodies (mAbs) to specific antigens, such as the TCR peptides of this invention, may be obtained by methods known to those skilled in the art. See, for example, Kohler and Milstein, *Nature* 256:495–497 (1975) and U.S. Pat. No. 4,376,110. Such antibodies may be of any immunoglobulin class, including IgG, IgM, IgE, IgA, IgD, and any subclass thereof.

Alternatively, antibodies can be prepared from polyclonal antisera taken from animals immunized with the TCR peptide, subjected to various purification schemes known in the art, and used directly for passive transfer of anti-TCR immunity.

Monoclonal antibodies of rodent origin are "humanized" by linking a cDNA molecule encoding the V region of the mAb to DNA encoding the human constant region, using any of several approaches described in Cabilly et al., U.S. Pat. No. 4,816,567 (Mar. 28, 1989) and Eur. Patent Pub. EP125023 (Nov. 14, 1984); Taniguchi et al., Eur. Patent Pub. EP171496 (Feb. 19, 1986); Morrison et al., Eur. Patent Pub. EP173494 (Mar. 5, 1986); Neuberger et al., PCT Pub. WO8601533 (Mar. 13, 1986); Kudo et al., Eur. Patent Pub. EP184187 (Jun. 11, 1986); Robinson et al., PCT Pub. WO 8702671 (May 7, 1987); Cabilly et al., *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Morrison, *Science*, 229:1202–1207 (1985); Neuberger et al., *Nature* 314:268–270 (1985); Takeda et al., *Nature* 314:452–454 (1985); Tan et al., *J. Immunol.* 135:3564–3567 (1985); Jones et al., *Nature* 321:522–525 (1986); Oi et al., *BioTechniques* 4:214 (1986); Sahagan et al., *J. Immunol.* 137:1066–1074 (1986); Sun et al., *Hybridoma* 5 (Supp. 1):S17–S19 (1986); Sun et al., *Proc. Natl. Acad. Sci. USA* 84:214–218 (1987); Liu et al., *Proc. Natl. Acad. Sci.* USA 84:3439–3443 (1987); Liu et al., *J. Immunol.* 139:3521–3526 (1987); Better et al., Science 240:1041–1043 (May 20, 1988); and Horwitz et al., *Proc. Natl. Acad. Sci.* USA 85:8676–8682 (1988)).

The preferred method of chimeric antibody production combines five elements: (1) Isolation of messenger RNA (mRNA) from a mouse B cell hybridoma line producing the monoclonal antibody, cloning and cDNA production therefrom; (2) Preparation of a full length cDNA library from purified mRNA, from which the appropriate variable (V) region gene segments of the light (L) and heavy (H) chain genes can be (i) identified with appropriate probes, (ii) sequenced, and (iii) made compatible with a constant (C) region gene segment; (3) Preparation of C region gene segment modules by cDNA preparation and cloning; (4) Construction of complete H or L chain coding sequences by linkage of the cloned specific immunoglobulin V region gene segments described in (2), above, to cloned human C region gene segment modules described in (3); and (5) Expression and production of chimeric L and H chains in selected hosts, including prokaryotic and eukaryotic cells.

Many vector systems are available for the expression of cloned H and L chain genes in mammalian cells (see Glover, D. M., ed., *DNA Cloning Vol. II*, pp143–238, IRL Press, 1985). Different approaches can be followed to obtain complete $H_2L_2$ antibodies. It is possible to co-express H and L chains in the same cells to achieve intracellular association and linkage of H and L chains into complete tetrameric $H_2L_2$ antibodies. The co-expression can occur by using either the same or different plasmids in the same host. Genes for both H and L chains can be placed into the same plasmid, which is then transfected into cells, thereby selecting directly for cells that express both chains. Alternatively, cells may be transferred first with a plasmid encoding one chain, for example the L chain, followed by transfection of the resulting cell line with an H chain plasmid containing a second selectable marker. Cell lines producing $H_2L_2$ molecules via either route can be transfected with plasmids encoding additional copies of H, L, or H plus L chains, in conjunction with additional selectable markers, to generate cell lines with enhanced properties, such as higher production of assembled $H_2L_2$ antibody molecules or enhanced stability of the transfected cell lines.

The chimeric antibodies of this invention have both the TCR-recognizing specificity of the mouse mAb and the biological properties of human antibodies, which include resistance to clearance in the human and much less immunogenicity (allowing multiple treatments).

The anti-TCR peptide antibodies (polyclonal, monoclonal and chimeric) of this invention can be used therapeutically as immunoconjugates (see for review: Dillman, R. O., *Ann. Int. Med.* 111:592–603 (1989)). They can be coupled to cytotoxic proteins, including ribosomal inhibitory proteins such as Ricin-A, Pseudomonas toxin, and Diphtheria toxin, as well as other proteins such as tumor necrosis factor. Toxins conjugated to antibodies or other ligands, are known in the art (see, for example, Olsnes et al., *Immunol. Today* 10:291–295 (1989)). An additional example of such a conjugated antibody is XomaZyme®-CD5 Plus, which is an anti-CD5 mAb conjugated to ricin A chain. This preparation is effective in prophylaxis and therapy of graft-versus-host disease, and of refractory rheumatoid arthritis in humans. This particular toxin-conjugated antibody is specific for most T lymphocytes and a subset of B lymphocytes. Cells having the CD5 marker drop rapidly in response to treatment. Since antibody to a TCR peptide will react with a much smaller proportion of total lymphocytes, higher doses of an anti-TCR antibody conjugated to ricin A will be tolerated by patients, or conversely, lower doses will be effective. Effective doses of a ricin A conjugated monoclonal antibody to a TCR peptide are in the range of about 0.005 to 0.5 mg/kg/day, with the preferred dose in the range of about 0.05 to 0.2 mg/kg/day.

The anti-TCR peptide antibodies of this invention can be conjugated to additional types of therapeutic moieties including, but not limited to, radionuclides and cytotoxic drugs, to treat individuals with autoimmunity or with malignant or lymphoproliferative disease. Non-limiting examples of radionuclides which can be coupled to antibodies and delivered in vivo to sites of antigen include $^{212}$Bi, $^{131}$I, $^{186}$Re, and $^{90}$Y. Such radionuclides exert their cytotoxic effect by locally irradiating the cells, leading to various intracellular lesions, as is well-known in the art of radiotherapy.

Cytotoxic drugs which can be conjugated to antibodies and subsequently used for in vivo therapy include, but are not limited to, daunorubicin, doxorubicin, methotrexate, and mitomycin C. Cytotoxic drugs interfere with critical cellular processes including DNA, RNA, and protein synthesis. For a fuller exposition of these classes of drugs which are known in the art, and their mechanisms of action, see Goodman et al., *Goodman and Gilman's The Pharmacological Basis of Therapeutics*, 7th Ed., Macmillan Publishing Co., (1985).

Treatment of an individual using the antibodies, fragments or derivatives of this invention comprises parenterally admininstering a single or multiple doses of the antibody, fragment or derivative thereof. The effective dose is a function of the individual antibody, the presence and nature of a conjugated therapeutic agent, the subject and his clinical status, and can vary from about 10 ng/kg body weight to about 100 mg/kg body weight. The route of administration may include IV, SC, intramuscular, intrapulmonary, intraperitoneal (IP), intranasal, intrathecal, intradermal, transdermal or other known routes.

Formulation of Peptides

The preclinical and clinical therapeutic use of the present invention in the treatment of disease or disorders will be best accomplished by those of skill, employing accepted principles of diagnosis and treatment. Such principles are known in the art, and are set forth, for example, in Braunwald et al., eds., *Harrison's Principles of Internal Medicine*, 11th Ed., McGraw-Hill, publisher, New York, N.Y. (1987).

The peptides and compositions of the present invention, or their functional derivatives, are well suited for the preparation of pharmaceutical compositions. The pharmaceutical compositions of the invention may be administered to any animal which may experience the beneficial effects of the compositions of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intradermal, intramuscular, intraperitoneal, transdermal, or buccal routes. Alternatively, or concurrently, administration may be by the oral route. The peptides and pharmaceutical compositions can be administered parenterally by bolus injection or by gradual perfusion over time.

The dosage administered will be dependent upon the age, sex, health, and weight of the recipient, kind of concurrent treatment, if any, frequency of treatment, and the nature of the effect desired. The dose ranges for the administration of the compositions of the present invention are those large enough to produce the desired effect, whereby, for example, an immune response to the peptide, as measured by DH or antibody production, is achieved, and the immune-related disease is significantly prevented, suppressed, or treated. The doses should not be so large as to cause adverse side effects, such as unwanted cross reactions, generalized immunosuppression, anaphylactic reactions and the like.

Preferred doses for humans range between about 0.001–25 mg/kg body weight.

In addition to peptides of the invention which themselves are pharmacologically active, pharmaceutical compositions may contain suitable pharmaceutically acceptable carriers comprising excipients and auxiliaries which facilitate processing of the active compounds into preparations which can be used pharmaceutically. Preferred compositions include the inclusion of an adjuvant, such as alum, or other adjuvants known in the art. (See, for example, Warren et al., *Ann. Rev. Immunol.* 4:369–388 (1986); Chedid, L., *Feder. Proc.* 45:2531–2560 (1986)).

To enhance delivery or bioactivity, the peptides can be incorporated into liposomes using methods and compounds known in the art.

Preparations which can be administered orally in the form of tablets and capsules, preparations which can be administered rectally, such as suppositories, and preparations in the form of solutions for injection or oral introduction, contain from about 0.001 to about 99 percent, preferably from about 0.01 to about 95 percent of active compound(s), together with the excipient.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the peptides in water-soluble form, for example, water-soluble salts. In addition, suspensions of the peptides as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The peptides are formulated using conventional pharmaceutically acceptable parenteral vehicles for administration by injection. These vehicles are nontoxic and therapeutic, and a number of formulations are set forth in *Remington's Pharmaceutical Sciences,* (supra). Nonlimiting examples of excipients are water, saline, Ringer's solution, dextrose solution and Hank's balanced salt solution. Formulations according to the invention may also contain minor amounts of additives such as substances that maintain isotonicity, physiological pH, and stability.

The peptides of the invention are preferably formulated in purified form substantially free of aggregates and other protein materials, preferably at concentrations of about 1.0 ng/ml to 100 mg/ml.

Effective doses of the peptides of this invention for use in preventing, suppressing, or treating an immune-related disease are in the range of about 1 ng to 100 mg/kg body weight. A preferred dose range is between about 10 ng and 10 mg/kg. A more preferred dose range is between about 100 ng and 1 mg/kg.

The immunogenicity of the peptide may be enhanced by including it in a longer peptide or chain or by conjugating it to "immunological" carriers, such as KLH, serum albumin, tetanus toxoid, and the like, using standard linking techniques. A variety of such methods is known in the art, e.g., use of condensing agents such as dicyclohexylcarbodiimide or use of linkers, such as those commercially available from Pierce Chemical Co., Rockford, Ill.

For the passive immunization with the TCR peptide-specific T cell preparations of this invention, the harvested T cells are suspended in a suitable vehicle, such as physiologically buffered saline, and injected into the subject in an amount of approximately $10^5$–$10^9$ cells per injection. Doses of TCR peptide-specific antibodies vary as a function of antibody species origin, isotype, affinity, nature (polyclonal, monoclonal, chimeric) and other characteristics which are known to one of skill. For example, a monoclonal antibody to a TCR peptide will be administered at a dose of between 0.01–50 mg/kg.

Also contemplated within the scope of this invention is passive immunization with a combination of protective T cells and TCR peptide-specific antibodies (polyclonal, monoclonal, or chimeric) in free or conjugated form.

The following examples are intended to be illustrative, but not to limit, the invention.

EXAMPLE I

Treatment of Human MS Patients With TCR Peptides

Currently, no effective treatment for MS is known. (Harrison's Principles of Internal Medicine, 12th ed. Wilson et al., McGraw Hill, Inc. 1991) Therapeutic efforts are directed toward amelioration of the acute episode, prevention of relapses or progression of the disease, and relief of symptoms. The clinical manifestations of MS depend upon which nerve group or region of the brainstem, cerebellar or spinal cord is involved. Spinal cord involvement is the predominating feature in most advanced cases of MS.

In acute episodes of disease, glucocorticoid treatment has been suggested as having the potential to lessen the severity of symptoms and speed recovery, however, even its proponents point out that ultimate recovery is not improved by this drug nor is the extent of permanent disability altered. ACTH is the preferred glucocorticoid of clinicians since the only controlled trials which demonstrated any efficacy of glucocorticoid therapy in episodes of MS and optic neuritis were performed with this drug. However, use of long term steroids is not advised.

Immunosuppressive agents such as azathioprine and cyclophosphamide have been claimed to reduce the number of relapses in several series, but there is no consensus about the efficacy of these drugs either.

The current recommendations for the treatment of MS revolve around attempting to avoid exacerbation of the symptoms. Patients are advised to avoid excess fatigue and extremes of temperature and eat a balanced diet. (The above discussion is primarily from Chapter 356 of Harrison's Principles of Internal Medicine, 12th ed. 1991.)

The above discussion clearly points out that there exists a desperate need for a clinically efficacious treatment for MS.

The present example provides the first demonstration of a therapy resulting in clinical improvement of MS patients. The clinical data presented are derived from two patients treated in vivo with TCR peptides. The results demonstrate the ability of the Vβ5.2 and Vβ6.1 peptides to suppress the autoimmune response to myelin basic protein (BP) without concurrent suppression of the immune system response. Most importantly, the data indicate the clinical efficacy of treating MS patients with TCR peptides.

Methods

Identification of TCR V Genes Used by BP-Specific T Cells. Blood T cells from MS patients and controls were selected for response to human BP. The responder T cell lines were cloned, and each BP-reactive clone was analyzed for the expression of TCR Vα and Vβ genes. In the MS patients studied, the inventor found a preferential utilization of TCR Vβ5.2 and Vβ6.1, whereas in one control donor 11 of 13 clones utilized Vβ14.

From the data, the inventor predicted that each patient would preferentially utilize a limited number (1 or 2) of Vβ genes in response to BP.

Selection of the Antigenic Peptides. The selection of the peptides used in this example was carried out according to the procedure and algorithm described above. Specifically, the regions of relevant TCR sequences were identified for synthesis on the basis of their predicted antigenic or immunogenic properties and/or their occurrence in the CDR2 region. Regions of the protein or peptide that were likely to be immunogenic or antigenic for t cells were identified, using the approaches and algorithms as described herein.

The above approach was used to select the peptide sequences useful for treating multiple sclerosis in humans. The size of the peptide selected for use in this example was largely determined by the requirement for immunogenicity, while maintaining the minimal epitope structure, such that a T cell or antibody specific for the peptide would recognize and react with the TCR on an intact T cell. Thus, it was important to identify antigenic regions of the marker TCR V gene sequence to be used for treatment. A number of sequences of peptides from human TCR Vβ genes were considered for this study. (TCR Vβ5.2 peptides: Vβ-26–43, Vβ5.2-39–59, Vβ5.2-59–78. TCR Vβ6.1 peptides: Vβ6.1-1–22, Vβ6.1-39–59, Vβ6.1-70–88.) The peptides selected were Vβ5.2(39–59) and Vβ6.1(39–59), on the basis of their increased recognition by T cells from MS patients.

The use of the above approach to select peptide sequences for use in treating MS patients exemplifies the success of this approach as described herein. For example, the peptides Vβ5.2(39–59 and Vβ6.1(39–59) were predicted by the above algorithms to be immunogenic for T cells. In fact, as described below, these peptides did produce T cell immunity and appear to be protecting the MS patients from autoimmune reactions to BP.

Treatment with TCR Peptides. The antigenicity of the selected peptide was assayed by determining whether there was a detectable frequency of response from the patient's T cells. Specifically, the differences in frequencies of T cells responding to the various peptides were assayed. The peptide eliciting the strongest frequency of response was then used.

Each patient was treated i.d. with 100 ug of TCR peptide in saline, once per week for 4 weeks. The patients were evaluated weekly for evidence of increased response to the peptides, measured by blood T cell frequency analyses in vitro and DTH response. Responses to the peptides were maintained by periodic booster injections of the peptides as needed. Additionally, the patients were evaluated every three months clinically for changes in ambulation index and Kurtzke score.

Parameters Measured. T cell responses to the TCR peptides Vβ5.2 and Vβ6.1, basic protein (BP) and HSV (Herpes simplex virus—used as a recall antigen) were evaluated by lymphocyte proliferation. Patient J. M. was treated with Vβ6.1, and T cell frequencies followed in response to both Vβ6.1 as well as to Vβ5.2 not given as therapy. Patient M. R. was treated with Vβ5.2 and was tested for responses to both Vβ5.2 and Vβ6.1.

Both patients were assessed for their response to BP due to the evidence that the frequency of BP or PLP reactive T cells is higher in MS patients than in normal, neurologic, or autoimmune controls (Allegretta et al., Science247:718 (1990); Link et al., Neurology 40:283 (1990); and Ota et al., Nature 346:183 (1990). The selective immunoregulation strategy offered by the TCR peptides of this invention, as used in this example, provides the first test for the hypothesis that myelin basic protein is a relevant autoantigen in MS.

Immune response to HSV was followed so as to determine whether the TCR therapy was suppressing the overall immune response of the patients. Based on the inventor's experimental model, the patients would show an increased response to the TCR peptide administered. This increased response to the TCR peptide would be coupled to a decreased response to BP. Additionally, the patients would not show a decreased response to HSV or to the other TCR peptide not used as therapy.

Results. The data obtained clearly demonstrate the utility of TCR therapy in MS patients. The data, which measure the frequency of antigen-reactive T cells may be summarized as follows: Patient J. M. (receiving TCR Vβ6.1) had a four fold increase in T cell response to Vβ6.1 (at 1 week post treatment), which tapered off to about a two fold increase (at week 4) vs pre-treatment). The myelin basic protein (BP) cell response was virtually undetectable by week 4 (below the limits of the assay). The response to Vβ5.2 stayed about the same (as expected, since this patient never received the Vβ5.2 peptide), whereas the response to HSV increased over the 4 weeks.

The data from patient M. R. (who received a Vβ5.2 TCR peptide) demonstrates a 30-fold increase in the Vβ5.2 reactive (regulatory) T cells, with a virtual disappearance of the BP reactive T cells by week 4. M. R.'s responses to Vβ6.1 (this patient never received this peptide) and HSV stayed about the same (FIGS. 12–14).

In addition to the demonstrated increase in the frequency of antigen-reactive T cells, patient J. M. also experienced a dramatic improvement in ambulation, while patient M. R. reports an increase in stamina (able to walk 400 yards without collapsing from exhaustion).

Prior to treatment with TCR peptides, patient J. M.'s ambulation had been progressively deteriorating. For a timed walk of 25 feet, J. M.'s time for walking this distance had progressed from 7 secs. to 12 secs. and then to 29 seconds.

Three months subsequent to treatment with the TCR peptide, J. M. demonstrated an improvement in ambulation. Not only was the deterioration arrested, but ambulation time was dramatically improved from 29 seconds to 21 seconds.

Discussion. The data demonstrate the dramatic ability of the TCR therapy to regulate the immune response to BP, thus providing a method of treatment for MS. The administration of Vβ5.2 and Vβ6.1 showed an increase in T cell response in MS patients. The corresponding decrease in T cell response to BP shows the positive therapeutic effect of the TCR peptide therapy on MS patients. Additionally, the absence of a decrease in the patients' response to HSV demonstrate that the immune system is not compromised by the TCR peptide therapy.

Although the above example utilizes a single peptide for each patient, the invention contemplates the use of a "cocktail" approach in treating patients. The cocktail approach could be useful in patients with clones demonstrating reactivity to more than one V gene region; therefore the cocktail administered to the patient could involve more than one antigenic peptide such as was used in the SJL mouse experiment (FIG. 15, Example X).

EXAMPLE II

Specificity of Human T Cell Clones Reactive To Immunodominant Epitopes of Myelin Basic Protein Introduction Myelin basic protein (MBP) is highly antigenic, and causes experimental autoimmune encephalomyelitis (EAE) in a variety of animal species when injected with adjuvants (Alvord, E. C., Jr., In Experimental Allergic Encephalomyelitis: A useful model for multiple sclerosis, Alvord, E. C., Jr., et al. (eds.), Alan R. Liss, Inc., New York, pp. 523–537 (1984)).

The encephalitogenic property of MBP is encompassed within a discrete number of immunodominant epitopes (about 10). Within each strain, one or more of these epitopes, in association with the available Class II MHC molecules, induces CD4+ T effector lymphocytes that home to the central nervous system (CNS), causing perivascular inflammatory lesions and nerve dysfunction (Zamvil et al., J.

Immunol. 139:1075 (1987); Offner, H., et al., J. Exp. Med. 170:355 (1989)).

The genetic background, including both MHC and non-MHC genes, influences which MBP epitopes are encephalitogenic (Beraud et al., J. Immunol. 136:511 (1986); Zamvil et al., J. Exp. Med. 162:2107 (1985)), the clinical course and severity of the disease (Fritz et al., J. Immunol. 134:2328 (1985); Hinrich et al., J. Exp. Med. 166:1906 (1987); Linthicum et al., J. Exp. Med. 155:31 (1982); Dietsch et al., J. Immunol. 142:1476 (1989); Mokhtarian et al., Nature (London) 309:356 (1984)), demyelination (Mokhtarian et al., Nature (London) 309:356 (1984)), and resistance mechanisms (Bernard, C. C., Clin. Exp. Immunol. 29:100 (1977); Welch et al., J. Immunol. 125:186 (1980); Varriale et al., J. Immunol. 125:186 (1989); Whitham et al., Cell. Immunol. 126:290 (1990)).

The spectrum of clinical and histologic signs induced by MBP-specific T cells resembles in many ways the human diseases multiple sclerosis (MS) and acute disseminated encephalomyelitis (AIDE) (Paterson, P. Y., Adv. Immunol. 5:131 (1966); Waksman et al., Proc. Soc. Exp. Biol. Med 175:282 (1984)). Consequently, human T cell recognition of MBP has been of considerable interest.

There are several lines of evidence that suggest the involvement of T cells, including those specific for human MBP, in the pathogenesis of MS. Genetic studies indicate linkage disequilibrium between T cell receptor V and C region genes within families with MS (Hauser et al., Neurology39:275 (1989); Beall et al., J. Cell. Biochem. 11D:223 (1987)) or among patients generally (Oksenberg et al., Proc. Natl. Acad. Sci. USA 86:988 (1989)). However, the actual involvement of MBP-reactive T cells in the pathogenesis of MS can only be demonstrated if selective regulation or removal of MBP-reactive T cells can affect the disease process. Such selective regulation is now possible in EAE.

In the present example, a synthetic TCR peptide was used to induce regulatory T cells and antibodies directed against the TCR on the pernicious T cells. This approach prevented the induction of EAE. Moreover, as demonstrated in the previous example, administration of the TCR peptide to clinically sick rats arrested disease progression and speeded recovery. The application of this approach for regulating potentially encephalitogenic T cells in MS patients depends on whether or not MBP-reactive T cells preferentially utilize a limited number of TCR V region genes in response to immunodominant epitopes of human MBP.

To this end, T cell lines from MS patients and controls were selected in a manner that allowed emergence of T cells that recognize immunodominant MBP epitopes. From these lines, 109 MBP-specific T cell clones were isolated and characterized for phenotype, epitope specificity, MHC restriction, and TCR V gene expression. The data demonstrate at the clonal level that T cells from MS patients recognize more and different MBP epitopes than do T cells from normal donors. Furthermore, in one MS donor with the disease-associated HLA-DR2/DQw1 haplotype, 4 of 8 T cell clones tested expressed the Vβ5.2 phenotype, indicating preferential TCR V gene use in response to MBP.

A. MATERIALS AND METHODS

Human Subjects: The MS patients evaluated in this study included 11 patients with clinically or laboratory-supported definite MS who were attending the Oregon Health Sciences University MS clinic. There were 7 females and 4 males (mean age of 46, range 34–67 years), who had MS for 6–35 years. The patients had an average ambulation index (AI) of 3.4±1.6 (range 1–6) and an average Kurtzke disability status score (KDSS) of 4.3±2.0 (range 2–4) (Kurtzke, J. F., Neurology15:654 (1965)).

The normal individuals included 6 female and 3 male employees (mean age of 36, range 25–55 years) from the Veterans Affairs Medical Center and Oregon Health Sciences University. These normal individuals were selected on the basis of positive PBL proliferation responses to human MBP as described previously (Vandenbark et al., J. Neurosci. Res. 23:21 (1989)).

All subjects were HLA-typed retrospective to T cell line selection by a standard serological method utilized by the Oregon Health Sciences University Transplantation Laboratory. The frequency of HLA Class II alleles (DR,DQ) showed an uneven distribution for DR2 (7 of 11 patients—63%—were DR2 positive; 3 of 9 normals—33%—were DR2 positive), that in general represented the expected occurrence for these two groups (Theofilopoulos, A. N., in Basic and Clinical Immunology, Stites et al. (eds.), Appleton and Lange Publishers, Los Altos, Calif., pp. 151–154 (1987)).

Antigens: Human (Hu-) MBP was extracted and purified from snap frozen human brain (Eylar et al., Arch. Biochem. Biophys. 132:34 (1969)). Peptides of Hu-MBP, including P1 (residues 45–89), P2 (residues 1–38) and P4 (residues 90–170), were obtained by peptic cleavage and purified by Sephadex, ion exchange chromatography, and high pressure liquid chromatography (Chou, C.H.-J., et al., J. Neurochem. 28:115 (1977)). A series of synthetic peptides corresponding to the Hu-MBP sequences 13–28, 39–54, 55–74, 72–84, 87–99, 90–109, 110–129, 130–149, and 149–170 was synthesized by the Merrifield solid-phase method and purified by HPLC according to methods described previously (Hashim et al., J. Neurosci. Res. 16:467 (1986)).

T Cell Lines: Human MBP-reactive T cell lines were selected from the blood of 11 MS patients and 9 normal individuals who were responsive to Hu-MBP in previous screening tests (Vandenbark et al., J. Neurosci. Res. 23:21 (1989)). Blood mononuclear cells (MNC) were separated by Ficoll density gradient centrifugation and cultured with 50 ug/ml Hu-MBP in complete medium (RPMI 1640 with 10% human AB serum, L-glutamine, sodium pyruvate and antibiotics) at a cell density $5 \times 10^5$ per well of a flat-bottomed 96-well plate for 5 days at 37° C. in a 5% $CO_2$ atmosphere. The stimulated cells were transferred into IL-2 rich medium (containing 50 u/ml recombinant IL-2, AMGEN Biologicals, Thousand Oaks, Calif.) for expanding activated T cells. When growth in IL-2 slowed, the T cells were re-stimulated with 25 ug/ml Hu-MBP presented by autologous monocytes contained in irradiated peripheral blood MNC (4,500 rad) at the ratio of 1:10 (T:MNC). The T cell lines were restimulated 4–5 times until the cell number was sufficient for assessing MBP epitope specificity, MHC restriction, and phenotype.

T Cell Cloning: T cell clones were obtained by limiting dilution of MBP-specific T cell lines that had been re-stimulated twice with Hu-MBP. After 4 days in IL-2-enriched medium, T lymphoblasts were diluted to 1, 10 and 30 cells/20 ul of culture medium containing Hu-MBP (50 ug/ml), IL-2 (50 u/ml) and irradiated MNC ($1.5 \times 10^6$), and the cell mixture was placed into each well of a 60-well Tarasaki microtest tray (NUNC Inc., Naperville, Ill.) (Lamb et al., J. Immunol. 128:233 (1982)). Recovery of human MBP-specific clones was most efficient when at least 10 Hu-MBP reactive line cells were seeded per well, producing a 20% rate of recovery. When only one line cell was seeded per well, the rate of recovery was 2%. Hu-MBP reactive T cells were recloned by seeding at 1 cell/well. The Tarasaki trays were incubated at 37° C. and 5% $CO_2$ for 7 days. For restimulation, the cells from each positive well were transferred to a single well of a round-bottomed 96-well plate, into which were added 200 ul of complete medium with 25 ug/ml Hu-MBP and $2\times10^5$ irradiated MNC. 50 µ/ml of IL-2 were added to the cells on the third day after stimulation and the cells maintained in IL-2 for another four days. When the cell number reached $2-4\times10^5$, the cultures were transferred into a 24 well plate in 1 ml, and re-stimulated with Hu-MBP in the presence of $3\times10^6$ autologous irradiated MNC, and later expanded in 2 ml of IL-2 rich medium.

Proliferation Assay: The specificity of the cell response was evaluated by incubating $2\times10^4$ T cells with $1\times10^5$ irradiated (4,500 rad) autologous blood MNC in 0.2 ml triplicate cultures in a 96 well, round bottomed microtiter plate in the absence of antigens and in the presence of 2 ug/ml Con A, 50 ug/ml Hu-MBP, 50 ug/ml Hu-MBP fragments (P1, P2 and P4), 50 ug/ml of synthetic peptides of Hu-MBP, and 1/200 diluted Herpes simplex virus (HSV) antigen (Whittaker M. A. Bioproducts, Walkersville, Md.). Microtiter cultures were incubated for 3 days at 37° C. at 5% $CO_2$, and were pulsed with 0.5 uBq $^3$H-TdR for the last 18 hr. The cells were harvested on glass fiber filters and incorporated $^3$H-TdR was counted using a β-scintillation counter. Proliferation was expressed as CPM of stimulated culture±SD (background subtracted). Backgrounds ranged from 200 to 2,000 CPM. MHC restriction was evaluated by incubating the T cells plus Hu-MBP, Hu-MBP fragments or synthetic peptides of Hu-MBP in the presence of antibodies specific for framework determinants of molecules from the HLA-DP, -DQ or -DR locus (antibodies were purchased from Becton Dickinson Pharmaceuticals, Mountain View, Calif.).

Phenotyping T Cells: T cell lines and clones were phenotyped using Leu 3a (anti-CD4+ T helper) and Leu 2a (anti-CD8+ T cytotoxic/suppressor) monoclonal antibodies (Becton Dickinson), as described previously (Vandenbark et al., J. Neuroimmunol. 8:103 (1985)). T cell clones were phenotyped for the expression of TCR Vβ chain gene products using mouse monoclonal antibodies specific for human TCR Vβ5.2/5.3 (5A), Vβ5.3 (5B), Vβ6.7, Vβ8.1, and Vβ12 (DIVERSI-T™ αβ TcR Screening Panel 1A, T Cell Sciences Inc., Cambridge, Mass.). Two×$10^5$ T cells were incubated with 5 ul of each antibody for 1 hr at 4° C., followed by 3 washes with medium containing 5% human AB serum and further incubation with FITC-conjugated goat anti-mouse IgG for 30 min. After 2 washes and fixation in 2% formaldehyde, the stained cells were evaluated for immunofluorescence using a FACScan flow cytometer.

B. RESULTS

Characterization of Hu-MBP Specific T Cell Lines from MS Patients and Normals. Hu-MBP specific T cell lines were selected from the blood of 11 patients with MS and 9 normal donors with previously demonstrated proliferation responses to Hu-MBP. Each line was selected from 30–50 million blood cells by repeated stimulation with whole Hu-MBP and expansion with IL-2. From previous experience in selecting rodent T cell lines, these conditions should allow expansion and focusing of representative T cell responses towards immunodominant Hu-MBP epitopes.

Figure 6:
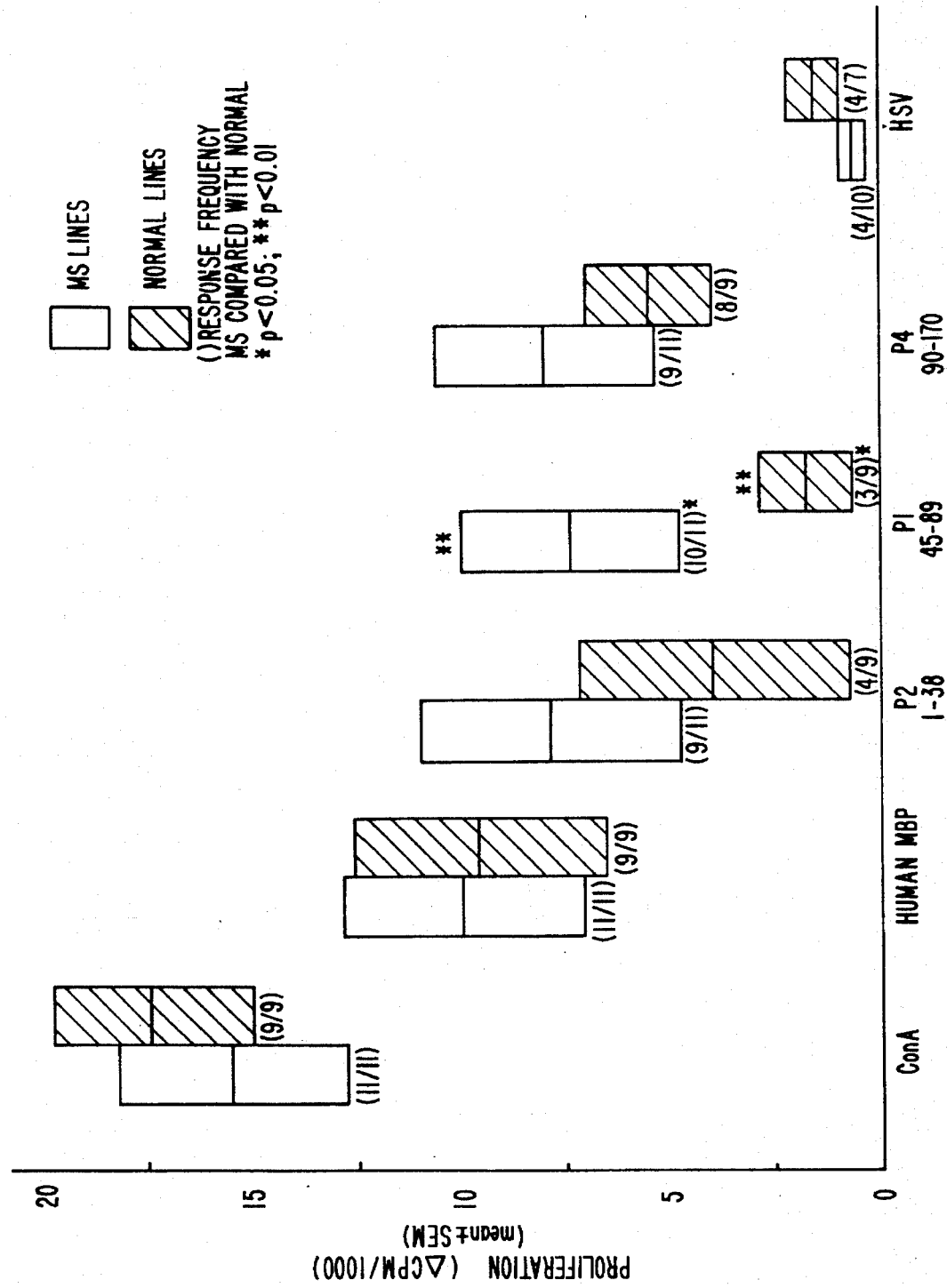
FIG. 6. Peptide specificity of human MPB-specific T cell lines from MS patients and normals.
Figure 7A:
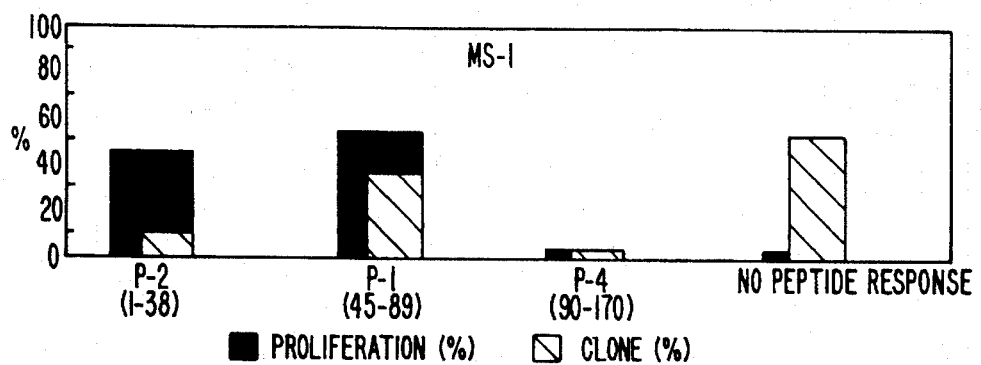
FIGS. 7(A,B,C,D and E). Percentage of total proliferation response of T cell lines from MS (FIGS. 7A, B and C) and normal (FIGS. 7D and E) donors directed at each peptide compared to percentage of total clones responding to each peptide.
Figure 7B:
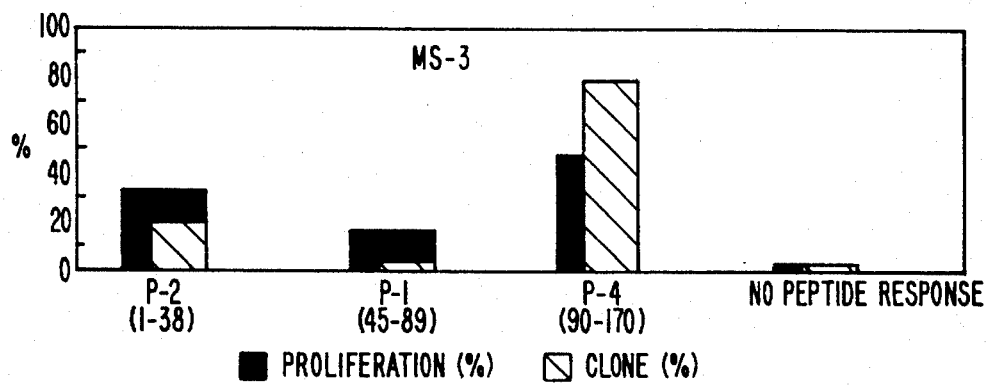
Figure 7C:
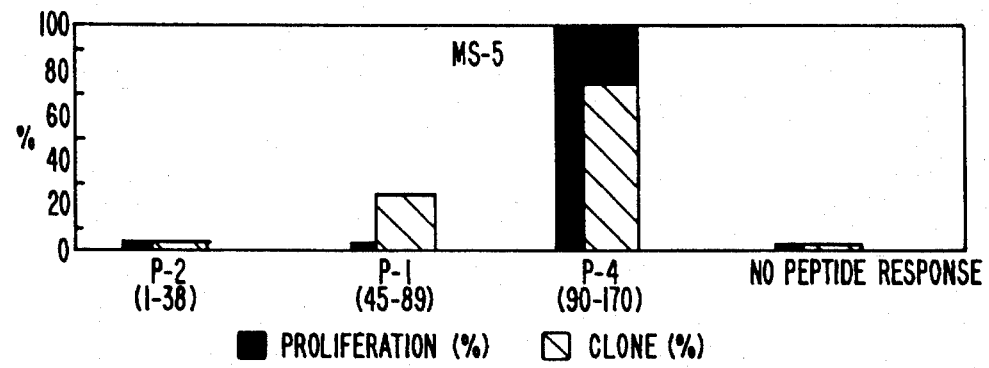
Figure 7D:
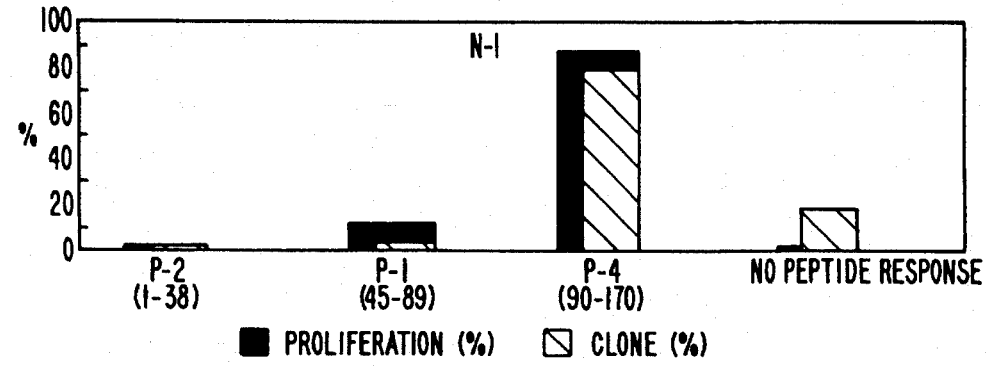
Figure 7E:
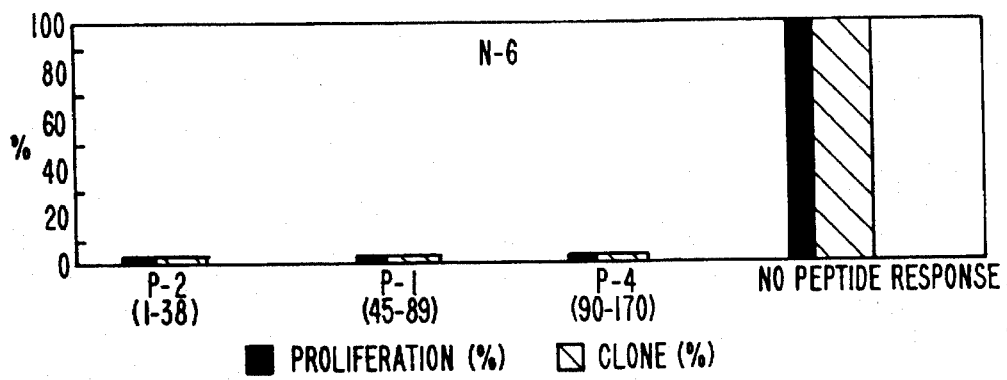

The T cell lines from MS patients and normal donors responded equally well to both Hu-MBP and Con A, with negligible responses to HSV antigens (FIG. 6). T cell lines were evaluated for response to highly purified enzymatic cleavage fragments spanning the entire sequence of Hu-MBP, including P1 (residues 45–89), P2 (residues 1–38) and P4 (residues 90–170). Eight of 11 MS lines responded to all 3 Hu-MBP fragments, two responded to 2 of 3 fragments, and only 1 line responded to a single fragment. In contrast, 5 of 9 normal lines responded to a single fragment, 3 lines responded to all fragments and 1 line did not respond to any fragment. The rate of responders to the 45–89 fragment was significantly greater in the MS group versus controls, and on average, the MS T cell lines were significantly more reactive to both the 45–89 (P1) and 1–38 (P2) fragments of Hu-MBP (FIG. 6). However, there was no difference in frequency or magnitude of response to the 90–170 (P4) fragment. All of the human T cell lines had a mixed phenotype of CD4+ and CD8+ T cells. However, the T cell lines from MS patients had a relatively higher rate of CD4+ and lower rate of CD8+ subpopulations compared to normal donors (78±13% versus 58±8% for CD4+ cells: 15±6% versus 30±12% for CD8+ cells, Table 1).

Selection and Characterization of Hu-MBP Specific T Cell Clones. Although the general range of immunodominant T cell epitopes on Hu-MBP can be inferred from the pattern of reactivity of T cell lines to Hu-MBP peptides, proof of T cell recognition must be derived from analysis of clones. To this end, a total of 109 human MBP-specific T cell clones from 7 MS T cell lines (50 clones) and 6 normal T cell lines (59 clones) were evaluated for response to Hu-MBP and Hu-MBP fragments and synthetic peptides. The T cell line donors were comparable except for HLA-DR2 distribution (86% of MS patients versus 33% of normals were DR2 positive; see Table 2).

All of the T cell clones responded to Hu-MBP, but not to Herpes simplexvirus (HSV) antigen, with a similar response level in both groups. In total, 48 T cell clones (distributed equally between the two groups) were phenotyped for CD4 and CD8 markers. Of these, 45 clones were CD4+ and 3 (from one normal donor) were CD8+ (Table 1). This predominance of CD4 + clones was expected from previous experience in rats and mice, but did not reflect the relative proportion of these subsets in the T cell lines from which the clones were derived (Table 1).

Clonal Specificities Reflect the Pattern of T Cell Line Responses. In order to establish the validity of the clonal analysis, it is important to evaluate how well the T cell clonal specificities represent the T cell line responses. In the lines which yielded sufficient clones for comparison, the number of clones responding specifically to a distinct fragment of MBP showed a significant correlation with the Hu-MBP fragment-directed response of the parent T cell line (paired Chi Square test, $p<0.05$).

Representative comparisons from 3 MS and 2 normal donors are shown in FIG. 7. Based on the pattern of T cell line responses, it was expected that more clones reactive to P1 and to P2 would be selected from the MS T cell lines than from control lines, but that the frequency of P4 reactive clones would be relatively equal. This indeed was the case, as is shown in Table 2. Unexpectedly, 46 of the 109 MBP-reactive T cell clones did not respond to any single fragment of Hu-MBP, even though the response to Hu-MBP was vigorous, ranging from 10,000 to 27,000 cpm with only 1,000–2,000 cpm background. This finding was more frequent in the normal group than in the MS group, largely on the basis of a single normal donor (Table 2).

Biased Clonal Specificities within P4. Although the P4 region of Hu-MBP represents the C terminal half of the molecule, approximately ⅔ (41 of 63) of the clones reactive to Hu-MBP peptides responded to this fragment. To identify epitope specificities, 23 of these clones from 4 normal and 4 MS donors were tested in a proliferation assay against a series of synthetic peptides corresponding to different portions of the P4 region. As is shown in Table 3, the clonal distribution was biased in normal donors towards the 110–129 sequence, and in MS donors towards the 130–149 sequence. Responses to the 149–171 sequence were similar in both groups, and only one MS clone responded to the 87–99 sequence (Table 3).

HLA-DR2 Is Capable of Restricting Multiple Hu-MBP Epitopes. The association of the HLA-DR2/DQw1 haplotype with MS suggests that these Class II molecules, especially DR2, could play a critical role in restricting CD4+ T cell responses to CNS autoantigens. To this end, the Hu-MBP epitopes recognized by 17 T cell clones from 3 HLA-DR2/DQw1 donors are summarized in Table 4. In total, this set of T cell clones recognized P2 (3 clones), P1 (1 clone), P4 (8 clones), or no peptide (5 clones). Within P4, 1 MS clone recognized the 87–99 epitope, 1 normal clone recognized the 110–129 epitope, 1 MS clone recognized the 130–149 epitope, and 4 clones (3 MS and 1 normal) recognized the 149–171 epitope. Responses in 7 of 7 P4-reactive clones tested were inhibited with anti-HLA-DR antibody, clearly implicating DR2 as the restriction element (Table 4). Since the DR locus is used predominantly in restricting human T cell responses to MBP, it is likely that the majority of the 10 untested clones were also DR2 restricted. In any case, it is clear that DR2 can restrict a wide variety of Hu-MBP epitopes in humans.

TCR Vβ Gene Usage by Hu-MBP Reactive T Cell Clones. The preferential use of TCR Vα and Vβ gene families by encephalitogenic MBP-specific T cells from rats and mice has led to successful vaccination and therapeutic strategies directed against common TCR sequences on the pernicious T cells. It is unknown, however, if a similar mechanism in humans leads to the restricted use of TCR V genes in response to MBP or other antigens. To begin the analysis of TCR V gene use, 38 T cell clones (19 from each group) were phenotyped for expression of Vβ gene products, using a panel of 5 monoclonal antibodies specific for Vβ5.2, Vβ5.3, Vβ6.7, Vβ8.1, and Vβ12 (Table 5). TCR V gene expression could be positively identified in six of the clones, all from MS donors: Two of these clones expressed Vβ6.7, whereas the other 4 clones expressed Vβ5.2. Of the Vβ5.2+ clones, 1 was from a DR2,4 donor, and 3 were from a DR2 homozygous donor. One additional clone from the DR2 homozygous donor expressed rearranged mRNA for Vβ5.2, indicating that in this individual, 4/8 clones analyzed use the same TCR Vβ gene in response to Hu-MBP, even though each has a distinct epitope specificity (Table 5).

C. DISCUSSION

The present example clearly demonstrates at the clonal level that MS patients have a more complex and altered pattern of T cell recognition of immunodominant Hu-MBP epitopes than do normal Hu-MBP responders. These data suggest an increased exposure to immunogenic forms of Hu-MBP in MS patients, thereby increasing the likelihood of inducing or perpetuating encephalitogenic T cells. The potential relevance of T cell recognition of Hu-MBP in human paralytic conditions such as MS must be viewed in light of the potent encephalitogenic function of MBP-reactive T cells in animals, and the increased frequency of activated MBP-reactive T cells in the blood and CSF of MS patients (Allegretta et al., Science 247:718 (1990); Link et al., Neurology40 (Suppl. 1):283 (1990)).

The T cell clones evaluated in this study were isolated from Hu-MBP specific T cell lines selected in vitro to allow the emergence of specificities directed at immunodominant Hu-MBP epitopes. Encephalitogenic determinants display imunodominance during the selection of rat and mouse T cell lines with whole MBP (Bourdette et al., Cell. Immunol. 112:351 (1988); Vandenbark et al., J. Immunol. 135:229 (1985)), and it is likely that T cells to immunodominant Hu-MBP determinants could also be encephalitogenic under permissive conditions. In this study, the immunodominant epitopes inferred from T cell line responses showed a significant correlation with the specificities identified through clonal analysis (FIG. 7).

These results validate conclusions drawn from the line data regarding specificity, and document that the clones which survived the selection procedure were representative of the Hu-MBP responsive T cell population within the lines.

However, the phenotype of the clones was uniformly CD4+ (with the exception of 3 clones from a single normal donor), even though the T cell lines all contained substantial levels of CD8+ T cells. It is not clear if the CD8+ T cells within the lines were Hu-MBP specific, or if they were simply carried in the lines by the relatively high levels of IL-2 added to the cultures. It was apparent, however, that the normal T cell lines consistently contained a higher percentage of CD8+ cells than the MS lines. One of the CD8+ clones could inhibit MBP-induced proliferation of a CD4+ clone from the same normal donor. Such regulatory CD8+ T cells, if present in increased numbers in vivo, could account for the lack of clinical disease in normal individuals with Hu-MBP reactive T cells. A critical level of these CD8+ T cells in conjunction with increased levels of adherent suppressor cells (similar to those observed in mice (Whitham et al., Cell. Immunol. 126:290 (1990))) could account for the inability to select Hu-MBP specific T cell lines from more than 60% of normal donors (Vandenbark et al., J. Neurosci. Res. 23:21 (1989)).

In contrast, T cell lines can be selected from more than 80% of MS patients. These regulatory cell types would not be expected to influence the efficiency of recovering MBP-specific T cell clones by limiting dilution directly from blood, without prior line selection, as reported by others (Hafler et al., J. Immunol. 139:68 (1987); Richert et al., J. Neuroimmunol. 23:55 (1989); Richert et al., Ann. Neurol. 26:342 (1989)).

T cell responses to Hu-MBP in MS patients included a broader range of specificities than the responses in normal individuals (FIG. 6). In addition to common epitopes, T cells from MS patients showed a biased response to the N terminal half of MBP and towards at least one epitope in the C terminal half of the molecule. The most consistent difference in response between MS and normal donors was to P1 (residues 45–89). Previous studies have shown that in MS, immuno-reactive fragments of Hu-MBP-like material are present in the cerebrospinal fluid (CSF), with the dominant antigenic form spanning residues 45–89 (Whitaker, J. N., J. Immunol. 129:2729 (1982)). The detectable concentration of this fragment increases in CSF after central nervous system injury, providing a feasible explanation for the increased occurrence of P1-reactive T cells in MS patients. The bias of MS responses to P2 and to the 130–149 epitope within P4 could also be explained by the release of immunoreactive fragments of Hu-MBP during demyelination, although MHC restriction effects cannot be ruled out as yet.

From animal studies, it is clear that long-term immunization with MBP induces an expanding repertoire of T cells to less and less dominant combinations of MHC and MBP epitopes (Offner et al., J. Exp. Med. 170:355 (1989)). These additional T cell specificities may or may not be encephalitogenic, depending on their ability to recognize homologous MBP. The increased complexity of Hu-MBP responsive T cell specificities in MS patients is consistent with increased exposure to immunogenic fragments of MBP released during demyelination, and it is conceivable that the long-term, chronic nature of MS involves the continuous induction or re-stimulation of encephalitogenic T cell specificities.

Approximately 40% of the Hu-MBP reactive T cell clones, especially the clones from normal T cell lines, did not respond to any Hu-MBP fragment. Such a response could involve junctional epitopes spanning the cleavage sites of Hu-MBP (e.g. residues 30–55 or 80–100), conformational epitopes destroyed by cleavage, or isoforms or post-translational variants of Hu-MBP lost during purification of cleavage fragments. Although the function of these cells in humans is unclear, similar cells occur at high frequency (50%) in EAE-recovered Lewis rats. Such T cells transfer delayed hypersensitivity responses to MBP, but do not transfer EAE or protection against EAE.

Responses in both MS and normal T cell clones were predominantly restricted by HLA-DR, although no strong association was found between any specific epitope and a given DR allele. HLA-DR2, which is over-represented in MS patients, was capable of restricting multiple epitopes of Hu-MBP, and some epitopes (e.g., 149–171) could be restricted by several HLA-DR alleles. In a previous T cell line study (Chou et al., J. Neurosci. Res. 23:207 (1989)), HLA-DR alleles were reported to be restricted to 26/33 Hu-MBP epitope-specific T cell responses, whereas HLA-DQ restricted 6/33 responses only in patients, and HLA-DP restricted a single normal donor response to P2.

The present data from T cell clones confirm the overwhelming restriction function of HLA-DR molecules on Hu-MBP recognition, as well as the ability of an undefined HLA-DP allele (from a different normal donor, DR7,?/DQw2,3) to restrict epitopes within the Hu-MBP 1–38 region recognized by three individual clones. However, no HLA-DQ restricted clones were found.

A major question regarding the use of TCR Vβ peptides to regulate T cell responses in humans is whether or not MBP-specific T cells utilize a limited set of V genes. The present data, using antibodies specific for only about 1/10th of the TCR Vβ repertoire, positively identified 6/38 clones, all from MS donors. In one HLA-DR2/DQw1 homozygous donor with chronic progressive MS, 4 of 8 T cell clones specific for different Mu-MBP epitopes expressed the same Vβ5.2 gene in the T cell receptor (all phenotypically Vβ5.2 positive clones were confirmed by PCR), suggesting for the first time a bias in TCR V gene use by humans in response to Hu-MBP. The use of the same TCR V region gene in response to different Hu-MBP epitopes is similar to MBP responses in rats and mice, and indicates that the choice of the TCR is not epitope driven.

One important practical implication of this observation is that biases in TCR repertoire can be ascertained without defining the epitope specificities of MBP-reactive clones. Table 6 presents PCR data which demonstrate that MBP-specific T cell clones from human MS patients are skewed in their TCR Vβ gene use. Total mRNA was extracted from individual T cell clones specific for human MBP from MS patients and normal donors, and rearranged TCR Vβ message was amplified by PCR and identified by specific probes. Preferential use of Vβ5.2 in MS donors MS-1 and MS-2, and preferential use of Vβ14 by normal donor N-1 by MBP-specific T cell clones was demonstrated. This provides additional support for the conclusion that humans also respond preferentially with V region genes to autoantigens such as MBP.

TABLE 1

Phenotype Distribution of M8P-Specific Cell Lines and Clones from MS Patients and Normal Individuals

| | T Cell Line | | T Cell Clone | | |
|---|---|---|---|---|---|
| Donor | CD4+ % | CD8+ % | #CD4+ | #CD8+ | Total # Tested |
| MS1(HL) | 86.0 | 7.5 | 5 | 0 | 5 |
| MS2(JH) | 52.4 | 25.8 | 5 | 0 | 5 |
| MS3(MD) | 93.5 | 15.5 | 6 | 0 | 6 |
| MS4(SO) | 76.8 | 17.0 | 1 | 0 | 1 |
| MS5(BS) | Not tested | | Not tested | | |
| MS6(MR) | 84.0 | 10.0 | 7 | 0 | 7 |
| MS7(RB) | 86.0 | 14.0 | Not tested | | |
| Total | 78.1 ± 13 | 14.9 ± 6 | 24 | 0 | 24 |
| N 1(BP) | 56.0 | 37.0 | 2 | 0 | 2 |
| N 2(MA) | Not tested | | 6 | 3 | 9 |
| N 3(LT) | 66.0 | 10.0 | 4 | 0 | 4 |
| N 4(DB) | 58.5 | 36.0 | 2 | 0 | 2 |
| N 5(HY) | 45.0 | 42.0 | 1 | 0 | 1 |
| N 6(JT) | 66.0 | 25.00 | 6 | 0 | 6 |
| Total | 59.3 + 8 | 30.0 + 12 | 21 | 3 | 24 |

TABLE 2

Peptide Specificities of T Cell Clones from MS Patients and Normal Individuals

| Donor | | | Clone number responding to | | | | |
|---|---|---|---|---|---|---|---|
| Name | Sex | HLA type | P2(1-38) | P1(45-89) | P4(90-170) | None | Total |
| MS1(NL) | F | DR1,2/DQw1 | 2 | 7 | 0 | 10 | 19 |
| MS2(JH) | F | DR7,?*/DQw2,3 | 3 | 0 | 2 | 1 | 4 |
| MS3(MD) | F | DR2,4/DQw1,3 | 2 | 0 | 8 | 0 | 10 |
| MS4(SO) | F | DR2,w6/DQw1 | 0 | 0 | 1 | 0 | 1 |
| MS5(BS) | M | DR2/DQw1 | 0 | 1 | 3 | 0 | 4 |
| MS6(MR) | M | DR2/DQw1 | 3 | 0 | 4 | 3 | 10 |
| MS7(RB) | M | DR2,7/DQw1 | 0 | 1 | 1 | 0 | 2 |
| | | | 10(20)** | 9(18)** | 17(34) | 14(28)** | 50(100) |

TABLE 2-continued

Peptide Specificities of T Cell Clones from MS Patients and Normal Individuals

| Donor | | | Clone number responding to | | | | |
|---|---|---|---|---|---|---|---|
| Name | Sex | HLA type | P2(1-38) | P1(45-89) | P4(90-170) | None | Total |
| MS8(LB) | F | DR4/DQw3 | | | | | |
| MS9(SS) | F | DR5,w6/DQw1,3 | | | | | |
| MS10(MB) | F | DR5,w6/DQw1,3 | | | | | |
| MS11(JS) | M | DR2/DQw1 | | | | | |
| N1(BP) | F | DR1,3/DQw1,2 | 0 | 0 | 4 | 1 | 5 |
| N2(MA) | F | DR3,w6/DQw1,2 | 2 | 0 | 16 | 2 | 20 |
| N3(LT) | F | DR2,7/DQw1,2 | 0 | 1 | 2 | 4 | 7 |
| N4(DB) | M | DR2/DQw1 | 0 | 0 | 1 | 2 | 3 |
| N5(HY) | M | DR4,7/DQw2,3 | 0 | 0 | 1 | 0 | 1 |
| N6(JT) | M | DR7/DQw2 | 0 | 0 | 0 | 23 | 23 |
| | | | 2(3) | 1(2) | 24(41) | 32(54) | 59(100) |
| N7(SO) | F | DR1,2/DQw1 | | | | | |
| N8(PP) | F | DRw8/DQw3 | | | | | |
| N9(LS) | F | Not tested | | | | | |

*Antigens in linkage disequilibrium with DR antigens are present, but expected antigens did not type clearly.
**( ) = % of total clones; compared to normals, $p < 0.01$.

TABLE 3

Epitope Specificities of P4-Reactive T Cell Clones from MS Patients and Normal Individuals

| Donor Number Total (DR2+) | Number of clones responding to | | | | | |
|---|---|---|---|---|---|---|
| | 87-99 | 91-109 | 110-129 | 130-149 | 149-171 | Total |
| MS  4(4) | 1 | 0 | 1** | 3**(2)* | 4(3)* | 9 |
| Normal  4(2) | 0 | 0 | 9(3)* | 0 | 5(2) | 14 |

*( ) Number of donors responded.
**Compared to normals, $p < 0.01$.

TABLE 4

Human MBP Epitope Specificities in DR2/DQw1 Homozygous Donors

| Donor | Clone | MBP | P2(1-38) | P1(45-89) | P4(90-170) | Epitope/allele |
|---|---|---|---|---|---|---|
| MS5(BS) | #24(14B7) | 3 ± 0 | 0 | 3 ± 0 | 0 | P1 |
| | #14(8B3) | 19 ± 1 | 0 | 0 | 27 ± 0 | P4 |
| | #5(5B9) | 49 ± 0 | 0 | 0 | 22 ± 2 | 149-171/DR |
| | #23(11D3) | 60 ± 4 | 0 | 0 | 31 ± 2 | 149-171/DR2 |
| MS6(MR) | #9(5D7) | 1 ± 0 | 0 | 0 | 0 | P2 |
| | #43(5D2) | 1 ± 0 | 2 ± 0 | 0 | 0 | P2 |
| | #52(8C4) | 2 ± 0 | 1 ± 0 | 0 | 0 | P2 |
| | #41(4F3) | 3 ± 0 | 0 | 0 | 1 ± 0 | 87-99/DR2 |
| | #48(10B7) | 2 ± 0 | 0 | 0 | 6 ± 0 | 130-149/DR2 |
| | #22(3C6) | 1 ± 0 | 0 | 0 | 1 ± 0 | 149-171/DR2 |
| | #4S(3C3) | 4 ± 0 | 0 | 0 | 2 ± 1 | 149-171/DR2 |
| | #40(D310) | 13 ± 0 | 0 | 0 | 0 | No Peptide |
| | #51(7B7) | 1 ± 0 | 0 | 0 | 0 | No Peptide |
| | #2(3A2) | 3 ± 0 | 0 | 0 | 0 | No Peptide |
| Normal 4(DB) | #36(9B4) | 4 ± 0 | 0 | 0 | 4 ± 0 | 110-129/DR2 |
| | #9(7E3) | 1 ± 0 | 0 | 0 | 0 | No Peptide |
| | #19(8C5) | 2 ± 0 | 0 | 0 | 0 | No Peptide |

TABLE 5

T Cell Receptor Vβ Chain Expression of MBP-Reactive T Cell Clones

| Donor | # of Clones Tested | # of Clones Identified | Name | CD4/CD8 | TcR* | Epitope/MHC |
|---|---|---|---|---|---|---|
| MS1(NL) | 2 | 1 | #47 | CD4+ | Vβ6.7 | HMBP/DR1,2** |
| MS2(JH) | 3 | 1 | #49 | CD4+ | Vβ6.7 | HMBP/DR7,?** |
| MS3(MD) | 6 | 1 | #26 | CD4+ | Vβ5.2 | 90-170/DR2,4 |
| MS4(SO) | 1 | 0 | — | — | — | — |
| MS6(MR) | 7 | 3 | #22 | CD4+ | Vβ5.2 | 149-171/DR2 |
|  |  |  | #41 | CD4+ | Vβ5.2 | 87-99/DR2 |
|  |  |  | #43 | CF4+ | Vβ5.2 | 1-38/DR2 |
| Total 5 | 19 | 6 |  |  |  |  |
| N 1(B) | 1 | 0 | — | — | — | — |
| N 2(MA) | 7*** | 0 | — | — | — | — |
| N 3(LT) | 3 | 0 | — | — | — | — |
| N 4(DB) | 3 | 0 | — | — | — | — |
| N 6(JT) | 5 | 0 | — | — | — | — |
| Total 5 | 19 | 0 |  |  |  |  |

*DIVERST-Tm αβ TcR screening panel 1A (T Cell Sciences, Inc., Cambridge, MA) included Vβ5a (Vβ5.2 and 5.3), Vβ5b (Vβ5.3), Vβ6 (Vβ6.7), Vβ8 (Vβ8.1) and Vβ12 (Vβ12) mAbs against TcR Vβ chain.
**Responded to whole Human MBP, but not to any peptides.
***Three CD8 + clones were included.

TABLE 6

BP-Specific TCR Vβ Gene Use

| Donor | HLA Type | # Clones | Vβ Gene |
|---|---|---|---|
| MS-1 | DR 1,2 | 13 | 5.2 |
|  |  | 1 | 5.1 |
| MS-2 | DR 2 | 4 | 5.2 |
|  |  | 4 | 3,4,6,9 |
| MS-3 | DR 2,4 | 1 | 5.2 |
| MS-4 | DR 2, W6 | 1 | 6 |
| N1 | DR 3, W6 | 12 | 14 |
| N2 | DR 4,7 | 1 | 2 |

Conclusion: BP-specific T cell clones are skewed in their TCR Vβ gene use, with Vβ5.2 expressed by 18/24 MS clones.

EXAMPLE III

Preferential Cell Receptor Vβ Gene Usage in Myelin Basic Protein Reactive T Cell Clones from Patients with Multiple Sclerosis Introduction Multiple sclerosis (MS) is an autoimmune disease in which T lymphocytes reactive to myelin basic protein (BP) could play a central role. According, the utility of the present invention was demonstrated by cloning T cells specific for BP from the blood of MS patients and normal individuals; followed by the analysis and expression of T cell receptor (TCR) variable (V) region genes. A remarkable bias for usage of Vβ5.2 and to a lesser extent Vβ6.1 was observed among BP-specific clones from patients but not from controls. Shared Vβ5.2 and Vβ6.1 suggests that the BP-specific clones derived from blood may be relevant to disease pathogenesis. These findings have important implications for the treatment of MS. This example analyzes the TCR Vα and Vβ genes expressed in BP-specific T cells selected from the blood of MS patients and normal individuals.

T cell clones specific for BP and other antigens were derived from peripheral blood mononuclear cells (PBMC) of MS patients and normal individuals, and characterized in terms of response to different BP regions. TCR Vβ and Vα gene expression in these clones was determined using PCR amplification (Oksenberg et al., Nature 345:344–346 (1990); Choi et al., Proc. Natl. Acad. Sci. USA 86:8941–8945 (1989)). A representative example of detected Vβ and Vα expression is shown in FIGS. 10A and 10B, respectively. Although referred to as Vβ5.2 in FIG. 10A, the Vβ5.2 and Vβ5.3 gene products cannot be distinguished since a sequence common to these V genes was used as primer. The clone analyzed in FIG. 10 was also shown to express cell surface TCR Vβ5.2/5.3 antigens by immunofluorescence analysis.

A detailed analysis of clones derived from three MS patients is shown in Table 7. BP-specific clones from patient NL showed a striking preferential usage of Vβ5.2. Surprisingly, specificity for different BP determinants appeared to be independent of this biased TCR Vβ gene usage. For example, clones specific for peptides 45–89 and 1–38, and BP-specific clones that were not stimulated by any of these peptides rearranged Vβ5.2 genes preferentially. Although Vα usage was determined for only four NL clones, the data suggest that Vα may be a major contributor to BP peptide specificity. Thus, Vα8 gene expression was identified in three clones specific for BP peptide 45–89 whereas Vα2 was rearranged in the one clone specific for peptide 1–38. With this limited analysis, however, a major contribution from α to β chain junctional regions (Jα, Dβ, Jβ) cannot be excluded. Despite common usage of Vβ5.2, many of the NL clones appear to be clonally unrelated, separated on the basis of peptide specificity, Vα expression, and minor Vβ gene expression. The clonal relatedness of certain sets, for example the seven Vβ5.2+ clones in which no peptide specificity was apparent, is currently unknown. Determining Vα expression and/or sequencing junctional regions would be the most straightforward way to answer this question. Four of 10 BP-specific clones derived from patient MR also utilized Vβ5.2. As in patient NL, clones with three distinct BP specificities used this particular Vβ gene. Three of six clones from WS also expressed Vβ5.2 genes, of which two utilized the same Vα and had the same specificity. In contrast to the frequent isolation of Vβ5.2+ clones that were BP specific, none of the clones reactive to other antigens or clones that were nonspecific utilized Vβ5.2 (Table 7).

It should be emphasized that great care was taken to avoid contamination of samples with amplified PCR products, and to exclude it as a contributor to the findings. Thus, in all cases, controls included negative reactions with Vβ5.2 and Vβ6.1-specific oligomers but with no RNA template. Whenever possible, freshly prepared RNA was also used to confirm an initially positive Vβ5.2+ clone. Furthermore, clones with different specificities and from different patients as well as from normal individuals were studied at similar times, and preferential Vβ5.2 usage was only detected in BP-specific clones from MS patients (see Tables 7 and 8). Finally, clones from patient MR were analyzed for surface expression of Vβ5.2 determining using a monoclonal anti-Vβ5.2 antibody and immunofluorescence analysis, and complete concordance between gene expression by PCR and cell surface expression by monoclonal antibody was observed.

A striking preferential usage of Vβ5.2 and to a lesser extent Vβ6.1 was apparent in BP-specific clones from seven patients but not from six normal donors (Table 8). Of 48 BP specific clones from MS patients analyzed by PCR for Vβ expression, 27 utilized Vβ5.2 and 0 of 15 non-BP-specific clones were Vβ5.2+ (p<0.001 by Fisher's exact test). In contrast, only two of 41 BP-specific clones from normal individuals were Vβ5.2+ (p<0.0001 by Chi-square analysis). The statistical significance of these comparisons is still evident if clones from patient NL are excluded, and the frequency of Vβ5.2+ BP-specific clones in patients is considered to be 14 of 34 (p<0.001 for comparison with BP-specific clones for normals or for comparison with non-BP-specific clones. In regards to the comparison of clones from patients and controls, six of the seven patients studied and only two of the six controls carried HLA-DR2, which is expected from the known frequencies of DR2 in the two populations. Still, only one of ten BP-specific clones from the DR2+ controls was Vβ5.2+ (p<0.01 compared to frequency in MS patients). The 54% frequency in patients is also much greater than the expected peripheral blood level (2.5–5.0%) (Choi et al., Proc. Natl. Acad. Sci. USA 86:8941–8945 (1989); Kappler et al., Science244:811–813 (1989)). Although overall frequencies of Vβ6.1+ BP-specific clones from patients compared with that from controls or compared with non-BP specific clones are not statistically different, the frequency (20%) is still much greater than that expected by chance (peripheral blood percentage predicted by PCR is 5–10%, (Choi et al., Proc. Natl. Acad. Sci. USA 86:8941 (1989)). Furthermore, if only clones that do not express Vβ5.2 are considered, the frequency of Vβ6.1 expression in BP-specific clones from patients compared with controls is statistically different (p<0.02).

Despite the absence of Vβ5.2+ clones, preferential Vβ usage was noted for BP-specific clones derived from normal individuals (Table 8). In one individual, 11 of 13 clones expressed Vβ14, and in two other Vβ7 predominated. No relationship with serologically-determined DR expression was discernable.

FIG. 11 shows a summary of Vα utilization in BP-specific clones from patients and controls. In contrast to Vβ usage, BP-specific clones from patients showed much more generalized Vα usage. Vα1, 2, 7, 8, and 10 families were well-represented among the 30 clones analyzed. Because of an initial emphasis on Vβ, it should be noted that only 4 clones from patient NL were analyzed for Vα expression. Perhaps the analysis of more clones might disclose more prominent Vα skewing. Surprisingly, preferential Vα usage was much more apparent in BP-specific clones among controls. Of 22 clones analyzed, 12 expressed Vα2 and eight expressed Vα15.

In the present report, peripheral blood cells were expanded initially in bulk culture by stimulation with intact human BP, prior to cloning by limiting dilution. Responses to BP peptide 84–102 which dominated the response in the Wucherpfennig study (Wucherpfennig et al., Science 248:1016–1019 (1990)), were notably rare in the current study. In addition, preferential Vβ5.2 expression in the current example appeared to be independent of BP-epitope specificity. Interestingly, this is similar to the preferential Vβ5.2 expression that has been found in mice and rats (Heber-Katz et al., Immunol. Today 10:164–169 (1989)).

Oksenberg et al., (Nature345:344 (1990) and manuscript submitted) used the PCR to analyze directly expression of TCR Vα and Vβ genes in brain samples from MS patients. Limited heterogeneity of both Vα and Vβ transcripts was observed. Interestingly, of nine HLA-DR2 patients, including eight with different DR2 (DW2) molecular phenotypes, eight demonstrated rearranged Vβ5.2 gene and seven demonstrated rearranged Vβ6.1 at the site of brain disease. The correlation with the findings of preferential Vβ5.2 and Vβ6.1 usage in BP-specific clones derived from the peripheral blood of patients in this example is remarkable. Together, the studies provide additional evidence suggesting that peripheral blood T cells are a reflection of cells involved in the central nervous system damage, and that BP-reactivity is a component of the pathogenic response in MS.

In summary, the data presented demonstrate preferential Vβ gene usage among BP-specific clones derived from the blood of MS patients. The implication that those clones may be pathogenetically important suggests that the limited TCR repertoire provides a specific target for therapeutic intervention. Both monoclonal antibodies and synthetic TCR peptides specific for the V regions used could be considered in this approach.

TABLE 7

TCR Vβ and Vα Usage in Clones Derived from Three MS Patients

| BP-Specific Clones | | | | Non-BP Specific Clones | | | |
|---|---|---|---|---|---|---|---|
| Patient-Clone | Specificity Antigen (BP peptide) | Vα | Vβ | Patient-Clone | Antigen Specificity | Vα | Vβ |
| NL-6 | BP(NR) | NT† | 5.2 | MR-C1 | PPD | NT | 8.1 |
| NL-25 | BP(NR) | NT | 5.2 > 14 | MR-C2 | PPD | 15 | 6.1 > 14 |
| NL-27 | SP(NR) | NT | 5.2 | MR-C7 | PPD | NT | 13.2 |
| NL-41 | BP(NR) | NT | 5.2 | | | | |
| NL-46 | BP(45-89) | NT | 5.1 | WS-3B3 | nonspecific | 9 | 15 |
| NL-47 | BP(45-89) | 2,8 | 5.2 | WS-7D5 | nonspecific | 14 | 19 |
| NL-53 | BP(45-89) | 8 | 5.2 | WS-8D3 | nonspecific | 7 | 13.1 |
| NL-54 | BP(NR) | NT | 5.2 | WS-8C7 | nonspecific | 8 | 6.1 > 20 |

TABLE 7-continued

TCR Vβ and Vα Usage in Clones Derived from Three MS Patients

| BP-Specific Clones | | | | Non-BP Specific Clones | | | |
|---|---|---|---|---|---|---|---|
| Patient-Clone | Specificity Antigen (BP peptide) | Vα | Vβ | Patient-Clone | Antigen Specificity | Vα | Vβ |
| NL-56 | BP(NR) | NT | 5.2 | WS-9D3 | nonspecific | 8 > 2 | 13.2 > 9 |
| NL-57 | BP(45-89) | NT | 5.2 | WS-13C7 | nonspecific | 1 | 13.1 > 10,6.1 |
| NL-59 | BP(45-89) | 8 > 6 | 5.2 | WS-6A2 | nonspecific | 8 | 10 |
| NL-63 | BP(NR) | NT | 5.2 | | | | |
| NL-97 | BP(1-38) | 2 | 5.2 | | | | |
| NL-101 | BP(NR) | NT | 5.2 | | | | |
| MR-21 | BP(NR) | NT | 5.2 | | | | |
| MR-22 | BP(90-170) | NT | 5.2 | | | | |
| MR-40 | BP(NR) | 7,11 | 6.1,9 | | | | |
| MR-41 | BP(90-170) | 1 | 5.2 | | | | |
| MR-43 | BP(45-89) | NT | 5.2 | | | | |
| MR-45 | BP(90-170) | 10 | 3 | | | | |
| MR-46 | BP(NR) | 1,14 | 9 | | | | |
| MR-48 | BP(90-170) | 7 | 19,15 | | | | |
| MR-51 | BP(NR) | 10 | 6.1 | | | | |
| MR-52 | BP(45-89) | 14 | 4 | | | | |
| WS-23 | BP(90-170) | 1 | 5.2 | | | | |
| WS-2B6 | BP(90-170) | 1 | 5.2 | | | | |
| WS-2C8 | BP(NR) | 7 | 12 | | | | |
| WS-2D5 | BP(NR) | 8 | 6.1 > 20,9 | | | | |
| WS-8D5 | BP(NR) | 10 | 6.1 | | | | |
| WS-14B7 | BP(NR) | NT | 5.2 | | | | |

Table 7

Clones were analyzed for Vβ and Vα expression by PCR and autoradiography as described in FIG. 10. Human BP-reactive T cell lines were selected from the blood of MS patients as previously described (Chou et al., J. Neurosci. Res., in press (1991)). Briefly, peripheral blood mononuclear cells (PBMC) were cultured with 50 μg/ml human BP for 5 days prior to transfer into IL-2 rich medium. When growth in IL-2 showed, T cells were restimulated one time with 25 μg/ml Hu-BP presented by irradiated autologous PBMC, and cloned by limiting dilution two times as described (Chou et al., J. Neurosci. Res., in press (1991)). All sixteen clones from MS-patients and 15 of 15 clones from normal individuals analyzed by immunofluorescence expressed CD4. For some clones, more than one Vβ or Vα band could be identified, although usually one band predominated in intensity especially when a lower number (25-30) of PCR cycles was employed. The specificity of T cell clones for BP, BP peptides, or other antigens was assessed by proliferation as described Chou et al., J. Neurosci. Res., in press (1991)). Clones labeled as nonspecific were generated in the presence of BP but failed to demonstrate a proliferative response to BP above background (stimulator cells alone). All BP-reactive clones were tested for response to BP peptides 1-38, 45-89, and 90-170 prepared by Dr. Selene Chou as described (Chou et al., J. Neurochem. 28:115-119 (1977)). NR indicates that a particular clone responded to BP but did not respond to any of these BP peptides. †NT—not tested.

TABLE 8

Summary of Vβ Utilization in Clones from MS Patients and Controls

| | HLA type | Tested | Specificity | Vβ5.2 | vβ6.1 | Other Vβs (# clones positive) |
|---|---|---|---|---|---|---|
| Patients | | | | | | |
| NL | DR1.2;DQw1 | 14 | BP | 13 | 0 | Vβ5.1 |
| MR | DR2;DQw1 | 10 | BP | 4 | 2 | Vβ9(2x),3,4,15,19 |
| | | 3 | PPD | 0 | 1 | Vβ8.1,13.2 |
| WS | DR2;DQw1 | 6 | BP | 3 | 2 | Vβ12 |
| | | 7 | nonspecific | 0 | 1 | Vβ131.1(2x), 10,13.2,15,19 |
| MD | DR2,4;DQw1,3 | 9 | BP | 4 | 1 | Vβ2,7,13.2,15 |
| JH | DR7,-;DQ21.2,3 | 7 | BP | 2 | 4 | Vβ8,9 |
| | | 1 | nonspecific | 0 | 0 | Vβ2 |
| | DR2,w6;DQw1 | 3 | BP | 0 | 1 | —* |
| | | 2 | nonspecific | 0 | 0 | Vβ4,7 |
| | | 2 | HSV | 0 | 0 | Vβ4,15 |
| RB | DR2,7:DQw1,2 | 1 | BP | 1 | 0 | none |
| Total | | 50 | BP | 27 | 10 | |

TABLE 8-continued

Summary of Vβ Utilization in Clones from MS Patients and Controls

| | HLA type | Tested | Specificity | Vβ5.2 | vβ6.1 | Other Vβs (# clones positive) |
|---|---|---|---|---|---|---|
| Controls | | 15 | other | 0 | 2 | |
| MA | DR3,w6;DQw1.2 | 13 | BP | 1 | 0 | Vβ14(11x),—* |
| | | 1 | nonspecific | 0 | 0 | Vβ13.1 |
| JT | DR7;DQw2 | 10 | BP | 0 | 3 | Vβ7(4x),15,18,20 |
| BP | DR1.3;DQw1,2 | 7 | BP | 0 | 1 | Vβ7(4x),18,20 |
| LT | DR2.7;DQw1,2 | 6 | BP | 0 | 0 | Vβ14(2x), 7,12,13.2,17,20 |
| DB | DR2;DQw1 | 4** | BP | 1 | 0 | —** |
| HY | DR4.7;DQw2,3 | 1 | BP | 0 | 0 | Vβ2 |
| | | 2 | nonspecific | 0 | 0 | Vβ13.1,17 |
| Total | | 41 | BP | 2 | 4 | |
| | | 3 | other | 0 | 0 | |

Table 8

TCR Vα and Vβ expression was analyzed for T cell clones selected from the blood of seven MS patients and six normal individuals. Patients were being followed at the Oregon Health Sciences University MS clinic, and had clinically and laboratory supported definite MS. The patients had an average ambulation index of 3.2±2.0 (range 2.6). Four patients had relapsing/remitting disease and three patients had chronic progressive disease. The normal individuals were from the Veterans Affairs Medical Center, selected on the basis of a positive proliferative response of PBMC to human BP in culture. All subjects were HLA-typed by standard serological methods at the Oregon Health Sciences University Transplantation laboratory. The uneven distribution of HLA DR2 expression (6 of 7 patients vs. 2 of 6 controls) reflects the frequency expected in MS patients versus the normal population.

In this analysis, only the predominant Vβ band for each clone is included. However, for some clones, 2 bands of nearly equal intensity are both recorded, and therefore the total number of Vβs may be greater than the number of clones analyzed. *No Vβ gene expression could be identified for those clones using the Vβ-specific oligomers described. †Three of these clones were only analyzed by monoclonal anti-Vβ antibodies (Kappler et al., Science 244:811–813 (1989)) directed to Vβ5.2/5.3, Vβ6.7, Vβ8.1, and Vβ12, and were negative.

EXAMPLE IV

Sequence Homology Between V Gene Families In The CDR2 Region

In light of the predicted and observed high level of biological activity for the CDR2 region, the inventor decided to look further into the CDR2 region and line up the peptides so as to assay for homology.

A remarkable homology was witnessed at the NH2-terminus. Six out of eight residues were homologous with the two nonhomologous ones at the C-terminus being conservative substitutions. This homology is noteworthy since, as discussed later, the clones selected against Vβ6.1 can recognize the Vβ5.2 epitope.

In an effort to further elucidate the relationship between the V gene families in the CDR2 region, the inventor also compared the Vβ14 epitope to Vβ12.2 and Vβ17.1. Ten out of the the first twelve residues from the NH2-terminus are homologous. There is less homology at the C-terminus; four out of nine residues line up. The following Table indicates the sequence homology.

TABLE 9

```
             NH2      CH3
        39 5    |   | 10      15       20
  ┌─ 5.2   A L G Q G P Q F I F Q Y Y E E E E R Q R G
  │        | | | | | |
  └─ 6.1 (S) L G Q G P E F L I Y F Q G T G A A D D S G
             | | |
  ┌─ 12.2  D P G H G L R L I H Y S Y G V K D T D K G
  │   38 | | | | | | | |     | |      | |
  └─ 17.1  D P G Q G L R L I Y Y S Q I V N D F Q K G
           | | | | | | | | | |    |       | |
     14.   D P G L G L R Q I Y Y S M N V E V T D K G
                 V
                 F
```

EXAMPLE V

Distinct T Cell Recognition of Myelin Antigens in Cerebrospinal Fluid of Multiple Sclerosis Patients The present example demonstrates for the first time that the cerebrospinal fluid (CSF) of MS patients contains significantly higher frequencies of T cells that respond to intact BP and, to a lesser degree, to a PLP peptide, than do those found in the blood of the same patients, or in the CSF of patients with other neurological diseases (OND). In contrast, both MS and OND patients have comparable levels of CSF T cells that respond only to cryptic fragments of BP not found in processed intact BP, suggesting a distinct processing pathway. The close proximity to the target organ of inflammatory levels of myelin antigen reactive T cells lends new support to their involvement in the MS disease process.

Previous studies suggested that the frequency of peripheral T cells specific for myelin antigens is too low to account for the extensive myelin damage observed in MS (Allegretta et al., Science247:718–721 (1990)); and (Ota et al., Nature 346:183–187 (1990)). However, there are few reports characterizing myelin antigen specific T cells from the CSF, which is in direct communication with the inflamed CNS parenchyma. BP- and PLP-specific T cells are recovered preferentially from the CNS of immunized animals after expansion in IL-2, indicating prior activation of these encephalitogenic specificities. In contrast, no BP-specific T cells can be recovered after IL-2 expansion from the lymph nodes, suggesting that CNS-derived T cells are in a different state of activation.

In preliminary studies, the IL-2 expansion step allowed recovery of 3 fold more BP-specific T cells from the CSF of MS patients than direct antigen stimulation, compared to blood analyses that produced comparable results using both methods. The IL-2 expansion step was used to recover activated, antigen specific T cell clones from the CSF, and direct antigen stimulation was used to assess blood T cell frequencies from 9 patients with definite MS (Poser et al., Ann. Neurol. 13:227–231 (1983)); and (Kurtzke, J. R. Neurology33:1444–1452 (1983)) and 6 patients with other neurologic conditions. Blood T cell frequencies were also established for 4 rheumatoid arthritis patients and 6 normal donors.

As is shown in Table 10, the CSF cellularity from the MS donors ranged from 0.5 to 15.5 per µl (an average of 3.5 cells/µl), with only one donor (MS1) having an elevated cell count (>5 cells/µl). A total of 300 IL-2 responsive T cell clones were isolated and characterized from a total of 528,000 CSF cells plated (0.06% recovery). The IL-2 expanded clones were then assessed for specific responses to intact human BP (Eylar et al., J. Biol. Chem. 246:5770–5782 (1971)), BP fragments 1–38 (P2), 45–89 (P1), and 90–170 (P4) (Chou et al., J. Neurochem.28:115–119 (1977)), the PLP peptide corresponding to residues 139–151, and to Herpes simplex virus (HSV). The $PLP_{139-151}$ peptide was chosen by virtue of its widespread activity upon initial screening in MS patients, and its demonstrated encephalitogenic activity in mice (Tuohy et al., J. Immunol. 142:1868–1873 (1988)). Of the 300 activated clones recovered for analysis, 71 clones (24%) responded specifically to whole BP but not to $PLP_{139-151}$ or HSV, and an additional 39 clones (13%) reacted to one of the three fragments of BP but not to the intact BP molecule (Table 10). In addition, 39 clones (13%) responded specifically to $PLP_{139-151}$ (Table 10). Thus, in total, BP- and $PLP_{139-151}$-specific clones represented 50% of the activated CSF T cells. In contrast, only 10 clones (3%) responded specifically to HSV. All of 14 BP-specific clones tested were of the CD4 phenotype, in agreement with previous results.

In many respects, the CSF from the OND group was similar to MS CSF. OND CSF contained from 0.5–22.5 cells per µl (an average of 5.3 cells/µl), with only one donor (OND3) having an elevated cell count (Table 38). A total of 112 IL-2 responsive T cell clones were isolated and tested for antigen specificity from a total of 223,000 cells plated (0.05% recovery), a rate comparable to that from MS CSF. However, of the 112 clones recovered, only 3 responded to intact BP, and 2 to $PLP_{139-151}$. Together, these specificities represented <5% of the IL-2 responsive clones, versus 37% for MS patients. Similar to MS patients, however, 19 clones (17%) responded to one of the BP fragments, but not to the intact BP molecule. Thus, in total, 21% of the IL-2 responsive clones from OND patients were specific for CNS antigens, versus 50% for MS patients. In addition, 37 clones (33%) responded to HSV antigen, a rate nearly 10 fold higher than for MS patients (Table 10).

The frequencies of CSF T cells specific for whole BP among the MS patients ranged from 5.6 to $40 \times 10^{-5}$, providing an average frequency of $22.1 \times 10^{-5}$ or 1 per 4,525 CSF cells (FIG. 24). This frequency of response to intact BP in MS CSF was >18 fold higher than in OND CSF (p<0.01), in which only $1.2 \times 10^{-5}$ (1 per 83,333) CSF cells responded to intact BP. The frequency of $PLP_{139-151}$ responsive T cells was also increased in MS versus OND CSF (9.5 vs $2.1 \times 10^{-5}$, p<0.05, FIG. 24). In contrast, the frequencies of T cell clones that responded only to one of the BP peptides but not intact BP were the same in MS and OND patients (13.4 vs $12.3 \times 10^{-5}$, FIG. 24). The frequency of T cells responsive to HSV was inversely related to the response to myelin antigens, the MS CSF containing a reduced frequency ($4.1 \times 10^{-5}$) and OND CSF an increased frequency ($30.5 \times 10^{-5}$) relative to BP and $PLP_{139-151}$.

Paired blood samples from MS patients and controls were analyzed by the limiting dilution assay (Lefkovits et al., Immun. Today 5:265–268 and 295–298 (1984)) to establish the precursor frequency of BP-, $PLP_{139-151}$, and HSV-reactive T cells. As is shown in FIG. 25, circulating BP-reactive T cells from MS patients occurred at a frequency of $0.61 \times 10^{-5}$ (1 per 164,000 cells). This frequency was significantly higher (p<0.01) than in OND patients, rheumatoid arthritis patients, or normal donors (0.14, 0.12, and $0.10 \times 10^{-5}$ respectively). In contrast, no differences were observed among the patient groups in blood T cell frequencies to $PLP_{139-151}$ (range, $0.11 \times 0.16 \times 10^{-5}$) or to HSV (range $6.4–12.3 \times 10^{-5}$, FIG. 25).

Compared to blood, the frequency of BP-reactive T cells in MS CSF was enriched 36 fold (p<0.001), and the frequency of $PLP_{139-151}$-reactive T cells, 73 fold (p<0.001). A similar enrichment of BP- and $PLP_{139-151}$-reactive T cells occurred in OND CSF (9 and 19 fold respectively, p<0.05). In contrast, T cells specific for HSV were decreased 3 fold in MS CSF (p<0.01), but were increased 3 fold in OND CSF compared to blood (p<0.05). The differences in myelin antigen-specific T cell frequencies may be underestimated, since blood T cell clones detected by limiting dilution analysis represent the maximum achievable frequency, not the actual recovered frequency as in the CSF. Unlike the CSF, in which IL-2 expansion provided more efficient recovery of antigen specific T cells, blood T cell frequencies established after IL-2 expansion or direct antigen stimulation were similar. These results suggest that the peripheral antigen specific T cells may also be in an "activated" state.

A critical question addressed by the results presented in the present example is whether myelin antigen-reactive T cells occur at frequencies sufficient to induce paralysis and demyelination in MS patients. The present data strongly suggest that myelin antigen-reactive T cells in CSF (but not in blood) are sufficient to cause inflammation: The frequency of BP-reactive T cells in the CSF (22/100,000) is comparable to that found in the CNS tissue of rats with paralytic EAE (Cohen et al., Cell. Immunol. 108:203–213 (1987)) (30/100,000), and to T cell levels observed in SK/SD or TT reactive donors (Geha, R. S. Clin. Immunol. Immunopathol. 19:196–205 (1981)); (Sohnle et al., J. Immunol. 127:612–615 (1981)); and (Ford et al., Cellular Immunol. 79:334–344 (1983)) (4–22/100,000). It is noteworthy that the frequency of response to HSV in the blood of the study patients (6–12/100,000) also fell within this range. Moreover, the frequency of specific T cells in the blood of Keyhole limpet hemocyanin (KLH) immunized donors was 4/100,000 (Ford et al., Cellular Immunol. 79:334–344 (1983)), a level capable of triggering strong dermal reactions in vivo 32. (Burger et al., Cellular Immunol. 29:410–416 (1977)).

Myelin antigen reactive T cells did not occur at inflammatory frequencies in the blood, however. Circulating MS T cell levels to BP (0.61/100,000) were significantly higher than in OND, RA, or normal donors (0.10–0.14/100,000), but the MS blood T cell levels were only slightly greater than the frequency of T cells specific for KLH in unimmunized, skin test-negative donors (Ford et al., Cellular Immunol. 79:334–344 (1983)); and (Burger et al., Cellular Immunol. 29:410–416 (1977)) (0.38/100,000). All of the groups in this example had comparably low levels of $PLP_{139-151}$ reactive T cells (0.11–0.16/100,000), and this "baseline" level was similar to frequencies of BP-specific T cell clones recovered from the blood of MS patients (0.04–0.11/100,000) reported by others (Allegretta et al., Science 247:718–721 (1990); and Ota et al., Nature 346:183–187 (1990)). Thus, blood T cell frequencies to myelin antigens: i) appear to be too low to cause inflammatory reactions in vivo; ii) may reflect in diluted numbers the CSF response; and iii) appear not to result from systemic immunization with natural or cross-reactive determinants. Relevant to these findings, 40 fold higher frequencies of mononuclear cells secreting IFN-γ after BP exposure were reported recently in the CSF (185/100,000) versus the blood (3–5/100,000) of MS patients (Olsson et al., J. Clin. Invest. 86:981–985 (1990)). However, it is not yet clear how many of these reactive cells were T lymphocytes bearing TCR specific for BP.

T cell recognition of BP in CSF involved two distinct patterns. One set of clones recognizing epitopes within the intact BP molecule was prevalent in MS patients (71/110 clones, 65%) but occurred infrequently in OND patients (3/22 clones, 13%). The specificity of the MS clones was skewed towards epitopes in the N terminal half of BP, with T cell clones specific for P1 (residues 45–89) or P2 (residues 1–38) together accounting for more than 60% (43/71) of this clonal type (FIG. 26). The remaining clones responded to P4 (residues 90–170, 20%) or to none of the peptides (20%). Comparatively, only 36% of BP-reactive T cell clones from the blood of the same MS patients were specific for P1 or P2 (FIG. 26). The biased T cell response to P1 and P2 fragments of BP is particularly noteworthy because these fragments were almost totally unrecognized (5%) by BP-specific T cell clones from the blood of normal BP responders.

The second variant set of T cell clones in CSF responded selectively to one of the BP fragments, but not to intact BP itself, and occurred at similar frequencies in both the MS and OND groups (FIG. 24). Such peptide-specific epitopes that are not preserved when intact antigen is processed and presented with MHC have been described as "cryptic" (Gammon et al., Immunol. Rev., 98:53–73 (1987)). The variant T cell clones in this recognized such "cryptic" epitopes in each of the BP fragments, including residues 43–89 (41% and 42% of BP fragment specific clones from MS and OND patients respectively), 1–38 (36% and 21% respectively), and 90–170 (23% and 37% respectively).

Studies in rats explain the significance of these two patterns of BP recognition. T cell recognition of homologous BP appears to be requisite for induction of the encephalitogenic process. T cells induced after immunization with intact BP respond to immunodominant and encephalitogenic BP epitopes that are preserved when the intact BP is "processed" by accessory cells (Chou et al., J. Neurosci. Res. 23:207–216 (1989)). In contrast, immunization with a synthetic BP fragment representing a truncated version of the encephalitogenic epitope in rats induced two distinct sets of T cell clones (Offner et al., J. Immunol. 141:3828–3832 (1988)): One set recognized the synthetic peptide and intact BP, and were encephalitogenic. A second variant set of T cells recognized only the synthetic epitope, but not intact BP, and were not encephalitogenic. Thus, the same peptide appeared to assume two different antigenic conformations, only one of which was retained when the intact BP molecule was "processed" naturally. That a similar dual sensitization occurs in humans is supported by the observation that synthetic peptides corresponding to residues 55–74, 87–99, and 110–129 of human BP were all recognized by both BP-reactive and peptide-specific T cell clones from CSF. It is noteworthy that within P4, blood-derived clones from the same patients responded most frequently to the 130–149 and 149–171 peptides of BP, but rarely to the 87–99 and 110–129 epitopes.

Taken together, the results presented above demonstrate that: 1) T cells specific for encephalitogenic myelin antigens comprise 50% of the activated, IL-2 responsive T cells in MS CSF; 2) the frequency of T cells specific for encephalitogenic myelin antigens is highly enriched in the CSF of MS patients compared to the periphery, and occurs at a level capable of instigating inflammatory responses; 3) CSF BP responses in MS patients can be distinguished from OND patient responses on the basis of recognition of intact BP; 4) the frequency of myelin antigen reactive clones is significantly higher in the CSF (BP and $PLP_{139-151}$) and blood (BP only) of MS patients versus controls; and 5) the BP epitope specificity of CSF clones is highly skewed towards N terminal epitopes.

TABLE 10

Recovery of T Cell Clones Specific for Myelin Antigens from the CSF of MS and OND Patients

| | CSF Cells | | Total | CSF Clone, Specific For: | | | | | | | |
| | | | | BP | | BP/Frag. | | PLP | | HSV | |
| Doner | #/μl | Total | Clone # | # | % | # | % | # | % | # | % |
|---|---|---|---|---|---|---|---|---|---|---|---|
| MS1(F) | 15.5 | 212,000 | 88 | 21 | 24 | 5 | 6 | 20 | 23 | 1 | 1 |
| MS2(F) | 4.2 | 80,000 | 26 | 10 | 38 | 7 | 27 | 1 | 4 | 1 | 4 |
| MS3(M) | 2.7 | 50,000 | 54 | 7 | 13 | 8 | 15 | 7 | 13 | 1 | 2 |
| MS4(M) | 0.5 | 10,000 | 12 | 3 | 25 | 5 | 42 | NT | — | NT | — |
| MS5(M) | 0.5 | 10,000 | 15 | 4 | 27 | 1 | 7 | 1 | 7 | NT | — |
| MS6(F) | 0.5 | 10,000 | 20 | 4 | 20 | 1 | 5 | 2 | 10 | 1 | 5 |
| MS7(M) | 1.5 | 30,000 | 30 | 11 | 37 | 3 | 10 | 4 | 13 | 0 | 0 |
| MS8(M) | 4.5 | 90,000 | 39 | 9 | 23 | 7 | 18 | 2 | 5 | 1 | 3 |
| MS9(M) | 1.8 | 36,000 | 16 | 2 | 13 | 2 | 13 | 2 | 13 | 5 | 31 |
| Total | | 528,000 | 300 | 71 | 24 | 39 | 13 | 39 | 13 | 10 | 3 |
| OND1(M) | 2.0 | 50,000 | 48 | 2 | 4 | 12 | 25 | 0 | 0 | 1 | 2 |
| OND2(F) | 3.3 | 48,000 | 10 | 0 | 0 | 1 | 10 | 0 | 0 | 9 | 90 |

TABLE 10-continued

Recovery of T Cell Clones Specific for Myelin
Antigens from the CSF of MS and OND Patients

| | CSF Cells | | Total | CSF Clone, Specific For: | | | | | | | |
|---|---|---|---|---|---|---|---|---|---|---|---|
| | | | | BP | | BP/Frag. | | PLP | | HSV | |
| Doner | #/µl | Total | Clone # | # | % | # | % | # | % | # | % |
| OND3(F) | 22.5 | 48,000 | 5 | 0 | 0 | 1 | 20 | 0 | 0 | 1 | 20 |
| OND4(F) | 0.5 | 10,000 | 10 | 0 | 0 | 3 | 30 | 1 | 10 | 5 | 50 |
| OND5(M) | 0.5 | 10,000 | 10 | 0 | 0 | 1 | 10 | 0 | 0 | 9 | 90 |
| OND6(F) | 2.7 | 57,000 | 29 | 1 | 3 | 1 | 3 | 1 | 3 | 12 | 41 |
| Total | | 223,000 | 112 | 3 | 3 | 19 | 17 | 2 | 2 | 37 | 33 |

Table 10

Patients received their care at Oregon Health Sciences University MS Center. MS patients had clinically definite MS, with a mean age of 47 years, range 34–58 years. Three of the MS patients had stable relapsing-remitting disease and 6 had chronic progressive disease; none changed clinically during the study. The mean duration of their disease was 16±8 years (range 6–32 years). The patients had an average Ambulation Index (AI) of 3.8±2.0 (range 2–8) and an average Kurtzke Disability Status Score (KDSS) of 4.5±2.1 (range 2–7). Patients were HLA-typed by a standard serological method at the Transplantation Laboratory of OHSU. HLA types were: MS1, DR1, 2/DQw1; MS2, DR2,4/DQw1, 3; MS3, DR2/DQw1; MS4, DR2/DQw1; MS5, DR2,7/DQw1; MS6, DR2,6/DQw1; MS7, DR2,4/DQw1,3; MS8, DR2/DQw1; MS9, not tested. OND patients had a mean age of 42 years, range 23–69 years. The diagnoses for the OND patients were: OND1, pituitary dysgerminoma; OND2, recent viral meningitis; OND3, coccidioidal meningitis and lacunar cerebral infarcts; OND4, diabetic peripheral neuropathy; OND5, previous laminectomies and chronic back pain; OND6, CNS vasculitis and cerebral infarcts. For each MS and OND patient, 20 ml of CSF was obtained by lumbar puncture without blood contamination. CSF cells were collected by centrifugation at 275 xg for 10 min and a portion was plated in IL-2 and IL-4 (50 U/ml for each, AMGEN) containing medium (RPMI 1640 with 10% AB serum, 1% L-glutamine, sodium pyruvate and antibiotics) at a density of 1,000 cells per well of a round-bottomed 96-well plate. After 14–21 days of expansion, the T cells were restimulated with 50 µg/ml specific antigens presented by $10^5$ autologous irradiated (4,500 rads) blood mononuclear cells, and response was measured after 72 hr by uptake of $^3$H-Tdy. Clones were scored as positive if the response to one of the antigens was 3× or >1,000 CPM over background. Human BP (Hu-BP) was extracted and purified from snap frozen brain. Fragments of Hu-BP, including P1 (residues 45–89), P2 (residues 1–38), and P4 (residues 90–170), were obtained from Dr. Selene Chou, Emory University, Atlanta, Ga., after peptic cleavage and purification. The sequence of $PLP_{139-151}$ is HCLGKWLGHPDKF.

EXAMPLE VI

Compositions of Peptides Useful to Treat EAE, as a Model of MS

Introduction

EAE is a well-recognized rat model of the human autoimmune disease, multiple sclerosis. Accordingly, the utility of the present invention was demonstrated by showing that the administration of the peptide representing the appropriate CDR2 peptide of the TCR which, in rats, is a marker TCR for EAE, prevents EAE in these animals. In this model, the disease is induced by injecting the subject rat with an encephalitogenic form of myelin basic protein, such as, for example, guinea pig basic protein (GPBP) or a synthetic peptide that corresponds to residues 72–89 of GPBP (GPBP(72–89)). Injection of either of these peptides in complete Freund's adjuvant (CFA) induces encephalitogenic T cell clones that utilize preferentially the rat homologs of mouse TCR Vα2 and Vβ8 genes (Chou, Y. K., et al., J. Neurosci. Res. 22:181–187 (1989); Burns, F. R., et al., J. Exp. Med. 169:27–39 (1989)).

The inventors reported the complete nucleotide and deduced amino-acid sequence for the rearranged rat TCR α and β chain genes (with sequence homology to the mouse Vα2 and Vβ8 families respectively) used in response to the major encephalitogenic epitope of basic protein, GPBP(72–89)(Burns, F. R., et al., supra). Within the TCR Vβ8 region, a 21-amino acid sequence was identified and synthesized that included the second complementarity determining region (CDR2) and was predicted to be immunogenic fort cells (based on the algorithms of Margalit et al. and Rothbard et al. (supra).

This peptide has the sequence: Asp-Met-Gly-His-Gly-Leu-Arg-Leu-Ile-His-Tyr-Ser-Tyr-Asp-Val-Asn-Ser-Thr-Glu-Lys-Gly and is termed "TCR $V_\beta 8(39–59)$."

A control peptide was synthesized from the corresponding region for a different TCR Vβ sequence that was homologous to the mouse Vβ14 family (Williams et al., supra).

Specific Immunity to TCR Peptide

Four rats were immunized by subcutaneous (SC) injection of 400 µg TCR peptide in CFA (100 µg Mycobacterium/rat) and peptide-specific immune responses were measured after 30 days.

To measure antibodies specific for TCR Vβ8(39–59) peptide, serum from the immunized rats was tested by direct ELISA. THe TCR peptide was coated onto plastic microplates (25 ng of TCR peptide/well). Serum dilutions were added and the plates incubated for 2 hours. The reaction was developed by addition of peroxidase-conjugated antibodies specific for Ig H and L chains. A chromogenic substrate for peroxidase was added and the colored reaction product was measured as the absorbance at 405 nm ($A_{405}$) using a colorimetric plate reader.

A 1:200 dilution of immune serum gave an absorbance of 0.63±0.12 units. Control sera from rats immunized with the control peptide (derived from the corresponding CDR2 region of an unrelated TCR chain, Vβ14) gave a reaction of only 0.02±0.01 units. Thus, a specific antibody response was obtained to the TCR peptide.

In addition, the rats showed a specific T cell response in vivo, measured as a delayed hypersensitivity (DH) reaction to intradermal (ID) challenge with the Vβ8(39–59) TCR peptide, but not with the Vβ14 peptide.

TCR Peptide-Specific Immunity Protects Against Clinical EAE

In addition to showing specific immunity toward the TCR peptide, the peptide-immunized rats were found to be protected against clinical EAE.

Immunization of Lewis rats with the TCR Vβ8(39–59) peptide, but not with the TCR Vβ14 peptide or saline, prevented completely the induction of EAE (Table 11). The Vβ8(39–59)-immunized rats developed both specific antibodies to the Vβ8(39–59) peptide and a delayed hypersensitivity (DH) response of 0.17 mm ear swelling to 50 μg TCR Vβ8(39–59) peptide. The control Vβ14 peptide also induced specific immunity to itself but did not confer protection against EAE.

TCR Peptide-Specific Immunity Generates Specific T Cells

In addition to demonstration of antibody production, DH, and protection against EAE, the TCR peptide elicited demonstrable antigen-specific (i.e., TCR peptide-specific) T cells.

Rats were immunized SC with 400 μg TCR Vβ8(39–59) peptide in CFA (containing 1 mg M. tuberculosis)and were challenged SC with either 50 μg GPBP in CFA at the same time or with 100 μg of GPBP 30 days later. Twenty days after the simultaneous challenge, draining lymph nodes (LN) were removed and lymphocyte suspensions prepared.

A fraction of the cells were tested for proliferative response to antigens or mitogens in vitro ($5 \times 10^5$ cells/well).

The remainder of the cells were restimulated in bulk culture (in 6 cm. diameter petri dishes) with the appropriate TCR peptide (50 μg/ml) for 3 days followed by transfer to IL-2 rich medium for an additional 4 days. These cells were subsequently tested for proliferative responses to antigens or and mitogens by restimulation in the presence of irradiated thymic accessory cells (($2 \times 10^4$ cells/well). In some cases, stimulation by TCR peptide was carried out in the presence of 2 μg/well monoclonal antibodies. Results are shown in Table 12 (underlined values show statistically significant responses).

Lymph node (LN) cells isolated from the protected rats responded to the TCR Vβ8(39–59) peptide as well as to GPBP and PPD (purified protein derivative of M. tuberculosis). This was further evidence for the concurrent presence of TCR-specific as well as autoantigen-specific T cell reactivity.

T-cell lines were selected from the LN of the protected rats that responded specifically to the Vβ8(39–59) but not to the Vβ14 peptide (Table 12). The TCR Vβ8(39–59)-specific T cells were strongly positive by immunofluorescence for the CD4 marker and weakly positive for the CD8 marker. The proliferative response to the Vβ8(39–59) peptide was restricted only by MHC class I molecules.

A GPBP-specific T-cell line was also selected from protected rats immunized with both the TCR Vβ8(39–59) peptide and GPBP. This line had an uncharacteristically low response to the encephalitogenic 72–89 peptide in comparison to its responsiveness to GPBP. Once selected and activated, GPBP-specific T cell line cells from TCR peptide-protected rats were encephalitogenic (administration of $10^7$ cells caused hind-leg paralysis in 3 rats), indicating that TCR Vβ8(39–59) peptide immunization did not result in the deletion of precursors of encephalitogenic T cells.

Mixing of the TCR Vβ8(39–59)-specific and BP-specific T cells did not impair the response to GPBP, even in the presence of the TCR peptide (Table 12). The presence of TCR Vβ8(39–59)-specific T cells, however, caused, an increased response to all of the peptides of GPBP except the encephalitogenic 72–89 sequence. The TCR peptide-specific T cells therefore altered the peptide recognition pattern of GPBP-reactive T cells, which provides evidence of the existence of cell-cell interactions.

Direct Interactions Between TCR Peptide-Specific and BP-Specific T Cells

T cells from the LN of the immunized rats were tested for responsiveness in vitro to attenuated Vβ8$^+$ or Vβ8$^-$ T cells. The stimulator T cells were irradiated (2500 R), and $2 \times 10^4$ cells were cultured (in the absence of additional accessory cells) with $2 \times 10^5$ isolated TCR-specific T cells for 3 days, pulsed for the last 18 hours with $^3$H-thymidine, and isotope uptake was measured by liquid scintillation spectroscopy.

In the absence of a stimulator T cell line, "background" responses were on the order of 7000 cpm (Table 13). When the stimulator line was specific for the GPBP S72–89 epitope, and therefore expressed the Vβ8 TCR, the response was 31,000 cpm. However, the when the stimulator line was specific for the GPBP 55–74 peptide, and therefore did not express the Vβ8 TCR, there was no significant response above background (8000 cpm). Thus, only $V_β8^+$ cells could be recognized by T cells specific for the TCR peptide, indicating the presence of direct recognition of the Vβ8 peptide on the target T cell by a regulatory Vβ8-specific T cell. The results indicate the direct recognition of the TCR sequence on the surface of the stimulator T cell. The TCR peptide-specific T cells, however, were not cytotoxic for the BP-reactive target cells.

Passive Transfer of EAE Protection by TCR Peptide-Specific T Cells

The protective ability of Vβ8(39–59) peptide-specific T cells was established by adoptive transfer. Rats injected with as few as $10^7$ Vβ8(39–59)-specific T cells did not develop EAE (Table 14). The transferred protection appeared to be T-cell mediated; Vβ8(39–59)-specific antibodies were not detectable in the serum of protected rats. DT results (Table 14) indicated that the adoptively transferred T cells could prevent the induction of EAE without compromising T cell recognition of other antigens.

Specificity of T Cell Lines Derived From Protected Rats

The ability of Vβ8(39–59)-specific T cells to (a) alter the response patterns of GPBP-specific T cell lines in vitro, (b) protect naive rats from EAE, and (c) reduce DH reactions in vivo, indicated that the pattern of response to BP epitopes might be altered in rats protected by TCR peptide-specific T cells. As shown in Table 15, LN cells from the EAE-protected animals responded well to the TCR peptide of GPBP as compared to LN cells from the control group. In contrast, LN cells from the protected group showed a significant response to the 87-99 peptide of BP, whereas LN cells from the control group did not respond to this peptide. The selection of a TCR Vβ8(39-59)-specific T cell line from the LN of adoptively protected rats (Table 15) indicated that TCR peptide-specific T cells had migrated to and persisted in the LN that drained the site of GPBP injection.

DISCUSSION

These results demonstrate for the first time the use of a synthetic peptide from the CDR2 region of the TCR to induce Vβ8-specific regulatory T cells that prevent the induction of EAE. Computer modeling of ternary interactions among TCR chains, antigenic peptides, and MHC restriction molecules is consistent with CDR involvement in peptide/MHC binding when the TCR is folded in an energetically favorable conformation (Davis et al. and Claverie et al., supra). The regulatory effects oft cells specific for CDR2 support the notion that this region has biological importance. Although the inventors do not intend to be bound by any particular theory, it seems unlikely that the responder T cell interacts directly with the functional TCR Vβ8 molecule on the target T cell surface. Indeed, it is conceivable that endogenous TCR peptide could be 'processed" and expressed preferentially on the T-cell surface in association with class I molecules (Long, E. O., Immunol. Today 10: 232–234 (1989)). If a natural form of the TCR peptide is associated with the MHC molecule on the T cell surface, the interacting TCR-specific T cell could interfere with normal T cell activation by a BP epitope.

Vaccination with attenuated T cells indicates that protective immunity is induced against target structures shared by different T cell clones specific for the same disease-inducing epitope, but do not implicate the TCR directly. The immunogenicity and immunoregulatory activity demonstrated here of a defined region of the TCR Vβ8 chain expressed by encephalitogenic T cells is an important step forward in understanding anti-idiotypic regulation, and provides-a clear explanation for the protective effects of the peptide immunization approach. The approach of the present invention, using a synthetic peptide to induce TCR peptide-specific antibodies, is of value in producing a variety of highly specific antibodies for assessing sequences important in TCR function. The potential regulatory properties of antibodies raised to the Vβ8(39-59) peptide are illustrated in Example VII.

TCR peptide vaccination has application in human autoimmune or malignant conditions that are characterized by common TCR V-gene usage.

TABLE 11

Immunization with TCR V$_B$8 Prevents Induction of EAE

| Immunization Protocol[2] | In-cidence | EAE Induction[1] | | |
|---|---|---|---|---|
| | | Day of Onset | Duration | Severity[3] |
| TCR Vβ8 peptide | 0/10 | — | — | — |
| TCR Vβ14 peptide | 4/4 | 14 ± 2 | 6 ± 2 | 3.1 ± 0.3 |
| Saline | 14/14 | 14 ± 2 | 6 ± 1 | 3.0 ± 0.5 |

[1]EAE was induced by SC challenge with 50 μg GPBP + 400 μg Mycobacteriain complete Freund's adjuvant (CFA) 30 days after TCR peptide (or saline) immunization.

TABLE 11-continued

Immunization with TCR V$_B$8 Prevents Induction of EAE

| Immunization Protocol[2] | In-cidence | EAE Induction[1] | | |
|---|---|---|---|---|
| | | Day of Onset | Duration | Severity[3] |

[2]Rats were injected SC with either: (1) 100 μg of the TCR peptide [DMGH-GLRLIHYSDVNSTEKG (single-letter code)] representing residues 39-59 of the rat cDNA clone Vβ510, homologous to the mouse Vβ8 family (Burns et al., J. Exp. Med. 169:27–39 (1989)); (2) 100 μg of TCR peptide [APG-GTLQQLFYSFNVGQSLF] representing residues 39-59 of the rat cDNA clone CRTB188 homologous to the mouse Vβ14 family (Williams, C.B. et al., J. Immunol. 142:1037-1035 (1989)); or (3) saline. The peptides or saline were mixed with CFA containing 100 μg Mycobacteria prior to injection.
[3]Values represent the mean of the maximum severity of EAE. 0, no signs; 0.5, lethargy, weight loss; 1, limp tail; 2, hind-leg weakness; 3, hind-quarter paralysis, incontinence; 4, moribund.

TABLE 12

Specificity of T Cell Lines Derived from Rats Protected from EAE by the TCR Vβ8 Peptide
T Cell Proliferation (cpm × 10⁻³)[1]

| Medium | 11 | 2 | 1 | 6 |
|---|---|---|---|---|
| Con A | 99 | 96 | 80 | 123 |
| TCR Vβ8(39-59) | 27 | 100 | 1 | 140 |
| +OX-6 (anti I-A) | — | 99 | — | — |
| +OX-17 (anti I-E) | — | 100 | — | — |
| +OX-18 (anti class 1) | — | 31 | — | — |
| +W3/25 (anti-CD4) | — | 105 | — | — |
| +OX-8 (anti-CD8) | — | 22 | — | — |
| TCR Vβ14 peptide | 10 | 2 | — | — |
| GPBP | 16 | 3 | 93 | 102 |
| 1-37 | 13 | — | 1 | 13 |
| 44-89 | 20 | — | 46 | 56 |
| 44-68 | 15 | 1 | 2 | 22 |
| 72-89 | 16 | 1 | 27 | 20 |
| +OX-6 | — | — | 1 | — |
| +OX-17 | — | — | 23 | — |
| +OX-18 | — | — | 27 | — |
| +W3/25 | — | — | 1 | — |
| +OX-8 | — | — | 26 | — |
| 87-99 | 12 | — | 1 | — |
| 90-170 | 13 | — | 1 | 14 |
| | | | | 149 |
| GPBP + Vβ8(39-59) | 30 | — | 55 | 149 |
| PPD | 48 | 2 | 1 | — |
| Rat BP | 11 | 1 | 9 | 9 |

Underlined values indicate significant stimulation. —, not done.

TABLE 13

Response of TCR Vβ8 Peptide-specific T Cell Line to Attenuated Vβ8⁺ or Vβ8⁻ T Cells

| Specificity of Stimulator Line | Vβ8 Expression of Stimulator Line | Proliferation of Responder T Cell Line (cpm × 10⁻³) |
|---|---|---|
| None added | | 7 + 2 |
| GPBP (S72-89) | + | 31 ± 3 |
| GPBP (55-74) | − | 8 ± 1 |

T cell line cells were irradiated (2,500 R) and 2 × 10⁴ cells (as stimulators) were mixed with 2 × 10⁵ TCR-specific responder T cells for 3 days. Cultures pulsed with ³H-thymidine for the final 18 h, the cells were harvested, and proliferation assessed as ³H-thymidine uptake. Background proliferation of irradiated T cells specific for GPBP (S72-89) and GPBP (55-74) was 0.1 and 0.2 cpm (×10⁻³), respectively.

TABLE 14

TCR Vβ8 Peptide-specific T-Cells Protect against EAE

| Transfer dose[1] | Induction of EAE (GPBP/CFA) | | | | DH (mm × 10⁻²) | |
|---|---|---|---|---|---|---|
| | Inci- dence | Day of Onset | Dura- tion | Sever- ity[2] | GBP | PPD[3] |
| None | 5/5 | 12 | 6.5 | 3.1 | 32 | 21 |
| $3 \times 10^7$ | 0/5 | — | — | 0 | 24 | 21 |
| $1 \times 10^7$ | 0/4 | — | — | 0 | ND | ND |

[1]T cell line cells were stimulated with TCR Vβ8 peptide plus thymic accessory cells for 3 days prior to intraperitoneal transfer into naive recipient rats. The recipient rats were challenged on the same day with GPP/CFA.
[2]Values represent the mean of the maximum severity of EAE. See legend to Table 11.
[3]Ear swelling in response to ID challenge with GPBP or PPD was measured 24 h. after challenge and represents a DH response to the antigen.

TABLE 15

Antigen Specificity of T Cell Lines Derived from the Lymph Nodes of Rats Protected from EAE by the Transfer of TCR Vβ8 Peptide-specific T Cells

| Transfer Protocol[1] | Stimulant | Proliferation (cpm × 10⁻³) | | |
|---|---|---|---|---|
| | | LN[2] | TCR Peptide Selected Line[3] | GPBP Selected Line |
| A. TCR Vβ8 peptide-specific T Cells | Medium | 7 | 2 | 5 |
| | Con A | 125 | 46 | 39 |
| | Vβ8 peptide | 90 | 52 | 6 |
| | GPBP | 80 | 0 | 16 |
| | 1-37 | 7 | ND | 6 |
| | 44-89 | 12 | ND | 17 |
| | 44-68 | 9 | 4 | 9 |
| | 72-89 | 12 | 3 | 11 |
| | 87-99 | 41 | 4 | 9 |
| | 90-170 | 12 | ND | 8 |
| B. Saline | Medium | 12 | Not selected | 6 |
| | Con A | 38 | | 88 |
| | Vβ8 peptide | 8 | | 6 |
| | GPBP | 32 | | 65 |
| | | 12 | | 6 |
| | | 34 | | 91 |
| | | 19 | | 24 |
| | | 29 | | 64 |
| | | 11 | | 6 |
| | | 11 | | 7 |

[1]Lymph node (LN) cells were collected 20 days after simultaneous injection of (A) $3 \times 10^7$ TCR Vβ8 peptide-specific T line cells, or (B) saline, along with GPBP/CFA.
[2]LN cells were tested directly (NL column).
[3]T cell lines were selected from these LN cells by culture with TCR Vβ8 peptide (second column) or GPBP (third column) followed by IL2 as described in. Underlined values indicate significant stimulation.

EXAMPLE VII

Antibodies Against a Synthetic TCR V Region Peptide Suppress EAE

This Example provides an evaluation of the effects of immunization with the TCR $V_\beta 8(39-59)$ peptide on EAE induced with the encephalitogenic guinea pig basic protein (GPBP) peptide, S87-99, and on antibody responses to GPBP peptides S49S or S87-99. Antibody responses against the TCR $V_\beta 8(39-59)$ peptide are described and the ability of these antibodies to react with $V_\beta 8^+$ T cells and to suppress clinical signs of EAE are evaluated.

The results demonstrate that the TCR $V_\beta 8(39-59)$ peptide can induce both protection against EAE and elevated titers of antibody specific for either of the GPBP epitopes which are encephalitogenic in Lewis rats. Furthermore, anti-TCR $V_\beta 8(39-59)$ antibodies are shown to suppress EAE independent of regulatory T cells. Thus, both humoral and cellular regulatory mechanisms are generated after immunization of the Lewis rats with the TCR $V_\beta 8(39-59)$ peptide.

A. MATERIALS AND METHODS

1. Peptide synthesis and purification.

All peptides used in this study were synthesized by a minor modification (Hashim et al., J. Neurosci. Res. 16: 467 (1986)) of the solid phase method (Merrifield J. Amer. Chem. Soc. 85: 2149 (1963)) using Boc-amino acid-resin-ester (Peninsula Laboratories, San Carlos, Calif.). The peptides (Table 16) were synthesized with t-Boc-L-amino acid derivatives, starting with t-Boc-L-Glycine-O-resin ester (0.65 mmole/g: 0.78 mmole). Coupling and deblocking reactions were routinely monitored by the Kaiser test (Kaiser et al., Anal. Biochem. 34: 595 (1970)) for free amino groups. Single deblocking and occasional double coupling reaction steps were sufficient for the synthesis of all peptides used in this study. Peptide Gp-S49S defines region 69-84 of GPBP and has a C-terminal glycine. Residue numbers of GPBP peptides used in this study correspond to those reported for bovine myelin basic protein (Eylar et al., J. Biol. Chem. 246: 5770 (1971)).

Peptides containing tryptophan were first treated with 10% piperidine for 30 minutes to remove the formyl blocking groups and then, like all other peptides, were cleaved from the resin, together with other side chain deprotection, by treatment with HF at 0° C. in the presence of anisole. After removal of the HF, the resin-peptide mixture was washed 4 times with ether and dried. The peptide was extracted with water, lyophilized and filtered through a Sephadex G10 column (2.5×100 cm) that was equilibrated with and eluted by 5% acetic acid. Acid insoluble peptides were extracted from the resin-peptide mixture with 0.03M ammonium carbonate, filtered on a Sephadex G10 column that was equilibrated with and eluted by 0.03M ammonium bicarbonate, and lyophilized. Further purification of the peptide was achieved using HPLC with a Bondapak C18 column equilibrated with 0.1% trifluoroacetic acid (TFA) in water and eluted with a linear gradient up to 40% acetonitrile containing 0.1% TFA over a period of 60 minutes. The purity of the peptides was documented by HPLC and by amino acid composition analysis.

2. Test and control peptides.

The TCR $V_\beta 8(39-59)$ peptide was synthesized according to the sequence identified by Burns et al. (J. Exp. Med. 169: 27 (1989)). As controls for TCR $V_\beta$ gene family specificity and for the CDR2 hypervariable region, additional peptides were synthesized, including TCR $V_\beta 14(39-59)$, which comprises the corresponding CDR2 of the $V_\beta 14$ gene family (Williams et al., J. Immunol. 142: 1027 (1989)), and TCR $V_\beta 8(25-41)$, corresponding to a sequence in the CDR1 region adjacent to peptide TCR $V_\beta 8(39-59)$ (Burns et al., op. cit.). Other control peptides included a series that defines specific regions of GPBP. Peptides Gp-S49S and Gp-S87-99 define respectively the major and minor encephalitogenic sequences for Lewis rats. Peptides Gp-S67 (residues 69–81) and Gp-S53 (residues 75–84) define respectively T cell and B cell epitopes within the major encephalitogenic epitope encompassed in peptide Gp-S49S (residues 69–84). Peptide Gp-S55-74 defines a non-encephalitogenic T cell determinant in Lewis rats (Offner et al., J. Exp. Med. 170: 355 (1989)), and Gp-NAc-1-16 encompasses the encephalitogenic sequence for the PL/J strain of mouse (Zamvil et al., Nature 324: 258 (1986)).

3. Peptide coupling to KLH.

Keyhole limpet hemocyanin (KLH) (Calbiochem Corp., La Jolla, Calif.) was dissolved in phosphate buffered saline (PBS), dialyzed against PBS at 4 °C. overnight and lyophilized. A known weight of KLH (8 mg or 1–2 μmoles) together with the peptide to be coupled (10 μmoles) were dissolved in 1 ml deionized water. After the pH was adjusted to 4.5 with 0.01N HCl, 375 mg of 1-ethyl-3 (3-dimethylaminopropyl)-carbodiimide (Pierce Chemical Co., Rockford, Ill.) in 0.5 ml water were added and the reaction mixture was stirred for 1 hour at room temperature. The mixture was then placed in dialysis bags and dialyzed against 3 changes of PBS at 4° C. and lyophilized. The amount of peptide coupled to KLH was calculated from the increase in mass of the non-dialyzable portion of the KLH.

4. Preparation of anti-peptide antibodies.

Male Lewis rats weighing 200–250 g were immunized with a single dose of 100 μg of the free peptide. The peptide was emulsified in complete Freund's adjuvant (CFA) and injected SC. Each rat received 100 μl of the emulsion containing 100 μg peptide and 100 μg M. butyricum. Likewise, Lewis rats were immunized with 100 μg of a particular peptide and challenged either simultaneously or at a later date with another peptide. Immunized rats were pre-bled from the tail vein before and at intervals after immunization.

New Zealand white rabbits, weighing 6–7 lbs., were pre-bled and immunized with 0.5 ml CFA emulsion containing 4 mg peptide and 2 mg *M. butyricum*. The emulsion was injected SC in multiple sites in the dorsal area of the neck and the tail. Rabbits were immunized either with the free peptide or with peptide conjugated to KLH. Immunized rabbits were boosted on days 7, 14 and 21 with 1 mg peptide emulsified in incomplete Freund's adjuvant and injected SC on the flank. All rabbits were bled via the ear vein after they were placed in restraining cages and tranquilized with acepromozine. To prevent hypovolemia, the amount of blood removed was replaced with sterile saline. Sera from individual rats or rabbits were prepared from clotted blood by centrifugation. All sera were decomplemented for 30 minutes at 56° C. and frozen in small aliquots to which sodium azide was added.

5. Preparation of immunoglobulin.

IgG was prepared from serum by published methods (Steinbuch et al., Arch. Biochem. Biophys. 134: 279 (1969)) and purified by ion exchange chromatography with DEAE-sephadex. The serum was diluted with one volume of 0.06M acetate buffer and the pH adjusted to 4.8 at room temperature. Caprylic acid, 6.8 g/100 ml serum, was added dropwise under vigorous stirring for 30 minutes. The mixture was then centrifuged, the supernatant was adjusted to pH 5.7, dialyzed against deionized water and lyophilized.

6. Antibody assays.

Antibody reactivity was determined by an adaptation for peptides (Hashim, G. A., et al., J. Neurosci. Res. 24: 222 (1989)) of the direct enzyme-linked immunosorbent assay (ELISA) and by the inhibition ELISA as described by Cleveland, W. L., et al. (Methods in Enzymol. 121: 95 (1986)). Peroxidase-labeled rabbit anti-rat or goat anti-rabbit immunoglobulin (affinity-purified H and L chains, Cooper Biomedical, Malvern, Pa.) was used together with O-phenylenediamine for enzyme substrate, and the optical density was measured at 450–650 nm in a colorimetric plate reader (Model Vmax, Molecular Devices, Mento, Calif.).

7. EAE Induction.

EAE was induced in male Lewis rats (225–250 g) as described (Hashim et al., J. Neurosci. Res. 24: 222 (1989)). Each rat received a single SC injection of a CFA emulsion containing 100 μg peptide and 100 μg *M. butyricum*. Immunized rats were inspected daily for clinical signs of EAE and were terminated between days 25 and 30 following challenge. At this time, sera from individual rats were collected, and the brain and spinal cord tissues were processed for histology.

8. Prevention and suppression of EAE in Lewis rat.

Male Lewis rats were immunized with 100 μg TCR $V_\beta 8(39-59)$ peptide emulsified in CFA and injected SC. The immunized rats were bled from the tail for antibody determination and were challenged with 100 μg of an encephalitogenic peptide (Gp-S49S or Gp-S87-99). Groups of rats were challenged either on the same day or on day 40–41 after they were immunized, based on the observed time course of anti-TCR $V_\beta 8(39-59)$ antibody production.

To study EAE suppression by anti-TCR $V_\beta 8(39-59)$ antibodies, Lewis rats were challenged with the encephalitogenic peptide Gp-S49S and injected intraperitoneally with either saline (control) or either Lewis rat or rabbit anti-TCR $V_\beta 8(39-59)$ IgG, given every other day for 14 days. Each rat received a total of either 49 or 70 mg rat or rabbit IgG, respectively, and was terminated on day 24 after the challenge. When injected in sterile saline over a period of 14 days, rabbit IgG remained at high levels in the circulation of recipient rats on days 12 and 24 after transfer and did not interfere with the development of anti-Gp-S49S antibodies.

9. Antibody staining of $V_\beta 8^+$ and $V_\beta 8^-$ T cells.

Rat or rabbit IgG (10 μg) from normal or TCR $V_\beta 8(39-59)$ immunized animals was incubated at various concentrations for 30 minutes with $10^6$ normal rat thymocytes (known to be mostly $V_\beta 8^-$) or a Gp-S49S-reactive, GPBP-specific T cell line (known to be $V_\beta 8^+$). After several washes, the cells were incubated with 10 μg mouse anti-rat or anti-rabbit IgG for an additional 30 minutes as an amplification step. After further washing, the cells were stained with fluoresceinated goat anti-mouse IgG (H+L chain specific), washed, fixed in 2% formalin, and evaluated for fluorescence intensity at 488 nm using a Coulter Epics C Cytofluorograph. The cells were gated electronically on the basis of forward angle versus right angle scatter patterns to include the major lymphocyte populations, which were then evaluated for FITC fluorescence.

B. RESULTS

1. Prevention of EAE by TCR $V_\beta 8(39-59)$ peptide immunization.

To evaluate prophylactic effects of anti-TCR $V_\beta 8(39-59)$ immunity on EAE induced by various encephalitogenic epitopes, Lewis rats were first immunized with the TCR $V_\beta 8(39-59)$ peptide, and 44 days later, EAE was induced with either Gp-S49S or Gp-S87-99. As is shown in Table 17, immunization with the TCR $V_\beta 8(39-59)$ peptide reduced markedly the severity of Gp-S49S-induced EAE, and prevented completely S87-99-induced EAE. Although histological scores in both protected groups were reduced, inflammation in the CNS was generally less affected by TCR $V_\beta 8(39-59)$ peptide immunization than were clinical parameters.

2. Suppression of EAE with the TCR $V_\beta 8(39-59)$ peptide.

To evaluate suppression of EAE, the TCR $V_\beta 8(39-59)$ peptide was given simultaneously with the encephalitogenic dose of GPBP or Gp-S49S. As is shown in Table 17, the TCR $V_\beta 8(39-59)$ peptide prevented GPBP-induced EAE in most rats, and markedly reduced the clinical severity in the remaining animals. A similar result was obtained in with Gp-S49S-induced EAE. In contrast, the TCR $V_\beta 14(39-59)$ control peptide had no suppressive effects on EAE (Table 17). Again, histological signs of EAE were relatively less affected by TCR $V_\beta 8(39-59)$ immunization than clinical signs.

3. Antibody responses against the TCR $V_\beta 8(39-59)$ peptide.

TCR $V_\beta 8$-specific antibodies raised against intact T cell clones (Owhashi, M., et al., J. Exp. Med. 168: 2153 (1988); Gascoigne, N. R. J., et al., Proc. Natl. Acad. Sci., USA 84: 2936 (1987); Kappler, J. W., et al., Nature 332: 35 (1988); Kappler, J. W., et al., Cell 49: 263 (1987); MacDonald, H. R., et al., Nature 332: 40 (1988)) have proven efficacious in the prevention and treatment of EAE in both Lewis rats (Owhashi et al., J. Exp. Med. 168: 2153 (1988)) and PL/J mice (Acha-Orbea et al., Cell 54: 263 (1988); Urban et al., Cell 54: 577 (1988)). It thus was very important to determine whether antibodies could be raised against the synthetic TCR $V_\beta 8(39-59)$ peptide, and if so, whether they had clinical utility.

Such antibodies could indeed be raised and were found to be clinically effective. Antibodies against TCR $V_\beta 8(39-59)$ were detected in the sera of Lewis rats as early as 7 days after a single injection of 100 μg of the free peptide in CFA (Table 18). Although a high degree of variability in the antibody response was observed, the antibody titers increased gradually over time. None of the TCR peptide-immunized rats developed any signs of EAE, and all remained healthy throughout the 41 day observation period.

Rabbits immunized with either the free or KLH-conjugated TCR $V_\beta 8(39-59)$ peptide produced much higher titers of antibodies than did rats (Table 18). Antibody titers remained high for over 6 months, showing detectable reactivity at dilutions of up to 1/320,000.

4. Antibody responses against the encephalitogenic peptide S49S.

Immunization of Lewis rats with GPBP or GP-S49S (residues 69–84) peptide induces antibodies that recognize several different epitopes, one of which is comprised of residues 82–84 (Asp-Glu-Asn) and is evidenced by antibody binding to Gp-S53 (residues 75–84) (Day et al., J. Neurosci. Res. 18: 214 (1987); Hashim, G. A., et al., J. Neurosci. Res. 17: 375 (1987)). These antibody responses depend on T cell help, which can be provided by encephalitogenic T cells specific for the GP-S49S peptide. Although immunization with the TCR $V_\beta 8(39-59)$ peptide prevents and suppresses EAE mediated by Gp-S49S-specific T cells of the helper phenotype, it is important to determine the effect of such immunization on anti-S49S antibody formation.

The antibody response to Gp-S49S was detected as early as 7 days after immunization with the Gp-S49S in CFA (Table 19). Periodic bleeding of the immunized rats showed marked increases in antibody titers to both Gp-S49S and Gp-S53 during the next 48 days, the anti-Gp-S53 response appearing only after the development and eventual recovery from EAE.

After preimmunization and protection against EAE with TCR $V_\beta 8(39-59)$, the 26 day antibody responses to Gp-S49S and Gp-S53 were elevated two to four fold relative to that in rats not treated with the TCR peptide (Table 19). Similarly, anti-S87-99 responses were increased >4 fold in rats preimmunized and protected with the TCR $V_\beta 8(39-59)$ peptide (Table 19). Thus, an immune response directed against $V_\beta 8^+$ T cells actually enhanced antibody responses to several distinct B cell epitopes of GPBP.

5. Specificity of anti-peptide antibodies.

Figure 1:
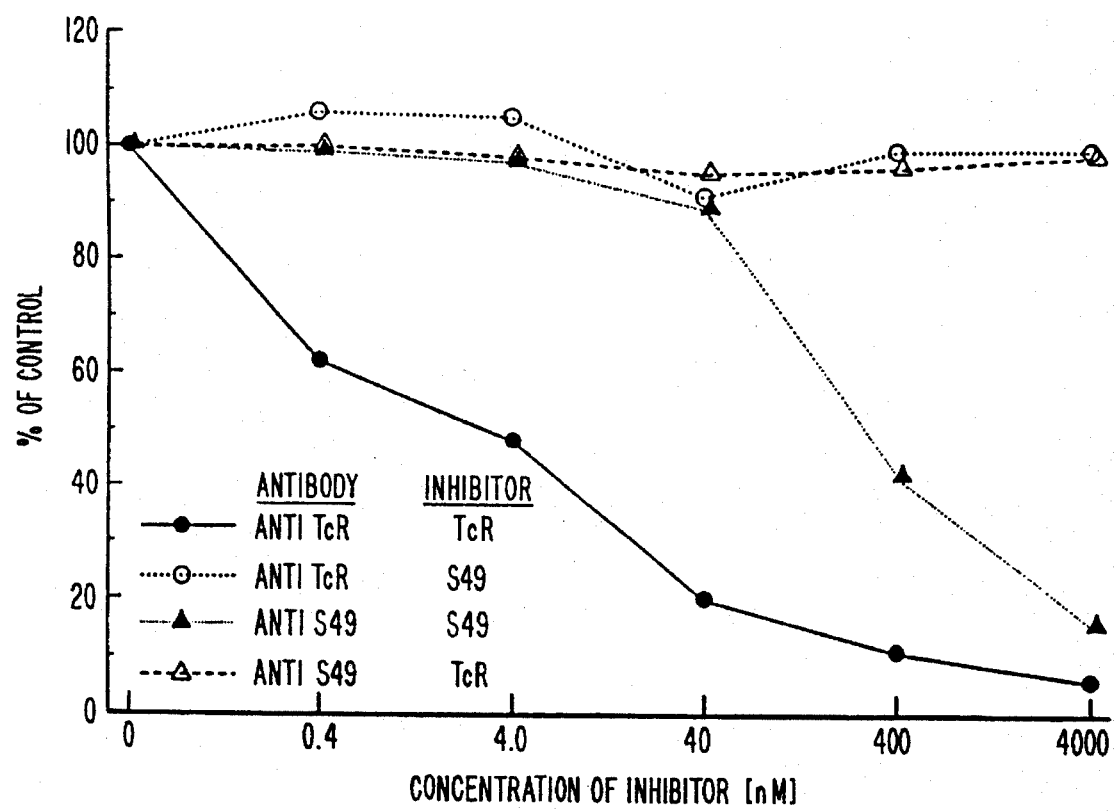
FIG. 1. Peptide-specific inhibition of antibody reactivity. Antisera from 4 rats immunized with either the TCR Vβ8(39–59) peptide alone or a combination of the TCR peptide and the GP-S49S MBP-derived autoantigen were pooled and diluted 40–360 fold. The antisera were tested for reactivity in direct ELISA with 25 ng peptide bound to microplate wells. This amount of peptide is equivalent to 10 pM TCR Vβ8(39–59) (MW=2390 daltons) or 15 pM GP-S49S (MW=1630 daltons). Varying concentrations of inhibitor peptides were added in a range of 0.005–50 μg/well. The Absorbance measurements were determined in triplicate wells, and the reactivity calculated as the % of uninhibited control wells.
Figure 2A:
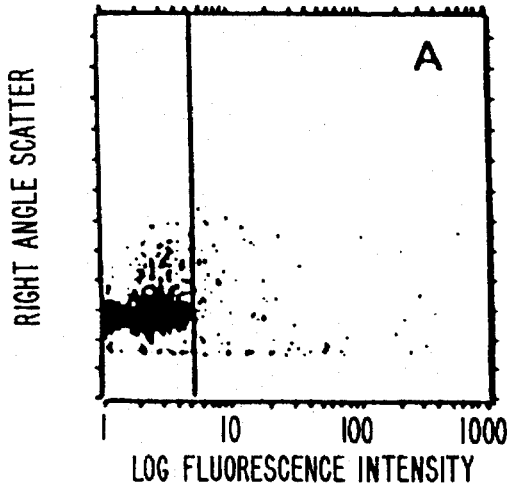
FIGS. 2(A,B,C and D). Antibodies to the TCR Vβ8(39–59) peptide stain Vβ8+ encephalitogenic T cells. Normal thymocytes (A and C) or GP-S49S-specific T line cells (B and D) were incubated with rabbit antibodies to TCR Vβ8(39–59), followed by a mouse anti-rabbit IgG facilitating antibody and fluorescein-labeled goat anti-mouse IgG antibody. Flow cytometric analysis of staining was performed using a Coulter Epics C Cytofluorograph. A and C represent dot-plots of 10,000 cells showing cell size versus fluorescence intensity; B and D represent the corresponding histograms. The fluorescence intensity of T line cells stained with anti-TCR Vβ8(39–59) antibody (>90% stained) is increased compared to the 5% of normal thymocytes which stained with this antibody. Both thymocytes and T line cells incubated with normal rabbit IgG as a control for anti-TCR Vβ8(39–59) IgG showed background levels of staining (dotted line in box D).
Figure 2B:
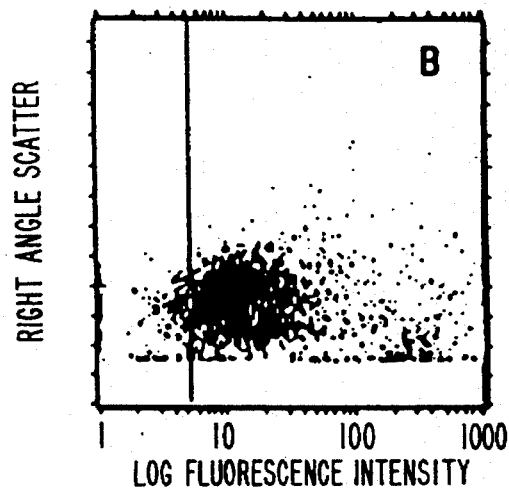
Figure 2C:
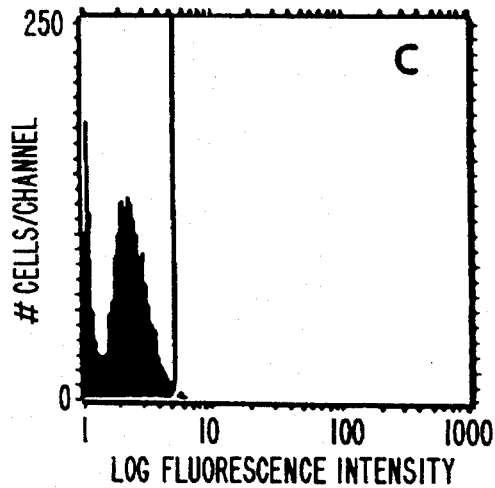
Figure 2D:
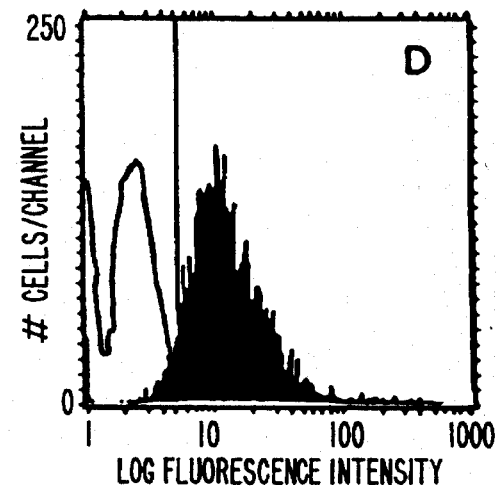

To evaluate the specificity of several antisera, binding to a panel of synthetic TCR and GPBP peptides was assessed. The results (Table 20), show that anti-Gp-S49 antiserum which recognized GP-S49S and its C-terminal fragment, Gp-S53, did not react with the N-terminal fragment of Gp-S49 (i.e., Gp-S67), with any other regions of GPBP, or with any of the TCR V region peptides. Similarly, rat or rabbit antisera to the TCR $V_\beta 8(39-59)$ peptide, recognized only the immunogen, and not other TCR sequences (including the 3 overlapping residues—AspMetGly—present on TCR $V_\beta 8(25-41)$, or GPBP peptides. Antisera from rats immunized simultaneously with TCR $V\beta 8(39-59)$ peptide plus Gp-S49S or Gp-S87-99 demonstrated the same specificity for each of the immunogens as antisera from singly-immunized rats (Table 15). The specificity of antibody reactivity to TCR $V_\beta 8(39-59)$ and to Gp-S49S was confirmed by peptide-specific, dose dependent inhibition of binding in ELISA (FIG. 1).

6. Antibodies to TCR $V_\beta 8(39-59)$ recognize $V_\beta 8^+$ T cells.

To interpret potential regulatory effects of antibodies to TCR $V_\beta 8(39-59)$, it was crucial to establish whether or not the peptide-specific antibodies interacted directly with $V_\beta 8^+$ T cells. To evaluate such reactivity, $V_\beta 8^+$ encephalitogenic T cells or normal thymocytes which are predominantly $V_\beta 8^-$ were incubated with rat or rabbit anti-TCR $V_\beta 8(39-59)$ IgG antibody, followed by mouse anti-rat or anti-rabbit facilitating antibody, and fluorescein-labeled goat anti-mouse IgG antibody. As is shown in FIG. 2, the rabbit IgG raised to the KLH-conjugated TCR $V_\beta 8(39-59)$ peptide caused an increased fluorescence intensity in the entire $V_\beta 8^+$ encephalitogenic T cell population (>90% positive versus a control antiserum), as opposed to approximately 5% of the normal thymocyte population. Rat IgG and rabbit IgG raised against unconjugated TCR peptide also stained selectively the $V_\beta 8^+$ T cells, although with less intensity. These results indicate that antibody to the TCR $V_\beta 8(39-59)$ peptide can bind specifically to $V_\beta 8^+$ T cells. None of the antisera were cytotoxic for $V_\beta 8^+$ T cells in the presence of complement, as measured by both chromium release or dye exclusion, suggesting that antibody binding altered T cell function without killing the cells.

7. Suppression of EAE with anti-TCR $V_\beta 8(39-59)$ antibody.

Lewis rats immunized with TCR $V_\beta 8(39-59)$ were not only protected against EAE, but developed circulating antibodies specific for the immunizing peptide. To evaluate the role of these antibodies in down-regulating EAE, Lewis rats were challenged with Gp-S49S in CFA and were then treated with TCR $V_\beta 8(39-59)$-specific IgG (rat or rabbit). Rats receiving Lewis rat IgG every other day for 12 days developed mild clinical signs of EAE with reduced histology in the brain, but more extensive lesions in the spinal cord compared to controls (Table 21). Rats receiving rabbit IgG developed minimal clinical signs with little change in histological scores (Table 21). Thus, passive administration of anti-TCR $V_\beta 8(39-59)$ antibodies over a 12 day period suppressed clinical but not histological signs of EAE.

C. DISCUSSION

The results presented herein constitute the first demonstration of the ability of a synthetic TCR V-region peptide to induce specific antibodies that can suppress the induction of EAE. These TCR $V_\beta 8(39-59)$ peptide-specific antibodies are able to bind T cells bearing the entire, intact TCR, and thereby alter the function of these cells without lysing them. Coupled with results presented in Example I, these results indicate that both antibody and cell-mediated immune responses can provide independent immunoregulatory actions on encephalitogenic T lymphocytes that utilize common V region genes in response to epitopes of MBP. Both regulatory mechanisms have potent preventative and suppressive effects on the induction of clinical signs of autoimmune disease.

The TCR $V_\beta 8(39-59)$ peptide, which was predicted to be a good T cell immunogen based on the algorithms of Margalit et al. and Rothbard et al. (supra), proved to be a potent B cell immunogen, especially in rabbits. The antibodies were highly specific for the immunizing peptide (by both direct reaction and inhibition assays), stained only $V_\beta 8^+$ T cells, and suppressed EAE mediated by $V_\beta 8^+$ T cells.

In conclusion, the synthetic peptide TCR $V_\beta 8(39-59)$ induced both T cell immunity and antibody production in Lewis rats. Both T cells and antibodies, alone or together, are capable of regulating the immune response to an encephalitogenic challenge. The ability of this TCR peptide to activate regulatory T cells and protective antibodies demonstrates the utility of this approach for the control of human autoimmune diseases.

TABLE 16

Amino Acid Sequence of Peptides Derived from the TCR
and Related Peptides from Myelin Basic Protein

```
                   39 40           45              50             55         59
TCR Vβ8(39–59):    AspMetGlyHisGlyLeuArgLeuIleHisTyrSerTyrAspValAsnSerThrGluLysGly 25           30           35            40 41
TCR Vβ8(25–41):    LysGlnAsnAsnAsnHisAsnAsnMetTyrTrpTyrArgGlnAspMetGly 39 40           45              50             55         59
TCR Vβ14(39–59):   AlaProGlyGlyThrLeuGlnGlnLeuPheTyrSerPheAsnValGlyGlnSerGluLeuVal 24          30           35            40 41
TCR Vβ14(24–41):   ThrValLysGlyThrSerAsnProAsnLeuTyrTrpTyrTrpGlyAlaProGly 69 70 71 72 73 74 75 76    79 80 81 82 83 84
Gp-S49S:           GlySerLeuProGlnLysSerGln-----ArgSerGlnAspGluAsn
Gp-S53:                                  SerGln-----ArgSerGlnAspGluAsn
Gp-S67:            GlySerLeuProGlnLysSerGln-----ArgSerGln 55          60       63      65              70         74
Gp-(S55–74):       SerGlyLysAspSerHisHisAlaThrArgThrThrHisTyrGlySerLeuProGlnLys
Gp-(S87–99):                   87         90           95            99
                               ValHisPhePheLysAsnIleValThrProArgThrPro
                   1              5             10              16
Gp-NAc(1–16):      N—Ac—AlaSerGlnLysArgProSerGlnHisGlySerLysTyrLeuAla
```

All peptides were synthesized by the solid phase method, purified by gel filtration and high pressure liquid chromatography as described in the methods section. Peptides from the TCR are numbered according to Burns et al. (supra) and Williams et al. (supra) and guinea pig muelin basic protein(GPBP) peptides are numbered according to Eylar et al. (J. Biol. Chem. 246:5770 (1971)). Peptide Gp-(S55–74) has an unnatural threonine for alanine substitution at position 63.

TABLE 17

Prevention and Suppression of EAE by Immunization with the TCR Vβ8(39-59) Peptide

| Antigen | Treatment Day | N | Clinical Score | Histological Score |
|---|---|---|---|---|
| GP-BP | 0 (Imm) | 8 | 3.1 ± 0.6 | ND |
| TCR Vβ8(39-59) | 0 (Imm) | 8 | 0.7 ± 0.3 | ND |
| GPBP | 0 (Chall) | | | |
| Gp-S49S | 0 (Imm) | 4 | 3.0 (2.5–4.0) | Br: 3.0 ± 0.8 Sc: 3.3 ± 0.5 |
| TCR Vβ8(39-59) | 0 (Imm) | 4 | 0.5 (0.5–0.5) | |
| Gp-S49S | 0 (Chall) | | | |
| TCR Vβ8(39-59) | 0 (Imm) | 8 | 0.8 (0.0–1.0) | Br: 1.8 ± 1.7 Sc: 2.8 ± 1.0 |
| Gp-S49S | 44 (Chall) | | | |
| Gp-(S87-99) | 0 (Imm) | 6 | 2.3 (1.5–3.0) | Br: 2.2 ± 1.1 Sc: 1.0 ± 0.0 |
| TCR Vβ8(39-59) | 0 (Imm) | 4 | 0.0 | Br: 0.5 ± 0.6 Sc: 0.8 ± 0.5 |
| Gp-(S87-99) | 44 (Chall) | | | |
| TCR Vβ14(39-59) | 0 (Imm) | 4 | 2.9 (1.5–4.0) | |
| Gp-S49S | 0 (Chall) | | | |

Groups of Lewis rats were immunized with the listed antigens on the indicated treatment days ("Imm"). Each rat received 2 SC injections in the base of the tail of 0.1 ml containing 100 μg free peptide emulsified in CFA. Immunized rats were challenged on indicated days ("Chall") with either the encephalitogenic GPBP (50 μg), Gp-S49S (100 μg) or Gp-(S87-99) (100 μg), injected in the foot pad as an emulsion (0.1 ml) in CFA. Rats were inspected daily for clinical signs of disease. Tissues were taken for histology 23 to 26 days after challenge. The clinical scores represent the mean of all rats per group and are scored as described in Table 11. Ranges of clinical scores appear in brackets. The histological scores of brain (Br) and spinal cord (Sc) of individual rats are based on the number of lesions: 1 = 1-2 lesions; 2 = 3-5; 3 = 6-8; 4 = 9 or more lesions in a hematoxylin-stained sagittal section of the brain or the entire length of the spinal cord.

TABLE 18

Antibody Response Against TCR Peptide Vβ8(39-59) in Lewis Rats and Rabbits

| Day After Challenge | Serum Dilution | N | Reactivity Against TCR Vβ8(39-59) | Clinical Signs of EAE |
|---|---|---|---|---|
| Lewis Rats | | | | |
| 7 | 1:40 | 4 | 90 (51–161) | None |
| 14 | 1:40 | 4 | 214 (83–471) | None |
| 21 | 1:40 | 4 | 115 (52–288) | None |
| 33 | 1:40 | 4 | 311 (44–712) | None |
| 41 | 1:40 | 12 | 466 (103–1132) | None |
| Rabbits | | | | |
| TCR Vβ8(39-59)-KLH conjugate: | | | | |
| 75 | 1:40,000 | | 482 | None |
| 160 | 1:80,000 | | 399 | |
| TCR Vβ8(39-59) free peptide: | | | | |
| 75 | 1:40,000 | | 133 | None |
| 160 | 1:80,000 | | 217 | |

Male Lewis rats (225-250 g) were challenged SC with 100 μg TCR Vβ8(39-59) + 100 μg M. butyricum in CFA. Each rat was bled from the tail vein on indicated days after challenge. Rabbits (6 lbs) received a course of immunization that is detailed in the Materials and Methods. Antibody reactivity of individual sera against TCR Vβ8(39-59) was documented by direct ELISA and the average reactivity of individual sera per group is presented as Absorbance Units ($\times 10^3$). In brackets are shown the ranges of antibody reactivity of all antisera per group. All sera were heat inactivated and diluted before assay against 25 ng of plated peptide. The term "None" designates the complete absence of clinical signs of EAE.

TABLE 19

Antibody Response Against Encephalitogenic Peptides in Rats
Immunized with TCR $V_\beta 8(39-59)$ Peptide During the Course of EAE

| Day after Challenge | Dilution | N | -Antisera Reactivity Against- | | | | Clinical Signs |
|---|---|---|---|---|---|---|---|
| | | | TCR $V_\beta 8$ (39-59) | Gp-S49S | Gp-S53 | Gp-(S87-99) | |
| No TCR Immunization Gp-S49S Challenge | | | | | | | |
| 7 | 1:40 | 6 | | 92 | 0 | | None |
| 14 | 1:40 | 5 | | 353 | 15 | | 6/6 HLP 1 died |
| 21 | 1:40 | 4 | | 1360 | 104 | | 4 recov. 1 died |
| 29 | 1:40 | 4 | | 935 | 222 | 19 | 4 recov. |
| 48 | 1:320 | 4 | | 1333 (10664) | 335 (2680) | 5 | 4 recov. |
| TCR $V_\beta 8(39-59)$ on d. 0 Gp-S49S on d. 48 Bleed on d. 74 | | | | | | None | |
| | 1:80 | | 629 (1258) | 875 (1750) | 455 (910) | 11 | 0/4 rats |
| No TCR Immunization GP-S(87-99) on d. 21 | | | | | | 4/4 | |
| | 1:40 | | | 10 | 8 | 14 | 550 | 2/4 HLP |
| TCR $V_\beta 8$-39-59 on day 0 Gp-S(87-99) on d. 44 Bleed on d. 65 | | | | | | None | |
| | 1:320 | | 621 (4968) | 38 | 46 | 348 (784) | 0/4 rats |

Rats were either immunized with 100 µg TCR $V_\beta 8(39-59)$ peptide or injected with saline and were challenged on indicated days with either Gp-S49S or GP(S87-99), SC in emulsion containing 100 µg *M. butyricum* in CFA. Rats were bled on the indicated days. Groups immunized with TCR $V_\beta 8(39-59)$ and challenged with either Gp-S49S or Gp-(S87-99) were terminated on days 26 and 21 after challenge, respectively. Antibody reactivity (binding to 25 ng/well of peptide) of individual sera was measured in direct ELISA. Results are presented as average Absorbance ($\times 10^3$) at 450-650 nm (automatically corrected for background). Theoretical Absorbances (shown in parentheses) were normalized to a 1:40 dilution. Hind leg paralysis (HLP) was accompanied by incontinence. Because of the severity of the disease, 2 of the Gp-S49S-challenged rats died on days 14 and 18, respectively. Variation within groups of 2-3 samples was less than 5%.

TABLE 20

Reactivity of Antibodies Against TCR $V_{\beta}8(39-59)$ and GPBP Peptides with a Panel of Synthetic Myelin Basic Protein and TCR β Chain Peptides

| $V_{\beta}8$ 39-59 | $V_{\beta}8$ 25-41 | $V_{\beta}14$ 39-59 | $V_{\beta}14$ 24-41 | Gp S49S | Gp S53 | Gp S67 | Gp S55-74 | Gp S87-99 | Gp N—Ac 1-16 |
|---|---|---|---|---|---|---|---|---|---|
| Rat anti-Gp-S49S: (1:160 dilution) | | | | | | | | | |
| 14 | 20 | 21 | 18 | 2211 | 1535 | 16 | 17 | 7 | 14 |
| Rat anti-TCR $V_{\beta}8(39-59)$: (1:160 dilution) | | | | | | | | | |
| 222 | 11 | 21 | 9 | 12 | 8 | 12 | 14 | 5 | 10 |
| Rat anti-TCR $V_{\beta}8(39-59)$ and Gp-S49S: (1:640 dilution) | | | | | | | | | |
| 421 | 16 | 20 | 11 | 2190<br>(8760) | 1639<br>(6556) | 8 | 14 | 5 | 12 |
| Rat anti-TCR $V_{\beta}8(39-59)$and Gp-(S87-99): (1:320 dilution) | | | | | | | | | |
| 621<br>(1242) | 13 | — | 18 | 38 | 6 | 8 | 14 | 348<br>(696) | 12 |
| Rabbit anti-TCR $V_{\beta}8(39-59)$-KLH: (1:40,000 dilution) | | | | | | | | | |
| 408<br>(102000) | 0 | 25 | 3 | 2 | 4 | 0 | 0 | 5 | 1 |

TABLE 20-continued

Reactivity of Antibodies Against TCR $V_\beta 8$(39-59) and GPBP Peptides
with a Panel of Synthetic Myelin Basic Protein and TCR β Chain Peptides

| $V_\beta 8$ 39-59 | $V_\beta 8$ 25-41 | $V_\beta 14$ 39-59 | $V_\beta 14$ 24-41 | Gp S49S | Gp S53 | Gp S67 | Gp S55-74 | Gp S87-99 | Gp N—Ac 1-16 |
|---|---|---|---|---|---|---|---|---|---|

Lewis rats were immunized with 100 μg of Gp-S49S, TcR $V_\beta 8$(39-59) or both, SC in Freund's adjuvant (100 μg *M. bityricum*/rat). Antisera were prepared between days 54 and 62 after immunization and pools of high titer antisera were made from 2 to 4 immunized rats. Rabbit antisera was isolated on day 43 after immunization with the TCR peptide conjugated to KLH. All antisera were heat-inactivated for 30 min at 57° C.. Antibody reactivity, at the indicated dilutions, against the various peptide antigens was measured by direct ELISA using rabbit anti-rat or goat anti-rabbit IgG (L + H)-peroxidase labeled. The values shown are the Absorbance measurements at 450-650 nm (×$10^3$). All figures were automatically corrected for background reactivity in the absence of plated peptides. Numbers in brackets represent theoretical Absorbance values calculated for a 1:160 dilution.

TABLE 21

Suppression of EAE in Lewis Rats by Passively Transferred Anti-TCR $V_\beta 8$(39-59) Antibodies

| Treatment | Antibody Against TCR Vβ8 (39-59) | Antibody Against GP-S49S | N | EAE Activity Clinical Scores | EAE Activity Histological Scores |
|---|---|---|---|---|---|
| No anti-TCR Ab | | | | | |
| Bleed: day 21 | 15 | 1360 | 6 | 3.1 (1.5–4.0) | Br: 3.3 ± 0.5 SC: 2.8 ± 1.0 |
| Rat anti-TCR | | | | | |
| Bleed: day 0 | 5 | 12 | 4 | 1.5 (1.5–2.0) | Br: 1.0 ± 1.0 Sc: 4.0 ± 0.0 |
| Bleed: day 12 | 149 | 165 | | | |
| Bleed: day 24 | 162 | (3014) | | | |
| Rabbit anti-TCR | | | | | |
| Bleed: day 0 | 10 | 16 | 6 | 0.7 (0.5–1.0) | Br: 2.2 ± 1.0 Sc: 2.7 ± 1.5 |
| Bleed: day 12 | 500 | 34 | | | |
| Bleed: day 24 | 130 | 322 | | | |

EAE was induced in Lewis rats by injection of 100 μl of emulsion containing 100 μg Gp-S49S and 100 μg *M. Butyricum* in the footpad. Beginning on the day of induction and every other day for 12 days, experimental groups received either 7 mg Lewis rat IgG (which contained 17 Absorbance Units/mg IgG) or 10 mg rabbit IgG (which contained 6570 Absorbance Units/mg IgG) from animals that had been immunized with TcR Vβ8(39-59). The IgG was dissolved in sterile saline and injected intraperitoneally. Treatment with non-immune rat or rabbit IgG did not influence the course of EAE. All animals were inspected daily for clinical signs of EAE, bled from the tail vein on indicated days. Sera were tested for antibody to TCR or GPBP peptide in direct ELISA (results are Absorbance × $10^3$). All animals were sacrificed on day 24 after EAE induction and brains (Br) and spinal cords taken for histological evaluation as described in the legend to Table 17.

EXAMPLE VIII

Clinical EAE in Rats Treated with TCR $V_\beta 8$(39-59) Peptides Before or After Onset of Disease The ability of the TCR Vβ8(39-59) given either SC (in adjuvant) or ID (in saline) to disrupt the disease process when given at various times after induction of EAE with GPBP was tested (Table 22). In Experiment 1, the TCR peptide was administered either on day 10 (line 2) or when the first rat in a group showed clinical signs of EAE (lines 3 and 4) at the time of onset. In both cases, with both routes of injection of the peptide, there was a significant reduction in the duration of the disease, though not in the severity or time of onset. The efficacy of the peptide given in saline via the ID route is of particular importance to human therapy, as it is preferred to SC injection in adjuvant.

In Experiment 2, the time of ID administration of the TCR peptide was varied, as was the dose. As shown in Table 22, 50 μg of the peptide administered on either days 0 (day of EAE induction), 7, or 14 resulted in a significant reduction in the duration of disease. A delay in onset of the disease was also observed. Furthermore, the percentage of animals showing signs of the disease decreased. A larger dose of the peptide (200 μg) appeared less efficacious than the lower dose, possibly due to a short-term overload of the peptide which could have comprised the immune response generated against the TCR. Treatment with a similarly sized peptide corresponding to an irrelevant TCR had no effect on onset, severity or incidence of EAE, but may have reduced the duration somewhat (last line of Table 22).

TABLE 22

Clinical EAE in Rats Treated with TCR Vβ8(39-59) Peptides Before or After Onset of Disease

| Treatment | Day | Day of Onset | Disease Severity | Disease Duration | Disease Incidence |
|---|---|---|---|---|---|
| Experiment 1 | | | | | |
| Control | — | 13.0 ± 0 | 3.0 ± 0 | 6.8 ± 0.8 | 5/5 |
| TCR (100 μg) (SC in CFA) | 10 | 14.0 ± 0.4 | 2.8 ± 0.4 | 3.2 ± 0.4 | 5/5 |
| TCR (100 μg) (SC in CFA) | 13 | 13.0 ± 0 | 3.0 ± 0 | 4.0 ± 0 | 5/5 |
| TCR (50 μg) (ID) | 13 | 13.4 ± 0.5 | 2.6 ± 0.4 | 3.2 ± 0.5 | 5/5 |
| Experiment 2 | | | | | |
| Control | — | 13.0 ± 0.5 | 3.0 ± 0 | 5.8 ± 0.4 | 6/6 |
| TCR (200 μg) (ID) | 13 | 14.0 ± 1.4 | 2.3 ± 0.8 | 3.0 ± 1.2 | 6/6 |
| TCR (50 μg) (ID) | 14 | 16.0 ± 1. | 1.7 ± 1.5 | 2.3 ± 2.0 | 4/6 |
| TCR (50 μg) (ID) | 7 | 15.0 ± 0.8 | 1.7 ± 1.4 | 2.0 ± 2.0 | 4/6 |
| TCR (50 μg) | 0 | 15.6 ± 2.6 | 1.8 ± 1.0 | 2.3 ± 1.6 | 5/6 |
| Control TCR (Vβ14(39-59) | 13 | 13.7 ± 0.5 | 2.5 ± 0.8 | 3.5 ± 0.5 | 6/6 |

TCR refers to the peptide TCR Vβ8(39-59).

EXAMPLE IX

T Cell Responses of LN Cells and TCR Peptide-Selected T Cell Lines From Rats Receiving TCR Peptide Therapy The proliferative responses and specificity of T cells in the draining LN (popliteal) of rats treated with TCR Vβ8(39-59) peptide for EAE on day 13 after disease induction were examined (Table 23). On day 0, Lewis rats received an EAE-inducing regimen of GP-BP+CFA SC into their hind footpads. On day 13, they were divided into three groups and received either saline (column 1), 100 µg TCR Vβ8(39-59) peptide (+CFA) SC in the hind footpads (column 2) or 50 µg of TCR Vβ8(39-59) in saline ID in the ear pinna. On day 20, about 7 days after onset of EAE, popliteal LNs were removed and T cell proliferative activity in response to the indicated antigens or mitogens were tested directly.

LN cells from control rats responded best to Con A, PPD, GPBP and GPBP (72-89), and GPBP (45-89) (which includes the 72–89 sequence and another immunogenic but non-encephalitogenic peptide). In contrast, LN cells from rats given the TCR peptide SC in CFA, did not show significant proliferative responses to GPBP or to any of the BP fragments. LN cells from rats treated ID with the TCR peptide esponded similarly to the control cells, with the exception of a reduced response to GPBP (72-89). In addition, the latter group showed an increased response to GPBP (90-170), which is not known to be encephalitogenic. This indicates that epitope switching had occurred. An aliquot of each of the above 3 groups of LN cells was stimulated in culture with either GPBP or with the TCR peptide for 3 days, and the cells expanded in IL-2 for 5 more days. The proliferative responses to the various antigens and mitogens of these selected T cells were examined, as above. The results are shown in Table 24.

Control T cells (Table 24, column 1) responded well to GPBP, GPBP (72-89), P1 and rat BP (indicating homologous recognition in the CNS). The last line of the Table indicates that when T cells of this group were injected into naive rats, they were encephalitogenic.

T cells from the group of animals treated with the TCR peptide in CFA, SC, and selected in culture with GPBP (column 2) responded poorly to GPBP, GPBP (72-89) and rat BP. The response to GPBP P1 was apparently due to the second (non-encephalitogenic) epitope, since the response to the GPBP (72-89) epitope was weak. The potent response to the TCR peptide indicated that a 7 day exposure (with no further selection with this peptide) was sufficient for anti-TCR peptide immunity. Of great significance is the obser- The cells from the above TCR-immunized animals, when selected in vitro with the TCR peptide rather than with GPBP (column 3), appeared to respond only to the TCR peptide (and, of course, the T cell mitogen, Con A).

Finally, cells from rats treated with the TCR peptide ID and selected in culture with GPBP (column 4) behaved essentially like the control cells. That is, they recognized the GPBP (72-89) encephalitogenic epitope and were able to transfer EAE. This indicates that encephalitogenic T cell precursors were still present in the rats treated in this manner and could be selected in culture. This suggests the possibility that the reduced duration of EAE seen in rats treated with TCR peptide ID (see Example III and Table 22) does not involve regulation of the draining LN cells. However, it is important to note that the LNs draining the site of ID injection (i.e., the cervical LN when ID injection is in the ear pinna) may show different regulatory properties.

TABLE 23

Proliferative Responses of LN Cells from Lewis Rats After EAE Induction and Treatment with TCR Peptides
T Cell Proliferation (cpm × $10^{-3}$)

| In Vitro Stimulus | Control | TCR Vβ8(39-59) 100 µg SC (in CFA) | 50 µg ID |
|---|---|---|---|
| Medium | 28 | 47 | 31 |
| Con A | 85 | 78 | 146 |
| PPD | 91 | 72 | 104 |
| TCR Vβ8(39-59) | 31 | 39 | 30 |
| GPBP | 49 | 50 | 44 |
| GPBP (72-89) | 44 | 38 | 37 |
| BPBP (87-99) | 37 | 36 | 34 |
| GPBP (45-89) | 48 | 50 | 49 |
| GPBP (1-38) | 30 | 47 | 34 |
| GPBP (90-170) | 36 | 54 | 44 |
| TCR Vβ8(39-59) + GPBP | 50 | 59 | 48 |

Results are shown as net $^3$H-thymidine incorporation of 5 × $10^5$ cells stimulated in microwells.

TABLE 24

Proliferative Responses of Peptide-Selected T Cells from Lewis Rats After EAE Induction and In Vivo Treatment with TCR Peptides

| Day 13 Inj: Selection with: | Control GPBP | TCR Vβ8(39–59) + CFA GPBP Vβ8(39–59) | | TCR Vβ8(39–59) ID GPBP |
|---|---|---|---|---|
| Intro Vitro: Stimulation: | | | | |
| Medium | 15 | 17 | 8 | 10 |
| Con A | 76 | 52 | 68 | 95 |
| PPD | 99 | 29 | 6 | 122 |
| TCR Vβ8(39–59) | 24 | 66 | 85 | 10 |
| GPBP + TCR | 110 | 82 | 105 | 127 |
| GPBP (72–89) | 51 | 20 | 12 | 52 |
| GPBP (45–89) | 73 | 38 | 9 | 78 |
| GPBP (1–38) | 13 | 19 | 11 | 12 |
| GPBP (90–170) | 23 | 25 | 10 | 12 |
| Rat BP | 46 | 14 | 4 | 36 |
| Ability to Transfer EAE | YES | NO | | YES | vation that these cells were unable to transfer EAE, indicating that the encephalitogenic clones could not be selected during culture in the presence of the GPBP antigen.

EXAMPLE X

Treatment of Experimental Autoimmune Encephalomyelitis with T Cell Receptor V Region Peptide Immunization of rats and mice with myelin basic protein (MBP) induces encephalitogenic T cells that express a limited repertoire of T cell receptor V region genes. Preceding examples demonstrate that a synthetic peptide from the Vβ8 sequence shared by most encephalitogenic rat T cell clones induces protection against EAE by stimulating specific regulatory T cells and antibodies. In the present example, the same TCR peptide, which corresponds to the 39–59 residues of the Vβ8 sequence and includes the second complementarity determining region, is demonstrated to be highly effective as therapy for EAE.

The TCR Vβ8-39-59 peptide, when given s.q. in complete Freund's adjuvant to rats with moderate EAE, halted disease progression and significantly shortened disease course. When the TCR peptide was given i.d. in the ear, the effects were delayed for 1 day, but again led to a faster resolution of clinical signs. MBP-selected T cell lines from the treated rats responded poorly to MBP, but retained reactivity to the TCR peptide and failed to transfer to normal recipients. The rapid clinical effect of the TCR peptide suggested triggering of a pre-existing regulatory network evoked in response to EAE development. In support of this concept, direct evidence is presented in the present example of T cell recognition of the TCR peptide in untreated rats undergoing EAE.

A. MATERIALS AND METHODS

Animals: Female Lewis rats, 6–8 weeks old, were obtained from Harlan Sprague Dawley (Indianapolis, Ind.). Rats were housed and maintained at the Portland VAMC Animal Resource Facility in accordance with Federal and Institutional guidelines.

Antigens: GP- or Rt-MBP was extracted and purified according to the method of Eylar (Eylar, E. H., et al., J. Biol. Chem. 246: 5770 (1971)). Enzymatic cleavage fragments of GP-MBP encompassing residues 1–37, 43–89, and 90–169, a synthetic peptide of GP-MBP corresponding to residues 72–89, and the synthetic peptides corresponding to the 39–59 residues of TCR Vβ8 and TCR Vβ14 were synthesized and purified as described previously (Vandenbark et al., Nature 341: 541 (1989); Eylar et al., J. Biol. Chem. 246: 5770 (1971)). These peptides were >90% pure by high pressure liquid chromatography analysis.

Clinical Protocols: EAE was induced in all experiments by a single subcutaneous (s.q.) injection in one hind footpad of 50 μg GP-MBP in complete Freund's adjuvant containing 100 μg heat killed M. tuberculosis H37RA (DIFCO, Detroit, Mich.). In the prevention protocol, rats were injected s.q. on one hind footpad 40 days prior to EAE induction with 100 μg TCR Vβ8-39-59 or TCR Vβ14-39-59 in CFA containing 100 μg M. tuberculosis. In suppression protocols, the TCR peptides were injected at the same time (100 μg s.q. in CFA, or 50 μg i.d. in 0.1 ml saline in the ear), 7 days (i.d.), or 11 days (i.d.) after challenge with GP-MBP. In the treatment protocols, the TCR peptides were given either s.q. in CFA or i.d. in the ear on the first day that clinical signs of EAE were noted (usually day 12 after challenge with GP-MBP). Animals were scored daily for clinical signs of EAE, using a rating scale of 0–4, in which 0=no signs; 1=limp tail; 2=hind leg weakness, ataxia; 3=hind quarter paralysis; 4=front and hind quarter paralysis, moribund condition. Treatment groups were compared with control groups for differences in maximum disease severity and duration of clinical signs by Student's unpaired t test. Delayed type hypersensitivity reactions were measured by the ear swelling assay (Offnet, H., et al., J. Exper. Med. 170: 355 (1989)) 24 and 48 hours after injection i.d. of 50 μg antigen. GP-MBP-specific T cell lines were selected from TCR peptide treated and untreated rats as described previously (Vandenbark et al., J. Immunol. 135: 223 (1985)). Ten million GP-MBP activated line cells were transferred i.p. into naive rats to test for encephalitogenic activity, scored as described above for actively induced EAE.

Lymphocyte Proliferation: Activation of T cells was measured by $^3$H-Tdy uptake. 500,000 lymph node cells or 20,000 line cells in the presence of 1 million irradiated thymic accessory cells were incubated with culture medium and antigens in microtiter wells for 18 hours prior to the addition of 0.5 μBq labeled thymidine. The cell cultures were harvested onto glass fiber filters and counted by liquid scintillation techniques. Mean CPM were calculated from triplicate cultures. Standard deviations (SD) from replicate cultures varied <10% from the mean value.

B. RESULTS

To evaluate the regulatory effect of the TCR peptides on EAE, the Vβ8-39-59 peptide, a control peptide Vβ14-39-59, or saline were injected prior to, simultaneously with, or after the injection of the encephalitogenic emulsion, GP-MBP/CFA. The average daily clinical scores of the most effective prevention, suppression, and treatment protocols are presented in FIGS. 3–5, and all groups tested are summarized in Table 25.

Figure 3:
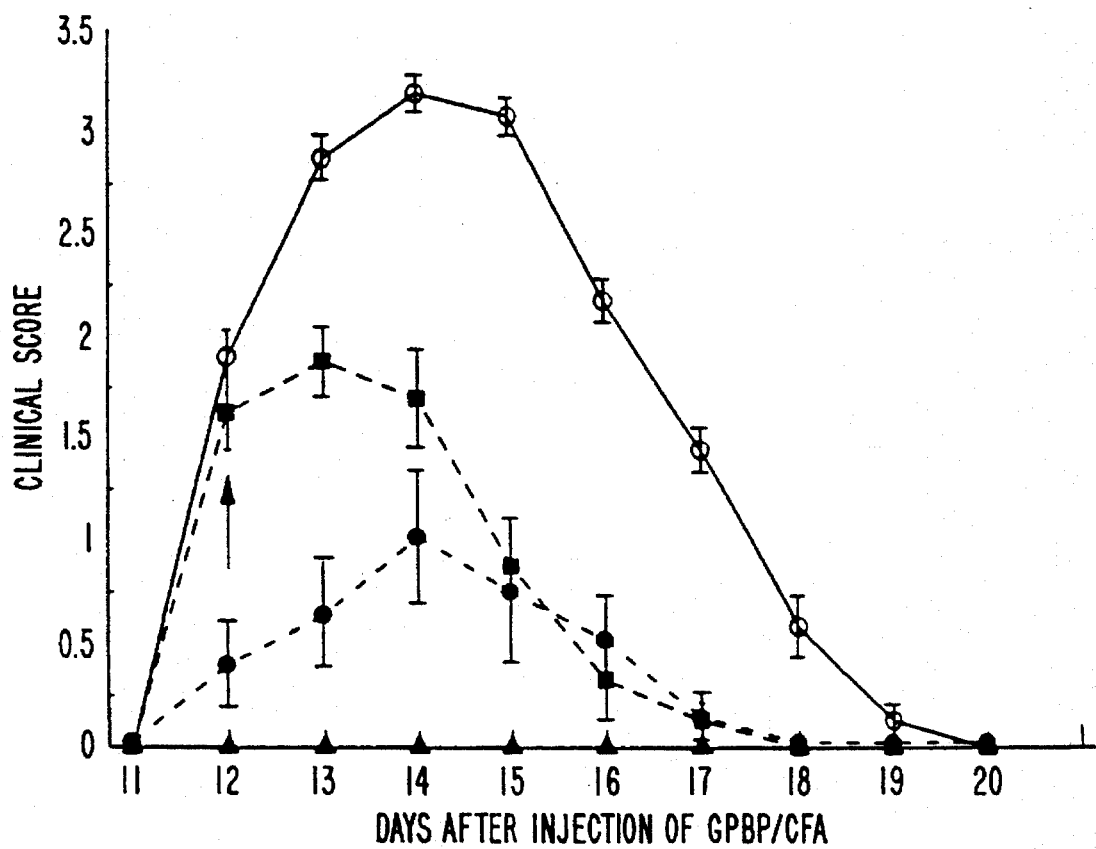
FIG. 3. Prevention, suppression and treatment of EAE with 50 μg TCR Vβ8-39-59 peptide/CFA. Rats were injected s.q. with the TCR peptide 40 days prior to, at the same time, or at disease onset 12 days after the induction of EAE with 50 μg GP-MBP/CFA.

Clinical effects of TCR/CFA. Injection of the Vβ8-39-59 peptide in CFA 40 days prior to challenge with GP-MBP induced complete protection against clinical EAE (FIG. 3). Furthermore, simultaneous injection of the peptide in CFA with the encephalitogenic emulsion suppressed EAE, reducing the incidence (8/13 in the treated group versus 26/26 in controls), severity (score of 1.3 versus 3.4), and duration (2.0 versus 6.6 days) of clinical disease (FIG. 3, Table 25). Rats injected 40 days prior to or at the same time as EAE induction with the Vβ14-39-59 peptide in CFA, or with CFA alone, developed EAE that was indistinguishable from the controls (Table 25).

To evaluate its therapeutic effects, the TCR Vβ8-39-59 peptide in CFA was injected s.q. into rats on the first day or onset of clinical signs. Rats at the time of this treatment exhibited hind leg weakness, ataxia, and incontinence (an average grade of 1.8). As is shown in FIG. 3, treatment with the TCR peptide/CFA prevented further progression of clinical signs and shortened the duration of EAE from 6.6 days (controls) to 3.5 days. Treatment with TCR Vβ14-39-59/CFA or CFA alone had no effect on clinical EAE (Table 25).

Figure 4:
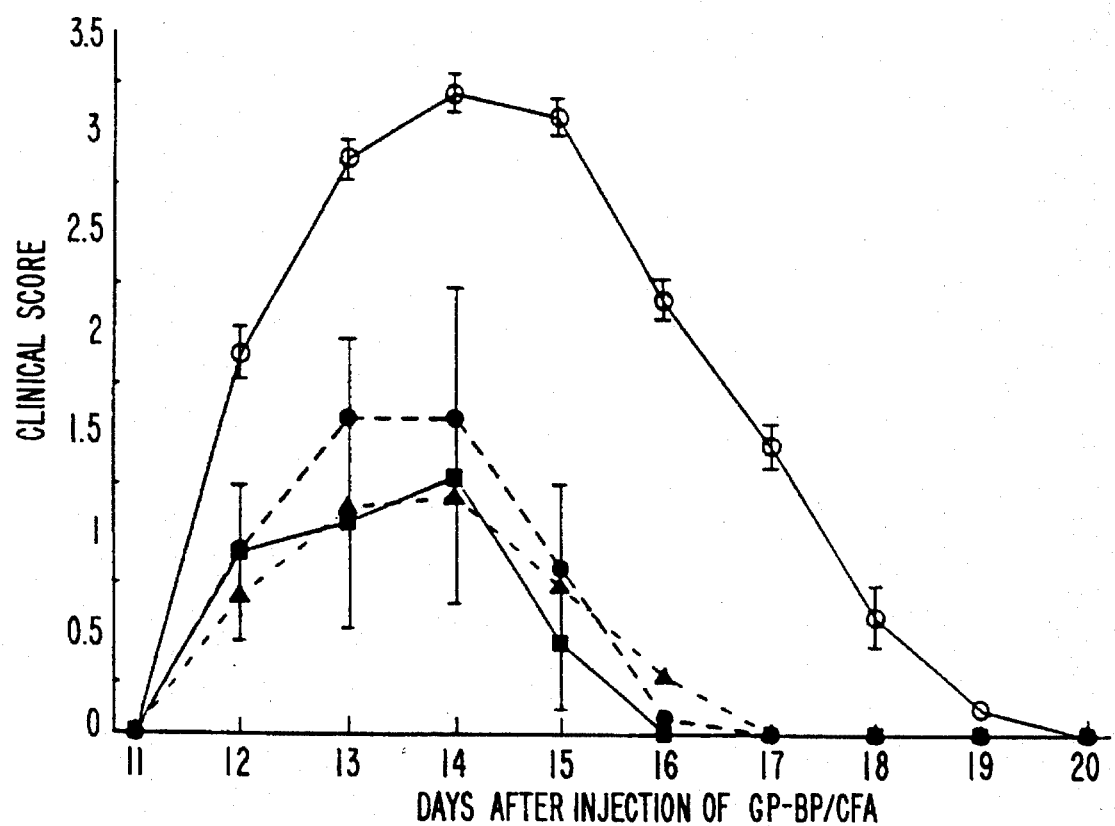
FIG. 4. Suppression of EAE with 50 μg TCR Vβ8-39-59 peptide given i.d. in the ear at the same time, or on days 7 or 11 after induction of EAE with 50 μg GP-MBP/CFA.

Clinical Effects of TCR Peptide Given i.d. To avoid the use of CFA, an evaluation was made of the effects on EAE of administering a saline solution of the TCR peptide intradermally in the ear. As is shown in FIG. 4, i.d. administration of 50 μg of the TCR peptide at the same time as the encephalitogenic challenge (day 0), or on days 7 or 11 after challenge, all had similar suppressive effects on EAE, reducing the maximum clinical severity from 3.4 to 1.7–1.8, and shortening the duration of EAE from 6.6 days to 3–4 days (Table 27).

Figure 5:
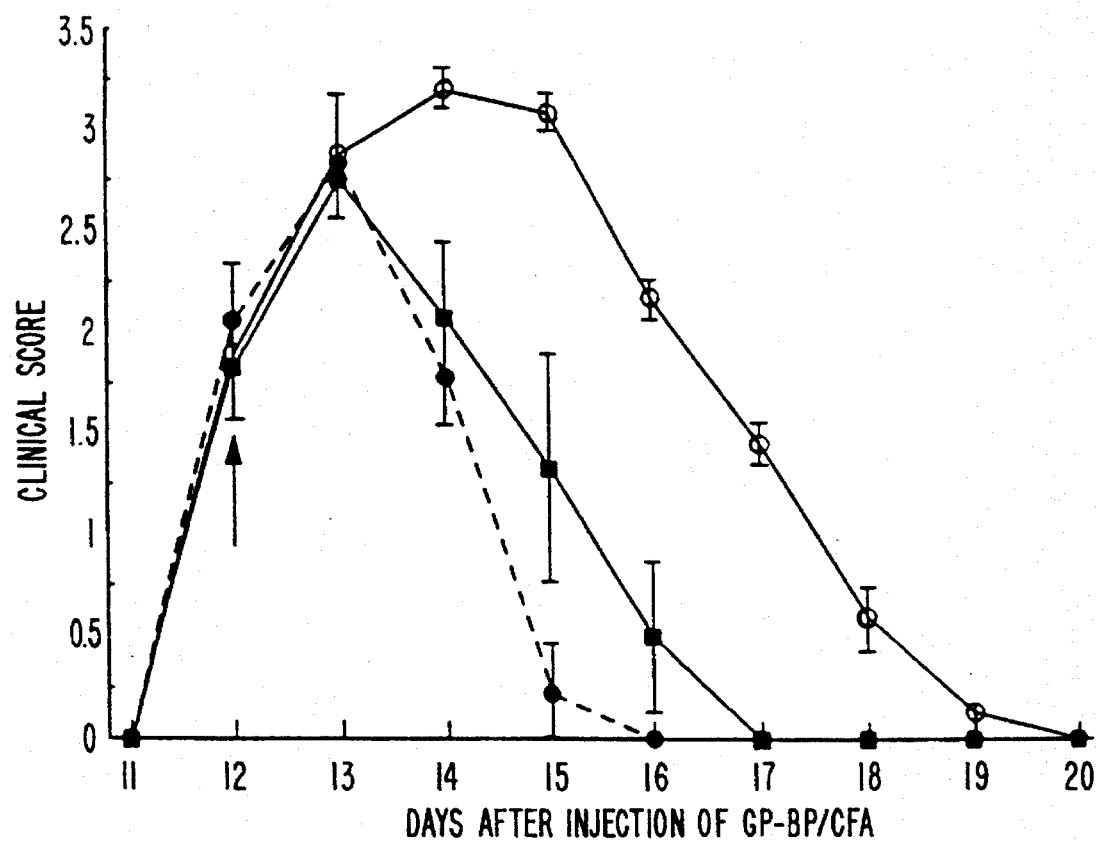
FIG. 5. Treatment of EAE with 10 or 50 μg TCR Vβ8-39-59 peptide given i.d. in the ear at onset of clinical signs (day 12) after induction of EAE with 50 μg GP-MBP/CFA.

When the TCR peptide was injected on the day clinical signs were first noted (average clinical score of 1.9), no clinical effect on EAE was observed during the first day; however, during subsequent days, the severity of EAE was reduced markedly versus controls (FIG. 5). The 50 μg/rat dose of TCR peptide caused a faster resolution of EAE (3.1 days) than the lower 10 μg/rat dose of peptide (4.0 days), compared to 6.6 days for the controls.

The rapid effect of the TCR Vβ8-39-59 peptide in resolving clinical EAE suggested that treatment with the peptide may have triggered a recall response to the TCR, induced initially in response to EAE. To document this possibility in vivo, rats undergoing or recovered from EAE induced with GP-MBP/CFA (without prior exposure to the TCR peptide)

had significant DTH response to the Vβ8 peptide (p<0.01 compared to naive or CFA immunized rats), but not to the Vβ14 peptide (Table 26). The magnitude of the response to Vβ8 peptide in rats undergoing EAE was understandably less than the response in rats immunized previously with a protective regime of TCR peptide in CFA (Table 26).

T cell responses in protected rats. To evaluate the effects of TCR Vβ8 peptide therapy on T cell responses, lymph node cells (LNC) draining the site of GP-MBP/CFA injection were tested for antigen-induced proliferation, and then expanded into T cell lines. As is shown in Table 27, LNC from rats treated with TCR Vβ8-39-59 had a high level of background proliferation (47,000 CPM), and similar responses to GP-MBP and other test antigens. T cell lines selected with GP-MBP (MBP/1st) responded weakly to the selecting antigen and not at all to Rt-MBP and GP-S72-89. The highest response of this line was to the TCR-Vβ8-39-59 peptide. With weak GP-MBP recognition and strong TCR response, it was not surprising that the T cell line failed to transfer clinical signs of EAE to naive rats (Table 27). A similar pattern of high TCR response and low reactivity to GP-MBP and other antigens was also observed in the T cell line (Vβ8/1st) selected with TCR Vβ8-39-59 (Table 27).

Figure 8A:
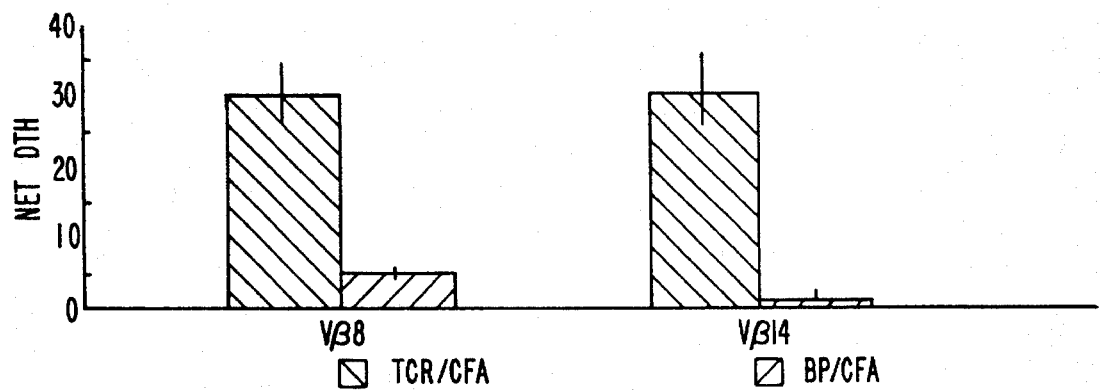
FIGS. 8A and B. Cellular responses to TCR Vβ8- and Vβ14 peptides from EAE-recovered and TCR peptide-immunized rats. DTH is given in mm/100 (8A) and proliferation in CPM/1000 (8B) both background subtracted.
Figure 8B:
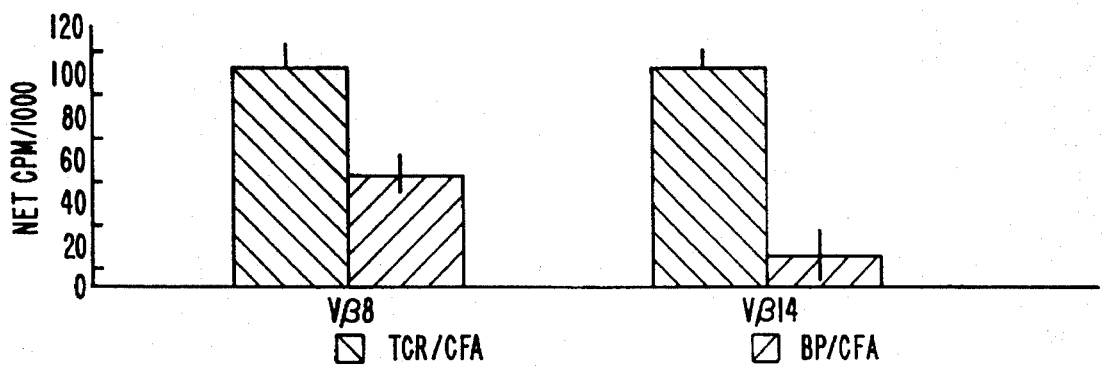

In contrast, LNC from untreated EAE-recovered rats responded predictably to GP-MBP, Rt-MBP, and GP-S72-89 (Table 27). Unexpectedly, however, these LNC also responded to the TCR Vβ8-39-59 peptide and to a lesser degree to the TCR Vβ14-39-59 peptide. When selected with GP-MBP, the resulting T cell line responded strongly to MBP epitopes, and transferred severe clinical EAE to naive recipients in spite of low-level residual activity to the TCR Vβ8 peptide (Table 27). Upon further selection with the TCR Vβ8 peptide, the specific response to this TCR peptide was amplified, although a low level response to GP-MBP and S72-89 persisted. Further selection with the TCR Vβ14 peptide amplified only Vβ14 reactive T cells. Thus, in both TCR-selected lines, the response pattern verified the presence of TCR reactive T cells from the LN of EAE-recovered rats. As shown in FIG. 8, strong DTH and proliferative responses were observed in animals preimmunized with the respective TCR peptides/CFA. Rats preimmunized with TCR Vβ8- but not with Vβ14 peptides were protected from subsequent challenge with GP-MBP/CFA. Significant DTH and strong proliferative responses to the TCR Vβ8-peptide were also observed in rats recovering from EAE that had never been immunized with the synthetic peptide, indicating that a natural regulatory response to the TCR Vβ8-peptide was induced as a consequence of the EAE disease process.

An additional well known MS model is EAE in mice, which, in contrast to rats, is characterized by a relapsing clinical progression. Groups of 6 SJL/J mice were injected with the 139-151 peptide of proteolipid apoprotein (PLP) in CFA. On the first day of the onset of clinical signs (day 14), the mice received 50 µg of a synthetic peptide corresponding to residues 1-17 of the TCR Vβ17 sequence by i.v., i.d., or s.q. administration. As shown in FIG. 9, both s.q. and i.d. injection of the TCR peptide reduced the severity and shortened the duration of disease in the initial episode and in relapsing EAE.

C. DISCUSSION

This example demonstrates clearly the therapeutic administration of the TCR Vβ8-39-59 peptide in EAE, which is consistent with previous examples demonstrating the effectiveness of the TCR peptide in preventing and suppressing EAE. The rapid clinical effect, as well as DTH and lymphocyte proliferation responses to the TCR peptide, indicate that T cell responses to the TCR Vβ8 peptide were already present in rats undergoing EAE that had never been immunized purposefully with the synthetic peptide.

Preimmunization with the Vβ8 peptide in CFA for 40 days prior to GP-MBP challenge was the most effective protocol tested (FIG. 3 and Table 25). It is apparent that this period of immunization is optimal for the induction of both protective T cells and antibodies to the TCR Vβ8 peptide. Injection of the TCR Vβ8 peptide at the same time as GP-MBP challenge was less protective than preimmunization, but this protocol still suppressed completely all clinical signs of EAE in more than 30% (6/19) of the rats (Table 25). In the remainder, the clinical course of EAE was shorter and milder. Injection of the TCR Vβ8 peptide after GP-MBP challenge but before onset of clinical EAE was also effective, completely preventing onset of EAE in 4/19 rats, and generally reducing disease severity and duration in the rest (Table 25).

A surprising aspect of the present example is the almost immediate clinical effect of the TCR Vβ8 peptide injected into sick animals. All rats receiving TCR peptide therapy recovered from EAE faster than controls. Those injected with TCR peptide in CFA did not progress clinically before recovery. Those injected with TCR peptide intradermally did progress the first day, but then recovered as fast as the TCR/CFA injected rats. Both the 10 µg and 50 µg doses of peptide speeded recovery, but the higher dose resolved EAE one day sooner than the lower dose.

The TCR peptide therapy appeared to be effective by down-regulating T cell responses to encephalitogenic determinants of GP-MBP. Lymph node cells from the GP-MBP-challenged, TCR peptide-treated rats had high levels of proliferating cells, but no specific BP responses (Table 27). However, T cell lines selected with GP-MBP proliferated in the presence of GP-MBP and TCR Vβ8 peptide, but not TCR Vβ14 peptide, indicating the presence of both effector and regulatory T cell specificities. That this cell mixture could not transfer EAE may be attributable to the apparent dominance of TCR Vβ8 reactive cells (net 49,000 CPM) over GP-MBP reactive cells (net 12,000 CPM) or S72–89 reactive cells (net 3,000 CPM). In contrast, LNC from EAE-recovered rats that were challenged initially with GP-MBP but not treated with TCR Vβ8 peptide recognized GP-MBP, Rt-MBP, and S72–89, and to a lesser degree the TCR Vβ8 and Vβ14 peptides (Table 27). T cell lines selected with GP-MBP were highly encephalitogenic, due most likely to the dominance of GP-MBP-reactive T cells (net 84,000 CPM) over TCR Vβ8-reactive T cells (net 9,000 CPM). The persistence of TCR Vβ8-peptide-reactive T cells in lines selected with GP-MBP is somewhat unusual in that T cell lines selected with one antigen typically lose responses to all other antigens. No cross-reactivity has been detected between GP-MBP and the TCR-Vβ8 peptide.

Lewis rats do not relapse spontaneously when EAE is induced with MBP/CFA. Although this monophasic course of EAE does not allow testing of TCR Vβ8-39-59 peptide therapy on relapsing disease, it does provide the opportunity to determine if the strong recovery mechanisms in this strain include immune responses to the TCR Vβ8 peptide. Lewis rat T cells that respond to either encephalitogenic determinant (72–84 or 87–99 sequence) of MBP utilize preferentially the Vα2/Vβ8 gene combination in their TCR. Injection of live or attenuated encephalitogenic T cells can induce protection against EAE, as well as idiotypic and "ergotypic" responses. The increased frequency of encephalitogenic T cells induced during EAE may have the same effect of perturbing the regulatory network, and it is conceivable that at least a part of this network is directed naturally at the TCR Vβ8-39-59 sequence.

The present data support this contention. Sick or recovered rats given the TCR Vβ8 peptide i.d. had small but significant DTH responses to this peptide, but no DTH to the corresponding Vβ14 peptide (Table 26). Furthermore, lymph node cells from recovered rats responded better to the Vβ8 TCR peptide, and T cells specific for either peptide could be enriched by in vitro selection techniques (Table 27). Together, those findings provide direct evidence for the natural induction of immunity to the TCR Vβ8-39-59 sequence expressed by encephalitogenic T cells. However, this may not be the only important determinant on the TCR, since other sequences within the TCR α or β chains also induce regulatory T cells and antibodies. The protective, suppressive and therapeutic effects of the TCR Vβ8-39-59 region clearly demonstrate its importance as a determinant for the idiotypic regulation of EAE.

Further, data presented for SJL/J mice, which experience a biphasic clinical course of EAE, demonstrate that administration of a TCR Vβ17 peptide at the onset of clinical signs reduces the severity and duration of symptoms during both the initial episode and relapse. This provides additional support for the importance of TCR V region peptides as tools in the treatment of autoimmune diseases modeled by EAE.

nized with either TCR Vβ18-39-59/CFA or TCR Vβ14-39-59/CFA were tested with either peptide. The ear swelling response (DTH) was measured 48 hours after the i.d. injection. In parentheses are shown the number of animals tested.

TABLE 25

Prevention, Suppression and Treatment of EAE with TCR $V_\beta$8-39-59 Peptide.

| Expt. Group | | Expts | EAE/TOTAL | Onset | Clinical EAE Max Clin. Signs | Duration |
|---|---|---|---|---|---|---|
| GP-BP/CFA only | | 5 | 26/26 | 12 | 3.4 ± 0.2 | 6.6 ± 0.9 |
| TCR/CFA | Day −40 | 4 | 0/20 | — | 0 ± 0 | 0 ± 0 |
| | Day 0 | 3 | 8/13 | 13 | 1.3 ± 1.1** | 2.0 ± 1.8** |
| | Day 10 | 1 | 5/5 | 13 | 2.8 ± 0.4 | 3.6 ± 0.9** |
| | Day onset | 4 | 20/20 | 12 | 2.3 ± 0.9** | 3.5 ± 1.4** |
| Saline/CFA | Day −40 | 2 | 8/8 | 12 | 3.3 ± 0.4 | 6.5 ± 0.9 |
| | Day 0 | 1 | 6/6 | 12 | 3.4 ± 0.3 | 6.6 ± 0.5 |
| | Day onset | 1 | 6/6 | 12 | 3.3 ± 0.2 | 6.7 ± 0.8 |
| Vβ14/CFA | Day −40 | 2 | 8/8 | 12 | 3.2 ± 0.3 | 6.1 ± 0.6 |
| | Day 0 | 1 | 6/6 | 12 | 3.3 ± 0.5 | 6.4 ± 0.3 |
| | Day onset | 1 | 4/4 | 12 | 3.0 ± 0.4 | 6.0 ± 1.5 |
| TCR i.d. | Day 0 | 1 | 5/6 | 15 | 1.8 ± 1.0** | 3.0 ± 1.8** |
| | Day 7 | 1 | 4/6 | 14 | 1.7 ± 1.4* | 2.0 ± 1.9** |
| | Day before onset | 1 | 6/8 | 12 | 1.8 ± 1.3* | 2.5 ± 2.1** |
| | 10 µg, day of onset | 1 | 6/6 | 12 | 2.8 ± 0.4 | 4.0 ± 0.9** |
| | 50 µg, day of onset | 1 | 9/9 | 12 | 2.8 ± 0.3 | 3.1± 0.3** |

*$p < 0.05$; **$p < 0.01$

TABLE 26

Delayed Hypersensitivity Responses to TCR Peptides

| | | 48 Hour DTH Response | | |
|---|---|---|---|---|
| Immunization Status | Ear Test | Vβ8-39-59 | Vβ14-39-59 | GP-BP |
| Normal or saline/CFA | Day 12 | 6 ± 3 (9) | 10 ± 4 (18) | 5 ± 3 (11) |
| GP-BP/CFA | Day 12* | 11 ± 2 (16)** | 11 ± 4 (8) | 35 ± 5 (14)** |
| TCR Vβ8 peptide/CFA | Day 30 | 36 ± 8 (30)** | 9 ± 3 (18) | ND |
| TCR Vβ814 peptide/CFA | Day 30 | 6 ± 3 (12) | 40 ± 4 (12)** | ND |

*EAE onset.
**$p < 0.01$ versus naive or saline/CFA immunized controls.

The DTH response was evaluated in naive Lewis rats or rats immunized with either GP-BP/CFA or saline/CFA without prior exposure to TCR peptides. Similarly, rats immu-

TABLE 27

T Cell Responses After Treatment of EAE with TCR Vβ8 39-59 Peptide/CFA

| Status[a] | Stim.[b] | Proliferation (CPM/1000) | | | | | | Passive EAE | |
|---|---|---|---|---|---|---|---|---|---|
| | | Control | GP-BP | Rt-BP | 72-89 | Vβ8 | Vβ14 | N | Severity |
| Treated | LNC | 47 ± 1 | 50 ± 7 | 49 ± 2 | 38 ± 4 | 39 ± 4 | ND | — | — |
| | BP/1st | 17 ± 1 | 29 ± 6 | 14 ± 2 | 20 ± 2 | 66 ± 6 | ND | 0/3 | 0 |
| | Vβ8/1st | 8 ± 1 | 6 ± 1 | 4 ± 1 | 12 ± 5 | 85 ± 2 | 8 ± 2 | — | — |
| Untreated | LNC | 24 ± 4 | 49 ± 5 | 40 ± 2 | 44 ± 5 | 34 ± 4 | 29 ± 4 | — | — |
| | BP/1st | 15 ± 3 | 99 ± 9 | 46 ± 3 | 51 ± 6 | 24 ± 3 | 17 ± 2 | 3/3 | 3.0 |
| | Vβ8/1st | 11 ± 4 | 23 ± 2 | 11 ± 4 | 18 ± 2 | 34 ± 2 | 11 ± 2 | — | — |
| | Vβ14/1st | 10 ± 1 | 11 ± 1 | ND | 8 ± 1 | 11 ± 1 | 25 ± 6 | — | — |

[a]Treated rats were injected s.q. with 50 μg TCR Vβ8-39-59 peptide/CFA on the first day of clinical EAE induced 12 days earlier with GP-BP/CFA. Untreated rats received only GP-BP/CFA
[b]LW cells collected after the untreated group recovered from EAE (day 21) were stimulated with GP-BP, TCR Vβ8-39-59 peptide, or TCR Vβ14-39-59 peptide, and were expanded in IL-2 prior to restimulation with the indicated antigens (indicated as BP/1st, Vβ8/1st, or Vβ14/1st). For EAE transfer studies, 10⁷ GP-BP activated T cells from treated (protected) and untreated groups were injected i.p. into naive rats.
Underlined values indicate significant difference versus control cultures.

EXAMPLE XI

TCR Treatment of PLP-Induced EAE in SJL/J Mice

In SJL/J mice, the PLP peptide encompassing residues 139–151 is the dominant determinant in whole CNS, and induces severe relapsing EAE. Almost half of the germline Vβ genes have been deleted in this mouse strain, including Vβ8 used preferentially by other rodent strains in response to myelin basic protein. Thus, there is a variety of other V genes used by encephalitogenic T cells, with a less pronounced bias.

Analysis of TCR V gene use in encephalitogenic T cell lines specific for the $PLP_{139-151}$ peptide revealed the presence of Vβ2, Vβ4, and Vβ17, and clones obtained from the line were found to express these V region genes. On this basis, SJL/J mice were treated subcutaneously on the first day of clinical signs with either 100 μg Vβ4 peptide (residues 42–63), 100 μg Vβ17 peptide (residues 1–17), or 100 μg of both peptides (FIG. 15). Mice treated with either the Vβ4 or the Vβ17 peptides developed less severe disease initially, but the remaining clinical course was similar to the untreated control group. Mice treated with both Vβ4 and Vβ17 did not progress clinically during the time that the controls were developing severe EAE. Thereafter, this group maintained a significantly lower disease score than the controls (FIG. 15)

These data demonstrate clearly that when multiple V region genes are involved in the encephalitogenic T cell response, a cocktail of TCR V region peptides is more effective than single peptides. Therefore, treatment of human diseases such as multiple sclerosis with a mixture of TCR V region peptides over-utilized in response to potential encephalitogenic molecules may be more effective than treatment with single peptides. These findings are particularly important and relevant based on the demonstration in Example III that two different V genes (Vβ5.2 and 6.1 ) are over-utilized by BP-reactive T cells from MS patients.

EXAMPLE XII

Protection Against EAE

Experimental autoimmune encephalomyelitis (EAE) in Lewis rats is a monophasic, self-limiting paralytic disease mediated by T lymphocytes specific for central nervous system (CNS) myelin proteins (Vandenbark et al., Prog. Clin. and Biolog. Res. 336: 93 (1990)), most notably basic protein (BP). Immunization with guinea pig (Gp)-BP causes the appearance 10 days later of a T cell subpopulation that (i) responds predominantly in culture to the 72-89 amino acid fragment of Gp-BP (Vandenbark et al., J. Immunol. 135: 229; Offner, H., et al., J. Immunol. 141: 3828; and Chou et al. J. Neurosci. Res. 22: 181), (ii) expresses the variable regions Vα2 and Vβ58.2 in their T cell receptors (TCR) (Burns et al., J. Exp. Med. 169: 27–39), and (iii) transfers paralytic signs of EAE adoptively to secondary recipients (Chou et al. J. Neurosci. Res. 22: 181). T cells having these characteristics that have been attenuated by irradiation or hydrostatic pressure can be used effectively as vaccines to cause a protective resistance to actively induced EAE (Cohen et al., In: Progress in Immunology-6. Proceedings of the 6th International Congress of Immunology Academic Press, New York, pp. 1–13) and (Offner et al., J. Neuroimmunol. 21: 13). The basis for this inducible resistance to disease is thought to involve an active auto-regulatory immune response by the host directed against immunogenic TCR epitopes of disease causing cells (Vandenbark et al., Nature 341: 541 ); (Hashim et al., J. Immunol. 144: 4621); (Offner et al., Prog. Clin. Biolog. Res. 336: 93 (1990)) and (Howell et al., Science 246: 668).

Within 14 days after immunization with Gp-BP, a period just prior to recovery from EAE, an additional T cell subpopulation appears in the periphery Offner et al., J. Exp. Med. 170: 355 (1984)), but not the CNS. This subpopulation (i) responds to another peptide fragment, 43-67, of Gp-BP, (ii) expresses a different TCR Vβ variable region gene, and (iii) is not encephalitogenic in rats probably because T cells of this population cannot recognize rat (Rt)-BP, which contains an extensive sequence variation near residue 60 (Alvord et al., In Experimental Allergic Encephalomyelitis: A Useful Model for Multiple Sclerosis. Alan R. Liss, Inc., NY, 146: 523–537). Of particular interest for the current example is the finding that a recently isolated T cell clone from this population, Clone C4, reactive to Gp-BP 43-67 and itself non-encephalitogenic, induces protective resistance against EAE caused by other clones reactive to Gp-BP 72-89. This clone is important since it represents the first description of an auto-antigen specific clone that can be used to down regulate the encephalitogenic activities of other clones specific for different epitopes of the same molecule.

This example is the result of studies designed to acquire a better understanding of the mechanism(s) through which clone C4$_{55-69}$ is able to induce resistance to EAE. The specificity and TCR Vβ sequences of three different Gp-BP specific T cell clones derived from rats recently recovered from EAE were compared: Clone C3 which is reactive to Gp-BP 72-89 and is encephalitogenic; Clone C4$_{55-69}$, non-encephalitogenic but capable of inducing resistance to EAE; and Clone C5, an inocuous clone reactive to Gp-BP, but not to any of the three major enzymatic cleavage fragments of Gp-BP. This example demonstrates more precisely that residues 55–69 act as a protective epitope of Gp-BP, the example also highlights TCR Vβ chain sequences expressed by these three different Gp-BP reactive T cell clones, and demonstrates that the EAE protective effect of clone C4 depends on its ability to induce a cross reactive immunity against a TCR epitope shared by most BP 72-89 specific encephalitogenic T cells.

MATERIALS AND METHODS

Animals: Lewis female rats (6–8 weeks old) were purchased from Harlan Sprague Dawley (Indianapolis, Ind.), and were housed and cared for in the Animal Resource Facility at the Portland VAMC according to institutional guidelines.

Antigens: Gp- and Rt-BP were prepared according the the method of Eylar et al. (Eylar et al., J. Biol. Chem. 246: 5770). Proteoytic cleavage fragments of Gp-BP were obtained and purified to contain >95% of the desired peptide by ion-exchange chromatography as described previously (Chou et al., J. Neurochem. 28: 115). Synthetic MBP peptides were prepared by solid phase techniques (Hashim et al., J. Neurosci. Res. 16: 467), and numbered according to the bovine BP sequence (Vandenbark et al., J. Immunol. 135: 223 (1985)).

Selection of T cell lines and clones: T cell lines were selected as described previously (Vandenbark et al., J. Immunol. 135: 223) from draining lymph nodes of rats immunized with Gp-BP/CFA after recovery from EAE. Supernatants from ConA stimulated Lewis rat splenocytes were used as the source of IL-2 used to expand antigen stimulated T cells.

T line cells were cloned by limiting dilution as described previously (Aalvord et al., in Experimental Allergic Encephalomyelitis: A Useful Model for Multiple Sclerosis, 146: 523–537 (1984)). After stimulation with BP, cells were placed in round bottom microtiter wells at densities of 4, 2, 1, and 0.5 cells/well in 0.2 ml growth medium, and incubated at 37C and 7% $CO_2$. After 7 days, cells were restimulated with 50 μg/ml BP using $10^5$ irradiated (1500 Rads) syngeneic thymocytes per well as antigen presenting cells. After 72 h, fresh growth medium was added to each well.

Plates were screened to determine the cloning efficiency and expanded clones were derived from plates with fewer than 60% positive wells, usually those seeded initially with 1 or 0.5 cells/well. Subsequent restimulation with BP was accomplished in 96-well flat bottom plates using $10^6$ irradiated thymocytes/well. After 72 h of stimulation, clones were refed with growth medium and expanded subsequently in 24-well flat bottom plates. Restimulation in 24-well plates was accomplished by using approximately $4 \times 10^5$ cloned cells in the presence of $10^6$ irradiated thymocytes and 25 μg BP. Cloned cells were eventually expanded to 6 and then 10 cm plastic Petri plates.

Proliferation assays: Proliferation assays were performed in 96-well microtiter plates. $2 \times 10^4$ T cells and $10^6$ irradiated thymocytes/well were incubated with stimulation medium only, ConA, or antigen at 37C in 7% $CO_2$. The cultures were incubated for 72 h, the last 18 h in the presence of 0.5 Bq $^3$H-Tdr. The cells were harvested onto glass fiber filters and TCR uptake was assessed by liquid scintillation. Mean CPM wre calculated from triplicate wells. The standard deviation from replicate wells varied <10% from the mean values.

Induction of EAE: Active EAE was induced by s.c. injection of 50 μg Gp-BP in CFA containing 100 μg Mycobacterium tuberculosis strain H37Ra (Difco Laboratories, Detroit, Mich.). Passive EAE was induced by injecting i.p. T cell clones that were stimulated with BP for 3 days using irradiated thymocytes as APC. Rats developing EAE were assessed daily for clinical signs using the following scale: 0=no signs; 1=limp tail; 2=hind limb weakness; 3=paraplegia; 4=paraplegia with forelimb weakness, moribund condition.

Transfer of DTH and protection: Delayed type hypersensitivity reactions were measured by the ear swelling assay (Offner et al., J. Neuroimmunol. 9: 147)) 24 and 48 h after injection i.d. of 20 μg antigen. Protection against actively induced EAE was evaluated after i.p. transfer of activated or resting (near the end of IL-2 dependent growth phase) T cell clones.

Phenotyping: Indirect immunofluorescence was performed as described earlier (Offner et al., J. Immunol. 139: 2395)) with FITC-conjugated goat anti-mouse IgG F(ab')$_2$ (GAM) antibody (TAGO, Burlingame, Calif.). T lymphocyte clones ($1 \times 10^6$) were washed in ice-cold PBS containing 2% FCS and 0.1% azide and pelleted by rapid centrifugation in a Dade immunofuge. Monoclonal antibodies specific for pan T cells (W3/13), CD4 (W3/25), CD8 (OX-8), I-A (OX-6), I-E (OX-17), or MHC class I (OX-18) (Bioproducts for Science, Indianapolis, Ind.) were added to separate cell pellets, vortexed, and incubated for 30 min on ice. Cells were washed three times with cold PBS, stained with FITC-GAM for 30 min on ice, and washed again. Lymphocytes were identified by characteristic high forward versus low side scatter and analyzed for green and/or red fluorescence intensity after excitation with 488 nm laser light using a Bectin-Dickinson FACS analyzer (Mountain View, Calif.). Histograms of 10,000 cells were collected for each analysis.

Determination of TCR Vβ utilization:

cDNA synthesis: Total cellular RNA was isolated from T cell clones by lysis in guanidinium isothicyanate and centrifugation through a cesium chloride cushion (Chirgwin et al., Biochemistry18: 5294)). Six μg total RNA was denatured in 10 mM MeMgOH (Alfa Products, Danvers, Mass.) and then converted to cDNA in Taq polymerase buffer; 50 mM KCl, 10 mM Tris-HCl pH8.3, 2.5 mM $MgCl_2$, 0.01% gelatin in the presence of 20 units RNA guard (Pharmacia, Piscataway, N.J.), 40 mM β-mercaptoethanol, 0.5 mM dNTPs, 1 μM Cβ specific oligonucleotide primer and 15 units AMV reverse transcriptase (Pharmacia, Sweden) in a 50 μl reaction. The Cβ oligonucleotide primer, 5'CATAGAAtTcCACTTGGCAGCGGAAGTGGT3' (Genosys, The Woodlands, Tex.) is specific for both rat TCR Cβ1 and 2. Bases in small letters denote changes from the TCR Cβ sequence made to create an EcoR1 restriction endonuclease site. Following incubation at 42C for 90 minutes, the reaction mixture was heated to 95C for 5 minutes to denature the DNA/RNA duplexes.

PCR amplification: The cDNA was amplified in a 100 μl volume containing 1.5 mM $MgCl_2$ Taq buffer, 2 μM Cβ oligonucleotide primer, 2 μM Vβ8 family specific oligonucleotide, 200 μM dNTPs and 2 units Taq DNA polymerase (Pharmacia). The Vβ8 specific oligonucleotide, 5'GGGCCGCGGAACACATGGAAGCTGCAGTCAC3', amplifies all known rat Vβ8 family members and contains a 5' SacII restriction endonuclease site. Each sample was overlayed with mineral oil and subjected to 30 amplification cycles of 1 min. at 92C, 1.5 rain at 55C, and 2 min at 72C in a thermocycler (Perkin Elmer, Norwalk, Conn.).

DNA sequencing: Following amplification, the samples were chloroform extracted to remove the mineral oil, ethanol precipitated, digested with SacII plus EcoR1 (New England Biolabs, Beverly, Mass.), and the resulting DNA was separated on a 1.4% agarose gel. The appropriate sized product was isolated directly from the agarose using Prep-A-Gene (Bio-Rad, Richmond, Calif.) and ligated into the SaclI/EcoR1 site of pBluescript II (Stratagene, San Diego, Calif.). The ligation mixture was transformed into the bacterial strain XL1-Blue (Stratagene). Miniprep DNA was prepared by standard methods (Maniatis et al., T., E. F. Fritsch, and J. Sambrook. 1989. Molecular cloning: A laboratory manual. Second edition. Cold Spring Harbor Laboratory, Cold Spring Harbor, N.Y.)) from randomly selected bacterial colonies and was sequenced on both strands by the dideoxy chain termination method (Sanger et al., Proc. Natl. Acad. Sci. USA 78: 2072))using the Sequenase sequencing system (U.S. Biochemical, Cleveland, Ohio).

RESULTS

Specificity of the protective clone $C4_{55-69}$ obtained from EAE-recovered rats. The inventor has demonstrated that clone C4, obtained from rats that spontaneously recovered from EAE, responded to the Gp-BP specific amino acid sequence encompassed within residues 43–67 and could protect naive rats from EAE induced by subsequent injection of Gp-BP/CFA. To analyze further its specificity, clone C4 was stimulated with a battery of synthetic peptides. As is shown in Table 28, clone C4 responded fully to the Gp-BP 50-69 and 55–69 peptides, and partially to the modified rat 55-74 sequence that differs from the Gp-BP sequence by a single T for A substitution at position 63. However, clone C4 did not respond at all to Rt-BP which has 3 amino acid differences from Gp-BP in this region (Chou et al., J. Neurochem. 28: 115 (1977)). These data demonstrate conclusively that the minimum Gp-BP epitope (residues 55–67) recognized by clone C4 is absent from Rt-BP, and accounts for the lack of induction of T cell clones of this specificity after immunization with Rt-BP. Hereafter, clone C4 will be designated $C4_{55-69}$.

Gp-BP-55–69 is a protective epitope against EAE in Lewis rats. The selection of an EAE protective clone responsive to Gp-BP-55-69 suggested that this synthetic epitope might have a more generalized protective activity against subsequent induction of EAE. Indeed, pre-immunization with Gp-BP-55-69 prior to challenge with Gp-BP/CFA prevented all signs of clinical EAE in 3 of 9 rats, and reduced significantly the severity and duration of EAE in the rest (FIG. 16).

Clone $C4_{55-69}$ protects against active and passive EAE. To evaluate the protective activity of clone $C4_{55-69}$, groups of Lewis rats were injected with 1–20 million $C4_{55-69}$ T cells, either 3 days after activation in vitro with Gp-BP or the Gp-BP 55–69 peptide, or just prior to antigen restimulation after growth had slowed in IL-2 rich supernatant (resting cells). Two weeks after injection of the T cells, the recipient rats were tested for their resistance to active EAE induced with Gp-BP/CFA, or passive EAE induced after transfer of activated Clone 3 T cells specific for the 72-89 sequence of Gp-BP ($C3_{72-89}$). AS is shown in Table 29, clone $C4_{55-69}$ cells, given either i.p. or i.v., induced partial to complete protection against active EAE in all recipients in a dose-dependent manner, compared to control rats that were not pre-injected with T cells. Those rats that developed milder EAE after injection with clone $C4_{55-69}$ had less clinical disability and shortened disease duration. Resting clone $C4_{55-69}$ T cells could also transfer protection, albeit somewhat less efficiently than activated cells (Table 29). In contrast to clone $C4_{55-69}$, a non-encephalitogenic clone $C5_{Gp-BP}$ specific for Gp-BP but not Gp-BP peptides exerted minimal protection against EAE (FIG. 17).

Clone $C4_{55-69}$ T cells were even more effective at preventing passive EAE than active EAE. As is shown in Table 31, clone $C4_{55-69}$ activated independently or in the presence of clone $C3_{72-89}$, protected all recipients against clinical EAE that developed in control rats 5–6 days after transfer of activated clone $C3_{72-89}$ cells.

Protection is not due to inactivation of clone $C3_{72-89}$ by clone $C4_{55-69}$. Conceivably, the protective activity of clone $C4_{55-69}$ might be related to its ability to inhibit the activation of encephalitogenic T cells such as clone $C3_{72-89}$. To evaluate this possibility, each clone was stimulated individually or in mixed culture with whole Gp-BP or one or both of the respective epitopes. As is shown in Table 30, the proliferation responses of both clone $C3_{72-89}$ and clone $C4_{55-69}$ were marginally inhibited (20–25%) when activated with one or both epitopes in mixed culture, compared to the sum of their individual activation levels. These results indicate that each clone responded to its respective epitope at a marginally reduced level in the presence of the other clone, and do not support the idea that clone $C4_{55-69}$ protects against EAE by inhibiting the activation of the encephalitogenic clone $C3_{72-89}$.

CNS histology. Evaluation of spinal cord sections revealed abundant perivascular lesions, both in clone $C4_{55-69}$ protected and control rats. However, injection of activated clone $C4_{55-69}$ T cells did not induce any detectable CNS lesions in the absence of an encephalitogenic challenge.

Identification of TCR Vβ genes expressed by clones from EAE-recovered rats. The persistence of CNS lesions in rats protected completely from clinical signs of EAE by clone $C4_{55-69}$ was reminiscent of protection induced by immunization with synthetic peptides from the TCR-$V\beta8_{39-59}$ sequence shared by Gp-BP-72-89 specific encephalitogenic T cell clones (Vandenbark et al., Nature 341: 541 (1989); and Hashim et al., J. Immunol. 144: 4621 (1990)). Although T cell lines responsive to the 43-67 epitope of Gp-BP did not express Vβ8.2 (Alvord et al., In Experimental Allergic Encephalomyelitis: A Useful Model for Multiple Sclerosis, Vol. 146, pp. 523–537, Alan R. Liss Inc., New York), it was conceivable that a related V region gene was utilized in the TCR specific for Gp-BP-43-67, and that a cross-reactive TCR idiotope induced anti-TCR-$V\beta8_{39-59}$ immunity. Alternatively, regulation might be induced by cross-reactive non-TCR determinants that appear during activation of clone $C4_{55-69}$ (e.g. "ergotypic" epitopes).

To assess the importance of T cell receptor gene usage on antigen recognition and function, TCR V region β chain families were identified for each of the three representative T cell clones (FIG. 18). Clones $C3_{72-89}$ and $C5_{Gp-BP}$ shared Vβ8.2 and Dβ1 sequences, but differed in Jβ use, the encephalitogenic clone $C3_{72-89}$ expressing Jβ2.3, and the non-encephalitogenic clone $C5_{Gp-BP}$ expressing Jβ1.1 (FIG. 18). In contrast, the protective clone $C4_{55-69}$ expressed Vβ8.6, Dβ2 and Jβ2.1.

Clone $C4_{55-69}$ induces DTH responses to both Vβ8.6+ and Vβ8.2+ T cells. Because of similarities in the Vβ8.2 and Vβ8.6 sequences, we hypothesized that injection of clone $C4_{55-69}$ (Vβ8.6+) would induce cellular cross-recognition of Vβ8.2+ T cells in vivo. To test this assertion, DTH (ear swelling) reactions to attenuated clone $C3_{72-89}$ (Vβ8.2+) and clone $C4_{55-69}$ T cells were assessed in rats passively immunized with clone $C4_{55-69}$ T cells and in naive control rats. As is shown in Table 32, rats passively immunized with $C4_{55-69}$ T cell clones had comparable DTH responses to both irradiated $C4_{55-69}$ (Vβ8.6+) and $C3_{72-89}$ (Vβ8.2+) T cells. This cellular recognition was directed mostly against cross-reactive determinants present on both "activated" and "resting" clone $C3_{72-89}$ and clone $C4_{55-69}$ cells (Table 32), thus indicating minimal contribution by "ergotypic" epitopes. Moreover, much of the DTH response observed to clone $C3_{72-89}$ could be attributed to the $V\beta8.2_{39-59}$ peptide (Table 32). In contrast to the potent induction of cross-reactive DTH by clone $C4_{55-69}$, clone $C5_{Gp-Bp}$, which expressed Vβ8.2 but was marginally protective, failed to induce a significant DTH response to the Vβ8.2$_{39-59}$ peptide (Table 32).

The ability of both activated and resting clone $C4_{55-69}$ to induce specific DTH responses against the Vβ8.2$_{39-59}$ peptide, and the relative inactivity of clone $C5_{Gp-BP}$ (which is Vβ8.2+) prompted a closer look at the expression of cell surface markers. FACS analysis of clones C3, C4, and C5 indicated similar levels of expression of CD4 (W3/25 monoclonal antibody), a pan T cell marker (W3/13), and Class I MHC (OX-18). However, the protective clone $C4_{55-69}$ expressed significantly higher levels of the activation marker I-A (OX-6, FIG. 19) and I-E (OX-17,) than either clone $C3_{72-89}$ or clone $C5_{Gp-BP}$ both during the resting phase (FIG. 19) and after activation (FIG. 19). Thus, although the precise contribution of I-A and I-E to induction of protection and anti-TCR immunity is unknown, it is apparent that clone $C4_{55-69}$ maintains higher levels of these activation markers than the other two clones.

The Vβ8.6$_{39-59}$ and Vβ8.2$_{39-59}$ peptides are highly cross-reactive. Analysis of the Vβ8.6 versus the Vβ8.2 sequences indicated only 4 amino acid differences within residues 39–59 (FIG. 18), as well as similar predicted T cell epitopes as determined by the presence of amphipathic alpha helices (Margalit et al., J. Immuno. 138: 2213)) and Rothbard-Taylor (RT) sequences (Rothbard et al., The EMBO Journal 7: 93)). To study possible cross-reactivity within these sequences, the TCR-Vβ8.6$_{39-59}$ peptide was synthesized for comparative studies with the TCR-Vβ8.2$_{39-59}$ peptide that has already been characterized extensively (Vandenbark et al., Nature 341: 541 (1989); Hashim et al., J. Immunol. 144: 4621 (1990); and Higgins et al., J. Immunol. 140: 440 (1988)).

A direct way to assess homologous and cross-recognition of the two TCR peptides in vivo is to immunize with each peptide in CFA and to measure DTH to both peptides. As is shown in Table 32, the Vβ8.6$_{39-59}$ and Vβ8.2$_{39-59}$ peptides were highly cross-reactive in vivo, with only a slightly stronger response observed to the immunizing versus the cross-reactive peptide. Similar cross reactivity was observed with antibodies to the two TCR peptides. These data demonstrate conclusively that immunization with either Vβ8.6+T cells or TCR-Vβ8.6$_{39-59}$ peptide can induce strong T cell cross-recognition of TCR-Vβ8.2$_{39-59}$, known to have both protective and therapeutic effects on EAE (Vandenbark et al., Nature 341: 541 (1989); Hashim et al., J. Immunol. 144: 4621 (1990); and Higgins et al., J. Immunol. 140: 440 (1988)). Similarly, cross reactivity between the two peptides was observed using a rabbit antibody specific for TCR Vβ8.2$_{39-59}$ that produced equivalent reactivity by ELISA to both of the TCR peptides (0.31 O.D. units to TCR Vβ8.2$_{39-59}$ and 0.33 O.D. units to TCR Vβ8.6$_{39-59}$ at a 1/40,000 serum dilution).

Treatment of EAE with Vβ8.6$_{39-59}$ peptide. The strong cross-reactivity of the Vβ8.6$_{39-59}$ and Vβ8.2$_{39-59}$ peptides predicted that the Vβ8.6 peptide should successfully treat rats with established EAE, as shown previously for the Vβ8.2 peptide (Higgins et al., J. Immunol. 140: 440 (1988)). As is shown in FIG. 20, injection of the TCR-Vβ8.6$_{39-59}$ peptide in saline either subcutaneously or intradermally on the first day of clinical EAE reduced significantly the severity and duration of EAE compared to rats injected with Vβ14$_{39-59}$ control peptide, or to untreated control rats. The resolution of EAE with TCR-Vβ8.6$_{39-59}$ was comparable to the effects of the TCR-Vβ8.2$_{39-59}$ peptide (FIG. 20).

DISCUSSION

The results presented above demonstrate that a TCR V region idiotype present on a non-encephalitogenic T cell clone can induce EAE-protective immunity directed at a cross-reactive TCR determinant commonly utilized by encephalitogenic T cells. The data illustrate that 1) the non-encephalitogenic 55-69 sequence of Gp-BP represents a protective epitope for EAE in Lewis rats, 2) Clone $C4_{55-69}$ specific for this epitope can induce potent protection against active and passive EAE after injection into naive rats, 3) the protective clone $C4_{55-69}$ expresses Vβ8.6 in its TCR, 4) the 39-59 sequence of Vβ8.6 is cross-reactive with the 39-59 sequence of Vβ8.2 utilized by encephalitogenic T cells in Lewis rats (Burns et al., J. Exp. Med. 169: 27 (1989)), and 5) the Vβ8.6$_{39-59}$ peptide has comparable activity to the Vβ8.2$_{39-59}$ peptide for treating rats with established EAE. Thus, it is probable that the protection against EAE induced by injecting the 55-69 peptide includes anti-TCR immunity directed at a cross-reactive TCR idiotope expressed on TCR Vβ8.6$_{39-59}$ by non-encephalitogenic T cells specific for the 55-69 determinant. However, other non-TCR determinants, as well as inhibitory properties of clone $C4_{55-69}$ itself, could also contribute to the observed protection.

Protection may have resulted from the efficient induction by clone $C4_{55-69}$ of anti-idiotypic regulation directed at the TCR of encephalitogenic T cell specificities. Firstly, clinically well rats protected by clone $C4_{55-69}$ still developed histological EAE, a pattern identical to the protection induced by the synthetic TCR Vβ8.2$_{39-59}$ peptide (Vandenbark et al., Nature 341: 541 (1989); Hashim et al., J. Immunol. 144: 4621 (1990)). Secondly, clone $C4_{55-69}$ induced strong T cell recognition of the encephalitogenic clone $C3_{72-89}$ and of the TCR Vβ8.2$_{39-59}$ sequence expressed by clone $C3_{72-89}$. Sequence analysis demonstrated clearly that clone $C4_{55-69}$ expressed Vβ8.6 in its TCR and that the Vβ8.6 and Vβ8.2 sequences were similar. The longest stretches of identical amino acids in Vβ8.2 and Vβ8.6 are in residues 1–11 and 44–54, but only the latter was predicted to be a T cell epitope and is included within a larger known antigenic peptide (ie. residues 39–59). Thirdly, the synthetic Vβ8.6$_{39-59}$ peptide was highly cross reactive in vivo with the Vβ8.2$_{39-59}$ peptide, and demonstrated comparable effects in modulating EAE.

The Gp-BP-55-69 specific, I-A restricted Clone 4 is the first clone reported to utilize Vβ8.6, a gene closely related to the Vβ8.2 gene preferentially utilized by encephalitogenic T cells specific for the 72–89 and 87–99 epitopes of Gp- and Rt-BP (Burns et al., J. Exp. Med. 169: 27 (1989); Alvord et al., In Experimental Allergic Encephalomyelitis: A Useful Model for Multiple Sclerosis, Vol. 146, pp. 523–537, Alan R. Liss Inc., New York; and Williams et al., Immunol. Res. 7: 339–350 (1988)). It is of further interest to note the distinct differences at the V-D-J junction that may account for the differences in specificity of the three clones evaluated in this study, especially clones $C3_{72-89}$ and $C5_{Gp-BP}$, that are otherwise identical in their use of Vβ8.2.

The recovery process in experimental autoimmune encephalomyelitis (EAE) is characterized by an increasing diversity of T cell clones directed at secondary epitopes of myelin basic protein. Of particular interest, residues 55–69 of guinea pig basic protein (Gp-BP) induce protection against EAE. A non-encephalitogenic T cell clone, $C4_{55-69}$, specific for this epitope transferred protection against both active and passive EAE. Clone $C4_{55-69}$ was found to express Vβ8.6 in its antigen receptor, and residues 39–59 of this sequence were found to be highly cross reactive with the corresponding 39–59 residues of Vβ8.2 known to induce protective anti-idiotypic T cells and antibodies. Like the TCR Vβ8.2$_{39-59}$ peptide, the Vβ8.6$_{39-59}$ sequence induced autoregulation and provided effective treatment of established EAE. Thus, the EAE-protective effect of the Gp-BP-55-69 sequence was most likely mediated by T cell clones such as $C4_{55-69}$ that could efficiently induce anti-TCR immunity directed at a cross-reactive regulatory idiotope.

TABLE 28

Proliferation Response of Clone $C4_{55-69}$ to BP Peptides

| Stimulant | Amino Acid Sequence (residues 50–74) | Response CPM/ 1000 ± S.D. |
|---|---|---|
| Medium | | 0.2 ± 0.1 |
| Con A | | 229 ± 15 |
| Gp-BP | -APKRGSGKDSHHAARTTHYGSLPQK- | 203 ± 7 |
| 43-67 | -APKRGSGKDSHHAARTTH | 249 ± 12 |
| 50-69 | APKRGSGKDSHHAARTTHYG | 277 ± 14 |
| 55-69 | SGKDSHHAARTTHYG | 247 ± 25 |
| Rt-BP | -APKRGSGKDSH--TRTTHYGSLPQK- | 0.2 ± 0.1 |
| 55-74 modified | SGKDSHHATRTTHYGSLPQK | 150 ± 15 |

Amino acids are designated by single letters. Hyphen (-) indicates additional residues. Underlined residues indicate differences relative to the homologous Rt-BP sequence. Five µg/ml ConA or 50 µg/ml of each peptide was cultured with 20,000 clone $C4_{55-69}$ cells and 1 million thymic accessory cells in 0.2 ml medium for 3 days, and proliferation was measured by uptake of $^3$H-Tdy.

TABLE 31

Coculture of clones $C3_{72-89}$ and $C4_{55-69}$

| | Proliferation (CPM/1000) | | |
|---|---|---|---|
| Antigen | $C3_{72-89}$ | $C4_{55-69}$ | $C3_{72-89}$ + $C4_{55-69}$ |
| Gp-BP | 40 ± 3 | 50 ± 9 | 91 ± 12 |
| Gp-BP-55-69 | 0 ± 0 | 90 ± 10 | 72 ± 7 (20%) |
| Gp-BP-72-89 | 45 ± 4 | 0 ± 0 | 34 ± 4 (24%) |
| Gp-BP-55-69 + 72-89 | 45 ± 5 | 78 ± 8 | 102 ± 10 (25%) |

50 µg of antigen was added to 10,000 cells of each clone stimulated in 0.2 ml medium in the presence of 1 million thymic accessory cells for 3 days. Proliferation was measured by uptake of $^3$H-Tdy. Responses of the clones without antigen or in the presence of irrelevant epitope ranged from 0.1–0.3 CPM/1000 and are rounded to 0. Parentheses in cocultures indicate the level of inhibition compared to the sum of responses.

TABLE 29

Protective Activity of Clone $C4_{55-69}$ T Cells Against Active EAE

| Clone Transferred | Route of Immunization | Number of Cells Transferred ($10^6$) | EAE in Affected Rats | | | |
|---|---|---|---|---|---|---|
| | | | Incidence (%) | Day Onset | Duration | Severity |
| None | — | — | 18/18 (100) | 12 ± 1 | 6.4 ± 0.8 | 3.0 ± 0.6 |
| $C4_{55-69}$ (A) | i.p | 10 | 4/11 (36) | 12 ± 2 | 3.7 ± 1.2* | 2.0 ± 0.8 |
| | | 20 | 3/6 (50) | 11 ± 0 | 2.3 ± 0.5* | 2.0 ± 0 |
| | i.v. | 1 | 5/6 (83) | 13 ± 2 | 3.0 ± 1.4* | 1.5 ± 0.3* |
| | | 5 | 1/6 (17) | 12 ± 0 | 3.0 ± 0* | 2.0 ± 0 |
| | | 10 | 2/6 (33) | 13 ± 1 | 3.0 ± 0* | 1.5 ± 0* |
| $C4_{55-69}$ (R) | i.v. | 10 | 2/3 (67) | 12 ± 0 | 2.0 ± 1.4* | 2.0 ± 0.7 |
| | i.p. | 10 | 5/5 (100) | 12 ± 2 | 5.6 ± 1.1 | 2.7 ± 0.3 |

Rats were challenged with GP-BP/CFA 2 weeks after passive transfer of T cell clones. (A) indicates that the cells were activated for 3 days with antigen and thymic APC. (R) indicates resting cells that had been cultured in IL-2 rich medium for 5–9 days. *indicates a significantly shorter disease duration or severity than controls (p < 0.05).

TABLE 30

Protective Activity of Clone $C4_{55-69}$ Against Passive EAE

| Clone Transferred | Number of Cells Transferred ($10^6$) | EAE in Affected Rats | | | |
|---|---|---|---|---|---|
| | | Incidence (%) | Day Onset | Duration | Severity |
| $C3_{72-89}$ | 7 | 5/5 (100) | 5 ± 1 | 6.8 ± 1.6 | 2.2 ± 0.2 |
| $C3_{72-89}$ + $C4_{55-69}$[a] | 7<br>10 | 0/5 (0) | NA | NA | NA |
| $C3_{72-89}$ + $C4_{55-69}$[b] | 14 | 0/6 (0) | NA | NA | NA |

[a] Clone $C3_{72-89}$ and clone $C4_{55-69}$ T cells were stimulated independently with Gp-BP plus thymic accessory cells for 3 days prior to separate transfer i.p. into naive rats.
[b] $2.5 \times 10^6$ clone $C3_{72-89}$ T cells and $2.5 \times 10^6$ clone $C4_{55-69}$ T cells were mixed and stimulated simultaneously with Gp-BP plus thymic accessory cells 3 days prior to transfer i.p. into naive rats.

TABLE 32

Passively Transferred Clone C4$_{55-69}$ T Cells
Induce Delayed Hypersensitivity Reactions to
Activated and Resting T Cells, and
TCR Peptides

| | Clone C4$_{55-69}$ | | Clone C3$_{72-89}$ | | | |
|---|---|---|---|---|---|---|
| Immunization | Vβ8.6+ Activated | T cells Resting | Vβ2+ Activated | T cells Resting | Vβ8.6$_{39-59}$ Peptide | Vβ8.2$_{39-59}$ Peptide |
| None | 9 ± 2 | 6 ± 3 | 10 ± 1 | 9 ± 4 | 2 ± 1 | 3 ± 1 |
| C4$_{55-69}$ (Vβ8.6+) | 36 ± 6 | 28 ± 4 | 33 ± 6 | 30 ± 4 | 20 ± 3 | 17 ± 2 |
| Vβ8.6$_{39-59}$ peptide | ND | ND | ND | ND | 34 ± 5 | 27 ± 4 |
| C5$_{Gp-BP}$ (Vβ8.2+) | ND | ND | ND | ND | 5 ± 2 | 6 ± 3 |
| Vβ8.2$_{39-59}$ peptide | ND | ND | ND | ND | 31 ± 7 | 39 ± 9 |

Rats received 5 million activated clone C4$_{55-69}$ or clone C5$_{Gp-BP}$ T cells i.p. 3–5 days prior to testing for DTH. Alternatively, rats were immunized 16–21 days with Vβ8.6$_{39-59}$ or Vβ8.2$_{39-59}$ peptides in CFA. DTH responses were detected by changes in ear thickness 48 h after i.d. injection of 200,000 irradiated clone C4$_{55-69}$ or clone C5$_{Gp-BP}$ T cells, or 50 μg TCR peptide in 50 μl saline. Underlined values were significantly greater than in naive rats.

EXAMPLE XIII

A Protective Idiotope in Experimental Encephalomyelitis

Synthetic TCR peptides expressed by encephalitogenic T cells can induce both cellular and humoral responses that protect against experimental encephalomyelitis. In the Lewis rat, encephalitogenic T cells predominantly express Vβ8.2, and a peptide in the CDR2 region representing residues 39-59 could both protect against and treat EAE. Similarly, the homologous and cross reactive 39-59 peptide from Vβ8.6 expressed by an EAE-protective clone also had protective and therapeutic activity against EAE. The consensus sequence between the Vβ8.2 and Vβ8.6 peptides, which included residues 44–54, was postulated to contain the protective idiotope. In this example the inventor demonstrates that this peptide, designated Vβ8-44-54, has comparable activity to the longer peptides for treating both active and passive EAE. Similar to the longer Vβ8.2-39-59 peptide, the Vβ8-44-54 peptide stimulates protective TCR peptide-specific CD4+, CD8$^{dim}$ T cells restricted by MHC I. This example shows for the first time the recovery of Vβ8-44-54 reactive T cell clones that express a variety of Vβ genes in their TCR, including Vβ8, 10, and 8.2 to which their TCR are directed. Taken together, these data establish that the Vβ8-44-54 sequence constitutes an important autoregulatory idiotope in EAE.

MATERIALS AND METHODS

Animals: Lewis female rats (6–8 weeks old) were purchased from Harlan Sprague Dawley (Indianapolis, Ind.), and were housed and cared for in the Animal Resource Facility at the Portland VAMC according to institutional guidelines.

Antigens: Gp-BP was prepared according the the method of Eylar et al. (Eylar et al., J. Biol. Chem. 246: 5770 (1971)). Synthetic TCR peptides were prepared by solid phase techniques, as described earlier herein.

Selection of T cell lines and clones: T cell lines were selected from draining lymph nodes of rats immunized with Gp-BP/CFA after recovery from EAE. Supernatants from ConA stimulated Lewis rat splenocytes were used as the source of IL-2 used to expand antigen stimulated T cells.

T line cells were cloned by limiting dilution as described herein. After stimulation with BP, cells were placed in round bottom microtiter wells at densities of 4, 2, 1, and 0.5 cells/well in 0.2 ml growth medium, and incubated at 37C and 7% CO$_2$. After 7 days, cells were restimulated with 50 μg/ml BP using 10$^5$ irradiated (1500 Rads) syngeneic thymocytes per well as antigen presenting cells. After 72 h, fresh growth medium was added to each well.

Plates were screened to determine the cloning efficiency and expanded clones were derived from plates with fewer than 60% positive wells, usually those seeded initially with 1 or 0.5 cells/well. Subsequent restimulation with BP was accomplished in 96-well flat bottom plates using 10$^6$ irradiated thymocytes/well. After 72 h of stimulation, clones were refed with growth medium and expanded subsequently in 24-well flat bottom plates. Restimulation in 24-well plates was accomplished by using approximately 4×10$^5$ cloned cells in the presence of 10$^6$ irradiated thymocytes and 25 μg BP. Cloned cells were eventually expanded to 6 and then 10 cm plastic Petri plates.

Proliferation assays: Proliferation assays were performed in 96-well microtiter plates. 2×10$^4$ T cells and 10$^6$ irradiated thymocytes/well were incubated with stimulation medium only, ConA, or antigen at 37C in 7% CO$_2$. The cultures were incubated for 72 h, the last 18 h in the presence of 0.5 Bq $^3$H-Tdr. The cells were harvested onto glass fiber filters and TCR uptake was assessed by liquid scintillation. Mean CPM wre calculated from triplicate wells. The standard deviation from replicate wells varied <10% from the mean values. In some experiments, azide free antibodies to MHC I (OX-18) or MHC II (OX-6, anti-I-A and OX-17, anti-I-E) were added to the cultures to evaluate which MHC molecules were used to restrict the T cell response to TCR Vβ8-44-54 peptide.

Induction of EAE: Active EAE was induced by s.c. injection of 10 μg Gp-BP in CFA containing 100 μg Mycobacterium tuberculosis strain H37Ra (Difco Laboratories, Detroit, Mich.). Passive EAE was induced by injecting i.p. T cell clones that were stimulated with BP for 3 days using irradiated thymocytes as APC. Rats developing EAE were assessed daily for clinical signs using the following scale: 0=no signs; 1=limp tail; 2=hind limb weakness; 3=paraplegia; 4=paraplegia with forelimb weakness, moribund condition.

Transfer of DTH and protection: Delayed type hypersensitivity reactions were measured by the ear swelling assay (Offner et al., J. Neuroimmunol. 9: 147 (1984)) 24 and 48 h after injection i.d. of 20 μg antigen. Protection against actively induced EAE was evaluated after i.p. transfer of activated or resting (near the end of IL-2 dependent growth phase) T cell clones.

Phenotyping: Indirect immunofluorescence was performed as described earlier (Offner et al., J. Immunol. 139: 2395 (1987)) with FITC-conjugated goat anti-mouse IgG F(ab')$_2$ (GAM) antibody (TAGO, Burlingame, Calif.). T lymphocyte lines or clones (1×10$^6$) were washed in ice-cold PBS containing 2% FCS and 0.1% azide and pelleted by rapid centrifugation in a Dade immunofuge. Monoclonal antibodies specific for pan T cells (W3/13), CD4 (W3/25), CD8 (OX-8), I-A (OX-6), I-E (OX-17), or MHC class I (OX-18) (Bioproducts for Science, Indianapolis, Ind.) were added to separate cell pellets, vortexed, and incubated for 30 min on ice. Cells were washed three times with cold PBS, stained with FITC-GAM for 30 min on ice, and washed again. Lymphocytes were identified by characteristic high forward versus low side scatter and analyzed for green and/or red fluorescence intensity after excitation with 488 nm laser light using a Bectin-Dickinson FACS analyzer (Mountain View, Calif.). Histograms of 10,000 cells were collected for each analysis.

Determination of TCR Vβ utilization:

cDNA synthesis: Total cellular RNA was isolated from T cell clones by lysis in guanidinium isothicyanate and centrifugation through a cesium chloride cushion (Chirgwin et al., Biochemistry 18: 5294 (1979)). Six μg total RNA was denatured in 10 mM MeMgOH (Alfa Products, Danvers, Mass.) and then converted to cDNA in Taq polymerase buffer; 50 mM KCl, 10 mM Tris-HCl pHS.3, 2.5 mM MgCl$_2$, 0.01% gelatin in the presence of 20 units RNA guard (Pharmacia, Piscataway, N.J.), 40 mM β-mercaptoethanol, 0.5 mM dNTPs, 1 μM Cβ specific oligonucleotide primer and 15 units AMV reverse transcriptase (Pharmacia, Sweden) in a 50 μl reaction. The Cβ oligonucleotide primer, 5'CATAGAAtTcCACTT GGCAGCGGAAGTGGT3' (Genosys, The Woodlands, Tex.) is specific for both rat TCR Cβ and 2. Bases in small letters denote changes from the TCR Cβ sequence made to create an EcoR1 restriction endonuclease site. Following incubation at 42C for 90 minutes, the reaction mixture was heated to 95C for 5 minutes to denature the DNA/RNA duplexes.

PCR amplification: The cDNA was amplified in a 100 μl volume containing 1.5 mM MgCl$_2$ Taq buffer, 2 μM Cβ oligonucleotide primer, 2 μM Vβ8 family specific oligonucleotide, 200 μM dNTPs and 2 units Taq DNA polymerase (Pharmacia). The Vβ8 specific oligonucleotide, 5'GGGC-CGCGGAACACATGGAAGCTGCAGTCAC3', amplifies all known rat Vβ8 family members and contains a 5' SacII restriction endonuclease site. Each sample was overlayed with mineral oil and subjected to 30 amplification cycles of 1 min. at 92C, 1.5 min at 55C, and 2 min at 72C in a thermocycler (Perkin Elmer, Norwalk, Conn.).

DNA sequencing: Following amplification, the samples were chloroform extracted to remove the mineral oil, ethanol precipitated, digested with SacII plus EcoR1 (New England Biolabs, Beverly, Mass.), and the resulting DNA was separated on a 1.4% agarose gel. The appropriate sized product was isolated directly from the agarose using Prep-A-Gene (Bio-Rad, Richmond, Calif.) and ligated into the SacII/EcoR1 site of pBluescript II (Stratagene, San Diego, Calif.). The ligation mixture was transformed into the bacterial strain XL1-Blue (Stratagene). Miniprep DNA was prepared by standard methods (Maniatis et al., Molecular cloning: A laboratory manual. Second edition. Cold Spring Harbor Laboratory, Cold Spring Harbor, N.Y. (1989)) from randomly selected bacterial colonies and was sequenced on both strands by the dideoxy chain termination method (Sanger et al., Proc. Natl. Acad. Sci. USA 78: 2072 (1977)) using the Sequenase sequencing system (U.S. Biochemical, Cleveland, Ohio).

RESULTS

Identification of a common TCR sequence in two protective Vβ8 peptides. Clinical EAE could be treated successfully with either the Vβ8.2-39-59 peptide expressed by encephalitogenic, Gp-BP reactive T cell clones, or the Vβ8.6-39-59 peptide expressed by a non-encephalitogenic, EAE-protective T cell clone (Eylar et al., J. Biol. Chem. 246: 5770 (1971)). Based on the sequences of these two peptides (Table 33), a consensus region that included residues 44–54 of both V genes was identified and synthesized for use in subsequent studies. This peptide has been designated Vβ8-44-54.

T cell and B cell epitopes in the Vβ8-44-54 peptide. To evaluate if the consensus Vβ8-44-54 peptide contained T cell epitopes cross-reactive with the larger Vβ8.2-39-59 peptide, rats were immunized with the Vβ8-44-54 peptide and DTH reactivity to each peptide was assessed by the ear swelling assay. As is shown in Table 34, highly significant ear swelling was observed to both peptides, although the response was somewhat greater to the Vβ8.2-39-59 peptide than to the Vβ8-44-54 peptide.

In contrast, antisera raised in rabbits to the Vβ8.2-39-59 and Vβ8.6-39-59 peptides reacted strongly by ELISA to both of the immunizing peptides, and to a lesser degree to the Vβ8.2-49-59 peptide. Neither antiserum, however, responded to the consensus Vβ8-44-54 peptide or to CDR1, CDR3 or Vβ14 TCR peptides (Table 35). These data clearly indicate that the Vβ8-44-54 peptide contains a cross-reactive T cell epitope, but lacks a cross-reactive B cell epitope compared to the Vβ8.2-39-59 and Vβ8.6-39-59 peptides.

Treatment of active and passive EAE with TCR peptides. To determine if the Vβ8-44-54 peptide retained the activity of the parent peptides to stimulate a protective anti-TCR response, each of the peptides were injected subcutaneously into Gp-BP/CFA immunized rats on the first day of clinical EAE. As is shown in FIG. 21, 100 μg of the Vβ8-44-54 peptide had comparable activity to both the Vβ8.2-39-59 and Vβ8.6-39-59 peptides in reducing severity and duration of actively induced EAE. In comparison, other peptides from the CDR1, CDR2, and CDR3 regions of the Vβ8.2 sequence had little therapeutic effect on EAE.

Although TCR peptides clearly have therapeutic activity in actively-induced EAE, their effects on passive disease have not been reported. Injection of either the parent Vβ8.2-39-59 peptide (FIG. 21A) or the shorter Vβ8-44-54 peptide (FIGS. 21A and 22) produced a marked reduction in the severity and duration of EAE induced passively by Vβ8.2+T cell lines specific for BP.

Characterization of T cells specific for Vβ8-44-54.

To characterize the T cell response to the consensus Vβ8-44-54 peptide, lymph node cells and T cell lines were stimulated with a variety of TCR peptides. Lymph nodes from rats immunized with Vβ8-44-54 peptide in CFA responded significantly to the consensus peptide and to a lesser degree to the longer 39-59 sequences represented in both the Vβ8.2 and Vβ8.6 genes, as well as to PPD as expected (Table 36). However, no response was observed to the Vβ8.2-49-59 sequence which had 6 overlapping residues with the immunizing Vβ8-44-54 peptide, or to the Vβ8.2-25-41 (CDR1 region) peptide, or to the Vβ14-39-59 peptide. T line cells that were repeatedly stimulated with Vβ8-44-54 peptide responded best to the selecting peptide, and to a lesser degree to the longer Vβ8.6-39-59 and Vβ8.2-39-59 peptides, but not to the other peptides or antigens tested (Table 33). The T cell response to the Vβ8-44-54 response was inhibited by 76% in the presence of antibody to MHC class I molecules, but not by antibodies to MHC class II (Table 36). The T line cells were >95% CD4+ and weakly CD8+ as described.

Protection transferred by the Vβ8-44-54 reactive T cell line. To assess protective activity within the Vβ8-44-54 specific T cell line, rats were simultaneously injected with an encephalitogenic dose of Gp-BP/CFA and 12 million activated T cells. As is shown in FIGS. 23A and B, rats receiving the TCR-specific T cells had a delayed onset and developed minimal signs of EAE compared to untreated controls that developed severe clinical EAE.

Isolation of Vβ8-44-54 reactive T cell clones. To characterize the anti-TCR peptide response on the clonal level, ten clones were isolated and characterized from the initial T cell line. As is shown in Table 37, each of the clones responded strongly to the Vβ8-44-54 peptide with stimulation indices ranging from 10× to 1300×, and weakly or not at all to the Vβ8.2-39-59 or Vβ8.6-39-59 peptides. Three of the four clones challenged with all three of the peptides responded selectively to the consensus Vβ8-44-54 peptide, whereas only one clone (B7) reflected the T cell line pattern of response characterized by response to Vβ8-44-54 >Vβ8.6-39-59 >Vβ8.2-39-59 (Table 37). Loss of viability of the clones precluded individual testing of EAE-protective activity.

V gene expression of anti-TCR Vβ8-44-54 reactive T cell line and clones. TCR Vβ gene expression was identified in the starting T cell line and in three of the Vβ8-44-54 reactive T cell clones, using the PCR technique. The T cell line expressed six detectable Vβ genes, including Vβ8.2, 8.6, 10, 12, 15 and 19 (Table 38), and two of these Vβ genes were identified in the TCR of the three T cell clones analyzed individually (clone B3 expressed Vβ10 and clones B9 and D4 expressed Vβ12, Table 38). As is shown in Table 37, each of the three clones had a distinct nucleotide and amino acid sequence through the VDJ region.

DISCUSSION

The data presented above demonstrate conclusively that both antigenic and EAE-regulatory activity resides in an 11 residue peptide representing a consensus sequence found within the Vβ8.2 and Vβ8.6 CDR2 peptides. This common peptide, Vβ8-44-54, has comparable activity in the treatment of both active and passive EAE, and similar to the longer Vβ8.2-39-59 peptide, stimulates protective TCR peptide-specific CD4+, CD8$^{dim}$ T cells restricted by MHC I. This example demonstrates for the first time that Vβ8-44-54 reactive T cell clones express a variety of Vβ genes in their TCR, in sharp contrast to the biased expression of Vβ8.2 by encephalitogenic BP-reactive T cells. Taken together, these data establish that the Vβ8-44-54 sequence constitutes an important autoregulatory idiotope in EAE.

The rapid clinical effect of TCR peptide therapy is apparently due to a boosting effect Of the TCR peptides on anti-TCR immunity that develops naturally during EAE as a consequence of the selective increase in Vβ8.2+ encephalitogenic T cell clones. Conceivably, treatment of EAE with any TCR Vβ8.2 peptide could affect the disease course, although one might expect the greatest activity with the most immunodominant epitopes. The Vβ8-44-54 peptide had much greater therapeutic activity than a CDR1 peptide (residues 25-41), a partially overlapping CDR2 peptide (residues 49–59), or a CDR3 peptide (residues 93–101). The activity of the Vβ8-44-54 peptide was related mainly to a dominant T cell epitope found also on the longer parent peptides, rather than to B cell determinants that were apparently absent on the consensus peptide. It is noteworthy that the Vβ8.2 CDR1 and CDR3 peptides did not contain predicted T cell epitopes (Margalit et al., J. Immuno. 138: 2213 (1987)); (Rothbard et al., The EMBO Journal 7: 93 (1988)), and neither could induce strong delayed hypersensitivity reactions in peptide immunized rats (Offnet et al., Prog. Clin. Biolog. Res. 336: 93 (1990)). In contrast, the Vβ8.2-49-59 peptide had predicted antigenic properties and antibody determinants, but induced only weak DTH reactions in Lewis rats. An additional CDR2 peptide, Vβ8.2-39-51 had no antigenic or protective activity. From these results, it is clear that the Vβ8-44-54 sequence represents the major T cell epitope in the CDR2 region, which is immunodominant when compared to CDR1 and CDR3.

The immunoregulatory activity of this epitope on actively induced EAE has been demonstrated clearly. With respect to passively-induced EAE, however, the induction period is shortened considerably from 12 to 3–4 days. The data (FIG. 22) support the conclusion that a 3–4 day exposure to the transferred T cells predisposed the recipients to the same TCR peptide boosting effects observed during treatment of active EAE (Howell et al., Science 246: 668 (1989)). An additional question that can be addressed in the passive model is the efficacy of the CDR2 peptides on lethal EAE induced with high doses of activated T cells. In this case, treatment with the Vβ8.2-39-59 peptide protected all of the recipients from lethal EAE (FIG. 21A) and allowed a relatively mild disease course. At lower T cell doses producing less severe EAE, both the Vβ8-44-54 and Vβ8.2-39-59 peptides had comparable therapeutic benefit.

Previously in Example IX, the inventor demonstrated that EAE-protective T cell lines specific for the Vβ8.2-39-59 peptide could be selected from peptide-immunized rats. These cells were strongly CD4+ and weakly CD8+, and the availability of the CD8 molecule helped explain the apparent MHC-I restriction of TCR peptide recognition. Similarly, this example demonstrates (Table 36) the selection of an EAE-protective T cell line specific for the Vβ8-44-54 peptide. In this line, recognition of the Vβ8-44-54 peptide involved CD4+, CD8$^{dim}$ T cells whose response was highly peptide specific and inhibitible by antibodies to MHC-I but not MHC-II.

The isolation of T cell lines and clones specific for the Vβ8-44-54 peptide (Table 37) allows for the first time an evaluation of the V gene repertoire involved in the recognition of a TCR idiotope. The predominant V gene (Vβ15) was distinct from the regulated V gene (Vβ8.2). However, at least some of the anti-Vβ8-44-54 reactive line cells also expressed Vβ8.2, raising the possibility that these regulatory cells, themselves, are subject to autoregulation. The mere presence of such Vβ8.2+ T cells precludes clonal deletion as the mechanism of immunoregulation, in support of previous data indicating non-cytolytic T—T interactions between Vβ8.2+ cells and anti-Vβ8.2-39-59 specific regulatory cells.

More generally, the data lend support to the notion that autoreactive T cells specific for TCR epitopes not only escape negative selection in the thymus, but also can be triggered with relative ease in animals that develop a highly focused response involving biased TCR V gene expression. These factors indicate that cellular and humoral recognition of TCR peptides represents an important autoregulatory mechanism in vivo that has application to the treatment of human immune-related diseases.

TABLE 33

Sequence of TCR Vβ8.2 and Vβ8.6 Peptides

| | |
|---|---|
| Vβ8.2-25-41 (CDR1) | KQNNNHNNMYWYRQDMG |
| Vβ8.2-39-59 (CDR2) | DMGHGLRLIHYSYDVNSTEKG |
| Vβ8-44-54 (CDR2) | LRLIHYSYDVN |
| Vβ8.6-39-59 (CDR2) | N..DE...........R.... |
| Vβ8.2-49-59 | YSYDVNSTEKG |
| Vβ8.2-Dβ1-Jβ1-93-101 (CDR3) | ASSDSSNTE |

TABLE 34

Delayed Type Hypersensitivity Response to Vβ88.2-39-59 and Vβ8-44-54 in Rats Immunized for 14 Days with Vβ8-44-54/CFA

| | Ear Swelling (mm/100) | |
|---|---|---|
| Ear Test Antigen | 24 h | 48 h |
| Vβ8.2-39-59 | 36 ± 8 | 41 ± 9 |
| Vβ8-44-54 | 26 ± 7 | 30 ± 8 |

Values represent mean ± S.D. of net ear swelling in 6 immunized rats. Background ear swelling in naive rats was 6 ± 1 mm for both peptides.

TABLE 35

Antibodies Raised Against TCR Vβ8.2-39-59 and Vβ8.6-39-59 Peptides Do Not Respond to Vβ8-44-54 Peptides

| | Synthetic β Chain TCR Peptides | | | | | | |
|---|---|---|---|---|---|---|---|
| Antiserum | Vβ8.2 39-59 | Vβ8 44-54 | Vβ8.6 39-59 | Vβ8.2 49-59 | Vβ8.2 25-41 | Vβ8.2 93-101 | Vβ14 39-59 |
| α-Vβ8.2-39-59 | 0.141 | 0.000 | 0.139 | 0.047 | 0.000 | 0.000 | 0.000 |
| α-Vβ8.6-39-59 | 1.347 | 0.000 | 1.025 | 0.151 | 0.000 | 0.000 | 0.000 |

Antisera were prepared in rabbits using a course of immunization with the free peptide emulsified with complete Freund's adjuvant. Antisera were tested at a 1:80,000 dilution. End titers were documented by ELISA and presented as O.D. units at 450 nm using a series of serum dilutions and 25 ng plated peptide per well in a 96-well plate.

TABLE 36

Response of T Cells from Vβ8-44-54/CFA Immunized Rats

| Antigen | Lymph Node Cells | T Cell Line |
|---|---|---|
| Medium | 14 ± 1 | 10 ± 2 |
| Con A | 293 ± 39 | 209 ± 8 |
| +OX-18 (MHC-I) | ND | 188 ± 13 (88%) |
| +OX-6 (MHC-II, I-A) | ND | 175 ± 11 (93%) |
| +OX-17 (MHC-II) | ND | 223 ± 15 (106%) |
| TCR Vβ8-44-54 | 54 ± 7 | 238 ± 5 |
| +OX-18 (MHC-I) | ND | 57 ± 20 (24%) |
| +OX-6 (MHC-II, I-A) | ND | 226 ± 17 (95%) |
| +OX-17 (MHC-II, I-E) | ND | 217 ± 10 (91%) |
| TCR Vβ8.2-39-59 | 38 ± 3 | 102 ± 10 |
| TCR Vβ8.2-49-59 | 14 ± 2 | 9 ± 2 |
| TCR Vβ8.2-25-41 | 14 ± 0 | 6 ± 1 |
| TCR Vβ8.6-39-59 | 32 ± 4 | 162 ± 3 |
| TCR Vβ14-39-59 | 18 ± 2 | 9 ± 1 |
| PPD | 152 ± 4 | 10 ± 1 |

TABLE 37

Specificity and TCR V Gene Use of Vβ8-44-54 Reactive T Cell Clones

| | Proliferation Response (CPM/1000) to: | | | | |
|---|---|---|---|---|---|
| Clone | Medium | Vβ8-44-54 | Vβ8.2-39-59 | Vβ8.6-39-59 | TCR Vβ Gene Expression |
| B3 | 1.6 | 57 | 1.1 | 1.3 | 10 |
| B7 | 0.1 | 11 | 3 | 6 | ND |
| B9 | 0.1 | 2 | ND | ND | 12 |
| B10 | 0.4 | 4 | ND | ND | ND |
| B11 | 0.2 | 9 | 0.7 | 0.3 | ND |
| C11 | 0.2 | 17 | ND | ND | ND |
| C12 | 0.1 | 108 | ND | ND | ND |
| C16 | 0.3 | 5 | ND | ND | ND |
| D1 | 0.1 | 130 | 0.8 | 0.8 | ND |
| D4 | 0.5 | 80 | ND | ND | 12 |
| Line | 10 | 238 | 102 | 162 | 8.2; 8.6; 10; 12; 15; 19 |

TABLE 38

Nucleotide and Amino Acid Sequences of TCR VβDβJβ
Region of T Cell Clones Specific for Vβ8-44-54 Determinant

| Clone | V | (N)D(N) | J |
|---|---|---|---|
| B3 Vβ10/ Jβ2.5 | CysAlaSerSer tgtgccagcagc | ProTrpGlyGlyIle ccctgggggggtatt | AsnGlnGluThr aaccaagagacc |
| B9 Vβ12/ Jβ1.4 | CysAlaSerSer tgtgccagcagc | AsnArgAlaGly aacagggctgga | GluArgLeu gaaagattg |
| D4 Vβ12/ Jβ2.7 | CysAlaSerSer tgtgccagcagc | PheGlnGlyAla tttcagggggcc | TyrGluGln tatgagcag |

EXAMPLE XIV

Treatment of Autoimmune Disease with a
Toxin-Conjugated Antibody to a TCR Peptide In the present example, a mAb is produced by immunizing mice with the TCR Vβ8(39-59) peptide and carrying out the methods for making a hybridoma as described above. The mAb is then conjugated to the ricin A chain, to yield an immunotoxin. The toxin conjugated antibody is injected into rats along at the same time as an encephalitogenic dose of GPBP (prophylaxis), and into other rats after onset of EAE (therapy).

Prophylactic treatment with the ricin A chain-conjugated anti-TCR peptide antibody (1–4 injections at doses of 0.05 to 0.2 mg/kg) results in a significantly reduced incidence and severity of EAE. Therapeutic treatment with similar doses of the conjugate results in a significant shortening of the duration and a lessening in the severity of the disease.

EXAMPLE XV

Treatment of Arthritis with TCR Peptides

The present example describes how human rheumatoid arthritis is treated by the composition and methods of the invention. It is modeled by two animal models: (1) Arthritis induced in susceptible mice by injection of Type II collagen (Stuart et al., Ann. Rev. Immunol. 2: 199–218 (1984) and (2) arthritis induced in susceptible rats by injection of Mycobacterial heat shock protein (HSP) (Van Eden, W., et al., Nature 331: 171–173 (1988)). Arthritogenic T cells responsive to collagen or HSP and capable of transferring the disease are selected in vitroin the presence of collagen or HSP using methods described above. The TCR associated with disease-mediating T cells is identified, and the presumptive amino acid sequence is determined by nucleic acid sequencing, as above. Using the algorithms of Margalit et al. and Rothbard et al. (supra), an immunogenic portion of the TCR that involves a CDR or hypervariable region is synthesized and used to immunize mice (for collagen arthritis) or rats (for adjuvant arthritis).

Animals treated with the TCR peptide in conjunction with disease induction are significantly protected from development of arthritis, as measured by joint swelling and by T cell reactivity to the arthritogen. Animals treated with the TCR peptide after onset of the disease show a significant shortening of the duration and a lessening in the severity of the symptoms of arthritis.

Passive immunization with antibodies induced against the TCR peptide associated with arthritis also show similar prophylactic and therapeutic effects on arthritis induction. Successful treatment is achieved by polyclonal antibodies, mAbs, chimetic antibodies, and immunotoxin-conjugated antibodies.

Passive immunization with T cells specific for the arthritis-associated TCR peptide induce protective immunity, both prophylactic and therapeutic, against development and progression of arthritis.

EXAMPLE XVI

Treatment of Thyroiditis with TCR Peptides

Human thyroiditis, including Hashimoto's thyroiditis and Graves' disease, is treated by the composition and methods of the invention as described in the present example. Although the precise nature of the target autoantigen is uncertain, immune reactivity to thyroglobulin and to thyrotrophin receptor, respectively, is associated with these diseases. Thyroiditis is modeled in mice by administration of thyroglobulin (Maron, R., et al., J. Exp. Med. 152: 1115–1120 (1980)). T cells responsive to thyroglobulin and to thyroid follicular cell antigens, and capable of transferring the disease, are selected in vitro in the presence of either thyroglobulin, thyroid cells, or thyroid cell membrane preparations using methods described above. The TCR associated with disease-mediating T cells is identified, and the presumptive amino acid sequence is determined by nucleic acid sequencing, as above. Using the algorithms of Margalit et al. and Rothbard et al. (supra), an immunogenic portion of the TCR that involves a CDR or hypervariable region is synthesized and used to immunize mice.

Animals treated with the TCR peptide in conjunction with disease induction are significantly protected from development of thyroiditis and and of T cell reactivity to the thyroid antigens. Animals treated with the TCR peptide after onset of the disease show a significant shortening of the duration and a lessening in the severity of the symptoms of thyroiditis.

Passive immunization with antibodies induced against the TCR peptide associated with thyroiditis also shows similar prophylactic and therapeutic effects on disease induction. Successful treatment is achieved by polyclonal antibodies, mAbs, chimeric antibodies, and immunotoxin-conjugated antibodies.

Passive immunization with T cells specific for the thyroiditis-associated TCR peptide induces protective immunity, both prophylactic and therapeutic, against development and progression of thyroiditis.

EXAMPLE XVII

Treatment of Diabetes with TCR Peptides

Insulin-dependent diabetes mellitus (IDDM), or type I diabetes, is an autoimmune disease characterized by immune reactivity directed to pancreatic islet (or beta) cells, resulting in the cells' destruction and shutdown of insulin production. The target antigens for this immune attack have not been characterized with certainty. The present example describes how IDDM is treated by the compositions and methods of this invention.

The disease is modeled in animals in which it occurs naturally, or can be induced in certain strains of mice (Kanasawa et al., Diabetologia 27: 113 (1984). Other mouse strains can be caused to exhibit this disease by transferring lymphocytes from the susceptible strains.

T cells responsive to pancreatic islet cell antigens and capable of transferring the disease are selected in vitro in the presence of either islet cells, or islet cell membrane preparations using methods described above. The TCR associated with disease-mediating T cells is identified, and the presumptive amino acid sequence is determined by nucleic acid sequencing, as above. Using the algorithms of Margalit et al. and Rothbard et al. (supra), an immunogenic portion of the TCR that involves a CDR or hypervariable region is synthesized and used to immunize mice.

Animals treated with the TCR peptide in conjunction with disease induction are significantly protected from development of diabetes and and of T cell reactivity to the islet cell antigens. Animals treated with the TCR peptide after onset of the disease show a significant shortening of the duration and a lessening in the severity of the symptoms of diabetes.

Passive immunization with antibodies induced against the TCR peptide associated with diabetes also show similar prophylactic and therapeutic effects on disease induction. Successful treatment is achieved by polyclonal antibodies, mAbs, chimeric antibodies, and immunotoxin-conjugated antibodies.

Passive immunization with T cells specific for the diabetes-associated TCR peptide induces protective immunity, both prophylactic and therapeutic, against development and progression of diabetes.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A purified or synthetic immunogenic T cell receptor peptide capable of reducing the severity of a T cell mediated disease, having an amino acid sequence of about 15 to 30 amino acids comprising at least a part of the second complementarity determining region of a T cell receptor characteristic of such T cell mediated disease, or a corresponding purified or synthetic immunogenic functional derivative that is a fragment, a variant or a chemical derivative of said peptide.

2. The T cell receptor peptide or functional derivative of claim 1 wherein the T cell receptor characteristic of a T cell mediated disease is of human origin.

3. The T cell receptor peptide or functional derivative of claim 1 wherein said complementarity determining region is from a T cell receptor beta chain.

4. The T cell receptor peptide or functional derivative of claim 1 comprising an amino acid sequence that overlaps said second complementarity determining region.

5. The T cell receptor peptide or functional derivative of claim 1 consisting of an amino acid sequence entirely within said second complementarity determining region.

6. The functional derivative of claim 1 that is a fragment.

7. The functional derivative of claim 1 that is a chemical derivative.

8. The functional derivative of claim 1 that is a variant.

9. The functional derivative of claim 1 encompassing a minimal epitope structure of said peptide.

10. A purified or synthetic immunogenic T cell receptor peptide capable of reducing the severity of a T cell mediated disease, having an amino acid sequence of about 15 to 30 amino acids comprising comprising at least a part of the second complementarity determining region of a T cell receptor characteristic of such T cell mediated disease.

11. The T cell receptor peptide of claim 10 wherein the T cell receptor characteristic of a T cell mediated disease is of human origin.

12. The T cell receptor peptide of claim 1 wherein said complementarity determining region is from a T cell receptor beta chain.

13. The T cell receptor peptide or functional derivative of claim 10 consisting essentially of an entire second complementarity determining region.

14. A pharmaceutical formulation comprising a therapeutically effective amount of the peptide or functional derivative of any of claims 1 to 13 and a pharmaceutically acceptable excipient.

15. A pharmaceutical formulation comprising:

one or a combination of purified or synthetic immunogenic T cell receptor peptides having an amino acid sequence of about 15 to 30 amino acids, each comprising an amino acid sequence encompassing at least a part of the second complementarity determining region of a T cell receptor characteristic of the a T cell mediated disease disease; or one or a combination of corresponding purified or synthetic immunogenic functional derivatives, comprising a fragment, a variant or a chemical derivative of a said peptide; or a combination of one or more of said peptides and one or more of said functional derivatives, present in an amount efffective to reduce the severity of a T cell mediated disease, and a pharmaceutically acceptable excipient.

16. A method for reducing the severity of a T cell mediated disease by administering to a mammal in need thereof an effective amount of a purified or synthetic immunogenic T cell receptor peptide comprising an amino acid sequence encompassing at least a part of the second complementarity determining region of a T cell receptor characteristic of the disease, or administering an effective amount of a corresponding purified or synthetic immunogenic functional derivative that is a fragment, a variant or a chemical derivative of said peptide.

17. The method of claim 16 wherein said amino acid sequence comprises the amino acids within 15 to 30 amino acids of said second complementarity determining region.

18. The method of claim 16 wherein the T cell receptor is of human origin.

19. The method of claim 17 wherein the T cell receptor is of of human origin.

20. The method of claim 16 wherein said peptide comprises 15 to 30 amino acids.

21. The method of claim 17 wherein said peptide comprises 15 to 30 amino acids.

22. The method of claim 18 wherein said peptide comprises 15 to 30 amino acids.

23. The method of claim 19 wherein said peptide comprises 15 to 30 amino acids.

24. The method of claim 16 wherein said complementarity determining region is from a T cell receptor beta chain.

25. The method of claim 17 wherein said complementarity determining region is from a T cell receptor beta chain.

26. The method of claim 18 wherein said complementarity determining region is from a T cell receptor beta chain.

27. The method of claim 19 wherein said complementarity determining region is from a T cell receptor beta chain.

28. The method of claim 20 wherein said complementarity determining region is from a T cell receptor beta chain.

29. The method of claim 16 wherein said functional derivative comprises an amino acid sequence that overlaps said second complementarity determining region.

30. The method of claim 17 wherein said functional derivative comprises an amino acid sequence that overlaps said second complementarity determining region.

31. The method of claim 18 wherein said functional derivative comprises an amino acid sequence that overlaps said second complementarity determining region.

32. The method of claim 19 wherein said functional derivative comprises an amino acid sequence that overlaps said second complementarity determining region.

33. The method of claim 20 wherein said functional derivative comprises an amino acid sequence that overlaps said second complementarity determining region.

34. The method of claim 24 wherein said functional derivative comprises an amino acid sequence that overlaps said second complementarity determining region.

35. The method of claim 16 wherein said T cell-mediated disease is rheumatoid arthritis, myasthenia gravis, encephalomyelitis, multiple sclerosis, thyroiditis, diabetes, inflammatory bowel disease, or systemic lupus erythematosus.

36. The method of claim 17 wherein said T cell-mediated disease is rheumatoid arthritis, myasthenia gravis, encephalomyelitis, multiple sclerosis, thyroiditis, diabetes, inflammatory bowel disease, or systemic lupus erythematosus.

37. The method of claim 18 wherein said T cell-mediated disease is rheumatoid arthritis, myasthenia gravis, encephalomyelitis, multiple sclerosis, thyroiditis, diabetes, inflammatory bowel disease, or systemic lupus erythematosus.

38. The method of claim 19 wherein said T cell-mediated disease is rheumatoid arthritis, myasthenia gravis, encephalomyelitis, multiple sclerosis, thyroiditis, diabetes, inflammatory bowel disease, or systemic lupus erythematosus.

39. The method of claim 20 wherein said T cell-mediated disease is rheumatoid arthritis, myasthenia gravis, encephalomyelitis, multiple sclerosis, thyroiditis, diabetes, inflammatory bowel disease, or systemic lupus erythematosus.

40. The method of claim 24 wherein said T cell-mediated disease is rheumatoid arthritis, myasthenia gravis, encephalomyelitis, multiple sclerosis, thyroiditis, diabetes, inflammatory bowel disease, or systemic lupus erythematosus.

41. The method of claim 29 wherein said T cell-mediated disease is rheumatoid arthritis, myasthenia gravis, encephalomyelitis, multiple sclerosis, thyroiditis, diabetes, inflammatory bowel disease, or systemic lupus erythematosus.

42. The method of claim 16, wherein said T cell receptor peptide or functional derivative comprises a sequence which consists entirely of amino acids within the CDR2.

43. The method of claim 16, wherein said T cell receptor peptide or functional derivative consists essentially of an entire second complementarity determining region.

44. The method of claim 16, wherein said functional derivative is a fragment of a T cell receptor peptide.

45. The method of claim 16 comprising administering a functional derivative that encompasses a minimal epitope structure of said peptide.

46. The method of claim 45 wherein said minimal epitope structure is recognizable by a T cell or antibody specific for said peptide.

47. The method of claim 16 wherein said functional derivative is a chemical derivative of said peptide.

48. The method of claim 16 wherein said functional derivative is a variant of said peptide.

49. The method of claim 48 comprising administering a functional derivative that encompasses a minimal epitope structure of said peptide.

50. The method of claim 49 wherein said minimal epitope structure is recognizable by a T cell or antibody specific for said peptide.

51. A method for reducing the severity of a T cell mediated disease by administering to a mammal in need thereof an effective amount of a purified or synthetic immunogenic T cell receptor peptide comprising an amino acid sequence encompassing at least a part of the second complementarity determining region of a T cell receptor characteristic of the disease.

52. The method of claim 51 wherein the T cell receptor is of human origin.

53. The method of claim 51 wherein said complementarity determining region is from a T cell receptor beta chain.

54. The method of claim 51 wherein said peptide consists essentially of an entire second complementarity determining region.

55. The method of claim 51 comprising administering an effective amount of a combination of purified or synthetic immunogenic T cell receptor peptides, each comprising an amino acid sequence encompassing at least a part of the second complementarity determining region of a T cell receptor characteristic of the disease.

56. The method of claim 16 comprising administering an effective amount of a combination of purified or synthetic immunogenic T cell receptor peptides, each comprising an amino acid sequence encompassing at least a part of the second complementarity determining region of a T cell receptor characteristic of the disease, or administering an effective amount of a combination of corresponding purified or synthetic immunogenic functional derivatives, each comprising a fragment, a variant or a chemical derivative of a said peptide, or administering an effective amount of a combination of one or more of said peptides and one or more of said functional derivatives.

* * * * *